(12) United States Patent
Jacobsen et al.

(10) Patent No.: US 9,695,200 B2
(45) Date of Patent: Jul. 4, 2017

(54) HETEROCYCLIC ITK INHIBITORS FOR TREATING INFLAMMATION AND CANCER

(71) Applicant: Confluence Life Sciences, Inc., St. Louis, MO (US)

(72) Inventors: Eric Jon Jacobsen, Chesterfield, MO (US); James Robert Blinn, O'Fallon, MO (US); John Robert Springer, Wentzville, MO (US); Susan L. Hockerman, Kirkwood, MO (US)

(73) Assignee: Confluence Life Sciences, Inc., St. Louis, MO (US)

( * ) Notice: Subject to any disclaimer, the term of this patent is extended or adjusted under 35 U.S.C. 154(b) by 0 days.

(21) Appl. No.: 15/005,627

(22) Filed: Jan. 25, 2016

(65) Prior Publication Data

US 2016/0213653 A1 Jul. 28, 2016

Related U.S. Application Data

(60) Provisional application No. 62/107,078, filed on Jan. 23, 2015.

(51) Int. Cl.
| | | |
|---|---|---|
| *A61K 31/5377* | (2006.01) | |
| *A61K 31/506* | (2006.01) | |
| *C07D 471/04* | (2006.01) | |
| *A61K 45/06* | (2006.01) | |
| *A61K 31/437* | (2006.01) | |
| *C07D 519/00* | (2006.01) | |

(52) U.S. Cl.
CPC ............ *C07D 519/00* (2013.01); *A61K 45/06* (2013.01); *C07D 471/04* (2013.01)

(58) Field of Classification Search
CPC .... A61K 45/06; A61K 31/506; A61K 31/437; A61K 31/5377; C07D 471/04; C07D 519/00
USPC .......................................................... 546/113
See application file for complete search history.

(56) References Cited

U.S. PATENT DOCUMENTS

| | | | | |
|---|---|---|---|---|
| 5,707,989 | A | 1/1998 | Himmelsbach | |
| 7,906,648 | B2 * | 3/2011 | Arnold .................. | C07D 471/04 546/113 |
| 8,242,280 | B2 * | 8/2012 | Chen ...................... | C07D 487/04 546/275.7 |
| 8,518,952 | B2 | 8/2013 | Braganza et al. | |
| 9,145,393 | B2 | 9/2015 | Jacobsen et al. | |
| 2007/0179156 | A1 | 8/2007 | Charrier et al. | |
| 2008/0280917 | A1 | 11/2008 | Albrecht et al. | |
| 2011/0294836 | A1 | 12/2011 | Song et al. | |
| 2012/0046295 | A1 * | 2/2012 | Charrier ............. | A61K 31/4985 514/249 |
| 2013/0281432 | A1 | 10/2013 | Currie et al. | |
| 2014/0315909 | A1 * | 10/2014 | Vankayalapati ..... | C07D 471/04 514/249 |
| 2015/0328227 | A1 | 11/2015 | Jacobsen et al. | |
| 2016/0213653 | A1 * | 7/2016 | Jacobsen ............. | A61K 31/437 |

FOREIGN PATENT DOCUMENTS

| | | | |
|---|---|---|---|
| EP | 2489663 | | 8/2012 |
| KR | 20120061011 | * | 6/2012 |
| WO | 0026211 A1 | | 5/2000 |
| WO | 02053543 A1 | | 7/2002 |
| WO | 2012031004 A1 | | 3/2012 |
| WO | 2013153539 A1 | | 10/2013 |
| WO | 2014172513 A1 | | 10/2014 |
| WO | 2015112847 A1 | | 7/2015 |
| WO | 2015112847 A3 | | 7/2015 |
| WO | WO2016000615 | * | 1/2016 |
| WO | 2016118951 A2 | | 7/2016 |
| WO | 2016118951 A3 | | 10/2016 |

OTHER PUBLICATIONS

Hong; Bioorganic & Medicinal Chemistry Letters 20 (2010) 7212-7215.*
Jung; Cancer Letters 316 (2012) 187-195.*
Hong; J. Med. Chem. 2012, 55, 5337-5349.*
Park; Org. Biomol. Chem., 2014, 12, 4644-4655.*
Jacobsen, EJ et al., New substituted heterocyclic compounds are interleukin-2-inducible T-cell kinase inhibitors, useful for treating e.g. cancer, autoimmune disorders, chronic inflammatory disorders, auto-inflammatory disorders, pain or inflammatory disorders, Confluence Life Science Inc., U.S. Pat. No. 9,145,393 B2, Notice of allowance, Apr. 22, 2015.
Jacobsen, EJ et al., Inhibition of interleukin-2-inducible T-cell kinase activity in a biological sample involves contacting biological sample with arylpyridinone compound or its pharmaceutically acceptable salt, hydrate, or solvate, Confluence Life Science Inc., US 20150328227 A1, Non-final rejection, Aug. 25, 2015.
Jacobsen, EJ et al., New substituted heterocyclic compounds are interleukin-2-inducible T-cell kinase inhibitors, useful for treating e.g. cancer, autoimmune disorders, chronic inflammatory disorders, auto-inflammatory disorders, pain or inflammatory disorders, Confluence Life Science Inc., WO 2015112847 A1—IPRP, Jul. 26, 2016.

* cited by examiner

*Primary Examiner* — Noble Jarrell
*Assistant Examiner* — Daniel Carcanague
(74) *Attorney, Agent, or Firm* — Dennis A. Bennett; Brock Levin

(57) ABSTRACT

Disclosed herein are heterocyclic compounds and compositions useful in the treatment of ITK mediated diseases, such as inflammation, having the structure of Formula (I):

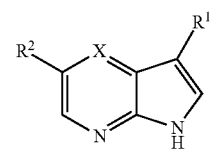

wherein $R^1$, $R^2$, and X are as defined in the detailed description. Methods of inhibition of ITK activity in a human or animal subject are also provided.

7 Claims, No Drawings

HETEROCYCLIC ITK INHIBITORS FOR TREATING INFLAMMATION AND CANCER

This application claims priority to U.S. provisional application No. 62/107,078 filed Jan. 23, 2015, the disclosure of which is incorporated by reference herein in its entirety.

The present disclosure relates to new heterocyclic compounds and compositions, and their application as pharmaceuticals for the treatment of disease. Methods of inhibition of ITK activity in a human or animal subject are also provided for the treatment diseases such as those caused by inflammation.

The Tec (tyrosine kinase expressed in hepatocellular carcinoma) family of tyrosine kinases (TFTK) consists of five family members: Tec, BTK (Bruton's tyrosine kinase), BMX (bone marrow kinase on the X chromosome also known as ETK), RLK (resting lymphocyte kinase also known as TXK) and ITK (interleukin-2 inducible T cell kinase, also known as EMT and TSK). These kinases are central to the regulation of hematopoietic cell biology and more specifically the development and activity of lymphocytes and myeloid cells (Horwood et al. (2012) Int. Rev. Immunol. 31, 87-103; Boucheron et al. (2012) Int. Rev. Immunol. 31, 133-154; Koprulu et al. (2009) Crit. Rev. Immunol. 29, 317-333). The TFTK have structural similarities to other non-receptor tyrosine kinases while exhibiting some family specific motifs resulting in a diversity of domain structures associated with complex localization, scaffolding and activation mechanisms. Generally, TFTK contain an amino terminal plekstrin homology domain (PH domain) involved in lipid interactions and membrane targeting followed by a BTK homology domain (BH) that binds $Zn^{2+}$ and an SH3 domain generally involved in proline rich domain binding. A phosphotyrosine binding SH2 domain and a carboxy terminal ATP binding kinase domain complete the TFTK structure (Mano, et al. (1999) Cytokine Growth Factor Rev. 10, 267-280). TFTK expression is generally limited to hematopoietic lineage cells with the exception of ETK and TEC that are expressed in the liver and endothelial cells, respectively (Smith, et al. (2011) Bioessays 23, 436-446). BMX is expressed in monocytes, granulocytes and cardiac endothelium while BTK is expressed in B cells and mast cells but not plasma cells and T cells. TEC, RLK and ITK are all expressed in T cells. To date the TFTK with the most clear biological role in T cells is ITK.

Antigen/MHC dependent activation of the T cell receptor (TCR) has been shown to transduce its signal through ITK. TCR stimulation results in the activation of the kinase LCK and subsequent phosphorylation of the immunoreceptor tyrosine-based activation motifs (ITAMs) on CD3 inducing the binding and activation of the kinase ZAP70. In turn, ZAP70 phosphorylates the adaptor proteins LAT and SLP-76, which together with LCK and other proteins forms a heteromultimeric signaling complex that activates PI3K and generates $PIP_3$ on the plasma membrane. ITK binds to this signaling complex via SH2 and SH3 domains and to $PIP_3$ through its PH domain, resulting in LCK dependent phosphorylation of ITK Y511 and subsequent ITK autophosphorylation of Y180. Activated ITK phosphorylates PLCγ1 that, once activated, hydrolyzes $PIP_2$ to the second messengers IP3 and DAG. The cellular consequences of these sequelae of events include calcium mobilization and flux, PKC and MEK/ERK pathway activation, and transcriptional activation via AP1, NFκactiv NFAT. As a critical enzyme in the TCR activation pathway ITK impacts T cell function in a number of ways including positive and negative selection, cellular differentiation, and cytokine production and release (Takesono, et al. (2002) J. Cell Science 115, 3039-3048; August, et al. (2012) Int. Rev. Immunol. 31, 155-165; Andreotti, et al. (2010) Cold Spring Harb. Perspect. Biol. 2, a002287 1-21).

The role of ITK in T cell function has been delineated through genetic knockdown/kinase inactivation of the ITK gene in rodents and through characterizing human ITK mutant individuals. Mice with a null mutation of the itk gene expressed a decreased number of mature T cells and a block in thymocyte development as well as a decreased TCR driven T cell proliferative response. Interestingly IL2 and CD28 signaling as well as PMA/ionomycin driven responses remained unchanged, suggesting that the ITK response is membrane proximal and stimuli specific (Liao et al. (1995) Immunity 3, 757-769). It appears that ITK is responsible for amplification of TCR signaling versus an 'on/off' switch, as dual knockdown of the T cell expressing TFTK, ITK and RLK in mice produce a more complete TCR inactivation phenotype compared with ITK genetic deletion alone (Schaeffer et al. (1999) Science 284, 638-641). In contrast to the modulatory effect that ITK appears to have on naïve T cell activation, it plays a more significant role in T helper cell differentiation. Several studies in ITK deficient mice have demonstrated a reduction in the Th2 protective response to parasitic infection (Fowell et al. (1999) Immunity 11, 399-409; Schaeffer et al. (2001) Nat. Immunol. 2, 1183-1188). This reduced Th2 response was linked to a decrease in concentrations of Th2 cytokines IL4, IL5, IL13 and IL10 (Schaeffer et al. (2001) Nat. Immunol. 2, 1183-1188) and to a reduction in RLK expression. In contrast to the ITK requirement for mounting Th2 driven responses, its impact on Th1 responses is modest. For example, IFNg production in ITK knockout cells is partially inhibited while the double ITK/RLK knockout has a more severe phenotype (Fowell et al. (1999) Immunity 11, 399-409; Schaeffer et al. (2001) Nat. Immunol. 2, 1183-1188; Miller et al. (2004) Immunity 21, 67-80). Evaluation of Th17 T helper cells in ITK knockout in vivo and in vitro studies demonstrated a reduction of IL17A mRNA and protein while having little impact on IL17F (Gomez-Rodriguez et al. (2009) Immunity, 31, 587-597). The role of ITK in cytotoxic CD8+ T cells was investigated using ITK knockout mice. Stimulation of CD8+ T cells deficient in ITK results in a reduction in activation of PLCg1, ERK and p38 MAPK and loss of $Ca^{2+}$ response resulting in decreased proliferative response and effector cytokine production (IL2, IL4 and IFNg) while not impacting cytolytic capacity of these cells (Atherly et al. (2006) J. Immunol. 176, 1571-1581). In addition to the defects observed in CD4+ and CD8+ T cells, natural killer T cell development and TCR stimulated response is reduced in ITK knockout cells and animals (Au-Yueng et al. (2007) J. Immunol. 179, 111-119; Felices et al. (2008) J. Immunol. 180, 3007-3018).

Rodent genetic knockout studies reflect the impact of enzyme expression, not necessarily its catalytic activity, on biological responses. As ITK, through its multiple domain structure, has a role in scaffolding, in addition to its catalytic role. It is important to delineate the impact of blocking each of these functions on cellular biology. Kinase activity-independent ITK activities include recruitment of the guanine nucleotide exchange factor VAV to the cell membrane associated with actin polymerization (PH and SH2 domain dependent) (Atherly et al. (2006) J. Immunol. 176, 1571-1581), antigen receptor stimulation, and receptor activation of SRF (Dombroski et al. (2005) J. Immunol., 174, 1385-1392). However, ITK knockout mice expressing an ITK kinase domain deleted transgene demonstrated that the kinase domain is essential for induction of a normal Th2 response (von Bonin et al. (2011) Exp. Dermatol. 20, 41-47).

The relationship between ITK expression and activity and human disease has recently been documented in studies characterizing individuals exhibiting mutations in the gene encoding this protein and or correlation between expression and disease. The ITK gene was found to be elevated in peripheral blood T cells from patients with moderate to severe atopic dermatitis, a Th2 driven chronic inflammatory skin disease (Hao et al. (2006) FEBS Letts., 580, 2691-2697). An investigation of disease-associated single nucleotide polymorphisms (SNP) in seasonal allergic rhinitis identified ITK as a significant risk factor (Matsumoto et al. (2002) Int. Arch. Allergy Immunol. 129, 327-340). A human primary immunodeficiency was uncovered in siblings that died from immune dysregulation resulting in lymphoproliferation following Epstein Barr Virus (EBV) infection. This disorder was linked to a missense (R335W) mutation in the SH2 domain of ITK resulting in structural instability and reduced steady state levels of the enzyme (Felices et al. (2008) J. Immunol., 180, 3007-3018). The finding was confirmed and extended in studies that identified three patients harboring a C1764G nonsense mutation in ITK resulting in a premature stop codon and reduced expression and/or activity of the protein. These patients presented with EBV-positive Hodgkin's Lymphoma (Huck et al. (2009) J. Clin. Invest. 119, 1350-1358). These two reports suggest that mutational disruption of the ITK gene in humans results in an autosomal recessive lymphoproliferative disorder and identify this kinase as a critical modulator in T cell biology.

In addition to the human genetic data summarized above, animal models support ITK as a therapeutic target for autoimmune and inflammatory disease. ITK knockout mice demonstrate reduced airway hypersensitivity and inflammation in models of allergic asthma (Stepensky et al. (2011) Haematologica, 96, 472-476; Mueller et al. (2003) J. Immunol., 170, 5056-5063; Ferrara et al. (2004) Pulm. Pharmacol. Ther. 17, 301-308). In a murine model of atopic dermatitis, ITK deficient mice do not develop inflammation while ITK inhibition reduces the response in wild type mice (Ferrara et al. (2006) J. Allerg. Clin. Immunol. 117, 780-786). The ITK dependent regulation of TCR dependent $Ca^{2+}$ mobilization and transcription factor induction makes it a critical factor in protecting against Influenza A and HIV infection and viral replication. ITK inhibitors have been shown to alter HIV replication at multiple stages and have the potential as effective HIV therapeutics (Sahu et al. (2008) J. Immunol. 180, 3833-3838).

From an oncology perspective, studies have demonstrated that ITK inhibitors selectively target the killing of acute lymphoblastic T-cell leukemia and cutaneous T-cell lymphoma while normal T cells are minimally impacted (Readinger et al. (2008) Proc. Nat. Acad. Sci. USA, 105, 6684-6689). ITK is highly expressed in transformed T-cell lines relative to normal T cells and other cancer cell lines. The impact of ITK inhibition on T cell tumors was confirmed in mouse xenograph models. Cancer evasion of the immune system as a result of tumor antigen tolerance induction versus priming is critical for tumor survival. Tumors that develop a microenvironment that induces T cell unresponsiveness demonstrate altered T cell gene expression suggesting skewing to the Th2 phenotype. ITK inhibition will favor Th1 differentiation and could be used to enhance cancer immunotherapy (Gao et al. (2012) Mol. Pharmacol., 82, 938-947; Horna et al. (2007) Curr. Cancer Drug Targ. 7, 41-53).

Compounds useful as dual ITK and JAK3 kinase inhibitors for the treatment of inflammation and immune disorders are reported in WO 2014172513 (pub. 23 Oct. 2014). Compounds described therein include 5-aryl-substituted pyrrolopyridines and pyrrolopyrazines where the 5-aryl group is substituted with acrylamide substituents.

Compounds useful as dual ITK and JAK3 kinase inhibitors for the treatment of inflammation and immune disorders are reported in US 20140315909 (pub. 23 Oct. 2014). Compounds described therein include 5-aryl-substituted pyrrolopyridines and pyrrolopyrazines where the 5-aryl group is substituted with acrylamide substituents.

Thus, in various embodiments, the present disclosure provides a compound, or a pharmaceutically acceptable salt, hydrate or solvate thereof, of Formula (I):

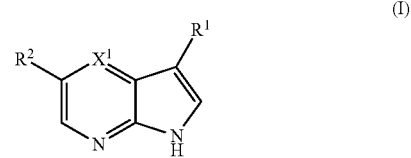

wherein:
$R^1$ is chosen from mono- and bicyclic aryl and heteroaryl, wherein $R^1$ may be optionally substituted with one or more $R^3$ substituents;
$R^2$ is chosen from heterocycloalkyl, aryl, and heteroaryl, each of which is substituted with one $R^4$ substituent, and any of which may be further optionally substituted with one or more $R^8$ substituents, or alternatively $R^2$ is $NR^{12}R^{13}$;
each $R^3$ is independently chosen from hydrogen, hydroxyl, cyano, $C_{1-6}$alkyl, hydroxy$C_{1-4}$alkyl, $C_{1-6}$alkoxyalkyl, aryl$C_{1-6}$alkyl, aryl$C_{1-6}$alkoxy, heteroaryl$C_{1-6}$alkyl, heteroaryl$C_{1-6}$alkoxy, aryloxy$C_{1-6}$alkyl, heteroaryloxy$C_{1-6}$alkyl, aryloxy$C_{1-6}$alkyl, heteroaryloxy$C_{1-6}$alkyl, cyclopropyl$C_{1-4}$alkyl, cyclopropyl$C_{1-4}$alkoxy, cyclopropoxy$C_{1-4}$alkyl, $C_{1-4}$alkylamino, $C_{1-4}$alkylarylamino, $C_{1-4}$alkylheteroarylamino, di($C_{1-4}$alkyl)amino, —C(O)$NR^6R^{6'}$, $C_{1-4}$alkanoyl, —C(O)aryl, —C(O)heteroaryl, —C(O)NHaryl, —C(O)NHheteroaryl, trifluoromethyl, and halo, wherein aryl and heteroaryl may be optionally substituted with $R^9$;
$R^4$ is chosen from $NR^5R^6$, —(CH$_2$)$_n$CR$^7$=CR$^9$C(O)CH$_3$, —(CH$_2$)$_n$CR$^7$=CR$^9$C(O)NR$^7$R$^{7'}$, and —(CH$_2$)$_n$CR$^7$=CR$^9$CN;
$R^5$ is chosen from cyano, —C(O)CF$_3$, —C(O)CH=CH$_2$, —C(O)CR$^7$=CH$_2$, —C(O)CH=CHR$^7$, —C(O)CR$^7$=CHR$^7$, —C(O)CH=CR$^7$R$^{7'}$, —C(O)CH=CHCH$_2$R$^8$, —C(O)CH=CHC(O)CH$_2$R$^8$, —COC(CN)=CHR$^6$, —C(O)(C(O)NH$_2$)=CHR$^6$, C(O)alkynylR$^7$, —S(O)$_2$CH=CH$_2$, —(CH$_2$)$_m$CR$^7$=CR$^9$C(O)CH$_3$, —(CH$_2$)$_m$CR$^7$=CR$^9$C(O)NR$^7$R$^{7'}$, and —(CH$_2$)$_m$CR$^7$=CR$^9$CN;
$R^6$ and $R^{6'}$ are each independently chosen from hydrogen, $C_{1-4}$alkyl, $C_{3-7}$cycloalkylalkyl, and phenyl$C_{1-4}$alkyl;
$R^7$ and $R^{7'}$ are each independently chosen from hydrogen, cyano, $C_{1-4}$alkyl, hydroxy$C_{1-4}$alkyl, $C_{1-4}$alkoxyalkyl, $C_{3-7}$cycloalkyl, $C_{3-7}$heterocycloalkyl, $C_{3-7}$heterocycloalkylalkyl, $(NR^6R^{6'})C_{1-4}$alkyl, aryl, and heteroaryl, wherein aryl and heteroaryl may be optionally substituted with one or more $R^9$;
$R^8$ is chosen from hydrogen, halo, cyano, $C_{1-4}$alkyl, aryl $C_{1-4}$alkyl, heteroaryl$C_{1-4}$alkyl, $C_{3-7}$cycloalkyl, hydroxyC$_{1-6}$alkyl, heterocycloalkylC$_{1-4}$alkyl, C$_{3-7}$heterocycloalkyl, hydroxyl, C$_{1-4}$alkoxy, C$_{3-7}$cycloalkoxy, C$_{3-7}$cycloalkoxyalkyl, heteroaryloxy, aryloxy, (NR$^6$R$^{6'}$)alkyl, arylalkoxy, C$_{1-4}$alkoxyC$_{1-4}$alkyl, amino, C$_{1-4}$alkylamino, di(C$_{1-4}$alkyl)amino, trifluoromethyl, aryl, and heteroaryl, wherein alkyl, heterocycloalkyl, aryl and heteroaryl may be optionally substituted with one or more R$^9$;

R$^9$ is chosen from hydrogen, halo, hydroxyl, C$_{1-4}$ alkyl, cyano, trifluoromethyl, alkanoyl, amino, amido, and aryl;

R$^{10}$ is chosen from hydrogen, C$_{1-4}$alkyl, C$_{1-4}$alkoxy, halo, trifluoromethyl, and cyano;

R$^{11}$ is chosen from hydrogen, C$_{1-4}$alkyl, C$_{3-7}$cycloalkylalkyl, heterocycloalkylalkyl, arylC$_{1-4}$alkyl, and heteroarylC$_{1-4}$alkyl, wherein aryl and heteroaryl may be optionally substituted with one or more R$^9$;

R$^{12}$ is a nitrogen-containing C$_{3-7}$heterocycloalkyl, wherein said nitrogen is further substituted by R$^5$;

R$^{13}$ is chosen from hydrogen, C$_{1-4}$alkyl, and C$_{3-7}$cycloalkylalkyl;

X is N or CR$^{11}$;

m is an integer chosen from 1, 2 and 3; and n is an integer chosen from 0, 1, 2, and 3.

Certain compounds disclosed herein may possess useful ITK inhibiting activity, and may be used in the treatment or prophylaxis of a disease or condition in which ITK plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting ITK. Other embodiments provide methods for treating an ITK-mediated disorder in a subject in need of such treatment, comprising administering to the subject a therapeutically effective amount of a compound or composition according to the present disclosure. Also provided is the use of certain compounds disclosed herein for use in the manufacture of a medicament for the treatment of a disease or condition ameliorated by the inhibition of ITK.

DETAILED DESCRIPTION

Abbreviations and Definitions

To facilitate understanding of the disclosure, a number of terms and abbreviations as used herein are defined below as follows:

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from n$_1$ ... to n$_2$" or "between n$_1$ ... and n$_2$" is used, where n$_1$ and n$_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values that it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon substituent having one or more double bonds and containing from 2 to 20 carbon atoms. In certain embodiments, the alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl substituents include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether substituent, wherein the term alkyl is as defined below. Examples of suitable alkyl ether substituents include methoxy, ethoxy, n-propoxy, iso-propoxy, n-butoxy, iso-butoxy, sec-butoxy, tert-butoxy, and the like.

The term "alkyl," as used herein, alone or in combination, refers to a straight-chain or branched-chain alkyl substituent containing from 1 to 20 carbon atoms. In certain embodiments, the alkyl will comprise from 1 to 10 carbon atoms. In further embodiments, the alkyl will comprise from 1 to 6 carbon atoms. Alkyl groups may be optionally substituted as defined herein. Examples of alkyl substituents include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) substituent wherein the term alkyl is as defined above and wherein the sulfur may be singly or doubly oxidized. Examples of suitable alkyl thioether substituents include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon substituent having one or more triple bonds and containing from 2 to 20 carbon atoms. In certain embodiments, the alkynyl comprises from 2 to 6 carbon atoms. In further embodiments, the alkynyl comprises from 2 to 4 carbon atoms. The term "alkynylene" refers to a carbon-carbon triple bond attached at two positions such as ethynylene (—C:::C—, —C≡C—). Examples of alkynyl substituents include ethynyl, propynyl, hydroxypropynyl, butyn-1-yl, Butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl" as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl substituent derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent substituent $C_6H_4$= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, the cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl substituent having the meaning as defined above wherein one or more hydrogens are replaced with a halogen. Specifically embraced are monohaloalkyl, dihaloalkyl and polyhaloalkyl substituents. A monohaloalkyl substituent, for one example, may have an iodo, bromo, chloro or fluoro atom within the substituent. Dihalo and polyhaloalkyl substituents may have two or more of the same halo atoms or a combination of different halo substituents. Examples of haloalkyl substituents include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon substituent, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, the heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, pyridinonyl, pyrimidinonyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

When a group or substituent is "chosen from mono- and bicyclic aryl and heteroaryl," what is meant is that the aryl and heteroaryl may each be monocyclic or bicyclic, and the group or substituent is chosen from monocyclic aryl, bicyclic aryl, monocyclic heteroaryl, and bicyclic heteroaryl.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each the heteroatom may be independently selected from the group consisting of nitrogen, oxygen, and sulfur In certain embodiments, the heterocycloalkyl will comprise from 1 to 4 heteroatoms as ring members. In further embodiments, the heterocycloalkyl will comprise from 1 to 2 heteroatoms as ring members. In certain embodiments, the heterocycloalkyl will comprise from 3 to 8 ring members in each ring. In further embodiments, the heterocycloalkyl will comprise from 3 to 7 ring members in each ring. In yet further embodiments, the heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four the members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbonyl," refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethylsilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that the group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

When terms such as "$R^6$ and $R^{6'}$ are each independently chosen from" and "$R^7$ and $R^{7'}$ are each independently chosen from" are used herein and followed by a list of group members, what is meant is that each occurrence of $R^6$, $R^{6'}$, $R^7$, and $R^{7'}$ is independent of every other occurrence.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

ITK inhibitor is used herein to refer to a compound that exhibits an IC50 with respect to ITK activity of no more than about 100 µM and more typically not more than about 50 µM, as measured in the ITK enzyme assay described generally herein below. IC50 is that concentration of inhibitor that reduces the activity of an enzyme (e.g., ITK) to half-maximal level. Certain compounds disclosed herein have been discovered to exhibit inhibition against ITK. In certain embodiments, compounds will exhibit an IC50 with respect to ITK of no more than about 10 µM; in further embodiments, compounds will exhibit an IC50 with respect to ITK of no more than about 5 µM; in yet further embodiments, compounds will exhibit an IC50 with respect to ITK of not more than about 1 µM; in yet further embodiments, compounds will exhibit an IC50 with respect to ITK of not more than about 200 nM, as measured in the ITK binding assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations that can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Gels for topical or transdermal administration may comprise, generally, a mixture of volatile solvents, nonvolatile solvents, and water. In certain embodiments, the volatile solvent component of the buffered solvent system may include lower (C1-C6) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. Several optional ingredients can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as stearic or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhaler or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Alternatively, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Alternatively, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies for inflammation include use of certain compounds of the disclosure with: (1) corticosteroids, including but not limited to cortisone, dexamethasone, and methylprednisolone; (2) nonsteroidal anti-inflammatory drugs (NSAIDs), including but not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE); (3) immunosuppressants, including but not limited to methotrexate (RHEUMATREX), leflunomide (ARAVA), azathioprine (IMURAN), cyclosporine (NEORAL, SANDIMMUNE), tacrolimus and cyclophosphamide (CYTOXAN); (4) CD20 blockers, including but not limited to rituximab (RITUXAN); (5) Tumor Necrosis Factor (TNF) blockers, including but not limited to etanercept (ENBREL), infliximab (REMICADE) and adalimumab (HUMIRA); (6) interleukin-1 receptor antagonists, including but not limited to anakinra (KINERET); (7) interleukin-6 inhibitors, including but not limited to tocilizumab (ACTEMRA); (8) interleukin-17 inhibitors, including but not limited to AIN457; (9) Janus kinase inhibitors, including but not limited to tasocitinib; and (10) syk inhibitors, including but not limited to fostamatinib.

Specific, non-limiting examples of possible combination therapies for the treatment of cancer include use of certain compounds of the disclosure with: (1) alkylating agents, including but not limited to cisplatin (PLATIN), carboplatin (PARAPLATIN), oxaliplatin (ELOXATIN), streptozocin (ZANOSAR), busulfan (MYLERAN) and cyclophosphamide (ENDOXAN); (2) anti-metabolites, including but not limited to mercaptopurine (PURINETHOL), thioguanine, pentostatin (NIPENT), cytosine arabinoside (ARA-C), gemcitabine (GEMZAR), fluorouracil (CARAC), leucovorin (FUSILEV) and methotrexate (RHEUMATREX); (3) plant alkaloids and terpenoids, including but not limited to vincristine (ONCOVIN), vinblastine and paclitaxel (TAXOL); (4) topoisomerase inhibitors, including but not limited to irinotecan (CAMPTOSAR), topotecan (HYCAMTIN) and etoposide (EPOSIN); (5) cytotoxic antibiotics, including but not limited to actinomycin D (COSMEGEN), doxorubicin (ADRIAMYCIN), bleomycin (BLENOXANE) and mitomycin (MITOSOL); (6) angiogenesis inhibitors, including but not limited to sunitinib (SUTENT) and bevacizumab (AVASTIN); and (7) tyrosine kinase inhibitors, including but not limited to imatinib (GLEEVEC), erlotinib (TARCEVA), lapatininb (TYKERB) and axitinib (INLYTA).

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating ITK-mediated disorders in a human or animal subject in need of such treatment comprising administering to the subject an amount of a compound disclosed herein effective to reduce or prevent the disorder in the subject, in combination with at least one additional agent for the treatment of the disorder that is known in the art. In a related aspect, certain embodiments provide therapeutic compositions comprising at least one compound disclosed herein in combination with one or more additional agents for the treatment of ITK mediated disorders.

Specific diseases to be treated by the compounds, compositions, and methods disclosed herein include autoimmune disorders, chronic inflammatory disorders, auto-inflammatory disorders, pain, inflammatory disorders, allergic disorders, autoimmune disorders and the like.

In some embodiments, the methods described herein are used to treat a patient in need thereof suffering from inflammatory disorders, allergic disorders, and autoimmune disorders. Examples of disorders include, but are not limited to asthma, rheumatoid arthritis, juvenile idiopathic arthritis, psoriatic arthritis, ankylosing spondylitis, psoriasis, contact hypersensitivity and inflammatory bowel disease.

Diseases to be treated by the compounds, compositions, and methods disclosed herein related to cancer include cancer specific to T-cells such as T-cell lymphoma and lymphoblastic T-cell leukemia.

Diseases to be treated by the compounds, compositions, and methods disclosed herein include HIV.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Compounds

Provided herein is a compound, or a pharmaceutically acceptable salt, hydrate or solvate thereof, of Formula (I):

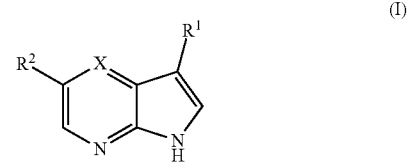

wherein:
$R^1$ is chosen from mono- and bicyclic aryl and heteroaryl, wherein $R^1$ may be optionally substituted with one or more $R^3$ substituents;
$R^2$ is chosen from heterocycloalkyl, aryl, and heteroaryl, each of which is substituted with one $R^4$ substituent, and any of which may be further optionally substituted with one or more $R^8$ substituents, or alternatively $R^2$ is $NR^{12}R^{13}$;
each $R^3$ is independently chosen from hydrogen, hydroxyl, cyano, $C_{1-6}$alkyl, hydroxy$C_{1-4}$alkyl, $C_{1-6}$alkoxyalkyl, aryl$C_{1-6}$alkyl, aryl$C_{1-6}$alkoxy, heteroaryl$C_{1-6}$alkyl, heteroaryl$C_{1-6}$alkoxy, aryloxy$C_{1-6}$alkyl, heteroaryloxy$C_{1-6}$alkyl, aryloxy$C_{1-6}$alkyl, heteroaryloxy$C_{1-6}$alkyl, cyclopropyl$C_{1-4}$alkyl, cyclopropyl$C_{1-4}$alkoxy, cyclopropoxy$C_{1-4}$alkyl, $C_{1-4}$alkylamino, $C_{1-4}$alkylarylamino, $C_{1-4}$alkylheteroarylamino, di($C_{1-4}$alkyl)amino, —C(O)NR$^6$R$^{6'}$, $C_{1-4}$alkanoyl, —C(O)aryl, —C(O)heteroaryl, —C(O)NHaryl, —C(O)NHheteroaryl, trifluoromethyl, and halo, wherein aryl and heteroaryl may be optionally substituted with $R^9$;
$R^4$ is chosen from NR$^5$R$^6$, —(CH$_2$)$_n$CR$^7$=CR$^9$C(O)CH$_3$, —(CH$_2$)$_n$CR$^7$=CR$^9$C(O)NR$^7$R$^{7'}$, and —(CH$_2$)$_n$CR$^7$=CR$^9$CN;
$R^5$ is chosen from cyano, —C(O)CF$_3$, —C(O)CH=CH$_2$, —C(O)CR$^7$=CH$_2$, —C(O)CH=CHR$^7$, —C(O)CR$^7$=CHR$^7$, —C(O)CH=CR$^7$R$^{7'}$, —C(O)CH=CHCH$_2$R$^8$, —C(O)CH=CHC(O)CH$_2$R$^8$, —COC(CN)=CHR$^6$, —C(O)(C(O)NH$_2$)=CHR$^6$, C(O)alkynylR$^7$, —S(O)$_2$CH=CH$_2$, —(CH$_2$)$_m$CR$^7$=CR$^9$C(O)CH$_3$, —(CH$_2$)$_m$CR$^7$=CR$^9$C(O)NR$^7$R$^{7'}$, and —(CH$_2$)$_m$CR$^7$=CR$^9$CN;
$R^6$ and $R^{6'}$ are each independently chosen from hydrogen, $C_{1-4}$alkyl, $C_{3-7}$cycloalkylalkyl, and phenyl$C_{1-4}$alkyl;
$R^7$ and $R^{7'}$ are each independently chosen from hydrogen, cyano, $C_{1-4}$alkyl, hydroxy$C_{1-4}$alkyl, $C_{1-4}$alkoxyalkyl, $C_{3-7}$cycloalkyl, $C_{3-7}$heterocycloalkyl, $C_{3-7}$heterocycloalkylalkyl, (NR$^6$R$^{6'}$)$C_{1-4}$alkyl, aryl, and heteroaryl, wherein aryl and heteroaryl may be optionally substituted with one or more $R^9$;
$R^8$ is chosen from hydrogen, halo, cyano, $C_{1-4}$alkyl, aryl$C_{1-4}$alkyl, heteroaryl$C_{1-4}$alkyl, $C_{3-7}$cycloalkyl, hydroxy$C_{1-6}$alkyl, heterocycloalkyl$C_{1-4}$alkyl, $C_{3-7}$heterocycloalkyl, hydroxyl, $C_{1-4}$alkoxy, $C_{3-7}$cycloalkoxy, $C_{3-7}$cycloalkoxyalkyl, heteroaryloxy, aryloxy, (NR$^6$R$^{6'}$)alkyl, arylalkoxy, $C_{1-4}$alkoxy$C_{1-4}$alkyl, amino, $C_{1-4}$alkylamino, di($C_{1-4}$alkyl)amino, trifluoromethyl, aryl, and heteroaryl, wherein alkyl, heterocycloalkyl, aryl and heteroaryl may be optionally substituted with one or more $R^9$;
$R^9$ is chosen from hydrogen, halo, hydroxyl, $C_{1-4}$ alkyl, cyano, trifluoromethyl, alkanoyl, amino, amido, and aryl;
$R^{10}$ is chosen from hydrogen, $C_{1-4}$alkyl, $C_{1-4}$alkoxy, halo, trifluoromethyl, and cyano;

R¹¹ is chosen from hydrogen, $C_{1-4}$alkyl, $C_{3-7}$cycloalkylalkyl, heterocycloalkylalkyl, aryl$C_{1-4}$alkyl, and heteroaryl$C_{1-4}$alkyl, wherein aryl and heteroaryl may be optionally substituted with one or more R⁹;

R¹² is a nitrogen-containing $C_{3-7}$heterocycloalkyl, wherein said nitrogen is further substituted by R⁵;

R¹³ is chosen from hydrogen, $C_{1-4}$alkyl, and $C_{3-7}$cycloalkylalkyl;

X is N or CR¹¹;

m is an integer chosen from 1, 2 and 3; and n is an integer chosen from 0, 1, 2, and 3.

In certain embodiments, R² is chosen from phenyl and pyridinyl, either of which is substituted with one R⁴ substituent, and either of which may be further optionally substituted with one or more R⁸ substituents.

In certain embodiments, R¹ is chosen from phenyl, pyridinyl, pyrimidinyl, pyrazinyl, pyridinonyl, pyrrolopyridinyl, and pyrrolopyrimidinyl, any of which may be optionally substituted with one or more R³ substituents.

In certain embodiments, when R¹ is phenyl, said phenyl is substituted with one or more R³ substituents; one R³ is C(O)NR⁶R⁶'; R⁶ is phenyl$C_{1-4}$alkyl; and R⁶' is hydrogen.

In certain embodiments, R⁴ is chosen from NR⁵R⁶ and —(CH₂)ₙCR⁷=CR⁹CN.

In certain embodiments, R⁴ is NR⁵R⁶; R⁵ is chosen from C(O)CH=CH₂ and —C(O)CH=CHCH₂R⁸; R⁶ is hydrogen; and R⁸ is di($C_{1-4}$alkyl)amino.

In certain embodiments, R⁴ is —(CH₂)ₙCR⁷=CR⁹CN; n is 0; R⁷ is hydrogen; R⁹ is amido.

In certain embodiments, the compound is chosen from the compounds in Tables 2 and 3.

In certain embodiments, the compound is chosen from:
N-(3-(3-(2-methoxypyridin-4-yl)-1H-pyrrolo[2,3-b]pyridin-5-yl)phenyl)acrylamide,
N-(3-(3-(pyridin-4-yl)-1H-pyrrolo[2,3-b]pyridin-5-yl)phenyl)acrylamide,
(E)-2-cyano-3-(3-(3-(pyridin-4-yl)-1H-pyrrolo[2,3-b]pyridin-5-yl)phenyl)acrylamide,
(E)-2-cyano-3-(3-(3-(2-methoxypyridin-4-yl)-1H-pyrrolo[2,3-b]pyridin-5-yl)phenyl)acrylamide,
N-(3-(3-(2-methoxypyridin-4-yl)-1H-pyrrolo[2,3-b]pyridin-5-yl)-5-(trifluoromethyl)phenyl)acrylamide,
N-(3-(3-(pyridin-3-yl)-1H-pyrrolo[2,3-b]pyridin-5-yl)phenyl)acrylamide,
N-(3-(3-(1-methyl-6-oxo-1,6-dihydropyridin-3-yl)-1H-pyrrolo[2,3-b]pyridin-5-yl)phenyl)acrylamide,
N-(5-(3-(pyridin-4-yl)-1H-pyrrolo[2,3-b]pyridin-5-yl)pyridin-3-yl)acrylamide,
N-(5-(3-(1-methyl-6-oxo-1,6-dihydropyridin-3-yl)-1H-pyrrolo[2,3-b]pyridin-5-yl)pyridin-3-yl)acrylamide,
N-(3-cyano-5-(3-(pyridin-4-yl)-1H-pyrrolo[2,3-b]pyridin-5-yl)phenyl)acrylamide,
N-(3-(3-(pyridin-4-yl)-1H-pyrrolo[2,3-b]pyridin-5-yl)-5-(trifluoromethyl)phenyl)acrylamide,
N-(3-(3-(2-methoxypyridin-4-yl)-1H-pyrrolo[2,3-b]pyridin-5-yl)phenyl)-N-methylacrylamide,
N-(3-methoxy-5-(3-(pyridin-4-yl)-1H-pyrrolo[2,3-b]pyridin-5-yl)phenyl)acrylamide,
(E)-4-morpholino-N-(3-(3-(pyridin-4-yl)-1H-pyrrolo[2,3-b]pyridin-5-yl)phenyl)but-2-enamide,
(E)-4-(dimethylamino)-N-(3-(3-(pyridin-4-yl)-1H-pyrrolo[2,3-b]pyridin-5-yl)phenyl)but-2-enamide,
N-(3-(3-(2-fluoropyridin-4-yl)-1H-pyrrolo[2,3-b]pyridin-5-yl)phenyl)acrylamide,
N-(3-(3-(2-methylpyridin-4-yl)-1H-pyrrolo[2,3-b]pyridin-5-yl)phenyl)acrylamide,
N-(5-(3-(2-fluoropyridin-4-yl)-1H-pyrrolo[2,3-b]pyridin-5-yl)pyridin-3-yl)acrylamide,
N-(5-(3-(2-methylpyridin-4-yl)-1H-pyrrolo[2,3-b]pyridin-5-yl)pyridin-3-yl)acrylamide,
N-(3-(3-(2-methoxy-6-methylpyridin-4-yl)-1H-pyrrolo[2,3-b]pyridin-5-yl)phenyl)acrylamide,
N-(3-(3-(6-methoxypyridin-3-yl)-1H-pyrrolo[2,3-b]pyridin-5-yl)phenyl)acrylamide,
N-(3-(3-(2-methoxy-6-(trifluoromethyl)pyridin-4-yl)-1H-pyrrolo[2,3-b]pyridin-5-yl)phenyl)acrylamide,
N-(3-(3-(2-(methylamino)pyridin-4-yl)-1H-pyrrolo[2,3-b]pyridin-5-yl)phenyl)acrylamide,
(E)-2-cyano-3-(3-(3-(2-methylpyridin-4-yl)-1H-pyrrolo[2,3-b]pyridin-5-yl)phenyl)acrylamide,
(E)-4-(dimethylamino)-N-(3-(3-(1-methyl-6-oxo-1,6-dihydropyridin-3-yl)-1H-pyrrolo[2,3-b]pyridin-5-yl)phenyl)but-2-enamide,
(E)-N-(3-(3-(2-methoxypyridin-4-yl)-1H-pyrrolo[2,3-b]pyridin-5-yl)phenyl)-4-morpholinobut-2-enamide,
N-(3-(3-(6-methoxypyrimidin-4-yl)-1H-pyrrolo[2,3-b]pyridin-5-yl)phenyl)acrylamide,
N-(6-methoxy-4-(3-(2-methoxypyridin-4-yl)-1H-pyrrolo[2,3-b]pyridin-5-yl)pyridin-2-yl)acrylamide,
N-(4-(3-(2-methoxypyridin-4-yl)-1H-pyrrolo[2,3-b]pyridin-5-yl)-6-morpholinopyridin-2-yl)acrylamide,
N-(3-(3-(o-tolyl)-1H-pyrrolo[2,3-b]pyridin-5-yl)phenyl)acrylamide,
N-(3-(3-(5-chloropyridin-3-yl)-1H-pyrrolo[2,3-b]pyridin-5-yl)phenyl)acrylamide,
N-(3-(3-(6-methylpyrimidin-4-yl)-1H-pyrrolo[2,3-b]pyridin-5-yl)phenyl)acrylamide,
N-(6-isopropoxy-4-(3-(2-methoxypyridin-4-yl)-1H-pyrrolo[2,3-b]pyridin-5-yl)pyridin-2-yl)acrylamide,
N-(3-(3-(6-fluoropyridin-3-yl)-1H-pyrrolo[2,3-b]pyridin-5-yl)phenyl)acrylamide,
N-(3-(3-(6-(cyclopropylmethoxy)pyridin-3-yl)-1H-pyrrolo[2,3-b]pyridin-5-yl)phenyl)acrylamide,
N-(3-(3-(6-(methylamino)pyridin-3-yl)-1H-pyrrolo[2,3-b]pyridin-5-yl)phenyl)acrylamide,
N-(3-(3-(pyrimidin-4-yl)-1H-pyrrolo[2,3-b]pyridin-5-yl)phenyl)acrylamide,
N-(3-(3-(1-(cyclopropylmethyl)-6-oxo-1,6-dihydropyridin-3-yl)-1H-pyrrolo[2,3-b]pyridin-5-yl)phenyl)acrylamide,
N-(3-(3-(3-methoxyphenyl)-1H-pyrrolo[2,3-b]pyridin-5-yl)phenyl)acrylamide,
N-(3-(3-(6-methoxy-4-methylpyridin-2-yl)-1H-pyrrolo[2,3-b]pyridin-5-yl)phenyl)acrylamide,
N-(3-(3-(naphthalen-1-yl)-1H-pyrrolo[2,3-b]pyridin-5-yl)phenyl)acrylamide,
N-(3-(3-(quinolin-4-yl)-1H-pyrrolo[2,3-b]pyridin-5-yl)phenyl)acrylamide,
N-(3-(3-(isoquinolin-5-yl)-1H-pyrrolo[2,3-b]pyridin-5-yl)phenyl)acrylamide,
N-(3-(3-(6-(methylamino)pyrimidin-4-yl)-1H-pyrrolo[2,3-b]pyridin-5-yl)phenyl)acrylamide,
N-(3-(3-(6-fluoropyridin-3-yl)-1H-pyrrolo[2,3-b]pyridin-5-yl)-5-(trifluoromethyl)phenyl)acrylamide,
N-(3-(3-(6-methoxypyridin-3-yl)-1H-pyrrolo[2,3-b]pyridin-5-yl)-5-(trifluoromethyl)phenyl)acrylamide,
N-(3-(3-(pyridin-3-yl)-1H-pyrrolo[2,3-b]pyridin-5-yl)-5-(trifluoromethyl)phenyl)acrylamide,
(E)-2-cyano-3-(3-methoxy-5-(3-(2-methoxypyridin-4-yl)-1H-pyrrolo[2,3-b]pyridin-5-yl)phenyl)acrylamide,
N-(3-(3-(2-fluoropyridin-4-yl)-1H-pyrrolo[2,3-b]pyridin-5-yl)-5-(trifluoromethyl)phenyl)acrylamide,
N-(3-(1H,1'H-[3,4'-bipyrrolo[2,3-b]pyridin]-5-yl)phenyl)acrylamide, (E)-2-cyano-3-(3-(3-(6-fluoropyridin-3-yl)-1H-pyrrolo[2,3-b]pyridin-5-yl)phenyl)acrylamide,
N-(3-(3-(quinolin-4-yl)-1H-pyrrolo[2,3-b]pyridin-5-yl)phenyl)acrylamide,
(E)-4-methoxy-N-(3-(3-(2-methoxypyridin-4-yl)-1H-pyrrolo[2,3-b]pyridin-5-yl)phenyl)but-2-enamide,
N-(3-(3-(1-(2-hydroxy-2-methylpropyl)-6-oxo-1,6-dihydropyridin-3-yl)-1H-pyrrolo[2,3-b]pyridin-5-yl)phenyl)acrylamide,
4-(5-(3-acrylamidophenyl)-1H-pyrrolo[2,3-b]pyridin-3-yl)-N-(2,4-dimethylphenyl)benzamide,
N-(6-methoxy-4-(3-(2-methoxypyridin-4-yl)-1H-pyrrolo[2,3-b]pyridin-5-yl)pyridin-2-yl)methacrylamide,
N-(3-(3-(1-oxo-1,2-dihydroisoquinolin-4-yl)-1H-pyrrolo[2,3-b]pyridin-5-yl)phenyl)acrylamide,
N-(4-(3-(2-methoxypyridin-4-yl)-1H-pyrrolo[2,3-b]pyridin-5-yl)-6-(1-methyl-1H-pyrazol-4-yl)pyridin-2-yl)methacrylamide,
N-(3-(3-(1H-indol-4-yl)-1H-pyrrolo[2,3-b]pyridin-5-yl)phenyl)acrylamide,
N-(3-(3-(2-methyl-1-oxo-1,2-dihydroisoquinolin-4-yl)-1H-pyrrolo[2,3-b]pyridin-5-yl)phenyl)acrylamide,
N-(5-(3-(6-methyl-7-oxo-6,7-dihydro-1H-pyrrolo[2,3-c]pyridin-4-yl)-1H-pyrrolo[2,3-b]pyridin-5-yl)pyridin-3-yl)acrylamide,
4-(5-(3-acrylamidophenyl)-1H-pyrrolo[2,3-b]pyridin-3-yl)-N-(4-isopropylphenyl)benzamide,
(E)-2-cyano-3-(3-(3-(pyrimidin-4-yl)-1H-pyrrolo[2,3-b]pyridin-5-yl)phenyl)acrylamide,
(E)-4-(dimethylamino)-N-(3-methoxy-5-(3-(2-methoxypyridin-4-yl)-1H-pyrrolo[2,3-b]pyridin-5-yl)phenyl)but-2-enamide,
N-(3-(3-(1H-pyrrolo[2,3-c]pyridin-4-yl)-1H-pyrrolo[2,3-b]pyridin-5-yl)phenyl)acrylamide,
(E)-N-(3-(3-(3-cyanophenyl)-1H-pyrrolo[2,3-b]pyridin-5-yl)phenyl)-4-(dimethylamino)but-2-enamide,
N-(3-(3-(2-methoxy-5-methylpyridin-4-yl)-1H-pyrrolo[2,3-b]pyridin-5-yl)phenyl)acrylamide,
N-(3-(3-(2-methoxypyridin-4-yl)-1H-pyrrolo[2,3-b]pyridin-5-yl)-5-(1-methyl-1H-pyrazol-4-yl)phenyl)acrylamide,
N-(3-(3-(2-methoxypyridin-4-yl)-1H-pyrrolo[2,3-b]pyridin-5-yl)phenyl)methacrylamide,
N-(3-(3-(benzofuran-4-yl)-1H-pyrrolo[2,3-b]pyridin-5-yl)phenyl)acrylamide,
N-(3-(3-hydroxypentan-3-yl)-5-(3-(2-methoxypyridin-4-yl)-1H-pyrrolo[2,3-b]pyridin-5-yl)phenyl)acrylamide,
(E)-4-(dimethylamino)-N-(3-(3-(pyridin-3-yl)-1H-pyrrolo[2,3-b]pyridin-5-yl)phenyl)but-2-enamide,
N-(3-(3-(pyridin-3-yl)-1H-pyrrolo[2,3-b]pyridin-5-yl)phenyl)methacrylamide,
N-(3-(3-(2-(cyclopropylmethyl)-1-oxo-1,2-dihydroisoquinolin-4-yl)-1H-pyrrolo[2,3-b]pyridin-5-yl)phenyl)acrylamide,
(E)-2-cyano-N-(3-(3-(2-methoxypyridin-4-yl)-1H-pyrrolo[2,3-b]pyridin-5-yl)phenyl)-4-methylpent-2-enamide,
N-(3-(3-(6-(cyclopropylmethyl)-7-oxo-6,7-dihydro-1H-pyrrolo[2,3-c]pyridin-4-yl)-1H-pyrrolo[2,3-b]pyridin-5-yl)phenyl)acrylamide,
(E)-N-(3-(1H,1'H-[3,4'-bipyrrolo[2,3-b]pyridin]-5-yl)phenyl)-4-(dimethylamino)but-2-enamide,
(E)-N-(3-(3-(1-(cyclopropylmethyl)-6-oxo-1,6-dihydropyridin-3-yl)-1H-pyrrolo[2,3-b]pyridin-5-yl)phenyl)-4-(dimethylamino)but-2-enamide,
N-(3-(3-(2-(methylamino)pyrimidin-4-yl)-1H-pyrrolo[2,3-b]pyridin-5-yl)phenyl)acrylamide,
N-(3-(3-(3-cyanophenyl)-1H-pyrrolo[2,3-b]pyridin-5-yl)phenyl)acrylamide,
(E)-3-(3-(3-(pyrimidin-4-yl)-1H-pyrrolo[2,3-b]pyridin-5-yl)phenyl)acrylamide,
N-(4-(3-(2-methoxypyridin-4-yl)-1H-pyrrolo[2,3-b]pyridin-5-yl)pyridin-2-yl)acrylamide,
N-(6-isopropyl-4-(3-(2-methoxypyridin-4-yl)-1H-pyrrolo[2,3-b]pyridin-5-yl)pyridin-2-yl)acrylamide,
N-(3-(3-(2-cyanopyridin-4-yl)-1H-pyrrolo[2,3-b]pyridin-5-yl)phenyl)acrylamide,
4-(5-(3-acrylamidophenyl)-1H-pyrrolo[2,3-b]pyridin-3-yl)picolinamide, and
N-(3-(1H,1'H-[3,5'-bipyrrolo[2,3-b]pyridin]-5-yl)phenyl)acrylamide,
or a pharmaceutically acceptable salt, hydrate or solvate thereof.

In certain embodiments, the compound is chosen from:
N-(3-(3-(2-methoxypyridin-4-yl)-1H-pyrrolo[2,3-b]pyridin-5-yl)phenyl)acrylamide,
(E)-2-cyano-3-(3-(3-(pyridin-4-yl)-1H-pyrrolo[2,3-b]pyridin-5-yl)phenyl)acrylamide,
N-(3-(3-(pyridin-4-yl)-1H-pyrrolo[2,3-b]pyridin-5-yl)-5-(trifluoromethyl)phenyl)acrylamide,
N-(3-methoxy-5-(3-(pyridin-4-yl)-1H-pyrrolo[2,3-b]pyridin-5-yl)phenyl)acrylamide,
N-(3-(3-(2-(methylamino)pyridin-4-yl)-1H-pyrrolo[2,3-b]pyridin-5-yl)phenyl)acrylamide,
(E)-4-(dimethylamino)-N-(3-(3-(2-methoxypyridin-4-yl)-1H-pyrrolo[2,3-b]pyridin-5-yl)phenyl)but-2-enamide,
N-(3-(3-(6-fluoropyridin-3-yl)-1H-pyrrolo[2,3-b]pyridin-5-yl)phenyl)acrylamide,
N-(3-(3-(pyrimidin-4-yl)-1H-pyrrolo[2,3-b]pyridin-5-yl)phenyl)acrylamide,
N-(3-(3-(1-(cyclopropylmethyl)-6-oxo-1,6-dihydropyridin-3-yl)-1H-pyrrolo[2,3-b]pyridin-5-yl)phenyl)acrylamide,
N-(3-(3-(6-(methylamino)pyrimidin-4-yl)-1H-pyrrolo[2,3-b]pyridin-5-yl)phenyl)acrylamide,
4-(5-(3-acrylamidophenyl)-1H-pyrrolo[2,3-b]pyridin-3-yl)-N-(4-isopropylphenyl)benzamide,
(E)-2-cyano-3-(3-(3-(pyrimidin-4-yl)-1H-pyrrolo[2,3-b]pyridin-5-yl)phenyl)acrylamide,
N-(3-(3-(2-methoxypyridin-4-yl)-1H-pyrrolo[2,3-b]pyridin-5-yl)-5-(1-methyl-1H-pyrazol-4-yl)phenyl)acrylamide,
(E)-N-(3-(1H,1'H-[3,4'-bipyrrolo[2,3-b]pyridin]-5-yl)phenyl)-4-(dimethylamino)but-2-enamide, and
N-(3-(3-(2-(methylamino)pyrimidin-4-yl)-1H-pyrrolo[2,3-b]pyridin-5-yl)phenyl)acrylamide,
or a pharmaceutically acceptable salt, hydrate or solvate thereof.

In certain embodiments, the compound is chosen from:
N-(3-(3-(2-methoxypyridin-4-yl)-1H-pyrrolo[2,3-b]pyridin-5-yl)phenyl)acrylamide,
(E)-4-(dimethylamino)-N-(3-(3-(2-methoxypyridin-4-yl)-1H-pyrrolo[2,3-b]pyridin-5-yl)phenyl)but-2-enamide,
N-(3-(3-(6-fluoropyridin-3-yl)-1H-pyrrolo[2,3-b]pyridin-5-yl)phenyl)acrylamide,
N-(3-(3-(pyrimidin-4-yl)-1H-pyrrolo[2,3-b]pyridin-5-yl)phenyl)acrylamide,
N-(3-(3-(6-(methylamino)pyrimidin-4-yl)-1H-pyrrolo[2,3-b]pyridin-5-yl)phenyl)acrylamide,
4-(5-(3-acrylamidophenyl)-1H-pyrrolo[2,3-b]pyridin-3-yl)-N-(4-isopropylphenyl)benzamide,
(E)-2-cyano-3-(3-(3-(pyrimidin-4-yl)-1H-pyrrolo[2,3-b]pyridin-5-yl)phenyl)acrylamide, N-(3-(3-(2-methoxypyridin-4-yl)-1H-pyrrolo[2,3-b]pyridin-5-yl)-5-(1-methyl-1H-pyrazol-4-yl)phenyl)acrylamide,
(E)-N-(3-(1H,1'H-[3,4'-bipyrrolo[2,3-b]pyridin]-5-yl)phenyl)-4-(dimethylamino)but-2-enamide, and
N-(3-(3-(2-(methylamino)pyrimidin-4-yl)-1H-pyrrolo[2,3-b]pyridin-5-yl)phenyl)acrylamide,
or a pharmaceutically acceptable salt, hydrate or solvate thereof.

In certain embodiments, the compound has formula (II):

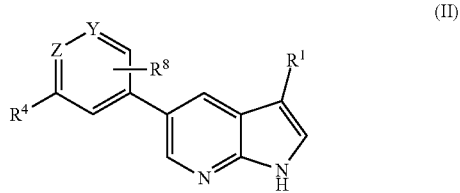

(II)

or a pharmaceutically acceptable salt, hydrate or solvate thereof, wherein:

Y and Z are independently chosen from $CR^8$, and N, provided that Y and Z are not both N;

$R^1$ is chosen from mono- or bicyclic aryl and heteroaryl, wherein $R^1$ may be optionally substituted with one or more $R^3$ substituents;

$R^3$ is independently chosen from hydrogen, hydroxyl, cyano, $C_{1-6}$alkyl, hydroxy$C_{1-4}$alkyl, $C_{1-6}$alkoxyalkyl, aryl$C_{1-6}$alkyl, aryl$C_{1-6}$alkoxy, heteroaryl$C_{1-6}$alkyl, heteroaryl$C_{1-6}$alkoxy, aryloxy$C_{1-6}$alkyl, heteroaryloxy $C_{1-6}$alkyl, cyclopropyl$C_{1-4}$alkyl, cyclopropyl$C_{1-4}$alkoxy, cyclopropoxy$C_{1-4}$alkyl, $C_{1-4}$alkylamino, $C_{1-4}$alkylarylamino, $C_{1-4}$alkylheteroarylamino, di($C_{1-4}$alkyl)amino, —$CONR^6R^{6'}$, $C_{1-4}$alkanoyl, —C(O)aryl, —C(O)heteroaryl, —C(O)NHaryl, —C(O)NHheteroaryl, trifluoromethyl, and halo, wherein aryl and heteroaryl may be optionally substituted with $R^9$;

$R^4$ is chosen from —$NR^5R^6$, —$(CH_2)_nCR^7$=$CR^9C(O)CH_3$, —$(CH_2)_nCR^7$=$CR^9C(O)NR^7R^{7'}$, and —$(CH_2)_nCR^7$=$CR^9CN$;

$R^5$ is chosen from cyano, —$C(O)CF_3$, —$C(O)CH$=$CH_2$, —$C(O)CR^7$=$CH_2$, —$C(O)CH$=$CHR^7$, —$C(O)CR^7$=$CHR^7$, —$C(O)CH$=$CR^7R^{7'}$, —$C(O)CH$=$CHCH_2R^8$, —$C(O)CH$=$CHC(O)CH_2R^8$, —$COC(CN)$=$CHR^6$, —$C(O)(C(O)NH_2)$=$CHR^6$, —$C(O)$alkynyl$R^7$, —$S(O)_2CH$=$CH_2$, —$(CH_2)_mCR^7$=$CR^9C(O)CH_3$, —$(CH_2)_mCR^7$=$CR^9C(O)NR^7R^{7'}$, and —$(CH_2)_mCR^7$=$CR^9CN$;

$R^6$ and $R^{6'}$ are each independently chosen from hydrogen, $C_{1-4}$alkyl, $C_{3-7}$cycloalkylalkyl, and phenyl-$C_{1-4}$alkyl;

$R^7$ and $R^{7'}$ are each independently chosen from hydrogen, cyano, $C_{1-4}$alkyl, hydroxy$C_{1-4}$alkyl, $C_{1-4}$alkoxyalkyl, $C_{3-7}$cycloalkyl, $C_{3-7}$heterocycloalkyl, $C_{3-7}$heterocycloalkylalkyl, ($NR^6R^{6'}$)$C_{1-4}$alkyl, aryl, and heteroaryl where aryl and heteroaryl may be optionally substituted with one or more $R^9$;

$R^8$ is chosen from hydrogen, halo, cyano, $C_{1-4}$alkyl, aryl$C_{1-4}$alkyl, heteroaryl$C_{1-4}$alkyl, $C_{3-7}$cycloalkyl, hydroxy$C_{1-6}$alkyl, heterocycloalkyl$C_{1-4}$alkyl, $C_{3-7}$heterocycloalkyl, hydroxyl, $C_{1-4}$alkoxy, $C_{3-7}$cycloalkoxy, ($NR^6R^{6'}$)alkyl, arylalkoxy, $C_{1-4}$alkoxy$C_{1-4}$alkyl, amino, $C_{1-4}$alkylamino, di($C_{1-4}$alkyl)amino, trifluoromethyl, aryl, heteroaryl, and heteroaryl$C_{1-4}$alkyl, wherein alkyl, heterocycloalkyl, aryl and heteroaryl may be optionally substituted with one or more $R^9$;

$R^9$ is chosen from hydrogen, halo, hydroxyl, $C_{1-4}$ alkyl, cyano, trifluoromethyl, alkanoyl, amino, amido, and aryl;

m is an integer chosen from 1, 2 and 3; and n is an integer chosen from 0, 1, 2, and 3.

In certain embodiments, the compound has formula (III):

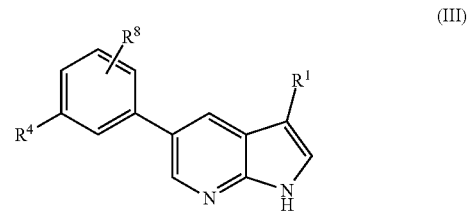

(III)

or a pharmaceutically acceptable salt, hydrate or solvate thereof, wherein:

$R^1$ is chosen from mono- or bicyclic aryl and heteroaryl, wherein $R^1$ may be optionally substituted with one or more $R^3$ substituents;

$R^3$ is independently chosen from hydrogen, hydroxyl, cyano, $C_{1-6}$alkyl, hydroxy$C_{1-4}$alkyl, $C_{1-6}$alkoxyalkyl, aryl$C_{1-6}$alkyl, aryl$C_{1-6}$alkoxy, heteroaryl$C_{1-6}$alkyl, heteroaryl$C_{1-6}$alkoxy, aryloxy$C_{1-6}$alkyl, heteroaryloxy $C_{1-6}$alkyl, cyclopropyl$C_{1-4}$alkyl, cyclopropyl$C_{1-4}$alkoxy, cyclopropoxy$C_{1-4}$alkyl, $C_{1-4}$alkylamino, $C_{1-4}$alkylarylamino, $C_{1-4}$alkylheteroarylamino, di($C_{1-4}$alkyl)amino, —$CONR^6R^{6'}$, $C_{1-4}$alkanoyl, —C(O)aryl, —C(O)heteroaryl, —C(O)NHaryl, —C(O)NHheteroaryl, trifluoromethyl, and halo, wherein aryl and heteroaryl may be optionally substituted with $R^9$;

$R^4$ is chosen from —$NR^5R^6$, —$(CH_2)_nCR^7$=$CR^9C(O)CH_3$, —$(CH_2)_nCR^7$=$CR^9C(O)NR^7R^{7'}$, and —$(CH_2)_nCR^7$=$CR^9CN$;

$R^5$ is chosen from cyano, —$C(O)CF_3$, —$C(O)CH$=$CH_2$, —$C(O)CR^7$=$CH_2$, —$C(O)CH$=$CHR^7$, —$C(O)CR^7$=$CHR^7$, —$C(O)CH$=$CR^7R^{7'}$, —$C(O)CH$=$CHCH_2R^8$, —$C(O)CH$=$CHC(O)CH_2R^8$, —$COC(CN)$=$CHR^6$, —$C(O)(C(O)NH_2)$=$CHR^6$, —$C(O)$alkynyl$R^7$, —$S(O)_2CH$=$CH_2$, —$(CH_2)_mCR^7$=$CR^9C(O)CH_3$, —$(CH_2)_mCR^7$=$CR^9C(O)NR^7R^{7'}$, and —$(CH_2)_mCR^7$=$CR^9CN$;

$R^6$ and $R^{6'}$ are each independently chosen from hydrogen, $C_{1-4}$alkyl, $C_{3-7}$cycloalkylalkyl, and phenyl$C_{1-4}$alkyl;

$R^7$ and $R^{7'}$ are each independently chosen from hydrogen, cyano, $C_{1-4}$alkyl, hydroxy$C_{1-4}$alkyl, $C_{1-4}$alkoxyalkyl, $C_{3-7}$cycloalkyl, $C_{3-7}$heterocycloalkyl, $C_{3-7}$heterocycloalkylalkyl, ($NR^6R^{6'}$)$C_{1-4}$alkyl, aryl, and heteroaryl where aryl and heteroaryl may be optionally substituted with one or more $R^9$;

$R^8$ is chosen from hydrogen, halo, cyano, $C_{1-4}$alkyl, aryl$C_{1-4}$alkyl, heteroaryl$C_{1-4}$alkyl, $C_{3-7}$cycloalkyl, hydroxy$C_{1-6}$alkyl, heterocycloalkyl$C_{1-4}$alkyl, $C_{3-7}$heterocycloalkyl, hydroxyl, $C_{1-4}$alkoxy, $C_{3-7}$cycloalkoxy, $C_{3-7}$cycloalkoxyalkyl, heteroaryloxy, aryloxy, ($NR^6R^{6'}$)alkyl, arylalkoxy, $C_{1-4}$alkoxy$C_{1-4}$alkyl, amino, $C_{1-4}$alkylamino, di($C_{1-4}$alkyl)amino, trifluoromethyl, aryl, and heteroaryl, wherein alkyl, heterocycloalkyl, aryl and heteroaryl may be optionally substituted with one or more $R^9$;

$R^9$ is chosen from hydrogen, halo, hydroxyl, $C_{1-4}$ alkyl, cyano, trifluoromethyl, $C(O)CH_3$, amido, and aryl;

$R^{10}$ is chosen from hydrogen, $C_{1-4}$alkyl, $C_{1-4}$alkoxy, halo, trifluoromethyl and CN;

m is an integer chosen from 1, 2 and 3; and n is an integer chosen from 0, 1, 2, and 3.

In certain embodiments, said phenyl of $R^1$ is substituted with one or more $R^3$ substituents; one $R^3$ is $C(O)NR^6R^{6'}$; $R^6$ is phenyl$C_{1-4}$alkyl; and $R^{6'}$ is hydrogen.

In certain embodiments, $R^4$ is chosen from $NR^5R^6$ and —$(CH_2)_nCR^7$=$CR^9CN$.

In certain embodiments, $R^4$ is $NR^5R^6$; $R^5$ is chosen from $C(O)CH$=$CH_2$ and —$C(O)CH$=$CHCH_2R^8$; $R^6$ is hydrogen; and $R^8$ is di($C_{1-4}$alkyl)amino.

In certain embodiments, $R^4$ is —$(CH_2)_nCR^7$=$CR^9CN$; n is 0; $R^7$ is hydrogen; $R^9$ is amido.

In certain embodiments, the compound is chosen from the compounds in Tables 2 and 3 having a phenyl at $R^2$, or a pharmaceutically acceptable salt, hydrate or solvate thereof.

In certain embodiments, the compound is chosen from:
N-(3-(3-(2-methoxypyridin-4-yl)-1H-pyrrolo[2,3-b]pyridin-5-yl)phenyl)acrylamide,
N-(3-(3-(pyridin-4-yl)-1H-pyrrolo[2,3-b]pyridin-5-yl)phenyl)acrylamide,
(E)-2-cyano-3-(3-(pyridin-4-yl)-1H-pyrrolo[2,3-b]pyridin-5-yl)phenyl)acrylamide,
(E)-2-cyano-3-(3-(3-(2-methoxypyridin-4-yl)-1H-pyrrolo[2,3-b]pyridin-5-yl)phenyl)acrylamide,
N-(3-(3-(2-methoxypyridin-4-yl)-1H-pyrrolo[2,3-b]pyridin-5-yl)-5-(trifluoromethyl)phenyl)acrylamide,
N-(3-(3-(pyridin-3-yl)-1H-pyrrolo[2,3-b]pyridin-5-yl)phenyl)acrylamide,
N-(3-(3-(1-methyl-6-oxo-1,6-dihydropyridin-3-yl)-1H-pyrrolo[2,3-b]pyridin-5-yl)phenyl)acrylamide,
N-(3-cyano-5-(3-(pyridin-4-yl)-1H-pyrrolo[2,3-b]pyridin-5-yl)phenyl)acrylamide,
N-(3-(3-(pyridin-4-yl)-1H-pyrrolo[2,3-b]pyridin-5-yl)-5-(trifluoromethyl)phenyl)acrylamide,
N-(3-(3-(2-methoxypyridin-4-yl)-1H-pyrrolo[2,3-b]pyridin-5-yl)phenyl)-N-methylacrylamide,
N-(3-methoxy-5-(3-(pyridin-4-yl)-1H-pyrrolo[2,3-b]pyridin-5-yl)phenyl)acrylamide,
(E)-4-morpholino-N-(3-(3-(pyridin-4-yl)-1H-pyrrolo[2,3-b]pyridin-5-yl)phenyl)but-2-enamide,
(E)-4-(dimethylamino)-N-(3-(3-(pyridin-4-yl)-1H-pyrrolo[2,3-b]pyridin-5-yl)phenyl)but-2-enamide,
N-(3-(3-(2-fluoropyridin-4-yl)-1H-pyrrolo[2,3-b]pyridin-5-yl)phenyl)acrylamide,
N-(3-(3-(2-methylpyridin-4-yl)-1H-pyrrolo[2,3-b]pyridin-5-yl)phenyl)acrylamide,
N-(3-(3-(2-methoxy-6-methylpyridin-4-yl)-1H-pyrrolo[2,3-b]pyridin-5-yl)phenyl)acrylamide,
N-(3-(3-(6-methoxypyridin-3-yl)-1H-pyrrolo[2,3-b]pyridin-5-yl)phenyl)acrylamide,
N-(3-(3-(2-methoxy-6-(trifluoromethyl)pyridin-4-yl)-1H-pyrrolo[2,3-b]pyridin-5-yl)phenyl)acrylamide,
N-(3-(3-(2-(methylamino)pyridin-4-yl)-1H-pyrrolo[2,3-b]pyridin-5-yl)phenyl)acrylamide,
(E)-2-cyano-3-(3-(3-(2-methylpyridin-4-yl)-1H-pyrrolo[2,3-b]pyridin-5-yl)phenyl)acrylamide,
(E)-4-(dimethylamino)-N-(3-(3-(1-methyl-6-oxo-1,6-dihydropyridin-3-yl)-1H-pyrrolo[2,3-b]pyridin-5-yl)phenyl)but-2-enamide,
(E)-N-(3-(3-(2-methoxypyridin-4-yl)-1H-pyrrolo[2,3-b]pyridin-5-yl)phenyl)-4-morpholinobut-2-enamide,
N-(3-(3-(6-methoxypyrimidin-4-yl)-1H-pyrrolo[2,3-b]pyridin-5-yl)phenyl)acrylamide,
N-(6-methoxy-4-(3-(2-methoxypyridin-4-yl)-1H-pyrrolo[2,3-b]pyridin-5-yl)pyridin-2-yl)acrylamide,
N-(4-(3-(2-methoxypyridin-4-yl)-1H-pyrrolo[2,3-b]pyridin-5-yl)-6-morpholinopyridin-2-yl)acrylamide,
N-(3-(3-(o-tolyl)-1H-pyrrolo[2,3-b]pyridin-5-yl)phenyl)acrylamide,
N-(3-(3-(5-chloropyridin-3-yl)-1H-pyrrolo[2,3-b]pyridin-5-yl)phenyl)acrylamide,
N-(3-(3-(6-methylpyrimidin-4-yl)-1H-pyrrolo[2,3-b]pyridin-5-yl)phenyl)acrylamide,
N-(3-(3-(6-fluoropyridin-3-yl)-1H-pyrrolo[2,3-b]pyridin-5-yl)phenyl)acrylamide,
N-(3-(3-(6-(cyclopropylmethoxy)pyridin-3-yl)-1H-pyrrolo[2,3-b]pyridin-5-yl)phenyl)acrylamide,
N-(3-(3-(6-(methylamino)pyridin-3-yl)-1H-pyrrolo[2,3-b]pyridin-5-yl)phenyl)acrylamide,
N-(3-(3-(pyrimidin-4-yl)-1H-pyrrolo[2,3-b]pyridin-5-yl)phenyl)acrylamide,
N-(3-(3-(1-(cyclopropylmethyl)-6-oxo-1,6-dihydropyridin-3-yl)-1H-pyrrolo[2,3-b]pyridin-5-yl)phenyl)acrylamide,
N-(3-(3-(3-methoxyphenyl)-1H-pyrrolo[2,3-b]pyridin-5-yl)phenyl)acrylamide,
N-(3-(3-(6-methoxy-4-methylpyridin-2-yl)-1H-pyrrolo[2,3-b]pyridin-5-yl)phenyl)acrylamide,
N-(3-(3-(naphthalen-1-yl)-1H-pyrrolo[2,3-b]pyridin-5-yl)phenyl)acrylamide,
N-(3-(3-(quinolin-4-yl)-1H-pyrrolo[2,3-b]pyridin-5-yl)phenyl)acrylamide,
N-(3-(3-(isoquinolin-5-yl)-1H-pyrrolo[2,3-b]pyridin-5-yl)phenyl)acrylamide,
N-(3-(3-(6-(methylamino)pyrimidin-4-yl)-1H-pyrrolo[2,3-b]pyridin-5-yl)phenyl)acrylamide,
N-(3-(3-(6-fluoropyridin-3-yl)-1H-pyrrolo[2,3-b]pyridin-5-yl)-5-(trifluoromethyl)phenyl)acrylamide,
N-(3-(3-(6-methoxypyridin-3-yl)-1H-pyrrolo[2,3-b]pyridin-5-yl)-5-(trifluoromethyl)phenyl)acrylamide,
N-(3-(3-(pyridin-3-yl)-1H-pyrrolo[2,3-b]pyridin-5-yl)-5-(trifluoromethyl)phenyl)acrylamide,
(E)-2-cyano-3-(3-methoxy-5-(3-(2-methoxypyridin-4-yl)-1H-pyrrolo[2,3-b]pyridin-5-yl)phenyl)acrylamide,
N-(3-(3-(2-fluoropyridin-4-yl)-1H-pyrrolo[2,3-b]pyridin-5-yl)-5-(trifluoromethyl)phenyl)acrylamide,
N-(3-(1H,1'H-[3,4'-bipyrrolo[2,3-b]pyridin]-5-yl)phenyl)acrylamide,
(E)-2-cyano-3-(3-(3-(6-fluoropyridin-3-yl)-1H-pyrrolo[2,3-b]pyridin-5-yl)phenyl)acrylamide,
N-(3-(3-(quinolin-4-yl)-1H-pyrrolo[2,3-b]pyridin-5-yl)phenyl)acrylamide,
(E)-4-methoxy-N-(3-(3-(2-methoxypyridin-4-yl)-1H-pyrrolo[2,3-b]pyridin-5-yl)phenyl)but-2-enamide,
N-(3-(3-(1-(2-hydroxy-2-methylpropyl)-6-oxo-1,6-dihydropyridin-3-yl)-1H-pyrrolo[2,3-b]pyridin-5-yl)phenyl)acrylamide,
4-(5-(3-acrylamidophenyl)-1H-pyrrolo[2,3-b]pyridin-3-yl)-N-(2,4-dimethylphenyl)benzamide,
N-(3-(3-(1-oxo-1,2-dihydroisoquinolin-4-yl)-1H-pyrrolo[2,3-b]pyridin-5-yl)phenyl)acrylamide,
N-(3-(3-(1H-indol-4-yl)-1H-pyrrolo[2,3-b]pyridin-5-yl)phenyl)acrylamide,
N-(3-(3-(2-methyl-1-oxo-1,2-dihydroisoquinolin-4-yl)-1H-pyrrolo[2,3-b]pyridin-5-yl)phenyl)acrylamide,
4-(5-(3-acrylamidophenyl)-1H-pyrrolo[2,3-b]pyridin-3-yl)-N-(4-isopropylphenyl)benzamide,
(E)-2-cyano-3-(3-(3-(pyrimidin-4-yl)-1H-pyrrolo[2,3-b]pyridin-5-yl)phenyl)acrylamide,
(E)-4-(dimethylamino)-N-(3-methoxy-5-(3-(2-methoxypyridin-4-yl)-1H-pyrrolo[2,3-b]pyridin-5-yl)phenyl)but-2-enamide,
N-(3-(3-(1H-pyrrolo[2,3-c]pyridin-4-yl)-1H-pyrrolo[2,3-b]pyridin-5-yl)phenyl)acrylamide,
(E)-N-(3-(3-(3-cyanophenyl)-1H-pyrrolo[2,3-b]pyridin-5-yl)phenyl)-4-(dimethylamino)but-2-enamide, N-(3-(3-(2-methoxy-5-methylpyridin-4-yl)-1H-pyrrolo[2,3-b]pyridin-5-yl)phenyl)acrylamide,
N-(3-(3-(2-methoxypyridin-4-yl)-1H-pyrrolo[2,3-b]pyridin-5-yl)-5-(1-methyl-1H-pyrazol-4-yl)phenyl)acrylamide,
N-(3-(3-(2-methoxypyridin-4-yl)-1H-pyrrolo[2,3-b]pyridin-5-yl)phenyl)methacrylamide,
N-(3-(3-(benzofuran-4-yl)-1H-pyrrolo[2,3-b]pyridin-5-yl)phenyl)acrylamide,
N-(3-(3-hydroxypentan-3-yl)-5-(3-(2-methoxypyridin-4-yl)-1H-pyrrolo[2,3-b]pyridin-5-yl)phenyl)acrylamide,
(E)-4-(dimethylamino)-N-(3-(3-(pyridin-3-yl)-1H-pyrrolo[2,3-b]pyridin-5-yl)phenyl)but-2-enamide,
N-(3-(3-(pyridin-3-yl)-1H-pyrrolo[2,3-b]pyridin-5-yl)phenyl)methacrylamide,
N-(3-(3-(2-(cyclopropylmethyl)-1-oxo-1,2-dihydroisoquinolin-4-yl)-1H-pyrrolo[2,3-b]pyridin-5-yl)phenyl)acrylamide,
(E)-2-cyano-N-(3-(3-(2-methoxypyridin-4-yl)-1H-pyrrolo[2,3-b]pyridin-5-yl)phenyl)-4-methylpent-2-enamide,
N-(3-(3-(6-(cyclopropylmethyl)-7-oxo-6,7-dihydro-1H-pyrrolo[2,3-c]pyridin-4-yl)-1H-pyrrolo[2,3-b]pyridin-5-yl)phenyl)acrylamide,
(E)-N-(3-(1H,1'H-[3,4'-bipyrrolo[2,3-b]pyridin]-5-yl)phenyl)-4-(dimethylamino)but-2-enamide,
(E)-N-(3-(3-(1-(cyclopropylmethyl)-6-oxo-1,6-dihydropyridin-3-yl)-1H-pyrrolo[2,3-b]pyridin-5-yl)phenyl)-4-(dimethylamino)but-2-enamide,
N-(3-(3-(2-(methylamino)pyrimidin-4-yl)-1H-pyrrolo[2,3-b]pyridin-5-yl)phenyl)acrylamide,
N-(3-(3-(3-cyanophenyl)-1H-pyrrolo[2,3-b]pyridin-5-yl)phenyl)acrylamide,
(E)-3-(3-(pyrimidin-4-yl)-1H-pyrrolo[2,3-b]pyridin-5-yl)phenyl)acrylamide,
N-(3-(3-(2-cyanopyridin-4-yl)-1H-pyrrolo[2,3-b]pyridin-5-yl)phenyl)acrylamide,
4-(5-(3-acrylamidophenyl)-1H-pyrrolo[2,3-b]pyridin-3-yl)picolinamide, and
N-(3-(1H,1'H-[3,5'-bipyrrolo[2,3-b]pyridin]-5-yl)phenyl)acrylamide,
or a pharmaceutically acceptable salt, hydrate or solvate thereof.

In certain embodiments, the compound has formula (IV):

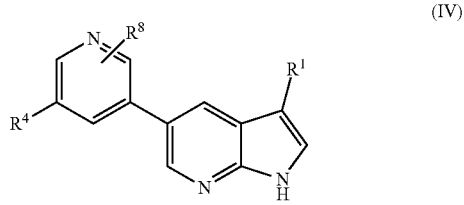

(IV)

or a pharmaceutically acceptable salt, hydrate or solvate thereof, wherein:
$R^1$ is chosen from mono- or bicyclic aryl and heteroaryl, wherein $R^1$ may be optionally substituted with one or more $R^3$ substituents;
$R^3$ is independently chosen from hydrogen, hydroxyl, cyano, $C_{1-6}$alkyl, hydroxy$C_{1-4}$alkyl, $C_{1-6}$alkoxyalkyl, aryl$C_{1-6}$alkyl, aryl$C_{1-6}$alkoxy, heteroaryl$C_{1-6}$alkyl, heteroaryl$C_{1-6}$alkoxy, aryloxy$C_{1-6}$alkyl, heteroaryloxy$C_{1-6}$alkyl, cyclopropyl$C_{1-4}$alkyl, cyclopropyl$C_{1-4}$alkoxy, cyclopropoxy$C_{1-4}$alkyl, $C_{1-4}$alkylamino, $C_{1-4}$alkylarylamino, $C_{1-4}$alkylheteroarylamino, di($C_{1-4}$alkyl)amino, —CONR$^6$R$^{6'}$, $C_{1-4}$alkanoyl, —C(O)aryl, —C(O)heteroaryl, —C(O)NHaryl, —C(O)NHheteroaryl, trifluoromethyl, and halo, wherein aryl and heteroaryl may be optionally substituted with $R^9$;
$R^4$ is chosen from —NR$^5$R$^6$, —(CH$_2$)$_n$CR$^7$=CR$^9$C(O)CH$_3$, —(CH$_2$)$_n$CR$^7$=CR$^9$C(O)NR$^7$R$^7$, and —(CH$_2$)$_n$CR$^7$=CR$^9$CN;
$R^5$ is chosen from cyano, —C(O)CF$_3$, —C(O)CH=CH$_2$, —C(O)CR$^7$=CH$_2$, —C(O)CH=CHR$^7$, —C(O)CR$^7$=CHR$^7$, —C(O)CH=CR$^7$R$^7$, —C(O)CH=CHCH$_2$R$^8$, —C(O)CH=CHC(O)CH$_2$R$^8$, —COC(CN)=CHR$^6$, —C(O)(C(O)NH$_2$)=CHR$^6$, —C(O)alkynylR$^7$, —S(O)$_2$CH=CH$_2$, —(CH$_2$)$_m$CR$^7$=CR$^9$C(O)CH$_3$, —(CH$_2$)$_m$CR$^7$=CR$^9$C(O)NR$^7$R$^7$, and —(CH$_2$)$_m$CR$^7$=CR$^9$CN;
$R^6$ and $R^{6'}$ are each independently chosen from hydrogen, $C_{1-4}$alkyl, $C_{3-7}$cycloalkylalkyl, and phenyl$C_{1-4}$alkyl;
$R^7$ and $R^{7'}$ are each independently chosen from hydrogen, cyano, $C_{1-4}$alkyl, hydroxy$C_{1-4}$alkyl, $C_{1-4}$alkoxyalkyl, $C_{3-7}$cycloalkyl, $C_{3-7}$heterocycloalkyl, $C_{3-7}$heterocycloalkylalkyl, (NR$^6$R$^{6'}$)$C_{1-4}$alkyl, aryl, and heteroaryl where aryl and heteroaryl may be optionally substituted with one or more $R^9$;
$R^8$ is chosen from hydrogen, halo, cyano, $C_{1-4}$alkyl, aryl$C_{1-4}$alkyl, heteroaryl$C_{1-4}$alkyl, $C_{3-7}$cycloalkyl, hydroxy$C_{1-6}$alkyl, heterocycloalkyl$C_{1-4}$alkyl, $C_{3-7}$heterocycloalkyl, hydroxyl, $C_{1-4}$alkoxy, $C_{3-7}$cycloalkoxy, $C_{3-7}$cycloalkoxyalkyl, heteroaryloxy, aryloxy, (NR$^6$R$^{6'}$)alkyl, arylalkoxy, $C_{1-4}$alkoxy$C_{1-4}$alkyl, amino, $C_{1-4}$alkylamino, di($C_{1-4}$alkyl)amino, trifluoromethyl, aryl, and heteroaryl, wherein alkyl, heterocycloalkyl, aryl and heteroaryl may be optionally substituted with one or more $R^9$;
$R^9$ is chosen from hydrogen, halo, hydroxyl, $C_{1-4}$ alkyl, cyano, trifluoromethyl, —C(O)CH$_3$, amido, and aryl;
$R^{10}$ is chosen from hydrogen, $C_{1-4}$alkyl, $C_{1-4}$alkoxy, halo, trifluoromethyl and CN;
m is an integer chosen from 1, 2 and 3; and
n is an integer chosen from 0, 1, 2, and 3.
In certain embodiments, $R^8$ is hydrogen.
In certain embodiments, $R^1$ is independently chosen from aryl and heteroaryl including phenyl, pyridine, pyrimidine, pyrazine, pyridinone, pyrrolopyridine, pyrrolopyrimidine, wherein each aromatic or heteroaromatic ring may be optionally substituted with one or more $R^3$ substituents.
In certain embodiments, the compound is chosen from the compounds in Tables 2 and 3 having a pyridinyl at $R^2$, or a pharmaceutically acceptable salt, hydrate or solvate thereof.
In certain embodiments, the compound is chosen from:
N-(5-(3-(pyridin-4-yl)-1H-pyrrolo[2,3-b]pyridin-5-yl)pyridin-3-yl)acrylamide,
N-(5-(3-(1-methyl-6-oxo-1,6-dihydropyridin-3-yl)-1H-pyrrolo[2,3-b]pyridin-5-yl)pyridin-3-yl)acrylamide,
N-(5-(3-(2-fluoropyridin-4-yl)-1H-pyrrolo[2,3-b]pyridin-5-yl)pyridin-3-yl)acrylamide,
N-(5-(3-(2-methylpyridin-4-yl)-1H-pyrrolo[2,3-b]pyridin-5-yl)pyridin-3-yl)acrylamide, and
N-(5-(3-(6-methyl-7-oxo-6,7-dihydro-1H-pyrrolo[2,3-c]pyridin-4-yl)-1H-pyrrolo[2,3-b]pyridin-5-yl)pyridin-3-yl)acrylamide,
or a pharmaceutically acceptable salt, hydrate or solvate thereof.

In certain embodiments, the compound has formula (V):

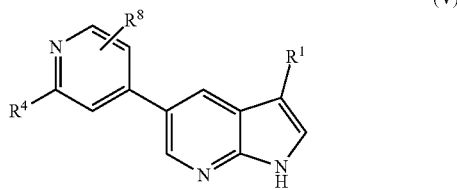

or a pharmaceutically acceptable salt, hydrate or solvate thereof, wherein:

$R^1$ is chosen from mono- or bicyclic aryl and heteroaryl, wherein $R^1$ may be optionally substituted with one or more $R^3$ substituents;

$R^3$ is independently chosen from hydrogen, hydroxyl, cyano, $C_{1-6}$alkyl, hydroxy$C_{1-4}$alkyl, $C_{1-6}$alkoxyalkyl, aryl$C_{1-6}$alkyl, aryl$C_{1-6}$alkoxy, heteroaryl$C_{1-6}$alkyl, heteroaryl$C_{1-6}$alkoxy, aryloxy$C_{1-6}$alkyl, heteroaryloxy$C_{1-6}$alkyl, cyclopropyl$C_{1-4}$alkyl, cyclopropyl$C_{1-4}$alkoxy, cyclopropoxy$C_{1-4}$alkyl, $C_{1-4}$alkylamino, $C_{1-4}$alkylarylamino, $C_{1-4}$alkylheteroarylamino, di($C_{1-4}$alkyl)amino, —CONR$^6$R$^{6'}$, $C_{1-4}$alkanoyl, —C(O)aryl, —C(O)heteroaryl, —C(O)NHaryl, —C(O)NHheteroaryl, trifluoromethyl, and halo, wherein aryl and heteroaryl may be optionally substituted with $R^9$;

$R^4$ is chosen from —NR$^5$R$^6$, —(CH$_2$)$_n$CR$^7$=CR$^9$C(O)CH$_3$, —(CH$_2$)$_n$CR$^7$=CR$^9$C(O)NR$^7$R$^{7'}$, and —(CH$_2$)$_n$CR$^7$=CR$^9$CN;

$R^5$ is chosen from cyano, —C(O)CF$_3$, —C(O)CH=CH$_2$, —C(O)CR$^7$=CH$_2$, —C(O)CH=CHR$^7$, —C(O)CR$^7$=CHR$^7$, —C(O)CH=CR$^7$R$^{7'}$, —C(O)CH=CHCH$_2$R$^8$, —C(O)CH=CHC(O)CH$_2$R$^8$, —COC(CN)=CHR$^6$, —C(O)(C(O)NH$_2$)=CHR$^6$, —C(O)alkynylR$^7$, —S(O)$_2$CH=CH$_2$, —(CH$_2$)$_m$CR$^7$=CR$^9$C(O)CH$_3$, —(CH$_2$)$_m$CR$^7$=CR$^9$C(O)NR$^7$R$^{7'}$, and —(CH$_2$)$_m$CR$^7$=CR$^9$CN;

$R^6$ and $R^{6'}$ are each independently chosen from hydrogen, $C_{1-4}$alkyl, $C_{3-7}$cycloalkylalkyl, and phenyl$C_{1-4}$alkyl;

$R^7$ and $R^{7'}$ are each independently chosen from hydrogen, cyano, $C_{1-4}$alkyl, hydroxy$C_{1-4}$alkyl, $C_{1-4}$alkoxyalkyl, $C_{3-7}$cycloalkyl, $C_{3-7}$heterocycloalkyl, $C_{3-7}$heterocycloalkylalkyl, (NR$^6$R$^{6'}$)$C_{1-4}$alkyl, aryl, and heteroaryl where aryl and heteroaryl may be optionally substituted with one or more $R^9$;

$R^8$ is chosen from hydrogen, halo, cyano, $C_{1-4}$alkyl, aryl$C_{1-4}$alkyl, heteroaryl$C_{1-4}$alkyl, $C_{3-7}$cycloalkyl, hydroxy$C_{1-6}$alkyl, heterocycloalkyl$C_{1-4}$alkyl, $C_{3-7}$heterocycloalkyl, hydroxyl, $C_{1-4}$ alkoxy, $C_{3-7}$cycloalkoxy, $C_{3-7}$cycloalkoxyalkyl, heteroaryloxy, aryloxy, (NR$^6$R$^{6'}$)alkyl, arylalkoxy, $C_{1-4}$alkoxy$C_{1-4}$alkyl, amino, $C_{1-4}$alkylamino, di($C_{1-4}$alkyl)amino, trifluoromethyl, aryl, and heteroaryl, wherein alkyl, heterocycloalkyl, aryl and heteroaryl may be optionally substituted with one or more $R^9$;

$R^9$ is chosen from hydrogen, halo, hydroxyl, $C_{1-4}$ alkyl, cyano, trifluoromethyl, —C(O)CH$_3$, amido, and aryl;

$R^{10}$ is chosen from hydrogen, $C_{1-4}$alkyl, $C_{1-4}$alkoxy, halo, trifluoromethyl and CN;

m is an integer chosen from 1, 2 and 3; and n is an integer chosen from 0, 1, 2, and 3.

In certain embodiments, $R^1$ is chosen from phenyl, pyridine, pyrimidine, pyrazine, pyridinone, pyrrolopyridine, and pyrrolopyrimidine, any of which may be optionally substituted with one or more $R^3$ substituents.

In certain embodiments, the compound is chosen from:

N-(6-isopropoxy-4-(3-(2-methoxypyridin-4-yl)-1H-pyrrolo[2,3-b]pyridin-5-yl)pyridin-2-yl)acrylamide, N-(6-methoxy-4-(3-(2-methoxypyridin-4-yl)-1H-pyrrolo[2,3-b]pyridin-5-yl)pyridin-2-yl)methacrylamide, N-(4-(3-(2-methoxypyridin-4-yl)-1H-pyrrolo[2,3-b]pyridin-5-yl)-6-(1-methyl-1H-pyrazol-4-yl)pyridin-2-yl)methacrylamide, N-(4-(3-(2-methoxypyridin-4-yl)-1H-pyrrolo[2,3-b]pyridin-5-yl)pyridin-2-yl)acrylamide, and N-(6-isopropyl-4-(3-(2-methoxypyridin-4-yl)-1H-pyrrolo[2,3-b]pyridin-5-yl)pyridin-2-yl)acrylamide, or a pharmaceutically acceptable salt, hydrate or solvate thereof.

In certain embodiments, the compound has formula (VI) or a regioisomer thereof:

or a pharmaceutically acceptable salt, hydrate or solvate thereof, wherein:

$R^1$ is chosen from mono- or bicyclic aryl and heteroaryl, wherein $R^1$ may be optionally substituted with one or more $R^3$ substituents;

$R^3$ is independently chosen from hydrogen, hydroxyl, cyano, $C_{1-6}$alkyl, hydroxy$C_{1-4}$alkyl, $C_{1-6}$alkoxyalkyl, aryl$C_{1-6}$alkyl, aryl$C_{1-6}$alkoxy, heteroaryl$C_{1-6}$alkyl, heteroaryl$C_{1-6}$alkoxy, aryloxy$C_{1-6}$alkyl, heteroaryloxy$C_{1-6}$alkyl, cyclopropyl$C_{1-4}$alkyl, cyclopropyl$C_{1-4}$alkoxy, cyclopropoxy$C_{1-4}$alkyl, $C_{1-4}$alkylamino, $C_{1-4}$alkylarylamino, $C_{1-4}$alkylheteroarylamino, di($C_{1-4}$alkyl)amino, —CONR$^6$R$^{6'}$, $C_{1-4}$alkanoyl, —C(O)aryl, —C(O)heteroaryl, —C(O)NHaryl, —C(O)NHheteroaryl, trifluoromethyl, and halo, wherein aryl and heteroaryl may be optionally substituted with $R^9$;

$R^4$ is chosen from —NR$^5$R$^6$, —(CH$_2$)$_n$CR$^7$=CR$^9$C(O)CH$_3$, —(CH$_2$)$_n$CR$^7$=CR$^9$C(O)NR$^7$R$^{7'}$, and —(CH$_2$)$_n$CR$^7$=CR$^9$CN;

$R^5$ is chosen from cyano, —C(O)CF$_3$, —C(O)CH=CH$_2$, —C(O)CR$^7$=CH$_2$, —C(O)CH=CHR$^7$, —C(O)CR$^7$=CHR$^7$, —C(O)CH=CR$^7$R$^{7'}$, —C(O)CH=CHCH$_2$R$^8$, —C(O)CH=CHC(O)CH$_2$R$^8$, —COC(CN)=CHR$^6$, —C(O)(C(O)NH$_2$)=CHR$^6$, —C(O)alkynylR$^7$, —S(O)$_2$CH=CH$_2$, —(CH$_2$)$_m$CR$^7$=CR$^9$C(O)CH$_3$, —(CH$_2$)$_m$CR$^7$=CR$^9$C(O)NR$^7$R$^{7'}$, and —(CH$_2$)$_m$CR$^7$=CR$^9$CN;

$R^6$ and $R^{6'}$ are each independently chosen from hydrogen, $C_{1-4}$alkyl, $C_{3-7}$cycloalkylalkyl, and phenyl$C_{1-4}$alkyl;

$R^7$ and $R^{7'}$ are each independently chosen from hydrogen, cyano, $C_{1-4}$alkyl, hydroxy$C_{1-4}$alkyl, $C_{1-4}$alkoxyalkyl, $C_{3-7}$cycloalkyl, $C_{3-7}$heterocycloalkyl, $C_{3-7}$heterocycloalkylalkyl, (NR$^6$R$^{6'}$)$C_{1-4}$alkyl, aryl, and heteroaryl where aryl and heteroaryl may be optionally substituted with one or more $R^9$;

$R^8$ is chosen from hydrogen, halo, cyano, $C_{1-4}$alkyl, aryl$C_{1-4}$alkyl, heteroaryl$C_{1-4}$alkyl, $C_{3-7}$cycloalkyl, hydroxy$C_{1-6}$alkyl, heterocycloalkyl$C_{1-4}$alkyl, $C_{3-7}$heterocycloalkyl, hydroxyl, $C_{1-4}$alkoxy, $C_{3-7}$cycloalkoxy, $C_{3-7}$cycloalkoxyalkyl, heteroaryloxy, aryloxy, $(NR^6R^{6'})$alkyl, arylalkoxy, $C_{1-4}$alkoxy$C_{1-4}$alkyl, amino, $C_{1-4}$alkylamino, di($C_{1-4}$alkyl)amino, trifluoromethyl, aryl, and heteroaryl, wherein alkyl, heterocycloalkyl, aryl and heteroaryl may be optionally substituted with one or more $R^9$;

$R^9$ is chosen from hydrogen, halo, hydroxyl, $C_{1-4}$ alkyl, cyano, trifluoromethyl, —C(O)CH$_3$, amido, and aryl;

$R^{10}$ is chosen from hydrogen, $C_{1-4}$alkyl, $C_{1-4}$alkoxy, halo, trifluoromethyl and CN;

$R^{11}$ is chosen from hydrogen, $C_{1-4}$alkyl, $C_{3-7}$cycloalkylalkyl, heterocycloalkylalkyl, aryl$C_{1-4}$alkyl, and heteroaryl$C_{1-4}$alkyl, wherein aryl and heteroaryl may be optionally substituted with one or more $R^9$;

U is O, S or $NR^{11}$;
V is N or $CR^{11}$;
W is N or $CR^{11}$;
m is an integer chosen from 1, 2 and 3; and
n is an integer chosen from 0, 1, 2, and 3.

In certain embodiments, $R^1$ is chosen from phenyl, pyridine, pyrimidine, pyrazine, pyridinone, pyrrolopyridine, and pyrrolopyrimidine, any of which may be optionally substituted with one or more $R^3$ substituents.

In certain embodiments, the compound is chosen from the compounds in Table 3 having a five-membered heteroaryl at $R^2$, or a pharmaceutically acceptable salt, hydrate or solvate thereof.

In certain embodiments, the compound has formula (VII):

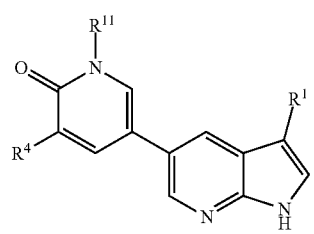

(VII)

or a pharmaceutically acceptable salt, hydrate or solvate thereof, wherein:

$R^1$ is chosen from mono- or bicyclic aryl and heteroaryl, wherein $R^1$ may be optionally substituted with one or more $R^3$ substituents;

$R^3$ is independently chosen from hydrogen, hydroxyl, cyano, $C_{1-6}$alkyl, hydroxy$C_{1-4}$alkyl, $C_{1-6}$alkoxyalkyl, aryl$C_{1-6}$alkyl, aryl$C_{1-6}$alkoxy, heteroaryl$C_{1-6}$alkyl, heteroaryl$C_{1-6}$alkoxy, aryloxy$C_{1-6}$alkyl, heteroaryloxy $C_{1-6}$alkyl, cyclopropyl$C_{1-4}$alkyl, cyclopropyl$C_{1-4}$alkoxy, cyclopropoxy$C_{1-4}$alkyl, $C_{1-4}$alkylamino, $C_{1-4}$ alkylarylamino, $C_{1-4}$alkylheteroarylamino, di($C_{1-4}$ alkyl)amino, —CONR$^6$R$^{6'}$, $C_{1-4}$ alkanoyl, —C(O)aryl, —C(O)heteroaryl, —C(O)NHaryl, —C(O)NHheteroaryl, trifluoromethyl, and halo, wherein aryl and heteroaryl may be optionally substituted with $R^9$;

$R^4$ is chosen from —NR$^5$R$^6$, —(CH$_2$)$_n$CR$^7$=CR$^9$C(O)CH$_3$, —(CH$_2$)$_n$CR$^7$=CR$^9$C(O)NR$^7$R$^{7'}$, and —(CH$_2$)$_n$ CR$^7$=CR$^9$CN;

$R^5$ is chosen from cyano, —C(O)CF$_3$, —C(O)CH=CH$_2$, —C(O)CR$^7$=CH$_2$, —C(O)CH=CHR$^7$, —C(O) CR$^7$=CHR$^7$, —C(O)CH=CR$^7$R$^{7'}$, —C(O) CH=CHCH$_2$R$^8$, —C(O)CH=CHC(O)CH$_2$R$^8$, —COC (CN)=CHR$^6$, —C(O)(C(O)NH$_2$)=CHR$^6$, —C(O)

alkynylR$^7$, —S(O)$_2$CH=CH$_2$, —(CH$_2$)$_m$CR$^7$=CR$^9$C(O) CH$_3$, —(CH$_2$)$_m$CR$^7$=CR$^9$C(O)NR$^7$R$^{7'}$, and —(CH$_2$)$_m$CR$^7$=CR$^9$CN;

$R^6$ and $R^{6'}$ are each independently chosen from hydrogen, $C_{1-4}$alkyl, $C_{3-7}$cycloalkylalkyl, and phenyl$C_{1-4}$ alkyl;

$R^7$ and $R^{7'}$ are each independently chosen from hydrogen, cyano, $C_{1-4}$alkyl, hydroxy$C_{1-4}$alkyl, $C_{1-4}$alkoxyalkyl, $C_{3-7}$cycloalkyl, $C_{3-7}$heterocycloalkyl, $C_{3-7}$heterocycloalkylalkyl, $(NR^6R^{6'})C_{1-4}$alkyl, aryl, and heteroaryl where aryl and heteroaryl may be optionally substituted with one or more $R^9$;

$R^8$ is chosen from hydrogen, halo, cyano, $C_{1-4}$alkyl, aryl$C_{1-4}$alkyl, heteroaryl$C_{1-4}$alkyl, $C_{3-7}$cycloalkyl, hydroxy$C_{1-6}$alkyl, heterocycloalkyl$C_{1-4}$alkyl, $C_{3-7}$heterocycloalkyl, hydroxyl, $C_{1-4}$alkoxy, $C_{3-7}$cycloalkoxy, $C_{3-7}$cycloalkoxyalkyl, heteroaryloxy, aryloxy, $(NR^6R^{6'})$alkyl, arylalkoxy, $C_{1-4}$alkoxy$C_{1-4}$alkyl, amino, $C_{1-4}$alkylamino, di($C_{1-4}$alkyl)amino, trifluoromethyl, aryl, and heteroaryl, wherein alkyl, heterocycloalkyl, aryl and heteroaryl may be optionally substituted with one or more $R^9$;

$R^9$ is chosen from hydrogen, halo, hydroxyl, $C_{1-4}$ alkyl, cyano, trifluoromethyl, —C(O)CH$_3$, amido, and aryl;

$R^{10}$ is chosen from hydrogen, $C_{1-4}$alkyl, $C_{1-4}$alkoxy, halo, trifluoromethyl and CN;

$R^{11}$ is chosen from hydrogen, $C_{1-4}$alkyl, $C_{3-7}$cycloalkylalkyl, heterocycloalkylalkyl, aryl$C_{1-4}$alkyl, and heteroaryl$C_{1-4}$alkyl, wherein aryl and heteroaryl may be optionally substituted with one or more $R^9$;

m is an integer chosen from 1, 2 and 3; and
n is an integer chosen from 0, 1, 2, and 3.

In certain embodiments, $R^1$ is chosen from phenyl, pyridine, pyrimidine, pyrazine, pyridinone, pyrrolopyridine, and pyrrolopyrimidine, any of which may be optionally substituted with one or more $R^3$ substituents.

In certain embodiments, the compound is chosen from the compounds in Table 3 having a pyridinone at $R^2$, or a pharmaceutically acceptable salt, hydrate or solvate thereof.

In certain embodiments, the compound has formula (VIII):

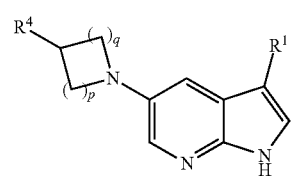

(VIII)

or a pharmaceutically acceptable salt, hydrate or solvate thereof, wherein:

$R^1$ is chosen from mono- or bicyclic aryl and heteroaryl, wherein $R^1$ may be optionally substituted with one or more $R^3$ substituents;

$R^3$ is independently chosen from hydrogen, hydroxyl, cyano, $C_{1-6}$alkyl, hydroxy$C_{1-4}$alkyl, $C_{1-6}$alkoxyalkyl, aryl$C_{1-6}$alkyl, aryl$C_{1-6}$alkoxy, heteroaryl$C_{1-6}$alkyl, heteroaryl$C_{1-6}$alkoxy, aryloxy$C_{1-6}$alkyl, heteroaryloxy $C_{1-6}$alkyl, cyclopropyl$C_{1-4}$alkyl, cyclopropyl$C_{1-4}$alkoxy, cyclopropoxy$C_{1-4}$alkyl, $C_{1-4}$alkylamino, $C_{1-4}$alkylarylamino, $C_{1-4}$alkylheteroarylamino, di($C_{1-4}$alkyl)amino, —CONR$^6$R$^{6'}$, $C_{1-4}$ alkanoyl, —C(O)aryl, —C(O)heteroaryl, —C(O)NHaryl, —C(O)NHheteroaryl, trifluoromethyl, and halo, wherein aryl and heteroaryl may be optionally substituted with $R^9$;

R⁴ is chosen from —NR⁵R⁶, —(CH₂)ₙCR⁷=CR⁹C(O)CH₃, —(CH₂)ₙCR⁷=CR⁹C(O)NR⁷R⁷', and —(CH₂)ₙCR⁷=CR⁹CN;

R⁵ is chosen from cyano, —C(O)CF₃, —C(O)CH=CH₂, —C(O)CR⁷=CH₂, —C(O)CH=CHR⁷, —C(O)CR⁷=CHR⁷, —C(O)CH=CR⁷R⁷', —C(O)CH=CHCH₂R⁸, —C(O)CH=CHC(O)CH₂R⁸, —COC(CN)=CHR⁶, —C(O)(C(O)NH₂)=CHR⁶, —C(O)alkynylR⁷, —S(O)₂CH=CH₂, —(CH₂)ₘCR⁷=CR⁹C(O)CH₃, —(CH₂)ₘCR⁷=CR⁹C(O)NR⁷R⁷', and —(CH₂)ₘCR⁷=CR⁹CN;

R⁶ and R⁶' are each independently chosen from hydrogen, C₁₋₄alkyl, C₃₋₇cycloalkylalkyl, and phenylC₁₋₄ alkyl;

R⁷ and R⁷' are each independently chosen from hydrogen, cyano, C₁₋₄alkyl, hydroxyC₁₋₄alkyl, C₁₋₄alkoxyalkyl, C₃₋₇cycloalkyl, C₃₋₇heterocycloalkyl, C₃₋₇heterocycloalkylalkyl, (NR⁶R⁶')C₁₋₄alkyl, aryl, and heteroaryl where aryl and heteroaryl may be optionally substituted with one or more R⁹;

R⁸ is chosen from hydrogen, halo, cyano, C₁₋₄alkyl, arylC₁₋₄alkyl, heteroarylC₁₋₄alkyl, C₃₋₇cycloalkyl, hydroxyC₁₋₆alkyl, heterocycloalkylC₁₋₄alkyl, C₃₋₇heterocycloalkyl, hydroxyl, C₁₋₄alkoxy, C₃₋₇cycloalkoxy, C₃₋₇cycloalkoxyalkyl, heteroaryloxy, aryloxy, (NR⁶R⁶')alkyl, arylalkoxy, C₁₋₄alkoxyC₁₋₄alkyl, amino, C₁₋₄alkylamino, di(C₁₋₄alkyl)amino, trifluoromethyl, aryl, and heteroaryl, wherein alkyl, heterocycloalkyl, aryl and heteroaryl may be optionally substituted with one or more R⁹;

R⁹ is chosen from hydrogen, halo, hydroxyl, C₁₋₄ alkyl, cyano, trifluoromethyl, —C(O)CH₃, amido, and aryl;

R¹⁰ is chosen from hydrogen, C₁₋₄alkyl, C₁₋₄alkoxy, halo, trifluoromethyl and CN;

m is an integer chosen from 1, 2 and 3;

n is an integer chosen from 0, 1, 2, and 3;

p and q are each independently an integer chosen from 1 and 2.

In certain embodiments, R¹ is chosen from phenyl, pyridine, pyrimidine, pyrazine, pyridinone, pyrrolopyridine, and pyrrolopyrimidine, any of which may be optionally substituted with one or more R³ substituents.

In certain embodiments, the compound is chosen from the compounds in Tables 2 and 3 having a heterocycloalkyl at R², or a pharmaceutically acceptable salt, hydrate or solvate thereof, or a pharmaceutically acceptable salt, hydrate or solvate thereof.

In certain embodiments, the compound is chosen from:
N-(1-(3-phenyl-1H-pyrrolo[2,3-b]pyridin-5-yl)azetidin-3-yl)acrylamide;
N-(1-(3-(2-methoxypyridin-4-yl)-1H-pyrrolo[2,3-b]pyridin-5-yl)azetidin-3-yl)acrylamide;
N-(1-(3-(6-methoxypyridin-3-yl)-1H-pyrrolo[2,3-b]pyridin-5-yl)azetidin-3-yl)acrylamide;
N-(1-(3-(2-methylpyridin-4-yl)-1H-pyrrolo[2,3-b]pyridin-5-yl)azetidin-3-yl)acrylamide;
N-(1-(3-(2-cyanopyridin-4-yl)-1H-pyrrolo[2,3-b]pyridin-5-yl)azetidin-3-yl)acrylamide;
N-(1-(3-(pyridin-4-yl)-1H-pyrrolo[2,3-b]pyridin-5-yl)azetidin-3-yl)acrylamide,
N-(1-(3-(2-(methylamino)pyridin-4-yl)-1H-pyrrolo[2,3-b]pyridin-5-yl)azetidin-3-yl)acrylamide,
(S)—N-(1-(3-(pyridin-4-yl)-1H-pyrrolo[2,3-b]pyridin-5-yl)pyrrolidin-3-yl)acrylamide,
(S)—N-(1-(3-(pyridin-4-yl)-1H-pyrrolo[2,3-b]pyridin-5-yl)pyrrolidin-3-yl)cyanamide, and
(S)—N-(1-(3-(pyridin-4-yl)-1H-pyrrolo[2,3-b]pyridin-5-yl)piperidin-3-yl)acrylamide, or a pharmaceutically acceptable salt, hydrate or solvate thereof.

In certain embodiments, p is 1 and q is 1.

In certain embodiments, the compound is chosen from the compounds in Tables 2 and 3 having an azetidinyl at R², or a pharmaceutically acceptable salt, hydrate or solvate thereof.

In certain embodiments, the compound is chosen from:
N-(1-(3-phenyl-1H-pyrrolo[2,3-b]pyridin-5-yl)azetidin-3-yl)acrylamide;
N-(1-(3-(2-methoxypyridin-4-yl)-1H-pyrrolo[2,3-b]pyridin-5-yl)azetidin-3-yl)acrylamide;
N-(1-(3-(6-methoxypyridin-3-yl)-1H-pyrrolo[2,3-b]pyridin-5-yl)azetidin-3-yl)acrylamide;
N-(1-(3-(2-methylpyridin-4-yl)-1H-pyrrolo[2,3-b]pyridin-5-yl)azetidin-3-yl)acrylamide;
N-(1-(3-(2-cyanopyridin-4-yl)-1H-pyrrolo[2,3-b]pyridin-5-yl)azetidin-3-yl)acrylamide;
N-(1-(3-(pyridin-4-yl)-1H-pyrrolo[2,3-b]pyridin-5-yl)azetidin-3-yl)acrylamide, and
N-(1-(3-(2-(methylamino)pyridin-4-yl)-1H-pyrrolo[2,3-b]pyridin-5-yl)azetidin-3-yl)acrylamide, or a pharmaceutically acceptable salt, hydrate or solvate thereof.

In certain embodiments, p is 2 and q is 1.

In certain embodiments, the compound is chosen from the compounds in Tables 2 and 3 having a pyrroldinyl at R², or a pharmaceutically acceptable salt, hydrate or solvate thereof.

In certain embodiments, the compound is chosen from:
(S)—N-(1-(3-(pyridin-4-yl)-1H-pyrrolo[2,3-b]pyridin-5-yl)pyrrolidin-3-yl)acrylamide and
(S)—N-(1-(3-(pyridin-4-yl)-1H-pyrrolo[2,3-b]pyridin-5-yl)pyrrolidin-3-yl)cyanamide, or a pharmaceutically acceptable salt, hydrate or solvate thereof.

In certain embodiments, p is 2 and q is 2.

In certain embodiments, the compound is chosen from the compounds in Tables 2 and 3 having a piperidinyl at R², or a pharmaceutically acceptable salt, hydrate or solvate thereof.

In certain embodiments, the compound is (S)—N-(1-(3-(pyridin-4-yl)-1H-pyrrolo[2,3-b]pyridin-5-yl)piperidin-3-yl)acrylamide, or a pharmaceutically acceptable salt, hydrate or solvate thereof.

In certain embodiments, the compound has formula (IX):

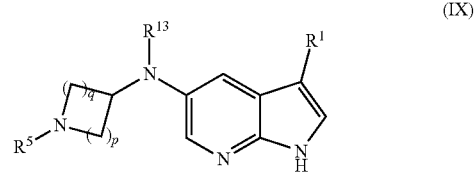

(IX)

or a pharmaceutically acceptable salt, hydrate or solvate thereof, wherein:

R¹ is chosen from mono- and bicyclic aryl and heteroaryl, wherein R¹ may be optionally substituted with one or more R³ substituents;

R² is chosen from heterocycloalkyl, aryl, heteroaryl, each of which is substituted with one R⁴ substituent, and any of which may be further optionally substituted with one or more R⁸ substituents, or alternatively R² is R¹²R¹³;

$R^3$ is independently chosen from hydrogen, hydroxyl, cyano, $C_{1-6}$alkyl, hydroxy$C_{1-6}$alkyl, $C_{1-6}$alkoxyalkyl, aryl$C_{1-6}$alkyl, aryl$C_{1-6}$alkoxy, heteroaryl$C_{1-6}$alkyl, heteroaryl$C_{1-6}$alkoxy, aryloxy$C_{1-6}$alkyl, heteroaryloxy $C_{1-6}$alkyl, cyclopropyl$C_{1-4}$alkyl, cyclopropyl$C_{1-4}$alkoxy, cyclopropoxy$C_{1-4}$alkyl, $C_{1-4}$alkylamino, $C_{1-4}$alkylarylamino, $C_{1-4}$alkylheteroarylamino, di($C_{1-4}$alkyl)amino, —C(O)NR$^6$R$^{6'}$, $C_{1-4}$alkanoyl, —C(O)aryl, —C(O)heteroaryl, —C(O)NHaryl, —C(O)NHheteroaryl, trifluoromethyl, and halo, wherein aryl and heteroaryl may be optionally substituted with $R^9$;

$R^4$ is chosen from NR$^5$R$^6$, —(CH$_2$)$_n$CR$^7$=CR$^9$C(O)CH$_3$, —(CH$_2$)$_n$CR$^7$=CR$^9$C(O)NR$^7$R$^{7'}$, and —(CH$_2$)$_n$CR$^7$=CR$^9$CN;

$R^5$ is chosen from cyano, —C(O)CF$_3$, —C(O)CH=CH$_2$, —C(O)CR$^7$=CH$_2$, —C(O)CH=CHR$^7$, —C(O)CR$^7$=CHR$^7$, —C(O)CH=CR$^7$R$^{7'}$, —C(O)CH=CHCH$_2$R$^8$, —C(O)CH=CHC(O)CH$_2$R$^8$, —COC(CN)=CHR$^6$, —C(O)(C(O)NH$_2$)=CHR$^6$, C(O)alkynylR$^7$, —S(O)$_2$CH=CH$_2$, —(CH$_2$)$_m$CR$^7$=CR$^9$C(O)CH$_3$, —(CH$_2$)$_m$CR$^7$=CR$^9$C(O)NR$^7$R$^{7'}$, and —(CH$_2$)$_m$CR$^7$=CR$^9$CN;

$R^6$ and $R^{6'}$ are each independently chosen from hydrogen, $C_{1-4}$alkyl, $C_{3-7}$cycloalkylalkyl, and phenyl$C_{1-4}$alkyl;

$R^7$ and $R^{7'}$ are each independently chosen from hydrogen, cyano, $C_{1-4}$alkyl, hydroxy$C_{1-4}$alkyl, $C_{1-4}$alkoxyalkyl, $C_{3-7}$cycloalkyl, $C_{3-7}$heterocycloalkyl, (NR$^6$R$^{6'}$)$C_{1-4}$alkyl, aryl, and heteroaryl, wherein aryl and heteroaryl may be optionally substituted with one or more $R^9$;

$R^8$ is chosen from hydrogen, halo, cyano, $C_{1-4}$alkyl, aryl$C_{1-4}$alkyl, heteroaryl$C_{1-4}$alkyl, $C_{3-7}$cycloalkyl, hydroxy$C_{1-6}$alkyl, heterocycloalkyl$C_{1-4}$alkyl, $C_{3-7}$heterocycloalkyl, hydroxyl, $C_{1-4}$alkoxy, $C_{3-7}$cycloalkoxy, $C_{3-7}$cycloalkoxyalkyl, heteroaryloxy, aryloxy, (NR$^6$R$^{6'}$)alkyl, arylalkoxy, $C_{1-4}$alkoxy$C_{1-4}$alkyl, amino, $C_{1-4}$alkylamino, di($C_{1-4}$alkyl)amino, trifluoromethyl, aryl, and heteroaryl, wherein alkyl, heterocycloalkyl, aryl and heteroaryl may be optionally substituted with one or more $R^9$;

$R^9$ is chosen from hydrogen, halo, hydroxyl, $C_{1-4}$ alkyl, cyano, trifluoromethyl, alkanoyl, amido, and aryl;

$R^{10}$ is chosen from hydrogen, $C_{1-4}$alkyl, $C_{1-4}$alkoxy, halo, trifluoromethyl, and cyano;

$R^{11}$ is chosen from hydrogen, $C_{1-4}$alkyl, $C_{3-7}$cycloalkylalkyl, heterocycloalkylalkyl, aryl$C_{1-4}$alkyl, and heteroaryl$C_{1-4}$alkyl, wherein aryl and heteroaryl may be optionally substituted with one or more $R^9$;

$R^{12}$ is a nitrogen-containing $C_{3-7}$heterocycloalkyl, wherein said nitrogen is further substituted by $R^5$;

$R^{13}$ is chosen from hydrogen, $C_{1-4}$alkyl, and $C_{3-7}$cycloalkylalkyl;

X is N or CR$^{11}$;

m is an integer chosen from 1, 2 and 3;

n is an integer chosen from 0, 1, 2, and 3;

p and q are each independently an integer chosen from 1, 2, and 3.

In certain embodiments, $R^1$ is chosen from phenyl, pyridine, pyrimidine, pyrazine, pyridinone, pyrrolopyridine, and pyrrolopyrimidine, any of which may be optionally substituted with one or more $R^3$ substituents.

In certain embodiments, p is 1 and q is 1.

In certain embodiments, p is 2 and q is 1.

In certain embodiments, p is 2 and q is 2.

In certain embodiments, p is 3 and q is 1.

In certain embodiments, the compound is chosen from the compounds in Table 3 having a an N-linked nitrogen-containing $C_{3-7}$heterocycloalkyl at $R^2$, wherein said nitrogen is further substituted by $R^5$, or a pharmaceutically acceptable salt, hydrate or solvate thereof.

Also provided are embodiments wherein any embodiment above may be combined with any one or more of these embodiments, provided the combination is not mutually exclusive. As used herein, two embodiments are "mutually exclusive" when one is defined to be something which is different than the other. For example, an embodiment wherein one group is ethyl is mutually exclusive with an embodiment in which the same group in the same position is hydrogen.

Also provided herein is a composition comprising a compound as disclosed herein, or a pharmaceutically acceptable salt, hydrate or solvate thereof, and a pharmaceutically acceptable carrier, adjuvant, or vehicle.

Methods of Treatment and Use

The present disclosure provides compounds and pharmaceutical compositions that inhibit kinase activity, particularly ITK activity and are thus useful in the treatment or prevention of disorders associated with ITK. Compounds and pharmaceutical compositions of the present disclosure selectively inhibit ITK and are thus useful in the treatment or prevention of a range of disorders associated with the activation of ITK which includes, but are not limited to respiratory diseases, allergic diseases, autoimmune diseases, inflammatory disorders, immunological disorders, proliferative disorders, transplant rejection, graft versus host disease, HIV, aplastic anemia, pain including inflammatory pain and other diseases and disorders associated with ITK.

In particular, the compounds of the present disclosure may be used to prevent or treat asthma, rheumatoid arthritis, juvenile idiopathic arthritis, psoriatic arthritis, ankylosing spondylitis, psoriasis, contact hypersensitivity and inflammatory bowel disease.

The compounds of the present disclosure may be used to prevent or treat T-cell lymphoma and lymphoblastic T-cell leukemia.

The compounds of the present disclosure may be used to prevent or treat HIV.

Compounds and pharmaceutically acceptable compositions of the present disclosure can be employed in combination therapies, that is, the compounds and pharmaceutically acceptable compositions may have potential utility in combination with other therapies for the treatment of immune, inflammatory, proliferative, and allergic disorders. Example includes but not limited to co-administration with steroids, leukotriene antagonists, anti-histamines, anti-cancer agents, protein kinase inhibitors, cyclosporine, or rapamycin.

The compounds of the present disclosure may be used to prevent or treat an ITK-mediated disorder by the sequential or co-administration of another therapeutic agent.

In certain embodiments, the therapeutic agent is selected from taxanes, inhibitors of bcr-abl, inhibitors of EGFR, DNA damaging agents, and antimetabolites.

In particular embodiments, the therapeutic agent is selected from paclitaxel, imatinib, dasatinib, nilotinib, erlotinib, Iressa, cisplatin, oxaliplatin, carboplatin, anthracyclines, ara-C and 5-FU.

In particular embodiments, the therapeutic agent is selected from camptothecin, doxorubicin, idarubicin, cisplatin, taxol, taxotere, vincristine, erlotinib, a MEK inhibitor, U0126, an ERK inhibitor, a cell cycle checkpoint inhibitor, vorinostat, imatinib, dasatinib, and nilotinib.

Compounds and pharmaceutical compositions of the present disclosure selectively inhibit ITK and are thus useful in the treatment or prevention of a range of disorders associated with the activation of ITK which includes, but are not limited to chronic obstructive pulmonary disease (COPD) such as irreversible COPD; asthma, such as bronchial, allergic, intrinsic, extrinsic and dust asthma, particularly chronic or inveterate asthma (for example, late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia; sinusitis, chronic rhinosinusitis, nasosinusal polyposis; pulmonary fibrosis; inflammatory bowel disease; Guillain-Barré syndrome, acute or chronic inflammation, rheumatoid arthritis, seronegative spondyloarthropathies (including ankylosing spondylitis, psoriatic arthritis and Reiter's disease), Behcet's disease, Sjogren's syndrome and systemic sclerosis; psoriasis, atopic dermatitis, contact dermatitis and other eczematous dermitides, sebonhoetic dermatitis, Lichen planus, Pemphigus, bullous Pemphigus, Epidermolysis bullosa, urticaria, angiodermas, vasculitides, erythema, cutaneous eosinophilias, uveitis, Alopecia areata and vernal conjunctivitis; Coeliac disease, proctitis, eosinopilic gastro-enteritis, mastocytosis, Crohn's disease, ulcerative colitis, food-related allergies which have effects remote from the gut, for example, migraine, rhinitis and eczema; multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, type II diabetes, nephritic syndrome, eosinophilia fascitis, hyper IgE syndrome, lepromatous leprosy, sezary syndrome and idiopathic thrombocytopenia pupura; tuberculosis; organ and bone marrow transplant rejection; graft-versus-host disease.

The compounds of the present disclosure are useful for the treatment of cancer such as, but are not limited to breast cancer, skin cancer, bone cancer, prostate cancer, liver cancer, lung cancer, non-small cell lung cancer, brain cancer, cancer of the larynx, gall bladder, pancreas, rectum, parathyroid, thyroid, adrenal, neural tissue, head and neck, colon, stomach, bronchi, and kidney cancer, basal cell carcinoma, squamous cell carcinoma, metastatic skin carcinoma, osteo sarcoma, Ewing's sarcoma, myeloma, giant cell tumor, small-cell lung tumor, islet cell tumor, primary brain tumor, lymphocytic and granulocytic tumors, hairy-cell tumor, adenoma, hyperplasia, medullary carcinoma, pheochromocytoma, mucosal neuromas, intestinal ganglioneuromas, ovarian tumor, cervical dysplasia, neuroblastoma, retinoblastoma, soft tissue sarcoma, malignant carcinoid, topical skin lesion, rhabdomyosarcoma, Kaposi's sarcoma, osteogenic sarcoma, malignant hypercalcemia, renal cell tumor, adenocarcinoma, glioblastoma multiforma, leukemias, lymphomas, malignant melanomas, and epidermoid carcinomas.

As ITK inhibitors are expected to reverse the immunosuppressive microenvironment of certain tumor types (e.g. colon, lung, breast), combination with checkpoint blockade antibodies targeting cell surface receptors such as CTLA4, PD-1, PD-L1, TIM-3, LAG3, VISTA or BTLA could particularly beneficial (Sharma P and J Allison. 2015. The future of immune checkpoint therapy. Science 348:56).

Accordingly, provided herein is a method of inhibiting ITK activity in a biological sample comprising contacting the biological sample with a compound as disclosed herein, or a pharmaceutically acceptable salt, hydrate or solvate thereof.

Also provided herein is a method of treating an ITK-mediated disorder in a subject in need thereof, comprising the step of administering to the subject a compound as disclosed herein, or a pharmaceutically acceptable salt, hydrate or solvate thereof.

In certain embodiments, the subject is a human.

In certain embodiments, the subject is a companion animal, exotic animal or farm animal.

In certain embodiments, the ITK-mediated disorder is selected from cancer, autoimmune disorders, chronic inflammatory disorders, auto-inflammatory disorders, pain, inflammatory disorders, and allergic disorders.

In certain embodiments, the ITK-mediated disorder is selected from asthma, rheumatoid arthritis, juvenile idiopathic arthritis, psoriatic arthritis, ankylosing spondylitis, psoriasis, contact hypersensitivity and inflammatory bowel disease.

In certain embodiments, the ITK-mediated disorder is selected from T-cell lymphoma and lymphoblastic T-cell leukemia.

In certain embodiments, the ITK-mediated disorder is selected from a solid tumor, colorectal cancer and a hematological tumor.

In certain embodiments, the ITK-mediated disorder is HIV.

Also provided herein is a method of treating an ITK-mediated disorder in a subject in need thereof, comprising the sequential or co-administration of a compound as disclosed herein, or a pharmaceutically acceptable salt, hydrate or solvate thereof, or a pharmaceutically acceptable salt thereof, and another therapeutic agent.

In certain embodiments, the therapeutic agent is selected from taxanes, inhibitors of bcr-abl, inhibitors of EGFR, DNA damaging agents, and antimetabolites.

In certain embodiments, the therapeutic agent is selected from Paclitaxel, Gleevec, dasatinib, nilotinib, Tarceva, Iressa, cisplatin, oxaliplatin, carboplatin, anthracyclines, AraC and 5-FU.

In certain embodiments, the therapeutic agent is selected from camptothecin, doxorubicin, idarubicin, Cisplatin, taxol, taxotere, vincristine, tarceva, a MEK inhibitor, U0126, an ERK inhibitor, a cell cycle checkpoint inhibitor, vorinostat, Gleevec, dasatinib, and nilotinib.

In certain embodiments, the therapeutic agent is an immune checkpoint inhibitor.

In certain embodiments, the immune checkpoint inhibitor is selected from nivolumab, pembrolizumab and ipilumimab.

In certain embodiments, the therapeutic agent is an immunotherapeutic agent.

In certain embodiments, the immunotherapeutic agent is selected from aPD1, aPDL1 and CTLA4.

Also provided herein is a compound as disclosed herein, or a pharmaceutically acceptable salt, hydrate or solvate thereof, for use in human therapy.

Also provided herein is a compound as disclosed herein, or a pharmaceutically acceptable salt, hydrate or solvate thereof, for use as a medicament.

Also provided herein is a compound as disclosed herein, or a pharmaceutically acceptable salt, hydrate or solvate thereof, for use in treating an ITK-mediated disease.

Also provided herein is the use of a compound as disclosed herein, for the manufacture of a medicament to treat an ITK-mediated disease.

General Synthetic Methods for Preparing Compounds

Compounds of the present invention can be prepared using methods illustrated in general synthetic schemes and experimental procedures detailed below. General synthetic schemes and experimental procedures are presented for purposes of illustration and are not intended to be limiting. Starting materials used to prepare compounds of the present invention are commercially available or can be prepared using routine methods known in the art. Representative procedures for the preparation of compounds of the invention are outlined in Schemes 1-4 below. Solvents and reagents, whose synthetic preparations are not described below, can be purchased at Sigma-Aldrich or Fisher Scientific.

Scheme 1 highlights the general synthesis of the 3,5-disubstituted pyrrolopyridines or 3,5-disubstituted pyrrolopyrazines. Reaction of halo 1a with an amine $R^{200}$ substituent in the presence of a base such as KOH in DMSO provides 1b. Alternatively, reaction of 1a with the desired amine under palladium-catalyzed coupling conditions using palladium(II) acetate and BINAP or other chelating ligands such as Ruphos, in the presence of a base such as potassium hexamethyldisilylazane in THF or dioxane provides 1b. In some cases 1a may need to be protected as the tosylate (at N1) for the coupling to occur to provide 1b (as the tosyl intermediate). In this case after coupling, deprotection using lithium hydroxide or cesium carbonate in a solvent such as THF or ethanol provides 1b. Aryl analogs of 1b ($R^{200}$=aryl) may be prepared by the reaction of 1a with an aryl or heteroaryl boronic acid using a palladium catalyst under Suzuki conditions. Iodination of 1b with a halogenating agent such as NIS furnishes 1c. Protection of the indole nitrogen of 1c using tosyl chloride and sodium hydride in a solvent such as THF or DMF provides 1d. Coupling of 1d with the desired boronic acid in the presence of a palladium catalyst such as bis(diphenylphosphino)ferrocene]dichloropalladium(II) (Pd(dppf)Cl$_2$) in dioxane or DMF gives 1e. Alternately 1d can converted to a boronate ester using a base such as potassium acetate, bis(pinacolato)diboron and a palladium catalyst followed by in situ addition of a aryl halide to provide 1e. In the case of pyridinones as $R^{100}$, the reagent must be alkylated with an appropriate alkyl halide using NaH in DMF. Often the protecting group is cleaved in this step. If not the desired final compounds may then be obtained by treating the intermediate with lithium hydroxide in dioxane to give 1e. In most cases $R^{200}$ may be manipulated to add an electrophile as detailed in schemes 2-4, following methods common to those skilled in the art.

Scheme 1.
Preparation of 3,5-Disubstituted Pyrrolopyridines and Pyrrolopyrazines

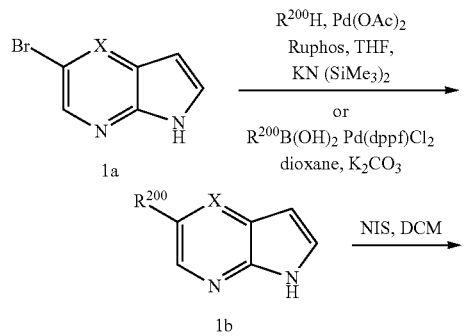

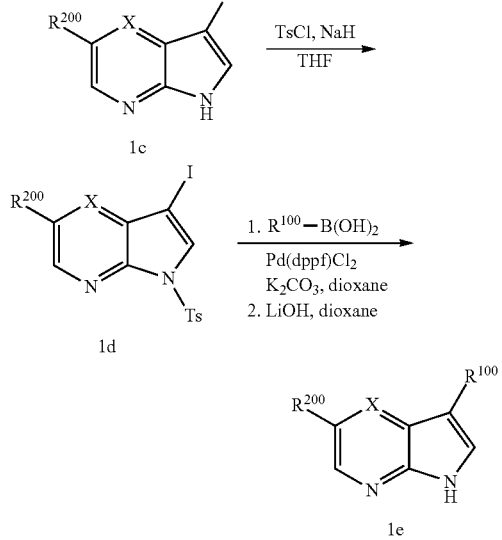

Scheme 2 highlights the synthesis of highlights the synthesis of the 5-amino substituted pyrrolopyridines or 5-substituted pyrrolopyrazines. Reaction of 1a with the desired amine using modified Buchwald conditions in the presence of a palladium catalyst such as palladium(II) acetate and Ruphos as the ligand and in a solvent such as dioxane or DMF gives 2a. Iodination of 2a with a halogenating agent such as NIS furnishes 2b. Protection of the indole nitrogen on 2b using tosyl chloride and sodium hydride in a solvent such as THF or DMF provides 2c. Coupling of 2c with the desired boronic acid in the presence of a palladium catalyst such as bis(diphenylphosphino)ferrocene]dichloropalladium(II) (Pd(dppf)Cl$_2$) in dioxane or DMF gives 2d. Alternately 2c can converted to a boronate ester using a base such as potassium acetate, bis(pinacolato)diboron and a palladium catalyst followed by in situ addition of a aryl halide to provide 2d. In the case of pyridinones as $R^{100}$, the reagent must be alkylated with an appropriate alkyl halide using NaH in DMF. Deprotection of the Boc carbamate of 2d using an acid such as HCl or TFA provides 2e. Reaction of 2e with the desired electrophile can then take place using the halide precursor or through amide coupling conditions using HATU or similar reagents in a solvent such as DCM or THF. The protecting group may then be removed using lithium hydroxide in dioxane to give 2f. If the tosyl protecting group is cleaved during the Suzuki coupling, then 2d (lacking the tosyl group) can be subsequently converted to 2e and then 2f in a similar fashion. In certain cases $R^{100}$ or $R^{500}$ bay be manipulated to a different substituent following methods common to those skilled in the art.

Scheme 2.
Preparation of 5-Amino Substituted Pyrrolopyridines and Pyrrolopyrazines

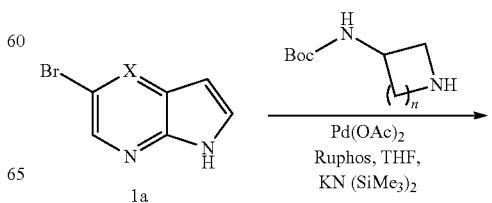

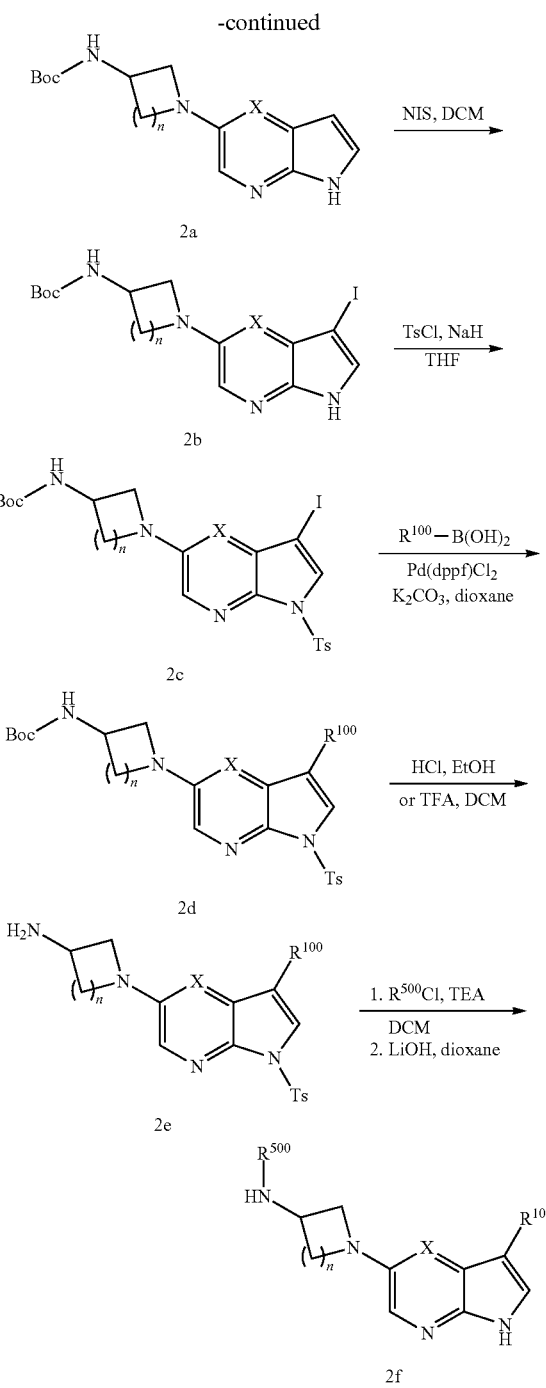

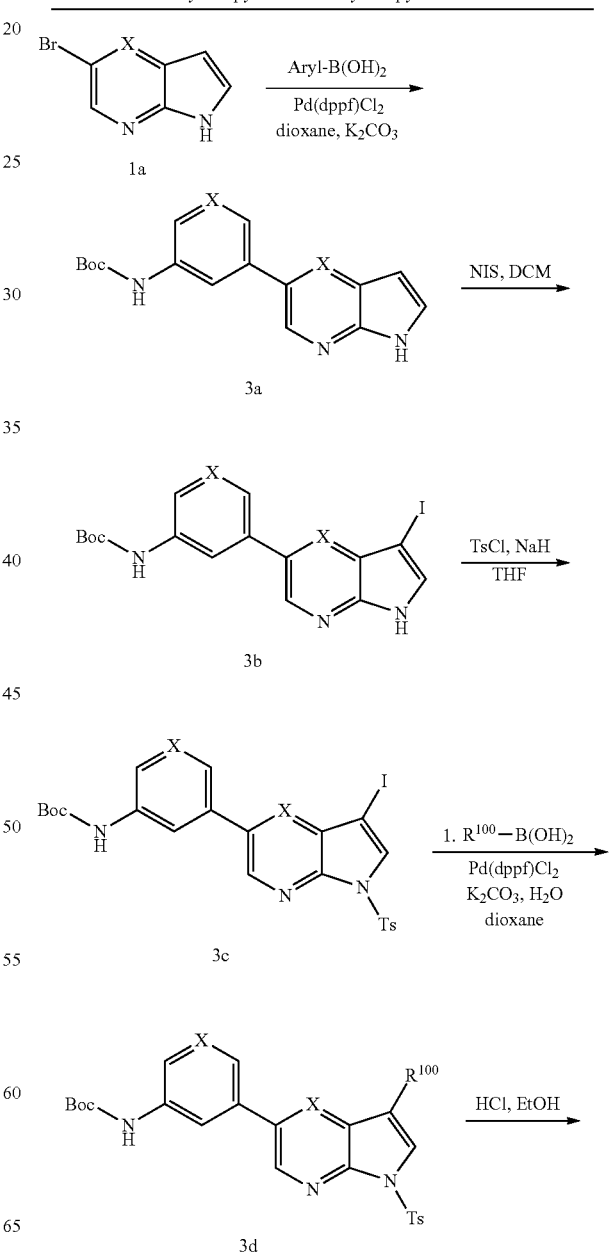

acetate, bis(pinacolato)diboron and a palladium catalyst followed by in situ addition of a aryl halide to provide 3d. In the case of pyridinones as $R^{100}$, the reagent must be alkylated with an appropriate alkyl halide using NaH in DMF. Deprotection of the Boc carbamate of 3d using an acid such as HCl or TFA provides 3e. Reaction of 3e with the desired electrophile can then take place through amide coupling conditions such as using O-(benzotriazol-1-yl)-N,N,N',N'-tetramethyluronium tetrafluoroborate (HTBU) and triethylamine as a base in a solvent such as THF to provide 3f. The tosyl group may be removed by treating 3f with lithium hydroxide in dioxane to give 3g. In certain cases $R^{100}$ or $R^{500}$ may be manipulated to a different substituent following methods common to those skilled in the art.

Scheme 3. Preparation of 4-Pyridinone or 4-Pyrimidinone Substituted Pyrrolopyridines and Pyrrolopyrazines Scheme 3 highlights the synthesis of the 5-aryl substituted pyrrolopyridines or pyrrolopyrazines. Reaction of 1a with an aryl or heteroaryl boronic acid using a palladium catalyst such as bis(diphenylphosphino)ferrocene]dichloropalladium (II) (Pd(dppf)Cl$_2$) under Suzuki conditions provides 3a. Iodination of 3a with a halogenating agent such as NIS furnishes 3b. Protection of the indole nitrogen on 3b using tosyl chloride and sodium hydride in a solvent such as THF or DMF provides 3c. Coupling of 3c with the desired boronic acid in the presence of a palladium catalyst such as bis(diphenylphosphino)ferrocene]dichloropalladium(II) (Pd(dppf)Cl$_2$) in dioxane or DMF gives 3d. Alternately 3c can converted to a boronate ester using a base such as potassium

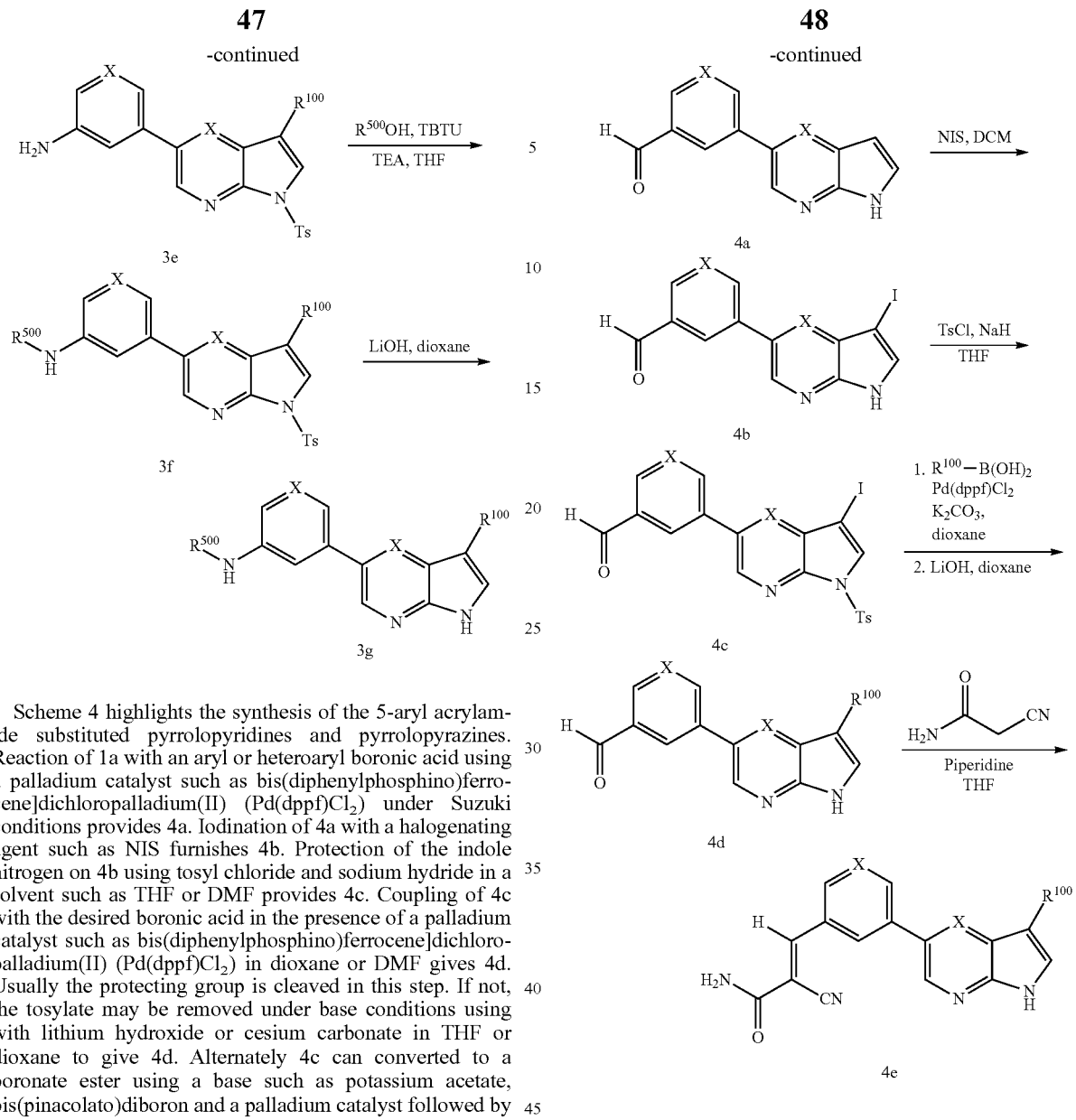

Scheme 4 highlights the synthesis of the 5-aryl acrylamide substituted pyrrolopyridines and pyrrolopyrazines. Reaction of 1a with an aryl or heteroaryl boronic acid using a palladium catalyst such as bis(diphenylphosphino)ferrocene]dichloropalladium(II) (Pd(dppf)Cl$_2$) under Suzuki conditions provides 4a. Iodination of 4a with a halogenating agent such as NIS furnishes 4b. Protection of the indole nitrogen on 4b using tosyl chloride and sodium hydride in a solvent such as THF or DMF provides 4c. Coupling of 4c with the desired boronic acid in the presence of a palladium catalyst such as bis(diphenylphosphino)ferrocene]dichloropalladium(II) (Pd(dppf)Cl$_2$) in dioxane or DMF gives 4d. Usually the protecting group is cleaved in this step. If not, the tosylate may be removed under base conditions using with lithium hydroxide or cesium carbonate in THF or dioxane to give 4d. Alternately 4c can converted to a boronate ester using a base such as potassium acetate, bis(pinacolato)diboron and a palladium catalyst followed by in situ addition of a aryl halide to provide 3d. In the case of pyridinones as $R^{100}$, the reagent must be alkylated with an appropriate alkyl halide using NaH in DMF. Reaction of 4d using a Knovenagel condensation with cyanoacetamide under mildly basic conditions gives 4e. In certain cases $R^{100}$ or $R^{500}$ may be manipulated to a different substituent following methods common to those skilled in the art.

Scheme 4.
Preparation of 5-Aryl Acrylamide Pyrrolopyridines and Pyrrolopyrazines

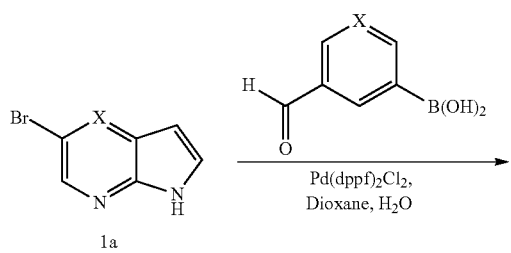

Scheme 5 highlights the synthesis of the 5-aryl acrylamide substituted pyrrolopyridines and pyrrolopyrazines lacking the nitrile as shown in Scheme 4. Reaction of 1a with an aryl or heteroaryl boronic acid using a palladium catalyst such as bis(diphenylphosphino)ferrocene]dichloropalladium (II) (Pd(dppf)Cl$_2$) under Suzuki conditions provides 5a. Iodination of 5a with a halogenating agent such as NIS furnishes 5b. Protection of the indole nitrogen on 5b using tosyl chloride and sodium hydride in a solvent such as THF or DMF provides 5c. Coupling of 5c with the desired aryl halide and bis(pinacolato)diboron in the presence of a palladium catalyst such as bis(diphenylphosphino)ferrocene] dichloropalladium(II) (Pd(dppf)Cl$_2$) in dioxane or DMF gives 5d. Alternatively coupling of 5c with the desired boronic acid in the presence of a palladium catalyst such as bis(diphenylphosphino)ferrocene]dichloropalladium(II) (Pd (dppf)Cl$_2$) in dioxane or DMF gives 5d. Reaction of 5d using a Horner-Emmonds reaction may be carried out with 5d using the desired olefination reagent to give 5e. The toslylate may be removed under base conditions using with lithium hydroxide or cesium carbonate in THF or dioxane to give 5f. In certain cases $R^{100}$ may be manipulated to a different substituent following methods common to those skilled in the art.

Scheme 5.
Preparation of 5-Aryl Acrylamide Pyrrolopyridines and Pyrrolopyrazines

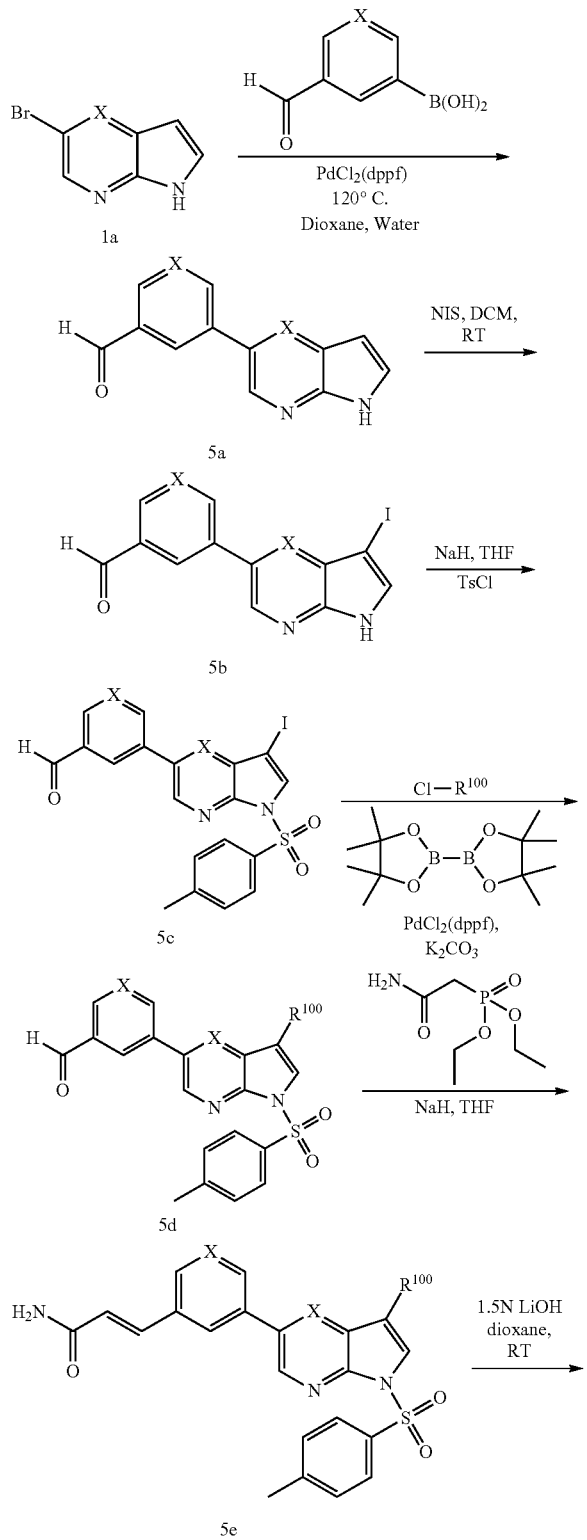

-continued

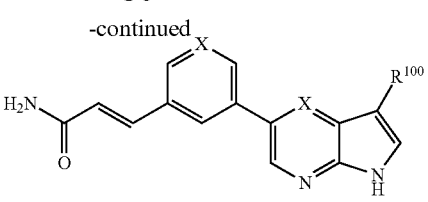

5f

The disclosure is further illustrated by the following examples.

EXAMPLES

Example 1: Preparation of N-(1-(3-Phenyl-1H-pyrrolo[2,3-b]pyridin-5-yl)azetidin-3-yl)acrylamide

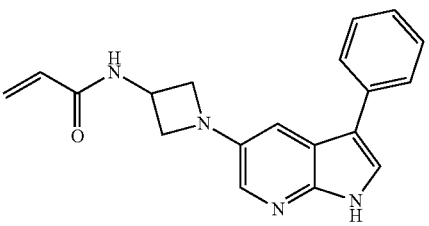 [SMILES: C=CC(=O)NC1CN(c2cnc3[nH]cc(-c4ccccc4)c3c2)C1]

Step 1: Preparation of tert-Butyl (1-(1H-pyrrolo[2,3-b]pyridin-5-yl)azetidin-3-yl)carbamate

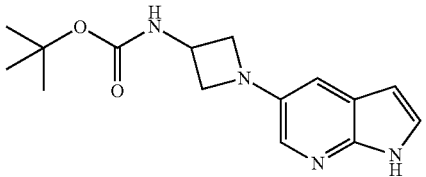 [SMILES: CC(C)(C)OC(=O)NC1CN(c2cnc3[nH]ccc3c2)C1]

A mixture of 5-bromo-1H-pyrrolo[2,3-b]pyridine (1.0 g, 5.1 mmol), tert-butyl azetidin-3-ylcarbamate hydrochloride (1.5 g, 7.2 mmol), Pd$_2$(dba)$_3$ (350 mg, 0.38 mmol), X-Phos (467 mg, 1 mmol) and Cs$_2$CO$_3$ (4.9 g, 15 mmol) in 1,4-dioxane/H$_2$O (15 mL/3 mL) was stirred under Ar at 135° C. with microwave for 2 h. After cooling the result mixture was poured into 30 mL water, and water layer was extracted with ethyl acetate (20 mL×3). The organic layers were combined, dried over Na$_2$SO$_4$ and concentrated. The residue was purified with normal phase chromatography (ethyl acetate/heptane) to give tert-butyl (1-(1H-pyrrolo[2,3-b]pyridin-5-yl) azetidin-3-yl)carbamate as a yellow solid (0.4 g, 27% yield): MS (ES) m/z 289 (M+H).

Step 2: Preparation of tert-Butyl (1-(3-iodo-1H-pyrrolo[2,3-b]pyridin-5-yl)azetidin-3-yl)carbamate

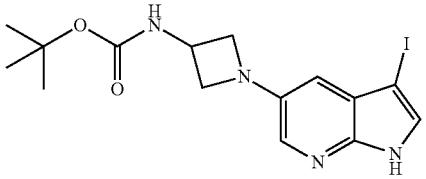 [SMILES: CC(C)(C)OC(=O)NC1CN(c2cnc3[nH]cc(I)c3c2)C1]

A mixture of tert-butyl (1-(1H-pyrrolo[2,3-b]pyridin-5-yl)azetidin-3-yl)carbamate (5.6 g, 19.4 mmol) and NIS (4.80 g, 21.4 mmol) in DMF (100 mL) was stirred at rt for 16 h. The resultant mixture was poured into 200 mL water. The solid was removed by filtration, washed with 50 mL water and dried in vacuo to give tert-butyl (1-(3-iodo-1H-pyrrolo[2,3-b]pyridin-5-yl)azetidin-3-yl)carbamate as a brown solid which was used without further purification (8.0 g, 99% yield): MS (ES) m/z 415 (M+H).

Step 3: Preparation of tert-Butyl (1-(3-iodo-1-tosyl-1H-pyrrolo[2,3-b]pyridin-5-yl)azetidin-3-yl)carbamate

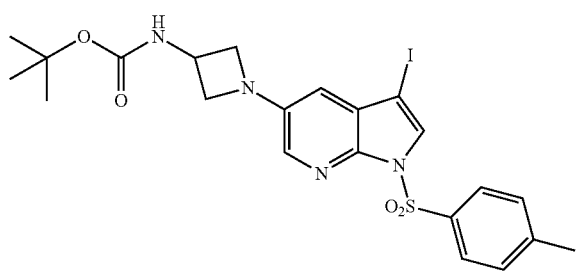 [SMILES: Cc1ccc(S(=O)(=O)n2cc(I)c3cc(N4CC(NC(=O)OC(C)(C)C)C4)cnc32)cc1]

A mixture of tert-butyl (1-(3-iodo-1H-pyrrolo[2,3-b]pyridin-5-yl)azetidin-3-yl)carbamate (8.0 g, 19.4 mmol, crude), TsCl (4.05 g, 21.3 mmol) and tetra-N-butyl ammonium bromide (TBAB) (800 mg, 2.40 mmol) in toluene/H$_2$O (80 mL/40 mL) was stirred at rt. Then NaOH (aq., 6 M, 40 mL) was added and the mixture was stirred at rt for 16 h. The result mixture was poured into 200 mL water. The water layer was extracted with ethyl acetate. The organic layers were combined, dried over Na$_2$SO$_4$ and concentrated. The residue was purified with normal phase chromatography (ethyl acetate/heptane) to give tert-butyl (1-(3-iodo-1-tosyl-1H-pyrrolo[2,3-b]pyridin-5-yl)azetidin-3-yl)carbamate as a white solid (4.1 g, 37% yield): $^1$H NMR (400 MHz, CDCl$_3$) δ 8.01 (d, J=8.8 Hz, 2H), 7.76 (s, 1H), 7.27-7.25 (m, 1H), 7.25 (d, J=8.8 Hz, 2H), 6.59-6.58 (m, 1H), 4.98 (bs, 1H), 4.65-4.63 (m, 1H), 4.26 (t, J=7.2 Hz, 4H), 3.66 (t, J=6.4 Hz, 4H), 2.37 (s, 3H), 1.45 (s, 9H); MS (ES) m/z 569 (M+H).

Step 4: Preparation of tert-Butyl (1-(3-phenyl-1-tosyl-1H-pyrrolo[2,3-b]pyridin-5-yl)azetidin-3-yl)carbamate

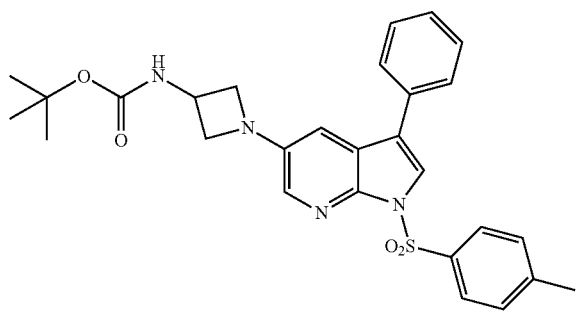 [SMILES: Cc1ccc(S(=O)(=O)n2cc(-c3ccccc3)c3cc(N4CC(NC(=O)OC(C)(C)C)C4)cnc32)cc1]

To a solution of tert-butyl (1-(3-iodo-1-tosyl-1H-pyrrolo[2,3-b]pyridin-5-yl)azetidin-3-yl)carbamate from step 3 (200 mg, 0.35 mmol) in 1,4-dioxane (2 mL) and water (0.5 mL) was added phenylboronic acid (43 mg, 0.35 mmol), potassium carbonate (145 mg, 1.05 mmol) and [1,1'-bis(diphenylphosphino)ferrocene]dichloropalladium(II) (13 mg, 0.017 mmol). The solution was treated with microwave radiation at 100° C. for one hour. After cooling, the resulting solution was partitioned between ethyl acetate and water. The organic layer was washed with water, brine and dried over magnesium sulfate. The solution was filtered and concentrated in vacuo. The crude material was purified using normal phase chromatography (ethyl acetate/heptane) to provide tert-butyl (1-(3-phenyl-1-tosyl-1H-pyrrolo[2,3-b]pyridin-5-yl)azetidin-3-yl)carbamate as a white solid (96 mg, 53% yield): MS (ES) m/z 519 (M+H).

Step 5: Preparation of N-(1-(3-Phenyl-1-tosyl-1H-pyrrolo[2,3-b]pyridin-5-yl)azetidin-3-yl)acrylamide

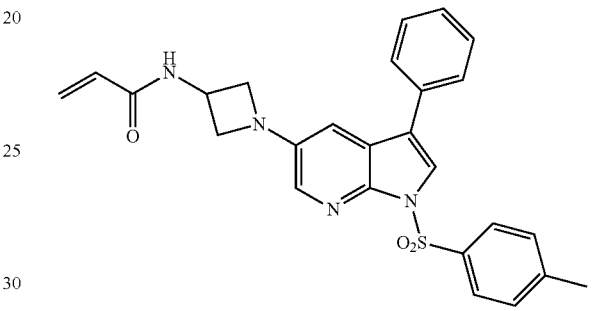

To a solution of tert-butyl (1-(3-phenyl-1-tosyl-1H-pyrrolo[2,3-b]pyridin-5-yl)azetidin-3-yl)carbamate from step 4 (96 mg, 0.18 mmol) in dichloromethane (5 mL) was added trifluoroacetic acid (2 mL) and the solution was stirred for 3 hours at ambient temperature. The solution was concentrated in vacuo to provide the amine salt as a green oil. The green oil was dissolved into dichloromethane (5 mL) and N,N-diisopropylethylamine (0.09 mL, 0.54 mmol) and acryloyl chloride (0.01 mL, 0.18 mmol) were added and the solution was stirred at ambient temperature for 30 minutes. The reaction was quenched with water and extracted with ethyl acetate. The organic layer was washed with water, brine and dried over magnesium sulfate. The solution was filtered and concentrated in vacuo to provide the crude coupled product. The material was purified using normal phase chromatography (ethyl acetate/heptane) to provide N-(1-(3-phenyl-1-tosyl-1H-pyrrolo[2,3-b]pyridin-5-yl)azetidin-3-yl)acrylamide (19 mg, 22% yield): MS (ES) m/z 473 (M+H).

Step 6: Preparation of N-(1-(3-Phenyl-1H-pyrrolo[2,3-b]pyridin-5-yl)azetidin-3-yl)acrylamide

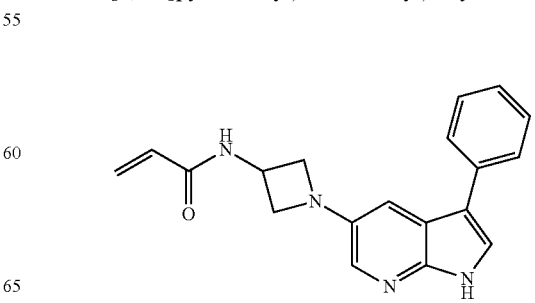

To a solution of N-(1-(3-phenyl-1-tosyl-1H-pyrrolo[2,3-b]pyridin-5-yl)azetidin-3-yl)acrylamide from step 5 (19 mg, 0.04 mmol) in 1,4-dioxane (1 mL) was added 1.5 M lithium hydroxide (1 mL) and the solution was stirred for 18 hours at ambient temperature. The reaction was partitioned between ethyl acetate and water. The organic layer was washed with water, brine and dried over magnesium sulfate. The solution was filtered and concentrated in vacuo to provide the crude coupled product. The material was purified using normal phase chromatography (dichloromethane/methanol) to provide N-(1-(3-phenyl-1H-pyrrolo[2,3-b]pyridin-5-yl)azetidin-3-yl)acrylamide as a yellow solid (3.5 mg, 27% yield): $^1$H NMR (400 MHz, DMSO-$d_6$) δ ppm, 11.62 (s, 1H), 8.79 (d, J=7.83 Hz, 1H), 7.76 (d, J=2.74 Hz, 1H), 7.68-7.67 (m, 3H), 7.44-7.40 (m, 2H), 7.27 (d, J=2.35 Hz, 1H), 7.24-7.20 (m, 1H), 6.26-6.19 (m, 1H), 6.15-6.10 (m, 1H), 5.65-5.62 (m, 1H), 4.72-4.71 (m, 1H), 4.24-4.21 (m, 2H), 3.67 (t, J=6.65 Hz, 2H); MS (ES) m/z 319 (M+H).

Example 2: Preparation of N-(1-(3-(2-Methoxypyridin-4-yl)-1H-pyrrolo[2,3-b]pyridin-5-yl)azetidin-3-yl)acrylamide

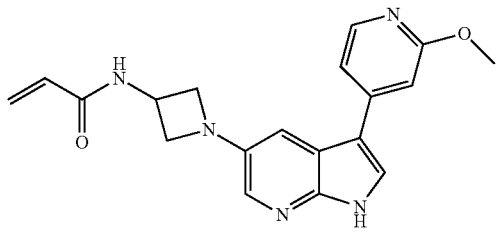 [SMILES: C=CC(=O)NC1CN(c2cnc3[nH]cc(-c4ccnc(OC)c4)c3c2)C1]

The title compound was prepared following Example 1, substituting 2-methoxy-4-pyridineboronic acid for phenylboronic acid in step 4: $^1$H NMR (400 MHz, DMSO-$d_6$) δ ppm, 11.96 (s, 1H), 8.84 (br. s, 1H), 8.13 (d, J=5.48 Hz, 1H), 8.08 (s, 1H), 7.71 (d, J=2.35 Hz, 1H), 7.35 (dd, J=5.48, 1.57 Hz, 1H), 7.31 (d, J=2.74 Hz, 1H), 7.07 (s, 1H), 6.27-6.21 (m, 1H), 6.15-6.10 (m, 1H), 5.65-5.62 (m, 1H), 4.74 (m, 1H), 4.25 (d, J=7.43 Hz, 2H), 3.88 (s, 3H), 3.72-3.68 (m, 2H); MS (ES) m/z 350 (M+H).

Example 3: Preparation of N-(1-(3-(6-Methoxypyridin-3-yl)-1H-pyrrolo[2,3-b]pyridin-5-yl)azetidin-3-yl)acrylamide

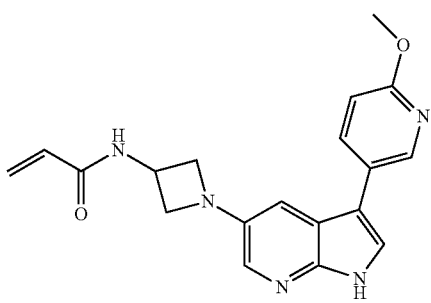 [SMILES: C=CC(=O)NC1CN(c2cnc3[nH]cc(-c4ccc(OC)nc4)c3c2)C1]

The title compound was prepared following Example 1, substituting 2-methoxy-5-pyridineboronic acid for phenylboronic acid in step 4: $^1$H NMR (400 MHz, DMSO-$d_6$) δ ppm, 11.63 (s, 1H), 8.79 (d, J=7.43 Hz, 1H), 8.50 (d, J=3.35 Hz, 1H), 8.02-7.99 (m, 1H), 7.76 (d, J=2.74 Hz, 1H), 7.69 (d, J=2.74 Hz, 1H), 7.24 (d, J=2.34 Hz, 1H), 6.89 (d, J=8.60 Hz, 1H), 6.26-6.19 (m, 1H), 6.15-6.10 (m, 1H), 5.65-5.62 (m, 1H), 4.74-4.67 (m, 1H), 4.22 (t, J=7.43 Hz, 2H), 3.88 (s, 3H), 3.69-3.65 (m, 2H); MS (ES) m/z 350 (M+H).

Example 4: N-(1-(3-(2-Methylpyridin-4-yl)-1H-pyrrolo[2,3-b]pyridin-5-yl)azetidin-3-yl)acrylamide

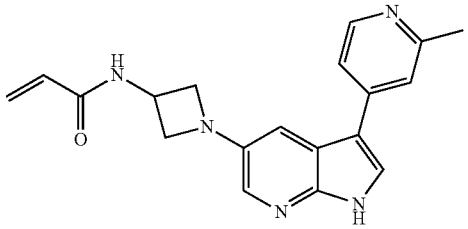 [SMILES: C=CC(=O)NC1CN(c2cnc3[nH]cc(-c4ccnc(C)c4)c3c2)C1]

The title compound was prepared following Example 1, substituting 2-methylpyridine-4-boronic acid for phenylboronic acid in step 4: $^1$H NMR (400 MHz, DMSO-$d_6$) δ ppm, 11.90 (s, 1H), 8.80 (d, J=7.05 Hz, 1H), 8.39 (d, J=5.48 Hz, 1H), 8.07 (d, J=2.73 Hz, 1H), 7.71 (d, J=2.74 Hz, 1H), 7.56 (s, 1H), 7.52 (d, J=5.09 Hz, 1H), 7.37 (d, J=2.34 Hz, 1H), 6.26-6.19 (m, 1H), 6.15-6.10 (m, 1H), 5.66-5.62 (m, 1H), 4.74-4.70 (m, 1H), 4.27-4.23 (m, 2H), 3.72-3.68 (m, 2H), 3.34 (s, 3H); MS (ES) m/z 334 (M+H).

Example 5: Preparation of N-(1-(3-(2-Cyanopyridin-4-yl)-1H-pyrrolo[2,3-b]pyridin-5-yl)azetidin-3-yl)acrylamide

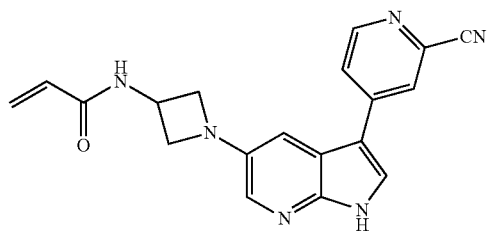 [SMILES: C=CC(=O)NC1CN(c2cnc3[nH]cc(-c4ccnc(C#N)c4)c3c2)C1]

The title compound was prepared following Example 1, substituting 2-cyanopyridine-4-boronic acid for phenylboronic acid in step 4: $^1$H NMR (400 MHz, DMSO-$d_6$) δ ppm, 11.81 (s, 1H), 8.79 (d, J=7.04 Hz, 1H), 8.11 (s, 1H), 8.06-8.04 (m, 1H), 7.97 (d, J=2.73 Hz, 1H), 7.71 (d, J=2.74 Hz, 1H), 7.66-7.60 (m, 2H), 7.34 (d, J=2.74 Hz, 1H), 6.26-6.19 (m, 1H), 6.15-6.10 (m, 1H), 5.65-5.62 (m, 1H), 4.74-4.69 (m, 1H), 4.24 (t, J=7.44 Hz, 2H), 3.71-3.68 (m, 2H); MS (ES) m/z 344 (M+H).

Example 6: Preparation of N-(3-(3-(2-Methoxypyridin-4-yl)-1H-pyrrolo[2,3-b]pyridin-5-yl)phenyl)acrylamide

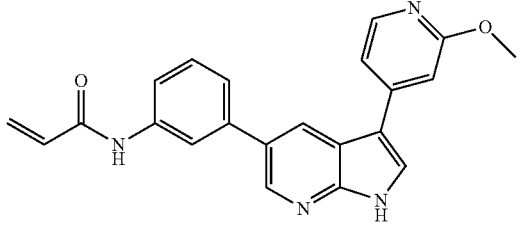 [SMILES: C=CC(=O)Nc1cccc(-c2cnc3[nH]cc(-c4ccnc(OC)c4)c3c2)c1]

Step 1: Preparation of tert-Butyl (3-(1H-pyrrolo[2,3-b]pyridin-5-yl)phenyl)carbamate

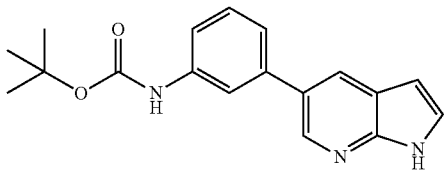 [SMILES: CC(C)(C)OC(=O)Nc1cccc(-c2cnc3[nH]ccc3c2)c1]

To a solution of 5-bromo-1H-pyrrolo[2,3-b]pyridine (196 mg, 1.00 mmol) in 1,4-dioxane (7 mL) and water (3 mL) was added 3-boc-aminophenylboronic acid (237 mg, 1.00 mmol), potassium carbonate (414 mg, 3.00 mmol) and [1,1'-bis(diphenylphosphino)ferrocene]dichloropalladium (II) (36 mg, 0.05 mmol). The solution was treated with microwave radiation at 120° C. for one hour. After cooling the resulting mixture was partitioned between ethyl acetate and water. The organic layer was washed with water, brine and dried over magnesium sulfate. The solution was filtered and concentrated in vacuo to provide the crude coupled product. The material was purified using normal phase chromatography (ethyl acetate/heptane) to provide tert-butyl (3-(1H-pyrrolo[2,3-b]pyridin-5-yl)phenyl)carbamate as a white solid (113 mg, 37% yield): MS (ES) m/z 310 (M+H).

Step 2: Preparation of tert-Butyl (3-(3-iodo-1H-pyrrolo[2,3-b]pyridin-5-yl)phenyl)carbamate

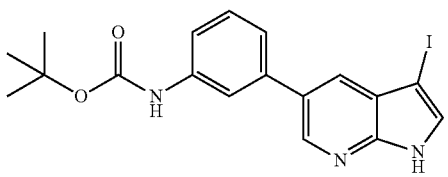 [SMILES: CC(C)(C)OC(=O)Nc1cccc(-c2cnc3[nH]cc(I)c3c2)c1]

To a solution of tert-butyl (3-(1H-pyrrolo[2,3-b]pyridin-5-yl)phenyl)carbamate from step 1 (309 mg, 1.00 mmol) in dichloromethane (5 mL) was added N-iodosuccinimide (225 mg, 1.00 mmol) and the solution was stirred for 2 hours at ambient temperature. The resulting white solid was collected by vacuum filtration to provide tert-butyl (3-(3-iodo-1H-pyrrolo[2,3-b]pyridin-5-yl)phenyl)carbamate (246 mg, 56% yield): MS (ES) m/z 436 (M+H).

Step 3: Preparation of tert-Butyl (3-(3-iodo-1-tosyl-1H-pyrrolo[2,3-b]pyridin-5-yl)phenyl)carbamate

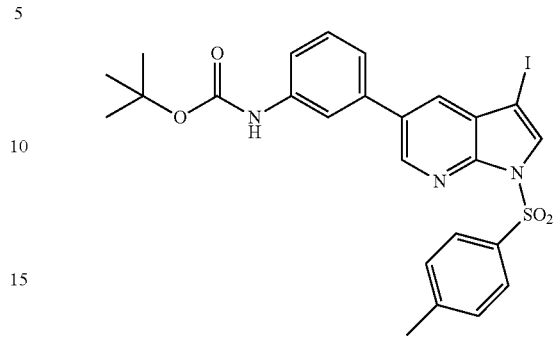

To a solution of tert-butyl (3-(3-iodo-1H-pyrrolo[2,3-b]pyridin-5-yl)phenyl)carbamate from step 2 (246 mg, 0.560 mmol) in tetrahydrofuran (3 mL) was added sodium hydride (60% mineral oil dispersion, 34 mg, 0.84 mmol) followed by p-toluenesulfonyl chloride (108 mg, 0.560 mmol) and the solution was stirred for 18 hours at ambient temperature. The reaction mixture was quenched with water and extracted with ethyl acetate. The organic layer was washed with water, brine and dried over magnesium sulfate. The solution was filtered and concentrated in vacuo to provide the crude coupled product. The material was purified using normal phase chromatography (ethyl acetate/heptane) to provide tert-butyl (3-(3-iodo-1-tosyl-1H-pyrrolo[2,3-b]pyridin-5-yl)phenyl)carbamate (325 mg, 98% yield): MS (ES) m/z 590 (M+H).

Step 4: Preparation of tert-Butyl (3-(3-(2-methoxypyridin-4-yl)-1-tosyl-1H-pyrrolo[2,3-b]pyridin-5-yl)phenyl)carbamate

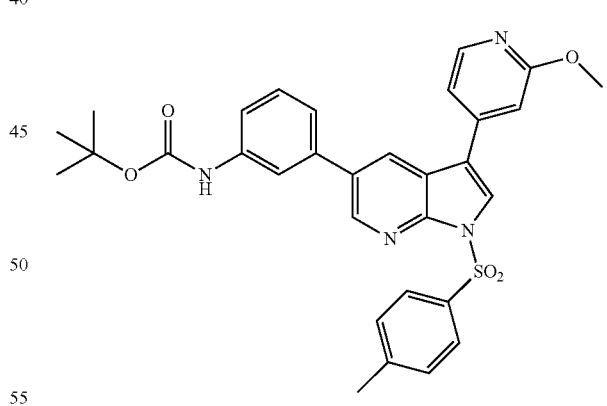

To a solution of tert-butyl (3-(3-iodo-1-tosyl-1H-pyrrolo[2,3-b]pyridin-5-yl)phenyl)carbamate from step 3 (125 mg, 0.210 mmol) in 1,4-dioxane (2 mL) and water (0.5 mL) was added 2-methoxy-4-pyridine boronic acid (32 mg, 0.21 mmol), potassium carbonate (87 mg, 0.63 mmol) and [1,1'-bis(diphenylphosphino)ferrocene]dichloropalladium(II) (8 mg, 0.01 mmol) and the solution was treated with microwave radiation at 100° C. for one hour. After cooling the resulting solution was partitioned between ethyl acetate and water. The organic layer was washed with water, brine and dried over magnesium sulfate. The mixture was filtered and concentrated in vacuo. The crude material was purified using normal phase chromatography (ethyl acetate/heptane) to provide tert-butyl (3-(3-(2-methoxypyridin-4-yl)-1-tosyl-1H-pyrrolo[2,3-b]pyridin-5-yl)phenyl)carbamate as a white solid (96 mg, 53% yield): MS (ES) m/z 571 (M+H).

Step 5: Preparation of N-(3-(3-(2-Methoxypyridin-4-yl)-1-tosyl-1H-pyrrolo[2,3-b]pyridin-5-yl)phenyl)acrylamide

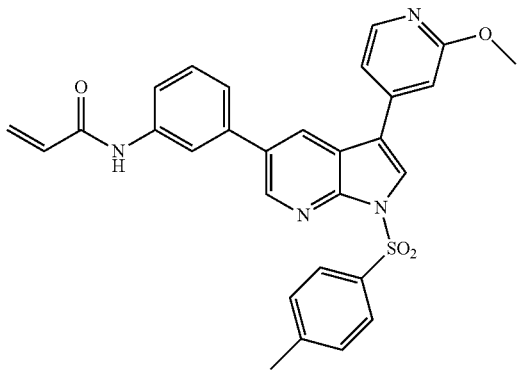 [SMILES: C=CC(=O)Nc1cccc(-c2cnc3c(c2)c(-c2ccnc(OC)c2)cn3S(=O)(=O)c2ccc(C)cc2)c1]

To a solution of tert-butyl (3-(3-(2-methoxypyridin-4-yl)-1-tosyl-1H-pyrrolo[2,3-b]pyridin-5-yl)phenyl)carbamate from step 4 (46 mg, 0.08 mmol) in dichloromethane (3 mL) was added trifluoroacetic acid (1 mL) and the solution was stirred for 1 hour at ambient temperature. The solution was concentrated in vacuo to provide the amine salt as a green oil. The green oil was dissolved into THF (1.5 mL) and triethylamine (0.033 mL, 0.24 mmol) was added followed by O-(benzotriazol-1-yl)-N,N,N',N'-tetramethyluronium tetrafluoroborate (38 mg, 0.12 mmol) and acrylic acid (0.005 mL, 0.08 mmol). The solution was stirred at ambient temperature for 2 hours. The reaction mixture was quenched with water and extracted with ethyl acetate. The organic layer was washed with water, brine and dried over magnesium sulfate. The mixture was filtered and concentrated in vacuo to provide the crude coupled product. The material was purified using normal phase chromatography (ethyl acetate/heptane) to provide N-(3-(3-(2-methoxypyridin-4-yl)-1-tosyl-1H-pyrrolo[2,3-b]pyridin-5-yl)phenyl)acrylamide (19 mg, 45% yield): MS (ES) m/z 525 (M+H).

Step 6: Preparation of N-(3-(3-(2-Methoxypyridin-4-yl)-1H-pyrrolo[2,3-b]pyridin-5-yl)phenyl)acrylamide

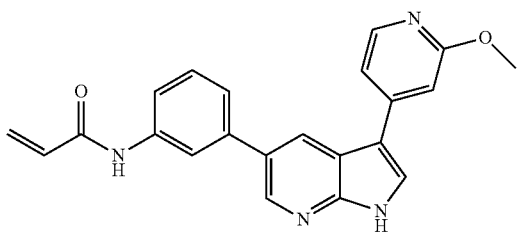 [SMILES: C=CC(=O)Nc1cccc(-c2cnc3[nH]cc(-c4ccnc(OC)c4)c3c2)c1]

To a solution of N-(3-(3-(2-methoxypyridin-4-yl)-1-tosyl-1H-pyrrolo[2,3-b]pyridin-5-yl)phenyl)acrylamide from step 5 (19 mg, 0.036 mmol) in 1,4-dioxane (1 mL) was added 1.5 M lithium hydroxide (1 mL) and the solution was stirred for 18 hours at ambient temperature. The reaction mixture was partitioned between ethyl acetate and water. The organic layer was washed with water, brine and dried over magnesium sulfate. The mixture was filtered and concentrated in vacuo to provide N-(3-(3-(2-methoxypyridin-4-yl)-1H-pyrrolo[2,3-b]pyridin-5-yl)phenyl)acrylamide as a white solid (8 mg, 60% yield): $^1$H NMR (400 MHz, DMSO-$d_6$) δ ppm, 12.34 (s, 1H), 10.29 (s, 1H), 8.56 (d, J=1.95 Hz, 1H), 8.46 (d, J=1.96 Hz, 1H), 8.26 (d, J=2.74 Hz, 1H), 8.18 (d, J=5.48 Hz, 1H), 7.98 (s, 1H), 7.76 (d, J=8.22 Hz, 1H), 7.52-7.44 (m, 3H), 6.51-6.44 (m, 1H), 6.32-6.27 (m, 1H), 5.81-5.78 (m, 1H), 3.89 (s, 3H); MS (ES) m/z 371 (M+H).

Example 7: Preparation of N-(3-(3-(pyridin-4-yl)-1H-pyrrolo[2,3-b]pyridin-5-yl)phenyl)acrylamide

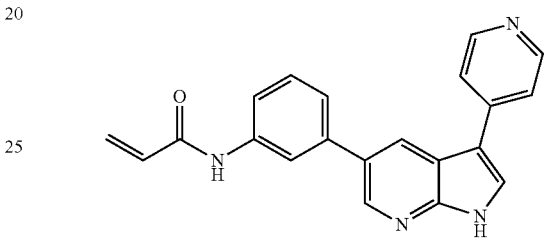

The title compound was prepared following Example 6, substituting 4-pyridine boronic acid, HCl salt for 2-methoxy-4-pyridine boronic acid in step 4: MS (ES) m/z 341 (M+H).

Example 8: Preparation of (E)-2-Cyano-3-(3-(3-(pyridin-4-yl)-1H-pyrrolo[2,3-b]pyridin-5-yl)phenyl)acrylamide

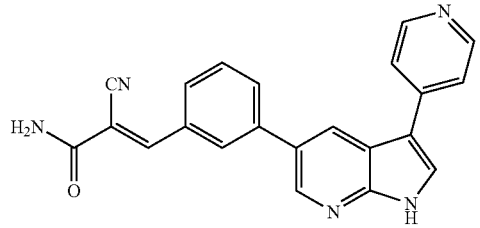 [SMILES: N#C/C(=C\c1cccc(-c2cnc3[nH]cc(-c4ccncc4)c3c2)c1)C(N)=O]

Step 1: Preparation of 3-(1H-Pyrrolo[2,3-b]pyridin-5-yl)benzaldehyde

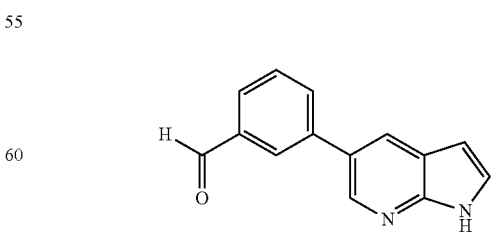

To a solution of 5-bromo-1H-pyrrolo[2,3-b]pyridine (200 mg, 1.01 mmol) in THF (3.00 mL) and water (1.00 mL) was added (3-formylphenyl)boronic acid (182 mg, 1.21 mmol)

and Pd(dppf)Cl$_2$ (8 mg, 10 mole %). The resulting solution was subjected to microwave irradiation at 120° C. for 1 hour. After cooling the reaction mixture was poured over celite and ethyl acetate (3.00 mL) was added. The organic layer was separated, dried over Na$_2$SO$_4$ and concentrated in vacuum to give crude desired product. The crude product was purified by column chromatography over silica gel (ethyl acetate:hexane gradient 5-95%) to afford the desired product as a yellow solid (190 mg, 90% yield): MS (ES) m/z 223 (M+H).

Step 2: Preparation of 3-(3-Iodo-1H-pyrrolo[2,3-b]pyridin-5-yl)benzaldehyde

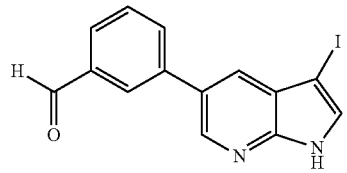 [SMILES: O=Cc1cccc(-c2cnc3[nH]cc(I)c3c2)c1]

To a solution of 3-(1H-pyrrolo[2,3-b]pyridin-5-yl)benzaldehyde (step 1, 250 mg, 1.12 mmol) in dichloromethane (3.00 mL) was added N-iodosuccinimide (303 mg, 1.32 mmol). The reaction mixture was stirred at 20° C. for 2 h. The precipitate was removed by filtration and washed with cold dichloromethane (2×5 mL) to afford the desired product as a tan solid which was used as is in the next step without further purification (349 mg, 96% yield): MS (ES) m/z 349 (M+H).

Step 3: Preparation of 3-(3-Iodo-1-tosyl-1H-pyrrolo[2,3-b]pyridin-5-yl)benzaldehyde

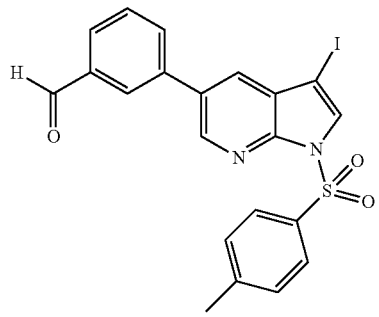 [SMILES: Cc1ccc(S(=O)(=O)n2cc(I)c3cc(-c4cccc(C=O)c4)cnc32)cc1]

To a solution of 3-(3-iodo-1H-pyrrolo[2,3-b]pyridin-5-yl)benzaldehyde (step 2, 250 mg, 0.716 mmol) in THF (2.00 mL) was added NaH (60% mineral oil dispersion, 27 mg, 1.1 mmol, 1.6 eq) at room temperature. The reaction mixture was stirred at room temperature for 15 min followed by the addition of tosyl chloride (163 mg, 0.859 mmol, 1.2 eq). The resulting solution was allowed to stir at room temperature overnight. The reaction was quenched with the addition of water (4.0 mL) followed by the addition of ethyl acetate (3.0 mL). The organic layer was separated, dried over Na$_2$SO$_4$, and concentrated in vacuo to give the crude product. The crude product was purified by column chromatography over silica gel (ethyl acetate:hexane gradient 5-95%) to afford the desired product as a yellow solid (302 mg, 84% yield): MS (ES) m/z 503 (M+H).

Step 4: Preparation of 3-(3-(Pyridin-4-yl)-1H-pyrrolo[2,3-b]pyridin-5-yl)benzaldehyde

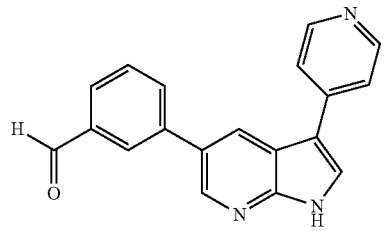 [SMILES: O=Cc1cccc(-c2cnc3[nH]cc(-c4ccncc4)c3c2)c1]

To a solution of 3-(3-iodo-1-tosyl-1H-pyrrolo[2,3-b]pyridin-5-yl)benzaldehyde (135 mg, 0.268 mmol) in THF (3.00 mL) and water (1.00 mL) was added 4-(dihydroxyboranyl)pyridin-1-ium chloride (182 mg, 1.21 mmol) and Pd(dppf)Cl$_2$ (21 mg, 10 mole %). The resulting solution was subjected to microwave irradiation at 120° C. for 1 hour. After cooling the reaction mixture was poured over celite and ethyl acetate (3.00 mL) was added. The organic layer was separated, dried over Na$_2$SO$_4$ and concentrated in vacuum to give crude product. The crude product was purified by column chromatography over silica gel (ethyl acetate:hexane gradient 5-95%) to afford the desired product as a yellow solid (54 mg, 67% yield): $^1$H NMR (400 MHz, DMSO-d$_6$) δ 12.36 (s, 1H), 10.14 (s, 1H), 8.69 (s, 1H), 8.57 (m, 2H), 8.36 (m, 1H), 8.30 (m, 1H), 8.19 (m, 1H), 7.92 (m, 1H), 7.87 (m, 2H), 7.74 (m, 1H); MS (ES) m/z 300 (M+H).

Step 5: Preparation of (E)-2-Cyano-3-(3-(3-(pyridin-4-yl)-1H-pyrrolo[2,3-b]pyridin-5-yl)phenyl)acrylamide

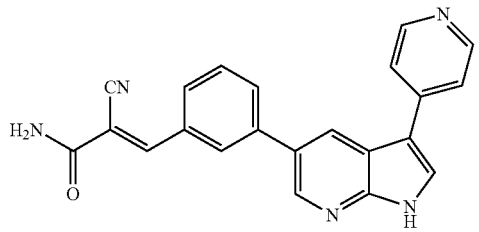 [SMILES: N#C/C(=C\c1cccc(-c2cnc3[nH]cc(-c4ccncc4)c3c2)c1)C(N)=O]

To a solution of 3-(3-(pyridin-4-yl)-1H-pyrrolo[2,3-b]pyridin-5-yl)benzaldehyde (step 4, 35.0 mg, 0.116 mmol) in THF (2.00 mL) was added 2-cyanoacetamide (12.0 mg, 0.140 mmol) and piperidine (19 µl, 0.20 mmol). The solution was allowed to stir at room temperature for 12 hours. The resulting precipitate was removed by filtration and washed with cold THF (2×5 mL) and dried on the filter paper under vacuum to afford title product (17 mg, 40% yield) as a pale yellow solid: 1H NMR (400 MHz, DMSO-d6) δ ppm, 12.40 (s, 1H), 8.68 (s, 2H), 8.56 (d, J=4.3 Hz, 2H), 8.35 (t, J=13.7 Hz, 3H), 8.08-8.06 (m, 1H), 7.98 (d, J=7.04 Hz, 2H), 7.87-7.86 (m, 3H), 7.71 (t, J=6.65 Hz, 1H); MS (ES) m/z 366 (M+H).

Example 9: Preparation of (E)-2-Cyano-3-(3-(3-(2-methoxypyridin-4-yl)-1H-pyrrolo[2,3-b]pyridin-5-yl)phenyl)acrylamide

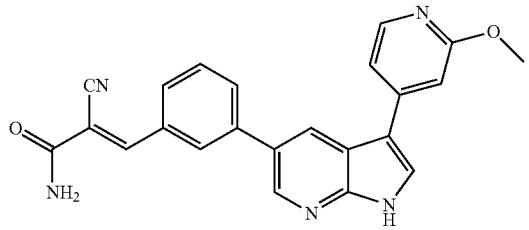 [SMILES: COc1cc(-c2c[nH]c3ncc(-c4cccc(/C=C(\C#N)C(N)=O)c4)cc23)ccn1]

Following Example 8 but substituting (2-methoxypyridin-4-yl)boronic acid for (pyridin-4-yl)boronic acid in Step 4 afforded the title compound (21 mg, 38% yield) as a tan solid: 1H NMR (400 MHz, DMSO-d6) δ ppm, 12.39 (s, 1H), 8.67-8.61 (m, 2H), 8.36-8.29 (m, 3H), 8.20-8.18 (m, 1H), 8.08-8.04 (m, 1H), 8.02-7.96 (m, 2H), 7.85 (s, 1H), 7.76-7.70 (m, 1H), 7.51-7.50 (m, 1H), 7.25 (s, 1H), 3.91 (s, 3H); MS (ES) m/z 396 (M+H).

Example 10: Preparation of N-(1-(3-(Pyridin-4-yl)-1H-pyrrolo[2,3-b]pyridin-5-yl)azetidin-3-yl)acrylamide

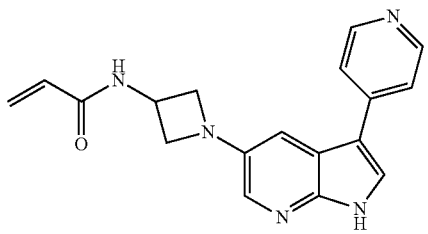 [SMILES: C=CC(=O)NC1CN(c2cnc3[nH]cc(-c4ccncc4)c3c2)C1]

The title compound was prepared following Example 1, substituting 4-pyridineboronic acid HCl salt for phenylboronic acid in step 4: $^1$H NMR (400 MHz, DMSO-d$_6$) δ ppm, 11.95 (s, 1H), 8.80 (d, J=7.43 Hz, 1H), 8.51 (d, J=6.26 Hz, 2H), 8.12 (d, J=2.74 Hz, 1H), 7.73-7.71 (m, 3H), 7.39 (d, J=2.73 Hz, 1H), 6.26-6.20 (m, 1H), 6.15-6.10 (m, 1H), 5.66-5.63 (m, 1H), 4.75-4.70 (m, 1H), 4.25 (t, J=7.44 Hz, 2H), 3.72-3.69 (m, 2H): MS (ES) m/z 320 (M+H).

Example 11: Preparation of N-(3-(3-(2-Methoxypyridin-4-yl)-1H-pyrrolo[2,3-b]pyridin-5-yl)-5-(trifluoromethyl)phenyl)acrylamide

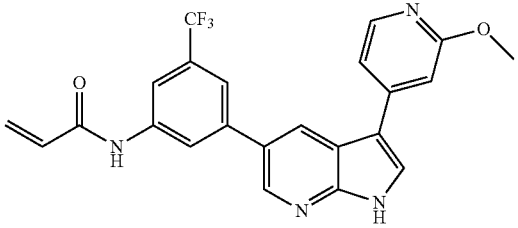 [SMILES: C=CC(=O)Nc1cc(-c2cnc3[nH]cc(-c4ccnc(OC)c4)c3c2)cc(C(F)(F)F)c1]

The title compound was prepared following Example 6, substituting pyrrolo[2,3-b]pyridine-5-boronic acid, pinacol ester for the 5-bromo-1H-pyrrolo[2,3-b]pyridine and N-boc-3-bromo-5-trifluoromethylaniline for 3-boc-aminophenylboronic acid in step 1: $^1$H NMR (400 MHz, DMSO-d$_6$) δ ppm, 12.41 (s, 1H), 10.63 (s, 1H), 8.62 (s, 1H), 8.57 (s, 1H), 8.30 (s, 1H), 8.26 (s, 1H), 8.19 (s, 1H), 8.13 (s, 1H), 7.49 (s, 1H), 7.25 (s, 1H), 6.48-6.45 (m, 1H), 6.37-6.33 (m, 1H), 5.88-5.81 (m, 1H), 3.91 (s, 3H); MS (ES) m/z 439 (M+H).

The following compounds in Table 1 were made using the methods described above. Spectral data for Examples 94-98 were not yet available; calculated molecular weights (ChemDraw 14.0) are provided, and mass spectroscopic analysis is expected to yield m/z values within 1 D of the calculated value.

TABLE 1

Compound Examples

| Ex. # | Structure | Name | Spectral Data |
|---|---|---|---|
| 12 | 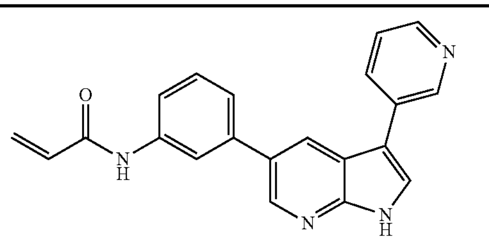 | N-(3-(3-(pyridin-3-yl)-1H-pyrrolo[2,3-b]pyridin-5-yl)phenyl)acrylamide | $^1$H NMR (400 MHz, DMSO-d$_6$) δ ppm, 12.21 (s, 1H), 10.28 (s, 1H), 9.03 (s, 1H), 8.57 (s, 1H), 8.49 (br. s, 1H), 8.44 (s, 1H), 8.21 (d, J = 7.43 Hz, 1H), 8.10 (s, 1H), 7.98 (s, 1H), 7.75 (d, J = 8.21 Hz, 1H), 7.51-7.48 (m, 3H), 6.51-6.44 (m, 1H), 6.29 (d, J = 17.61 Hz, 1H), 5.79 (d, J = 10.17 Hz, 1H). MS (ES) m/z 341 (M + H). |
| 13 | 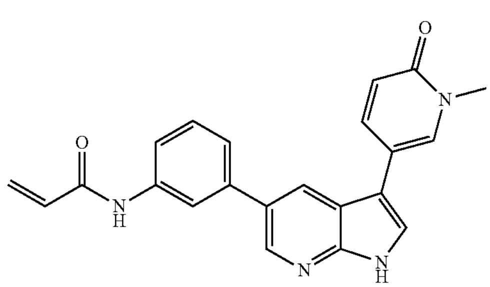 [SMILES: C=CC(=O)Nc1cccc(-c2cnc3[nH]cc(-c4ccc(=O)n(C)c4)c3c2)c1] | N-(3-(3-(1-methyl-6-oxo-1,6-dihydropyridin-3-yl)-1H-pyrrolo[2,3-b]pyridin-5-yl)phenyl)acrylamide | $^1$H NMR (400 MHz, DMSO-d$_6$) δ ppm, 11.93 (s, 1H), 10.24 (s, 1H), 8.50 (s, 1H), 8.36 (s, 1H), 8.08 (s, 1H), 7.95 (s, 1H), 7.87 (d, J = 9.78 Hz, 1H), 7.78 (s, 1H), 7.74 (d, J = 8.22 Hz, 1H), 7.49-7.43 (m, 2 H), 6.51 (d, J = 8.22 Hz, 1H), 6.45 (d, J = 9.78 Hz, 1H), 6.28 (d, J = 16.82 Hz, 1H), 5.78 (d, J = 9.78 Hz, 1H), 3.57 (s, 3H). MS (ES) m/z 371 (M + H). |

TABLE 1-continued

Compound Examples

| Ex. # | Structure | Name | Spectral Data |
|---|---|---|---|
| 14 | 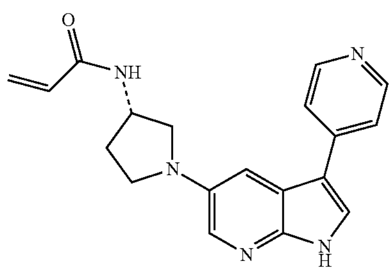 [SMILES: C=CC(=O)N[C@H]1CCN(c2cnc3[nH]cc(-c4ccncc4)c3c2)C1] | (S)-N-(1-(3-(pyridin-4-yl)-1H-pyrrolo[2,3-b]pyridin-5-yl)pyrrolidin-3-yl)acrylamide | $^1$H NMR (400 MHz, DMSO-$d_6$) δ ppm, 11.84 (s, 1H), 8.51 (d, J = 6.26 Hz, 2H), 8.42 (d, J = 7.04 Hz, 1H), 8.07 (d, J = 3.13 Hz, 1H), 7.85 (d, J = 2.74 Hz, 1H), 7.72 (d, J = 5.87 Hz, 2H), 7.40 (s, 1H), 6.29-6.22 (m, 1H), 6.15-6.10 (m, 1H), 5.62-5.59 (m, 1H), 4.58-4.47 (m, 1H), 3.64-3.60 (m, 1H), 3.42-3.34 (m, 1H), 1.97-1.90 (m, 2H), 0.85-0.84 (m, 2H). MS (ES) m/z 334 (M + H). |
| 15 | 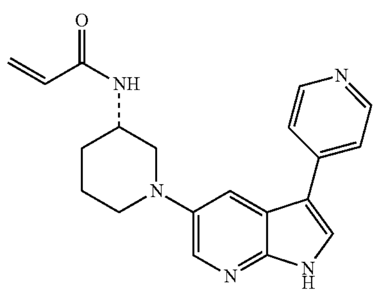 [SMILES: C=CC(=O)N[C@H]1CCCN(c2cnc3[nH]cc(-c4ccncc4)c3c2)C1] | (S)-N-(1-(3-(pyridin-4-yl)-1H-pyrrolo[2,3-b]pyridin-5-yl)piperidin-3-yl)acrylamide | $^1$H NMR (400 MHz, DMSO-$d_6$) δ ppm, 11.98 (s, 1H), 8.53 (d, J = 5.87 Hz, 2H), 8.16-8.14 (m, 2H), 8.11 (d, J = 2.74 Hz, 1H), 7.88 (d, J = 2.35 Hz, 1H), 7.76-7.74 (m, 2H), 6.34-6.27 (m, 1H), 6.16-6.11 (m, 1H), 5.62-5.59 (m, 1H), 4.03-3.93 (m, 1H), 3.57-3.54 (m, 1H), 3.49-3.46 (m, 1H), 2.90-2.85 (m, 1H), 2.74-2.67 (m, 1H), 1.92-1.85 (m, 2H), 1.70-1.67 (m, 1H), 1.45-1.42 (m, 1H). MS (ES) m/z 348 (M + H). |
| 16 | 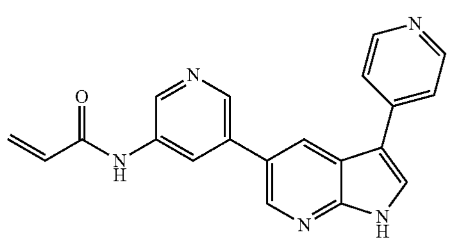 [SMILES: C=CC(=O)Nc1cncc(-c2cnc3[nH]cc(-c4ccncc4)c3c2)c1] | N-(5-(3-(pyridin-4-yl)-1H-pyrrolo[2,3-b]pyridin-5-yl)pyridin-3-yl)acrylamide | MS (ES) m/z 342 (M + H). |
| 17 | 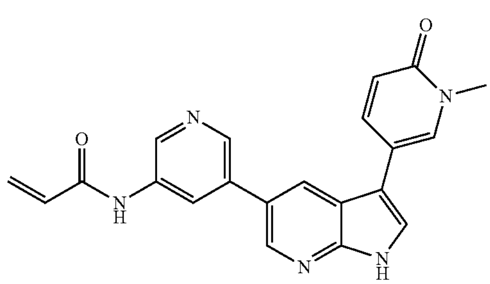 | N-(5-(3-(1-methyl-6-oxo-1,6-dihydropyridin-3-yl)-1H-pyrrolo[2,3-b]pyridin-5-yl)pyridin-3-yl)acrylamide | $^1$H NMR (400 MHz, DMSO-$d_6$) δ ppm, 12.06 (s, 1H), 10.90 (s, 1H), 8.94 (s, 1H), 8.72 (s, 1H), 8.53 (s, 1H), 8.46 (s, 1H), 8.11 (s, 1H), 7.88 (s, 1H), 7.83 (s, 1H), 6.52-6.50 (m, 1H), 6.34-6.30 (m, 1H), 5.83-5.80 (m, 1H), 3.56 (s, 3H). MS (ES) m/z 372 (M + H). |
| 18 | 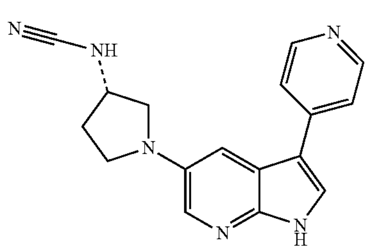 [SMILES: N#CN[C@H]1CCN(c2cnc3[nH]cc(-c4ccncc4)c3c2)C1] | (S)-N-(1-(3-(pyridin-4-yl)-1H-pyrrolo[2,3-b]pyridin-5-yl)pyrrolidin-3-yl)cyanamide | $^1$H NMR (400 MHz, DMSO-$d_6$) δ ppm, 11.85 (s, 1H), 8.52 (br. s, 2H), 8.07 (br. s, 1H), 7.85 (br. s, 1H), 7.74 (br. s, 2H), 7.42 (br. s, 1H), 7.17 (br. s, 1H), 4.08-3.99 (m, 1H), 3.62-3.54 (m, 1H), 3.52-3.45 (m, 1H), 3.43-3.36 (m, 1H), 2.31-2.23 (m, 1H), 2.07-1.99 (m, 1H). MS (ES) m/z 305 (M + H). |

TABLE 1-continued

Compound Examples

| Ex. # | Structure | Name | Spectral Data |
|---|---|---|---|
| 19 | 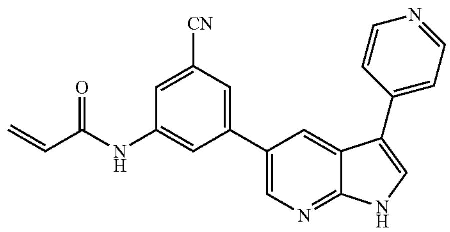 [SMILES: C=CC(=O)Nc1cc(C#N)cc(-c2cnc3[nH]cc(-c4ccncc4)c3c2)c1] | N-(3-cyano-5-(3-(pyridin-4-yl)-1H-pyrrolo[2,3-b]pyridin-5-yl)phenyl)acrylamide | $^1$H NMR (400 MHz, DMSO-d$_6$) δ ppm, 12.40 (s, 1H), 10.59 (s, 1H), 8.66 (s, 1H), 8.62 (s, 1H), 8.58 (d, J = 6.26 Hz, 2H), 8.30 (s, 1H), 8.23 (s, 1H), 8.17 (s, 1H), 8.09 (s, 1H), 7.87 (d, J = 6.26 Hz, 2H), 6.45 (d, J = 10.17 Hz, 1H), 6.34 (d, J = 17.22 Hz, 1H), 5.86 (d, J = 9.39 Hz, 1H). MS (ES) m/z 366 (M + H). |
| 20 | 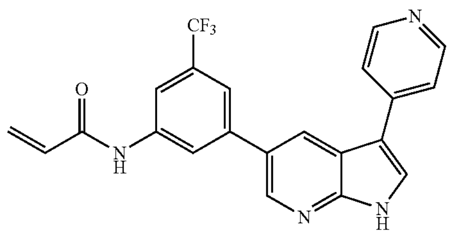 [SMILES: C=CC(=O)Nc1cc(-c2cnc3[nH]cc(-c4ccncc4)c3c2)cc(C(F)(F)F)c1] | N-(3-(3-(pyridin-4-yl)-1H-pyrrolo[2,3-b]pyridin-5-yl)-5-(trifluoromethyl)phenyl)acrylamide | $^1$H NMR (400 MHz, DMSO-d$_6$) δ ppm, 12.40 (s, 1H), 10.60 (s, 1H), 8.64-8.58 (m, 4H), 8.31 (s, 1H), 8.26 (s, 1H), 8.14 (s, 1H), 7.86 (br. s, 3 H), 6.52-6.44 (m, 1H), 6.35 (d, J = 16.82 Hz, 1H), 5.86 (d, J = 6.65 Hz, 1H). MS (ES) m/z 409 (M + H). |
| 21 | 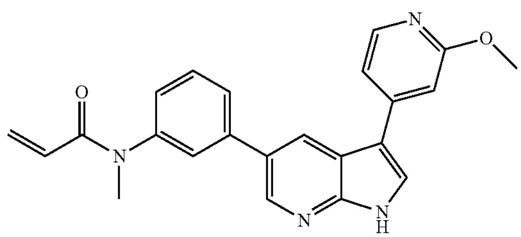 [SMILES: C=CC(=O)N(C)c1cccc(-c2cnc3[nH]cc(-c4ccnc(OC)c4)c3c2)c1] | N-(3-(3-(2-methoxypyridin-4-yl)-1H-pyrrolo[2,3-b]pyridin-5-yl)phenyl)-N-methylacrylamide | $^1$H NMR (400 MHz, DMSO-d$_6$) δ ppm, 12.31 (s, 1H), 8.63 (s, 1H), 8.54 (s, 1H), 8.27 (s, 1H), 8.17 (s, 1H), 7.79 (br. s, 2H), 7.59-7.59 (m, 1H), 7.47 (s, 1H), 7.29 (d, J = 6.65 Hz, 1H), 7.22 (s, 1H), 6.19 (br. s, 2H), 5.60 (br. s, 1H). 3.89 (s, 3H), 3.34 (s, 3H). MS (ES) m/z 385 (M + H). |
| 22 | 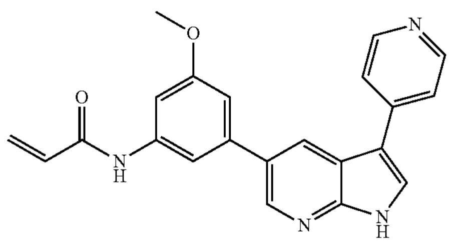 [SMILES: C=CC(=O)Nc1cc(OC)cc(-c2cnc3[nH]cc(-c4ccncc4)c3c2)c1] | N-(3-methoxy-5-(3-(pyridin-4-yl)-1H-pyrrolo[2,3-b]pyridin-5-yl)phenyl)acrylamide | $^1$H NMR (400 MHz, DMSO-d6) δ ppm, 12.35 (s, 1H), 10.29 (s, 1H), 8.53 (m, 4H), 8.27 (d, J = 2.4 Hz, 1H), 7.83 (m, 2H), 7.50 (m, 2H), 7.07 (m, 1H), 6.47 (m, 1H), 6.28 (m, 1H), 5.78 (m, 1H), 3.83 (m, 3H). MS (ES) m/z 371 (M + H). |
| 23 | 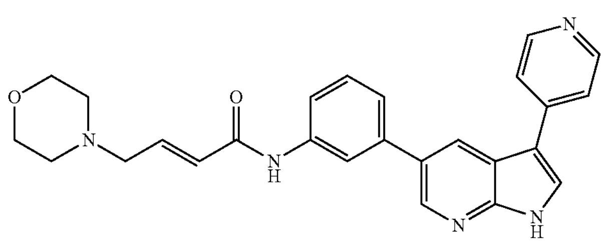 [SMILES: O=C(/C=C/CN1CCOCC1)Nc1cccc(-c2cnc3[nH]cc(-c4ccncc4)c3c2)c1] | (E)-4-morpholino-N-(3-(3-(pyridin-4-yl)-1H-pyrrolo[2,3-b]pyridin-5-yl)phenyl)but-2-enamide | $^1$H NMR (400 MHz, DMSO-d$_6$) δ ppm, 12.33 (s, 1H), 10.17 (s, 1H), 8.57-8.56 (m, 3H), 8.52 (s, 1H), 8.27 (s, 1H), 7.97 (s, 1H), 7.82 (d, J = 4.70 Hz, 2H), 7.74 (d, J = 6.65 Hz, 1H), 7.50-7.43 (m, 2H), 6.78-6.74 (m, 1H), 6.32 (d, J = 15.26 Hz, 1H), 3.61 (br. s, 4H), 3.14 (d, J = 4.69 Hz, 2H), 2.40 (br. s, 4H). MS (ES) m/z 440 (M + H). |
| 24 | 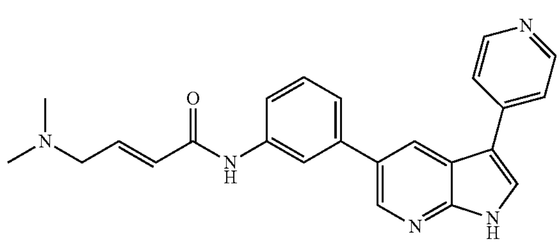 [SMILES: CN(C)C/C=C/C(=O)Nc1cccc(-c2cnc3[nH]cc(-c4ccncc4)c3c2)c1] | (E)-4-(dimethylamino)-N-(3-(3-(pyridin-4-yl)-1H-pyrrolo[2,3-b]pyridin-5-yl)phenyl)but-2-enamide | $^1$H NMR (400 MHz, DMSO-d$_6$) δ ppm, 12.74 (s, 1H), 10.46 (s, 1H), 8.69-8.65 (m, 3H), 8.60 (s, 1H), 8.03 (s, 1H), 7.74 (d, J = 7.82 Hz, 1H), 7.57-7.50 (m, 2H), 7.48 (d, J = 8.22 Hz, 2H), 7.11 (d, J = 7.83 Hz, 1H), 6.81-6.74 (m, 1H), 6.50 (d, J = 15.26 Hz, 1H), 3.98 (br. s, 2H), 2.82 (s, 6H). MS (ES) m/z 398 (M + H). |

TABLE 1-continued

Compound Examples

| Ex. # | Structure | Name | Spectral Data |
|---|---|---|---|
| 25 | 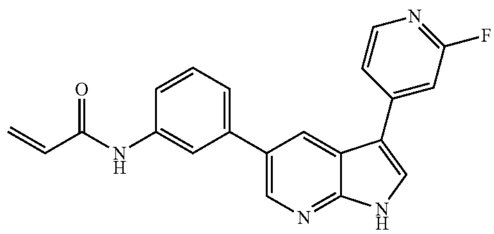 [SMILES: C=CC(=O)Nc1cccc(-c2cnc3[nH]cc(-c4ccnc(F)c4)c3c2)c1] | N-(3-(3-(2-fluoropyridin-4-yl)-1H-pyrrolo[2,3-b]pyridin-5-yl)phenyl)acrylamide | $^1$H NMR (400 MHz, DMSO-$d_6$) δ ppm, 12.45 (s, 1H), 10.27 (s, 1H), 8.57 (s, 2H), 8.39 (s, 1H), 8.23 (d, J = 4.69 Hz, 1H), 7.98 (br. s, 2H), 7.71 (d, J = 7.43 Hz, 1H), 7.53 (br. s, 2H), 7.42 (d, J = 7.04 Hz, 1H), 6.45 (s, 1H), 6.31 (s, 1H), 5.79 (d, J = 9.78 Hz, 1H). MS (ES) m/z 359 (M + H). |
| 26 | 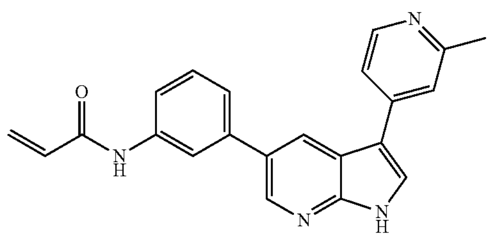 [SMILES: C=CC(=O)Nc1cccc(-c2cnc3[nH]cc(-c4ccnc(C)c4)c3c2)c1] | N-(3-(3-(2-methylpyridin-4-yl)-1H-pyrrolo[2,3-b]pyridin-5-yl)phenyl)acrylamide | $^1$H NMR (400 MHz, DMSO-$d_6$) δ ppm, 12.28 (s, 1H), 10.26 (s, 1H), 8.54 (s, 1H), 8.52 (s, 1H), 8.44 (d, J = 5.08 Hz, 1H), 8.22 (s, 1H), 7.98 (s, 1H), 7.76 (d, J = 7.82 Hz, 1H), 7.67 (d, J = 5.09 Hz, 1H), 7.52-7.45 (m, 2H), 6.51-6.44 (m, 1H), 6.29 (d, J = 16.04 Hz, 1H), 5.78 (d, J = 10.18 Hz, 1H), 2.53 (s, 3H). MS (ES) m/z 355 (M + H). |
| 27 | 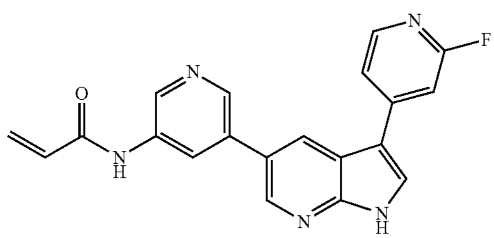 [SMILES: C=CC(=O)Nc1cncc(-c2cnc3[nH]cc(-c4ccnc(F)c4)c3c2)c1] | N-(5-(3-(2-fluoropyridin-4-yl)-1H-pyrrolo[2,3-b]pyridin-5-yl)pyridin-3-yl)acrylamide | No NMR. MS (ES) m/z 360 (M + H). |
| 28 | 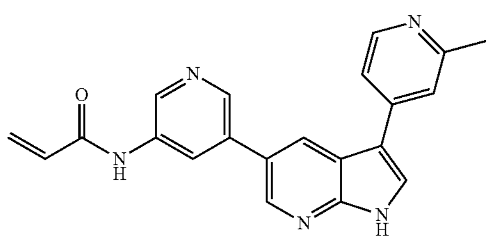 | N-(5-(3-(2-methylpyridin-4-yl)-1H-pyrrolo[2,3-b]pyridin-5-yl)pyridin-3-yl)acrylamide | No NMR. MS (ES) m/z 356 (M + H). |
| 29 | 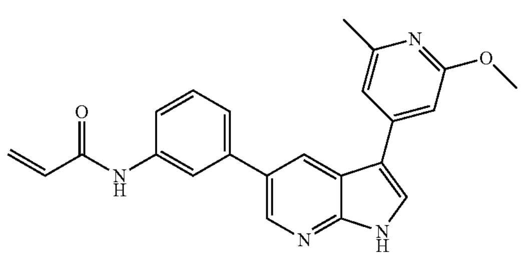 [SMILES: C=CC(=O)Nc1cccc(-c2cnc3[nH]cc(-c4cc(C)nc(OC)c4)c3c2)c1] | N-(3-(3-(2-methoxy-6-methylpyridin-4-yl)-1H-pyrrolo[2,3-b]pyridin-5-yl)phenyl)acrylamide | $^1$H NMR (400 MHz, DMSO-$d_6$) δ ppm, 12.26 (s, 1H), 10.26 (s, 1H), 8.54 (s, 1H), 8.44 (s, 1H), 8.18 (s, 1H), 7.97 (s, 1H), 7.76 (d, J = 7.43 Hz, 1H), 7.48-7.46 (m, 2H), 7.29 (s, 1H), 6.98 (s, 1H), 6.48-6.44 (m, 1H), 6.29 (d, J = 16.83 Hz, 1H), 5.78 (d, J = 10.17 Hz, 1H), 3.88 (s, 3H), 2.46 (s, 3H). MS (ES) m/z 385 (M + H). |
| 30 | 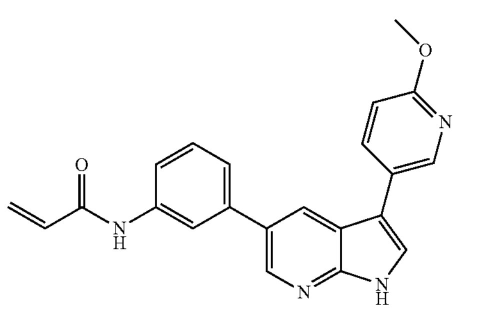 [SMILES: C=CC(=O)Nc1cccc(-c2cnc3[nH]cc(-c4ccc(OC)nc4)c3c2)c1] | N-(3-(3-(6-methoxypyridin-3-yl)-1H-pyrrolo[2,3-b]pyridin-5-yl)phenyl)acrylamide | $^1$H NMR (400 MHz, DMSO-$d_6$) δ ppm, 12.04 (s, 1H), 10.24 (s, 1H), 8.59 (s, 1H), 8.55 (s, 1H), 8.36 (s, 1H), 8.10 (d, J = 8.61 Hz, 1H), 7.98 (s, 1H), 7.92 (s, 1H), 7.74 (d, J = 8.22 Hz, 1H), 7.52-7.50 (m, 1H), 7.46-7.42 (m, 1H), 6.93 (d, J = 8.61 Hz, 1H), 6.50-6.43 (m, 1H), 6.29 (d, J = 16.83 Hz, 1H), 5.78 (d, J = 11.74 Hz, 1H), 3.90 (s, 3H). MS (ES) m/z 371 (M + H). |

TABLE 1-continued

Compound Examples

| Ex. # | Structure | Name | Spectral Data |
|---|---|---|---|
| 31 | 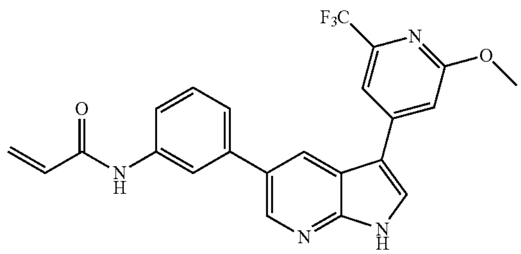 [SMILES: C=CC(=O)Nc1cccc(-c2cnc3[nH]cc(-c4cc(OC)nc(C(F)(F)F)c4)c3c2)c1] | N-(3-(3-(2-methoxy-6-(trifluoromethyl)pyridin-4-yl)-1H-pyrrolo[2,3-b]pyridin-5-yl)phenyl)acrylamide | $^1$H NMR (400 MHz, DMSO-$d_6$) δ ppm, 12.48 (s, 1H), 10.27 (s, 1H), 8.57 (s, 1H), 8.48 (s, 1H), 8.47 (s, 1H), 7.99 (s, 1H), 7.87 (s, 1H), 7.75 (d, J = 7.44 Hz, 1H), 7.52-7.45 (m, 3H), 6.52-6.45 (m, 1H), 6.29 (d, J = 15.65 Hz, 1H), 5.79 (d, J = 5.79 Hz, 1H), 3.96 (s, 3H). MS (ES) m/z 439 (M + H). |
| 32 | 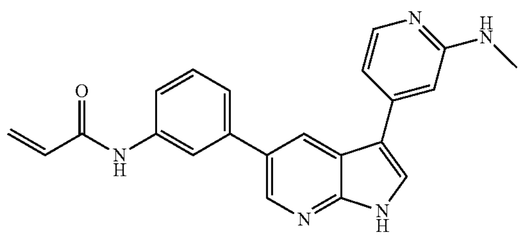 | N-(3-(3-(2-(methylamino)pyridin-4-yl)-1H-pyrrolo[2,3-b]pyridin-5-yl)phenyl)acrylamide | $^1$H NMR (400 MHz, DMSO-$d_6$) δ ppm, 12.17 (s, 1H), 10.26 (s, 1H), 8.53 (s, 1H), 8.45 (s, 1H), 8.06 (s, 1H), 7.99 (d, J = 5.08 Hz, 1H), 7.96 (s, 1H), 7.76 (br. s, 1H), 7.49 (d, J = 4.30 Hz, 2H), 6.90-6.88 (m, 1H), 6.51-6.44 (m, 1H), 6.29 (d, J = 17.21 Hz, 1H), 5.78 (d, J = 12.52 Hz, 1H), 2.82 (d, J = 5.09 Hz, 3H). MS (ES) m/z 370 (M + H). |
| 33 | 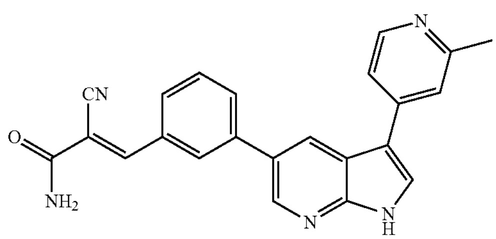 [SMILES: Cc1cc(-c2c[nH]c3ncc(-c4cccc(/C=C(\C#N)C(N)=O)c4)cc23)ccn1] | (E)-2-cyano-3-(3-(3-(2-methylpyridin-4-yl)-1H-pyrrolo[2,3-b]pyridin-5-yl)phenyl)acrylamide | $^1$H NMR (400 MHz, DMSO-d6) δ ppm, 12.35 (s, 1H), 8.64 (d, J = 6.64 Hz, 2H), 8.43 (d, J = 4.69 Hz, 1H), 8.38 (s, 1H), 8.33 (s, 1H), 8.24 (s, 1H), 8.04 (d, J = 7.82 Hz, 1H), 7.94 (d, J = 7.43 Hz, 2H), 7.80 (s, 1H), 7.70 (m, 2H), 7.65 (s, 1H), 2.53 (s, 3H). MS (ES) m/z 380 (M + H). |
| 34 | 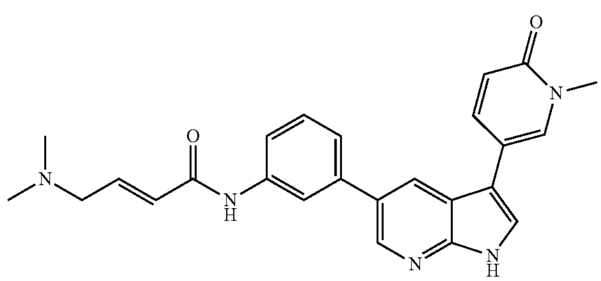 | (E)-4-(dimethylamino)-N-(3-(3-(1-methyl-6-oxo-1,6-dihydropyridin-3-yl)-1H-pyrrolo[2,3-b]pyridin-5-yl)phenyl)but-2-enamide | MS (ES) m/z 428 (M + H). |
| 35 | 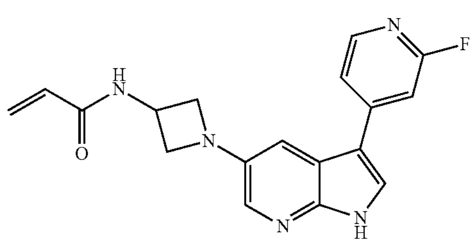 [SMILES: C=CC(=O)NC1CN(c2cnc3[nH]cc(-c4ccnc(F)c4)c3c2)C1] | N-(1-(3-(2-fluoropyridin-4-yl)-1H-pyrrolo[2,3-b]pyridin-5-yl)azetidin-3-yl)acrylamide | $^1$H NMR (400 MHz, DMSO-$d_6$) δ ppm, 12.06 (s, 1H), 8.77 (d, J = 6.65 Hz, 1H), 8.22 (s, 1H), 8.17 (d, J = 5.09 Hz, 1H), 7.72 (br. s, 2H), 7.45 (s, 1H), 7.40 (s, 1H), 6.26-6.20 (m, 1H), 6.13 (d, J = 16.82 Hz, 1H), 5.64 (d, J = 12.52 Hz, 1H), 4.74-4.69 (m, 1H), 4.26 (t, J = 7.43 Hz, 2H), 3.74-3.70 (m, 2H). MS (ES) m/z 338 (M + H). |
| 36 | 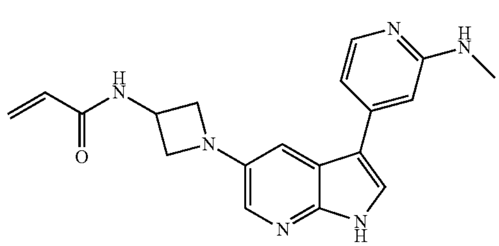 [SMILES: C=CC(=O)NC1CN(c2cnc3[nH]cc(-c4ccnc(NC)c4)c3c2)C1] | N-(1-(3-(2-(methylamino)pyridin-4-yl)-1H-pyrrolo[2,3-b]pyridin-5-yl)azetidin-3-yl)acrylamide | No NMR. MS (ES) m/z 349 (M + H). |

TABLE 1-continued

Compound Examples

| Ex. # | Structure | Name | Spectral Data |
|---|---|---|---|
| 37 | 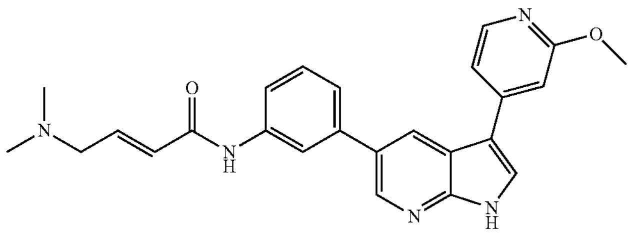 | (E)-4-(dimethylamino)-N-(3-(3-(2-methoxypyridin-4-yl)-1H-pyrrolo[2,3-b]pyridin-5-yl)phenyl)but-2-enamide | $^1$H NMR (400 MHz, DMSO-d6) δ ppm, 12.32 (d, J = 8.1 Hz, 1H), 10.21 (s, 1H), 8.55 (d, J = 2.0 Hz, 1H), 8.45 (d, J = 2.0 Hz, 1H), 8.25 (d, J = 2.8 Hz, 1H), 8.18 (d, J = 5.6 Hz, 1H), 7.98 (s, 1H), 7.74 (d, J = 8.0 Hz, 1H), 7.46 (m, 3H), 7.19 (s, 1H), 6.76 (m, 1H), 6.31 (d, J = 15.2 Hz, 1H), 3.90 (s, 3H), 3.11 (d, J = 5.6 Hz, 2H), 2.21 (s, 6H). MS (ES) m/z 428 (M + H). |
| 38 | 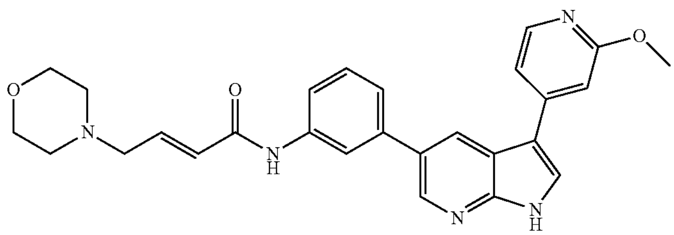 [SMILES: COc1cc(-c2c[nH]c3ncc(-c4cccc(NC(=O)/C=C/CN5CCOCC5)c4)cc23)ccn1] | (E)-N-(3-(3-(2-methoxypyridin-4-yl)-1H-pyrrolo[2,3-b]pyridin-5-yl)phenyl)-4-morpholinobut-2-enamide | $^1$H NMR (400 MHz, DMSO-d$_6$) δ ppm, 12.31 (s, 1H), 10.17 (s, 1H), 8.55 (s, 1H), 8.45 (s, 1H), 8.24 (s, 1H), 8.18 (s, 1H), 7.96 (s, 1H), 7.52-7.43 (m, 4H), 7.19 (s, 1H), 6.79-6.73 (m, 1H), 6.35-6.30 (m, 1H), 3.90 (s, 3H), 3.61 (br. s, 2 H), 3.57 (s, 2H), 3.14 (d, J = 6.26 Hz, 2H), 2.41 (br. s, 4H). MS (ES) m/z 470 (M + H). |
| 39 | 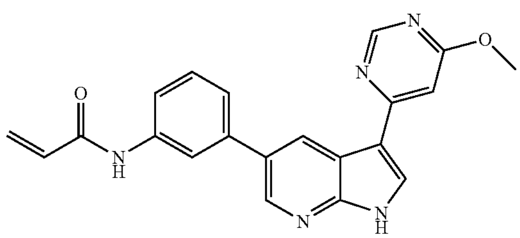 | N-(3-(3-(6-methoxypyrimidin-4-yl)-1H-pyrrolo[2,3-b]pyridin-5-yl)phenyl)acrylamide | $^1$H NMR (400 MHz, DMSO-d6) δ ppm, 12.45 (s, 1H), 10.32 (s, 1H), 8.86 (d, J = 2.0 Hz, 1H), 8.82 (d, J = 0.8 Hz, 1H), 8.56 (m, 2H), 7.97 (s, 1H), 7.78 (d, J = 7.6 Hz, 1H), 7.46 (m, 3H), 6.48 (m, 1H), 6.32 (d, J = 1.6 Hz, 1H), 6.27 (d, J = 2.0 Hz, 1H), 5.80 (d, J = 2.0 Hz, 1H), 5.78 (d, J = 2.0 Hz, 1H), 3.96 (s, 3H). MS (ES) m/z 372 (M + H). |
| 40 | 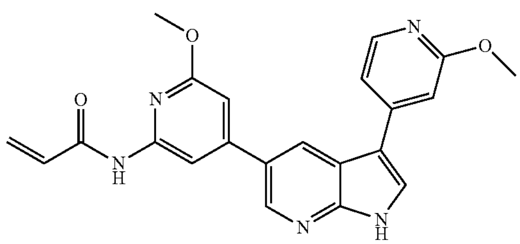 [SMILES: C=CC(=O)Nc1cc(-c2cnc3[nH]cc(-c4ccnc(OC)c4)c3c2)cc(OC)n1] | N-(6-methoxy-4-(3-(2-methoxypyridin-4-yl)-1H-pyrrolo[2,3-b]pyridin-5-yl)pyridin-2-yl)acrylamide | $^1$H NMR (400 MHz, DMSO-d$_6$) δ ppm, 12.41 (s, 1H), 10.59 (s, 1H), 8.62 (s, 1H), 8.55 (s, 1H), 8.27 (s, 1H), 8.18 (s, 2H), 7.46 (d, J = 5.87 Hz, 1H), 7.21 (s, 1H), 7.04 (s, 1H), 6.72-6.66 (m, 1H), 6.32 (d, J = 15.65 Hz, 1H), 5.80 (d, J = 11.74 Hz, 1H), 3.94 (s, 3H), 3.90 (s, 3H). MS (ES) m/z 402 (M + H). |
| 41 | 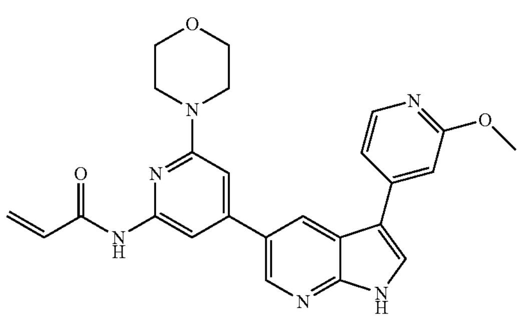 [SMILES: C=CC(=O)Nc1cc(-c2cnc3[nH]cc(-c4ccnc(OC)c4)c3c2)cc(N2CCOCC2)n1] | N-(4-(3-(2-methoxypyridin-4-yl)-1H-pyrrolo[2,3-b]pyridin-5-yl)-6-morpholinopyridin-2-yl)acrylamide | $^1$H NMR (400 MHz, DMSO-d$_6$) δ ppm, 12.41 (s, 1H), 10.33 (s, 1H), 8.60 (s, 1H), 8.51 (s, 1H), 8.26 (s, 1H), 8.19 (d, J = 5.48 Hz, 1H), 7.87 (s, 1H), 7.45 (d, J = 5.87 Hz, 1H), 7.20 (s, 1H), 6.94 (s, 1H), 6.69-6.62 (m, 1H), 6.29 (d, J = 17.60 Hz, 1H), 5.77 (d, J = 9.78 Hz, 1H), 3.90 (s, 3H), 3.74 (br. s, 4H), 3.58 (br. s, 4H). MS (ES) m/z 457 (M + H). |
| 42 | 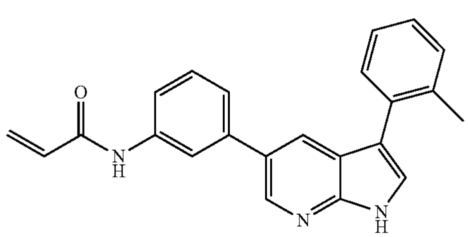 [SMILES: C=CC(=O)Nc1cccc(-c2cnc3[nH]cc(-c4ccccc4C)c3c2)c1] | N-(3-(3-(o-tolyl)-1H-pyrrolo[2,3-b]pyridin-5-yl)phenyl)acrylamide | $^1$H NMR (400 MHz, DMSO-d6) δ ppm, 11.98 (s, 1H), 10.21 (s, 1H), 8.55 (d, J = 2.0 Hz, 1H), 7.92 (d, J = 2.4 Hz, 2H), 7.71 (m, 1H), 7.65 (d, J = 2.4 Hz, 1H), 7.42 (m, 3H), 7.36 (m, 2H), 7.28 (m, 1H), 6.44 (m, 1H), 6.27 (dd, J = 2.0 Hz, J = 14.8 Hz 1H), 5.77 (m, 1H), 2.33 (s, 1H). MS (ES) m/z 354 (M + H). |

TABLE 1-continued

Compound Examples

| Ex. # | Structure | Name | Spectral Data |
|---|---|---|---|
| 43 | 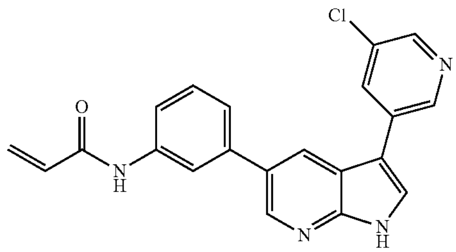 [SMILES: C=CC(=O)Nc1cccc(-c2cnc3[nH]cc(-c4cncc(Cl)c4)c3c2)c1] | N-(3-(3-(5-chloropyridin-3-yl)-1H-pyrrolo[2,3-b]pyridin-5-yl)phenyl)acrylamide | $^1$H NMR (400 MHz, DMSO-d6) δ ppm, 12.31 (s, 1H), 10.27 (s, 1H), 9.02 (d, J = 2.0 Hz, 1H), 8.57 (d, J = 2.0 Hz, 1H), 8.51 (d, J = 2.4 Hz, 1H), 8.47 (d, J = 2.0 Hz, 1H), 8.32 (t, J = 2.0 Hz, 1H), 8.21 (d, J = 2.0 Hz, 1H), 7.98 (s, 1H0, 7.76 (d, j = 7.6 Hz, 1H), 7.53 (d, J = 7.6 Hz, 1H), 7.46 (t, J = 7.6 Hz, 1H), 6.48 (m, 1H), 6.31 (d, J = 1.6 Hz, 1H), 6.27 (d, J = 2.0 Hz, 1H), 5.80 (d, J = 2.0 Hz, 1H), 5.77 (d, J = 2.0 Hz, 1H). MS (ES) m/z 375 (M + H). |
| 44 | 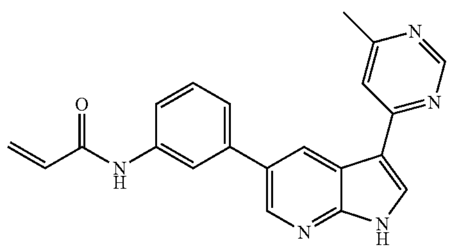 [SMILES: C=CC(=O)Nc1cccc(-c2cnc3[nH]cc(-c4cc(C)ncn4)c3c2)c1] | N-(3-(3-(6-methylpyrimidin-4-yl)-1H-pyrrolo[2,3-b]pyridin-5-yl)phenyl)acrylamide | $^1$H NMR (400 MHz, DMSO-d6) δ ppm, 12.47 (s, 1H0, 10.31 (s, 1H), 9.01 (m, 2H), 8.57 (m, 2H), 7.98 (s, 1H), 7.91 (s, 1H), 7.79 (d, J = 8.0 Hz, 1H), 7.46 (m, 2H), 6.49 (m, 1H), 6.29 (dd, J = 2.0 Hz, 1.6 Hz, 1H), 5.79 (dd, J = 1.6 Hz, J = 8.4 Hz, 1H), 2.50 (t, J = 1.6 Hz, 3H). MS (ES) m/z 356 (M + H). |
| 45 | 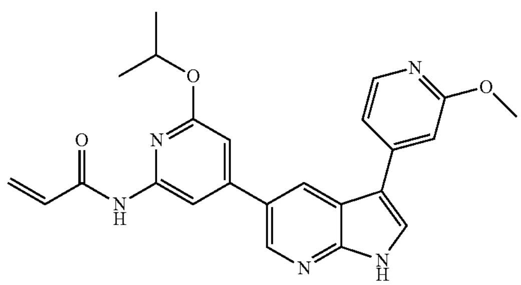 [SMILES: C=CC(=O)Nc1cc(-c2cnc3[nH]cc(-c4ccnc(OC)c4)c3c2)cc(OC(C)C)n1] | N-(6-isopropoxy-4-(3-(2-methoxypyridin-4-yl)-1H-pyrrolo[2,3-b]pyridin-5-yl)pyridin-2-yl)acrylamide | $^1$H NMR (400 MHz, DMSO-d$_6$) δ ppm, 12.43 (s, 1H), 10.54 (s, 1H), 8.60 (s, 1H), 8.55 (s, 1H), 8.28 (s, 1H), 8.18 (br. s, 1H), 8.14 (s, 1H), 7.47 (br. s, 1H), 7.23 (s, 1H), 6.98 (s, 1H), 6.73-6.65 (m, 1H), 6.32 (d, J = 16.83 Hz, 1H), 5.80 (d, J = 11.34 Hz, 1H), 5.34 (br. s, 1H), 3.90 (s, 3H), 1.36 (s, 3H), 1.34 (s, 3H). MS (ES) m/z 430 (M + H). |
| 46 | 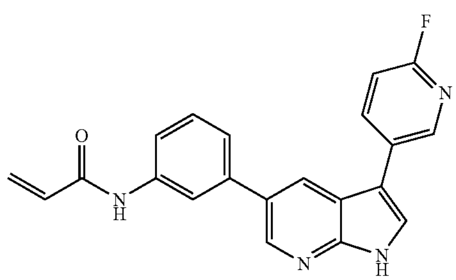 [SMILES: C=CC(=O)Nc1cccc(-c2cnc3[nH]cc(-c4ccc(F)nc4)c3c2)c1] | N-(3-(3-(6-fluoropyridin-3-yl)-1H-pyrrolo[2,3-b]pyridin-5-yl)phenyl)acrylamide | $^1$H NMR (400 MHz, DMSO-d$_6$) δ ppm, 12.21 (s, 1H), 10.28 (s, 1H), 8.67 (s, 1H), 8.56 (s, 1H), 8.42-8.39 (m, 2H), 8.08 (s, 1H), 7.98 (s, 1H), 7.74 (d, J = 7.83 Hz, 1H), 7.52 (d, J = 7.43 Hz, 1H), 7.47-7.43 (m, 1H), 7.28 (d, J = 5.87 Hz, 1H), 6.51-6.44 (m, 1H), 6.29 (d, J = 17.60 Hz, 1H), 5.79 (d, J = 12.12 Hz, 1H), MS (ES) m/z 359 (M + H). |
| 47 | 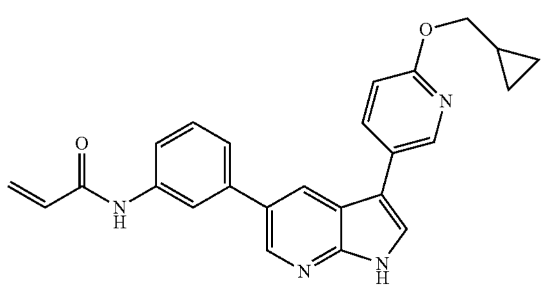 [SMILES: C=CC(=O)Nc1cccc(-c2cnc3[nH]cc(-c4ccc(OCC5CC5)nc4)c3c2)c1] | N-(3-(3-(6-(cyclopropylmethoxy)pyridin-3-yl)-1H-pyrrolo[2,3-b]pyridin-5-yl)phenyl)acrylamide | $^1$H NMR (400 MHz, DMSO-d$_6$) δ ppm, 12.06 (s, 1H), 10.28 (s, 1H), 8.54 (br. s, 2H), 8.35 (s, 1H), 8.10 (d, J = 9.00 Hz, 1H), 7.98 (s, 1H), 7.93 (s, 1H), 7.74 (d, J = 7.43 Hz, 1H), 7.51 (d, J = 6.65 Hz, 1H), 7.47-7.43 (m, 1H), 6.93 (d, J = 8.61 Hz, 1H), 6.48-6.44 (m, 1H), 6.29 (d, J = 15.26 Hz, 1H), 5.79 (d, J = 10.95 Hz, 1H), 4.14 (d, J = 6.65 Hz, 1H), 1.32-1.21 (m, 1H), 0.57 (d, J = 7.82 Hz, 2H), 0.34 (d, J = 4.70 Hz, 2H). MS (ES) m/z 411 (M + H). |

TABLE 1-continued

Compound Examples

| Ex. # | Structure | Name | Spectral Data |
|---|---|---|---|
| 48 | 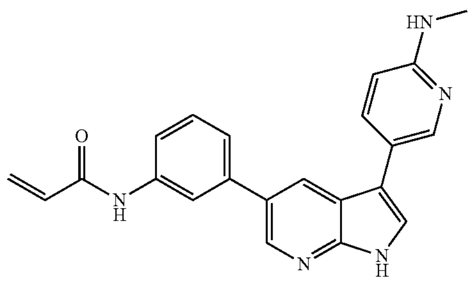 [SMILES: C=CC(=O)Nc1cccc(-c2cnc3[nH]cc(-c4ccc(NC)nc4)c3c2)c1] | N-(3-(3-(6-(methylamino)pyridin-3-yl)-1H-pyrrolo[2,3-b]pyridin-5-yl)phenyl)acrylamide | $^1$H NMR (400 MHz, DMSO-d$_6$) δ ppm, 11.89 (s, 1H), 10.28 (s, 1H), 8.52 (s, 1H), 8.41 (s, 1H), 8.30 (s, 1H), 7.96 (s, 1H), 7.78-7.75 (m, 3H), 7.50-7.42 (m, 2H), 6.56 (d, J = 8.21 Hz, 1H), 6.50 (s, 1H), 6.45 (d, J = 10.57 Hz, 1H), 6.29 (d, J = 16.04 Hz, 1H), 5.78 (d, J = 10.17 Hz, 1H), 2.81 (d, J = 4.30 Hz, 3H). MS (ES) m/z 370 (M + H). |
| 49 | 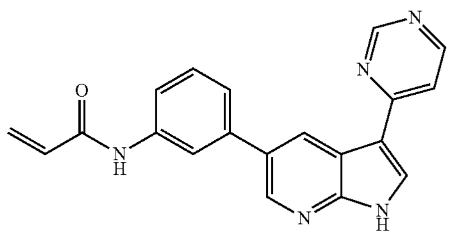 [SMILES: C=CC(=O)Nc1cccc(-c2cnc3[nH]cc(-c4ccncn4)c3c2)c1] | N-(3-(3-(pyrimidin-4-yl)-1H-pyrrolo[2,3-b]pyridin-5-yl)phenyl)acrylamide | $^1$H NMR (400 MHz, DMSO-d6) δ ppm, 12.58 (s, 1H), 10.33 (s, 1H), 9.16 (d, J = 0.8 Hz, 1H), 9.01 (d, J = 2.4 Hz, 1H), 8.68 (d, J = 5.6 Hz, 1H) 8.63 (s, 1H), 8.57 (d, J = 2.0 Hz, 1H), 8.01 (m, 2H), 7.78 (d, J = 6.8 Hz, 1H), 7.46 (m, 2H), 6.49 (m, 1H), 6.29 (dd, J = 1.6 Hz, J = 15.2 Hz, 1H), 5.79 (dd, J = 1.6 Hz, J = 8.4 Hz, 1H). MS (ES) m/z 342 (M + H). |
| 50 | 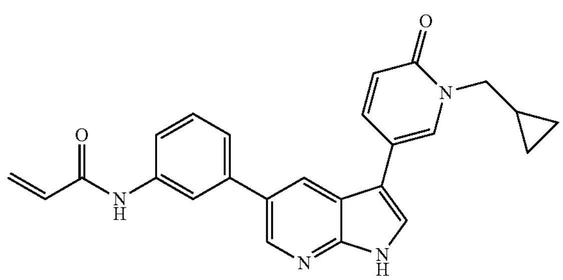 [SMILES: C=CC(=O)Nc1cccc(-c2cnc3[nH]cc(-c4ccc(=O)n(CC5CC5)c4)c3c2)c1] | N-(3-(3-(1-(cyclopropylmethyl)-6-oxo-1,6-dihydropyridin-3-yl)-1H-pyrrolo[2,3-b]pyridin-5-yl)phenyl)acrylamide | $^1$H NMR (400 MHz, DMSO-d$_6$) δ ppm, 11.97 (s, 1H), 10.26 (s, 1H), 8.52 (s, 1H), 8.32 (s, 1H), 8.10 (s, 1H), 8.02 (s, 1H), 7.86 (d, J = 9.00 Hz, 1H), 7.80 (s, 1H), 7.69 (d, J = 8.61 Hz, 1H), 7.47-7.43 (m, 2H), 6.53 (d, J = 9.00 Hz, 1H), 6.50-6.43 (m, 1H), 6.28 (d, J = 16.83 Hz, 1H), 5.78 (d, J = 10.96 Hz, 1H), 3.86 (d, J = 7.04 Hz, 2H), 1.30-1.23 (m, 1H), 0.50 (d, J = 7.04 Hz, 2H), 0.45-0.44 (m, 2H). MS (ES) m/z 411 (M + H). |
| 51 | 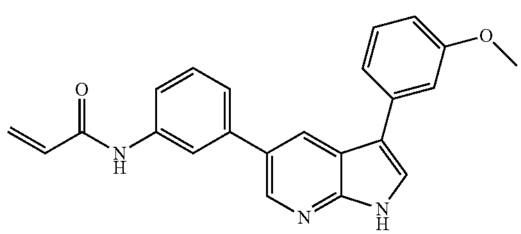 [SMILES: C=CC(=O)Nc1cccc(-c2cnc3[nH]cc(-c4cccc(OC)c4)c3c2)c1] | N-(3-(3-(3-methoxyphenyl)-1H-pyrrolo[2,3-b]pyridin-5-yl)phenyl)acrylamide | $^1$H NMR (400 MHz, DMSO-d$_6$) δ ppm, 12.07 (s, 1H), 10.28 (s, 1H), 8.54 (s, 1H), 8.37 (s, 1H), 7.99 (s, 1H), 7.96 (s, 1H), 7.72 (br. s, 1H), 7.47 (s, 2H), 7.39-7.37 (m, 2H), 7.28 (s, 1H), 6.87 (br. s, 1H), 6.46-6.43 (m, 1H), 6.29 (d, J = 15.26 Hz, 1H), 5.78 (d, J = 10.17 Hz, 1H), 3.84 (s, 3H). MS (ES) m/z 370 (M + H). |
| 52 | 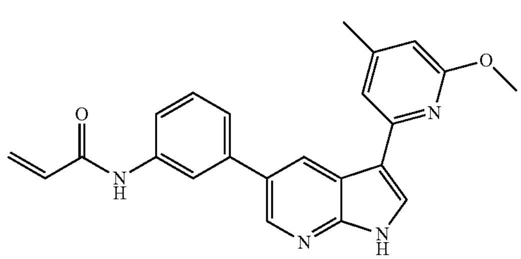 [SMILES: C=CC(=O)Nc1cccc(-c2cnc3[nH]cc(-c4cc(C)cc(OC)n4)c3c2)c1] | N-(3-(3-(6-methoxy-4-methylpyridin-2-yl)-1H-pyrrolo[2,3-b]pyridin-5-yl)phenyl)acrylamide | $^1$H NMR (400 MHz, DMSO-d6) δ ppm, 12.11 (d, J = 4.4 Hz, 1H), 10.28 (s, 1H), 9.11 (d, J = 2.4 Hz, 1H), 8.55 (d, J = 2.4 Hz, 1H), 8.28 (s, 1H), 8.19 (s, 1H), 7.59 (d, J = 2.8 Hz, 1H), 7.45 (d, J = 4.8 Hz, 2H), 7.40 (s, 1H), 6.49 (m, 2H), 6.30 (dd, J = 1.6 Hz, J = 14.8 Hz, 1H), 5.79 (dd, J = 1.6 Hz, J = 8.4 Hz, 1H), 4.03 (s, 3H), 2.32 (s, 3H). MS (ES) m/z 385 (M + H). |

TABLE 1-continued

Compound Examples

| Ex. # | Structure | Name | Spectral Data |
|---|---|---|---|
| 53 | 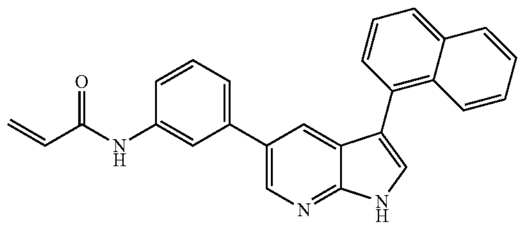 [SMILES: C=CC(=O)Nc1cccc(-c2cnc3[nH]cc(-c4cccc5ccccc45)c3c2)c1] | N-(3-(3-(naphthalen-1-yl)-1H-pyrrolo[2,3-b]pyridin-5-yl)phenyl)acrylamide | ¹H NMR (400 MHz, DMSO-d$_6$) δ ppm, 12.18 (s, 1H), 10.19 (s, 1H), 8.60 (s, 1H), 8.02 (d, J = 8.61 Hz, 2H), 7.97 (d, J = 7.43 Hz, 1H), 7.85-7.83 (m, 3H), 7.68 (s, 1H), 7.64-7.60 (m, 2H), 7.57-7.48 (m, 2H), 7.38 (br. s, 2H), 6.44-6.37 (m, 1H), 6.24 (d, J = 16.82 Hz, 1H), 5.75 (d, J = 10.18 Hz, 1H). MS (ES) m/z 390 (M + H). |
| 54 | 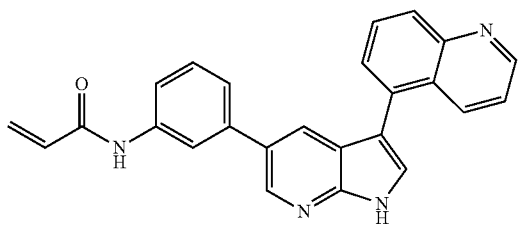 [SMILES: C=CC(=O)Nc1cccc(-c2cnc3[nH]cc(-c4cccc5ncccc45)c3c2)c1] | N-(3-(3-(quinolin-5-yl)-1H-pyrrolo[2,3-b]pyridin-5-yl)phenyl)acrylamide | ¹H NMR (400 MHz, DMSO-d$_6$) δ ppm, 12.26 (s, 1H), 10.20 (s, 1H), 8.94 (s, 1H), 8.60 (s, 1H), 8.42 (d, J = 8.61 Hz, 1H), 8.06 (d, J = 9.79, 1H), 7.90-7.88 (m, 4H), 7.76 (d, J = .6.65 Hz, 1H), 7.69 (br. s, 1H), 7.56-7.50 (m, 1H), 7.40 (br. s, 2H), 6.44-6.38 (m, 1H), 6.25 (d, J = 17.60 Hz, 1H), 5.75 (d, J = 10.17 Hz, 1H). MS (ES) m/z 391 (M + H). |
| 55 | 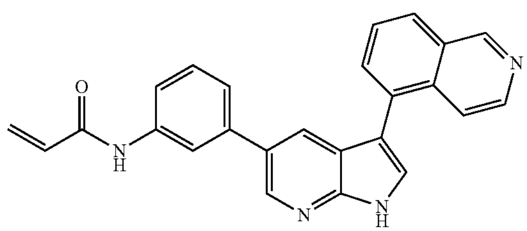 [SMILES: C=CC(=O)Nc1cccc(-c2cnc3[nH]cc(-c4cccc5cnccc45)c3c2)c1] | N-(3-(3-(isoquinolin-5-yl)-1H-pyrrolo[2,3-b]pyridin-5-yl)phenyl)acrylamide | ¹H NMR (400 MHz, DMSO-d$_6$) δ ppm, 12.31 (s, 1H), 10.21 (s, 1H), 9.35 (s, 1H), 8.64 (s, 1H), 8.62 (s, 1H), 8.24 (br. s, 1H), 8.03 (br. s, 1H), 7.92-7.89 (m, 3H), 7.78-7.70 (m, 3H), 7.40 (s, 2H), 6.40 (br. s, 1H), 6.25 (d, J = 17.60 Hz, 1H), 5.76 (br. s, 1H). MS (ES) m/z 391 (M + H). |
| 56 | 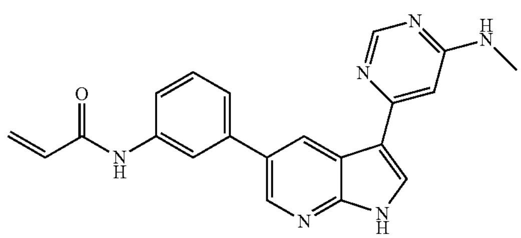 [SMILES: C=CC(=O)Nc1cccc(-c2cnc3[nH]cc(-c4cc(NC)ncn4)c3c2)c1] | N-(3-(3-(6-(methylamino)pyrimidin-4-yl)-1H-pyrrolo[2,3-b]pyridin-5-yl)phenyl)acrylamide | ¹H NMR (400 MHz, DMSO-d6) δ ppm, 12.72 (s, 1H), 10.30 (s, 1H), 8.66 (d, J = 2.4 Hz, 1H), 8.50 (m, 2H), 8.32 (m, 1H), 7.96 (s, 1H), 7.78 (m, 1H), 7.46 (m, 2H), 7.13 (s, 1H), 6.91 (s, 1H), 6.48 (m, 1H), 6.28 (m, 1H), 5.80 (m, 1H), 2.86 (s, 3H). MS (ES) m/z 371 (M + H). |
| 57 | 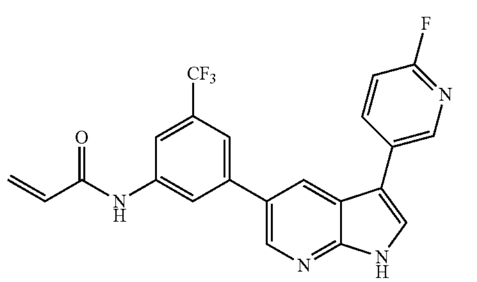 [SMILES: C=CC(=O)Nc1cc(-c2cnc3[nH]cc(-c4ccc(F)nc4)c3c2)cc(C(F)(F)F)c1] | N-(3-(3-(6-fluoropyridin-3-yl)-1H-pyrrolo[2,3-b]pyridin-5-yl)-5-(trifluoromethyl)phenyl)acrylamide | ¹H NMR (400 MHz, DMSO-d$_6$) δ ppm, 12.28 (s, 1H), 10.60 (s, 1H), 8.71 (s, 1H), 8.62 (s, 1H), 8.54 (s, 1H), 8.42-8.41 (m, 1H), 8.23 (s, 1H), 8.12 (d, J = 13.69 Hz, 1H), 7.88 (s, 1H), 7.29 (d, J = 7.43 Hz, 1H), 6.50-6.43 (m, 1H), 6.34 (d, J = 17.61 Hz, 1H), 5.85 (d, J = 11.35 Hz, 1H). MS (ES) m/z 427 (M + H). |
| 58 | 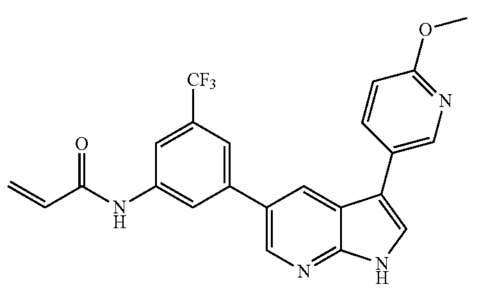 [SMILES: C=CC(=O)Nc1cc(-c2cnc3[nH]cc(-c4ccc(OC)nc4)c3c2)cc(C(F)(F)F)c1] | N-(3-(3-(6-methoxypyridin-3-yl)-1H-pyrrolo[2,3-b]pyridin-5-yl)-5-(trifluoromethyl)phenyl)acrylamide | ¹H NMR (400 MHz, DMSO-d$_6$) δ ppm, 12.11 (s, 1H), 10.57 (s, 1H), 8.64 (s, 1H, 8.60 (s, 1H), 8.47 (s, 1H), 8.22 (s, 1H) 8.13 (s, 1H), 8.11 (s, 1H), 7.95 (s, 1H), 7.86 (s, 1H), 6.93 (d, J = 8.21 Hz, 1H), 6.47-6.43 (m, 1H), 6.33 (d, J = 15.65 Hz, 1H), 5.85 (d, J = 10.17 Hz), 3.91 (s, 3H). MS (ES) m/z 439 (M + H). |

TABLE 1-continued

Compound Examples

| Ex. # | Structure | Name | Spectral Data |
|---|---|---|---|
| 59 | 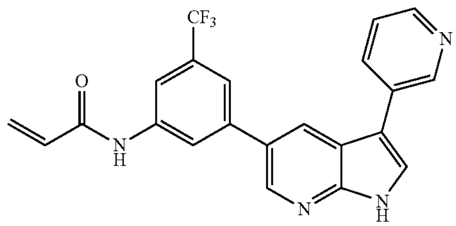 [SMILES: C=CC(=O)Nc1cc(-c2cnc3[nH]cc(-c4cccnc4)c3c2)cc(C(F)(F)F)c1] | N-(3-(3-(pyridin-3-yl)-1H-pyrrolo[2,3-b]pyridin-5-yl)-5-(trifluoromethyl)phenyl)acrylamide | $^1$H NMR (400 MHz, DMSO-d$_6$) δ ppm, 12.28 (s, 1H), 10.61 (s, 1H), 9.07 (s, 1H), 8.62 (s, 1H), 8.55 (s, 1H), 8.49 (s, 1H), 8.24-8.12 (m, 4H), 7.88 (s, 1H), 7.50-7.47 (m, 1H), 6.50-6.44 (m, 1H), 6.34 (d, J = 17.22 Hz, 1H), 5.70 (d, J = 9.78 Hz, 1H). MS (ES) m/z 409 (M + H). |
| 60 | 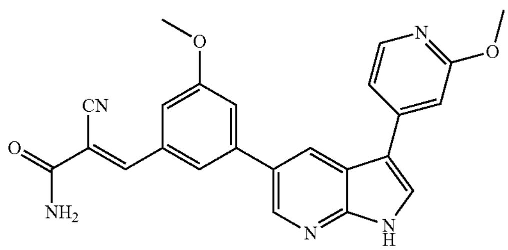 [SMILES: COc1cc(/C=C(\C#N)C(N)=O)cc(-c2cnc3[nH]cc(-c4ccnc(OC)c4)c3c2)c1] | (E)-2-cyano-3-(3-methoxy-5-(3-(2-methoxypyridin-4-yl)-1H-pyrrolo[2,3-b]pyridin-5-yl)phenyl)acrylamide | $^1$H NMR (400 MHz, DMSO-d6) δ ppm, 12.34 (s, 1H), 8.65 (d, J = 2.0 Hz, 1H), 8.58 (d, J = 2.0 Hz, 1H), 8.30 (s, 1H), 8.26 (s, 1H), 8.18 (d, J = 5.6 Hz, 1H), 7.92 (m, 2H), 7.59 (m, 2H), 7.49 (dd, J = 1.6 Hz, J = 4.0 Hz, 1H), 7.23 (d, J = 0.8 Hz, 1H), 3.91 (d, J = 10.4 Hz, 6H). MS (ES) m/z 426 (M + H). |
| 61 | 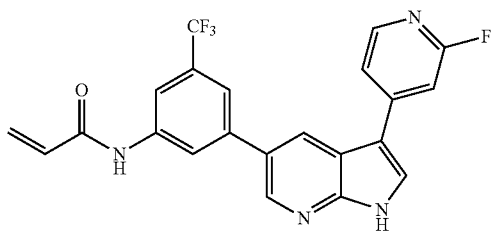 [SMILES: C=CC(=O)Nc1cc(-c2cnc3[nH]cc(-c4ccnc(F)c4)c3c2)cc(C(F)(F)F)c1] | N-(3-(3-(2-fluoropyridin-4-yl)-1H-pyrrolo[2,3-b]pyridin-5-yl)-5-(trifluoromethyl)phenyl)acrylamide | $^1$H NMR (400 MHz, DMSO-d$_6$) δ ppm, 12.54 (s, 1H), 10.62 (s, 1H), 8.68 (s, 1H), 8.62 (s, 1H), 8.43 (s, 1H), 8.26-8.24 (m, 2H), 8.13 (br. s, 1H), 7.90-7.86 (m, 2H), 7.67 (br. s, 1H), 6.51-6.45 (m, 1H), 6.34 (d, J = 16.82 Hz, 1H), 5.86 (d, J = 10.56 Hz, 1H). MS (ES) m/z 427 (M + H). |
| 62 | 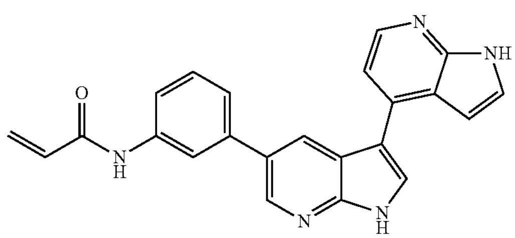 [SMILES: C=CC(=O)Nc1cccc(-c2cnc3[nH]cc(-c4ccnc5[nH]ccc45)c3c2)c1] | N-(3-(1H,1'H-[3,4'-bipyrrolo[2,3-b]pyridin]-5-yl)phenyl)acrylamide | $^1$H NMR (400 MHz, DMSO-d$_6$) δ ppm, 12.32 (s, 1H), 11.72 (s, 1H), 10.27 (s, 1H), 8.59 (s, 1H), 8.39 (s, 1H), 8.28 (d, J = 4.30 Hz, 1H), 8.12 (s, 1H), 7.96 (s, 1H), 7.76-7.74 (m, 2H), 7.51-7.41 (m, 4H), 6.69 (s, 1H), 6.49-6.42 (m, 1H), 6.28 (d, J = 16.44 Hz, 1H), 5.78 (d, J = 11.34 Hz, 1H). MS (ES) m/z 380 (M + H). |
| 63 | 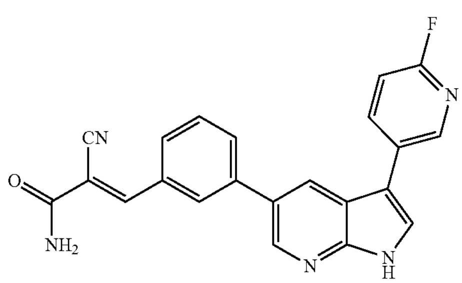 [SMILES: N#C/C(=C\c1cccc(-c2cnc3[nH]cc(-c4ccc(F)nc4)c3c2)c1)C(N)=O] | (E)-2-cyano-3-(3-(3-(6-fluoropyridin-3-yl)-1H-pyrrolo[2,3-b]pyridin-5-yl)phenyl)acrylamide | $^1$H NMR (400 MHz, DMSO-d6) δ ppm, 12.22 (s, 1H), 8.69 (m, 1H), 8.66 (m, 1H), 8.55 (s, 1H), 8.35 (s, 1H), 8.32 (s, 1H), 8.01 (m, 2H), 7.97 (m, 2H), 7.80 (m, 2H), 7.63 (s, 1H), 7.35 (s, 1H). MS (ES) m/z 384 (M + H). |
| 64 | 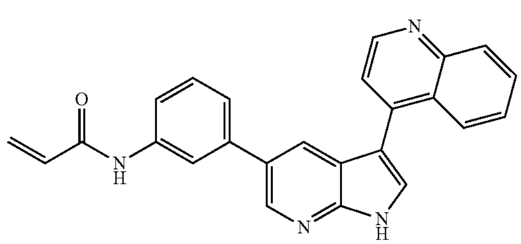 [SMILES: C=CC(=O)Nc1cccc(-c2cnc3[nH]cc(-c4ccnc5ccccc45)c3c2)c1] | N-(3-(3-(quinolin-4-yl)-1H-pyrrolo[2,3-b]pyridin-5-yl)phenyl)acrylamide | $^1$H NMR (400 MHz, DMSO-d$_6$) δ ppm, 12.45 (s, 1H), 10.22 (s, 1H), 8.96 (d, J = 3.52 Hz, 1H), 8.62 (s, 1H), 8.20 (d, J = 9.39 Hz, 1H), 8.12 (d, J = 9.00 Hz, 1H), 8.06 (s, 2H), 7.91 (s, 1H), 7.83-7.80 (m, 1H), 7.70 (d, J = 4.70 Hz, 2H), 7.65-7.61 (m, 1H), 7.42 (s, 2H), 6.46-6.39 (m, 1H), 6.26 (d, J = 17.22 Hz, 1H), 5.76 (d, J = 10.17 Hz, 1H). MS (ES) m/z 391 (M + H). |

TABLE 1-continued

Compound Examples

| Ex. # | Structure | Name | Spectral Data |
|---|---|---|---|
| 65 | 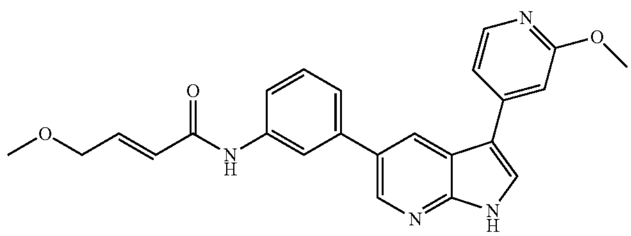 | (E)-4-methoxy-N-(3-(3-(2-methoxypyridin-4-yl)-1H-pyrrolo[2,3-b]pyridin-5-yl)phenyl)but-2-enamide | $^1$H NMR (400 MHz, DMSO-d6) δ ppm, 12.34 (d, J = 2.4 Hz, 1H), 10.23 (s, 1H), 8.55 (d, J = 2.0 Hz, 1H), 8.45 (d, J = 2.0 Hz, 1H), 8.26 (d, J = 2.8 Hz, 1H), 8.18 (d, J = 5.6 Hz, 1H), 7.98 (s, 1H), 7.74 (d, J = 8.0 Hz, 1H), 7.46 (m, 3H), 7.20 (d, J = 0.8 Hz, 1H), 6.83 (m, 1H), 6.36 (m, 1H), 4.41 (m, 2H), 3.90 (s, 3H), 3.35 (s, 3H). MS (ES) m/z 414 (M + H). |
| 66 | 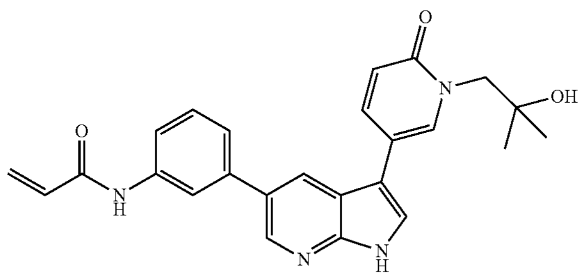 [SMILES: C=CC(=O)Nc1cccc(-c2cnc3[nH]cc(-c4ccc(=O)n(CC(C)(C)O)c4)c3c2)c1] | N-(3-(3-(1-(2-hydroxy-2-methylpropyl)-6-oxo-1,6-dihydropyridin-3-yl)-1H-pyrrolo[2,3-b]pyridin-5-yl)phenyl)acrylamide | $^1$H NMR (400 MHz, DMSO-d$_6$) δ ppm, 11.96 (s, 1H), 10.30 (s, 1H), 8.53 (s, 1H), 8.39 (s, 1H), 8.04 (br. s, 2H), 7.85 (d, J = 8.22 Hz, 1H), 7.80 (br. s, 1H), 7.65 (br. s, 1H), 7.47 (br. s, 2H), 6.54 (d, J = 9.00 Hz, 1H), 6.49-6.48 (m, 1H), 6.30 (d, J = 16.83 Hz, 1H), 5.80 (d, J = 10.17 Hz, 1H), 4.91 (s, 1H), 4.04 (s, 2H), 1.14 (s, 6H). MS (ES) m/z 429 (M + H). |
| 67 | 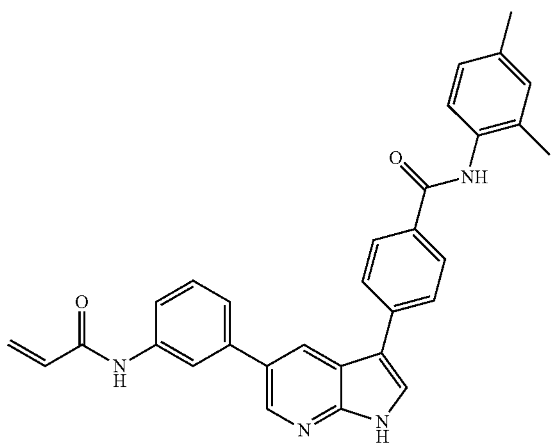 [SMILES: C=CC(=O)Nc1cccc(-c2cnc3[nH]cc(-c4ccc(C(=O)Nc5ccc(C)cc5C)cc4)c3c2)c1] | 4-(5-(3-acrylamidophenyl)-1H-pyrrolo[2,3-b]pyridin-3-yl)-N-(2,4-dimethylphenyl)benzamide | $^1$H NMR (400 MHz, DMSO-d$_6$) δ ppm, 12.21 (s, 1H), 10.29 (s, 1H), 9.81 (s, 1H), 8.56 (s, 1H), 8.49 (s, 1H), 8.12-8.06 (m, 3H), 8.01 (s, 1H), 7.95 (d, J = 7.83 Hz, 2H), 7.73 (br. s, 1H), 7.50-7.47 (m, 2H), 7.22 (br. s, 1H), 7.10 (s, 1H), 7.04 (br. s, 1H), 6.53-6.42 (m, 1H), 6.29 (d, J = 15.65 Hz, 1H), 5.79 (d, J = 8.61 Hz, 1H), 2.30 (s, 3H), 2.22 (s, 3H). MS (ES) m/z 487 (M + H). |
| 68 | 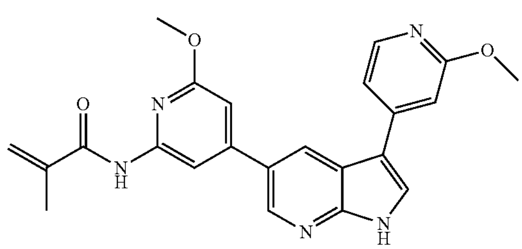 [SMILES: C=C(C)C(=O)Nc1cc(-c2cnc3[nH]cc(-c4ccnc(OC)c4)c3c2)cc(OC)n1] | N-(6-methoxy-4-(3-(2-methoxypyridin-4-yl)-1H-pyrrolo[2,3-b]pyridin-5-yl)pyridin-2-yl)methacrylamide | $^1$H NMR (400 MHz, DMSO-d6) δ ppm, 12.32 (s, 1H), 9.85 (s, 1H), 8.56 (d, J = 2.0 Hz, 1H), 8.44 (d, J = 2.0 Hz, 1H), 8.24 (s, 1H), 8.19 (d, J = 5.6 Hz, 1H), 7.59 (s, 1H), 7.51 (m, 1H), 7.45 (m, 1H), 7.19 (s, 1H), 7.06 (d, J = 1.6 Hz, 1H), 5.85 (s, 1H), 5.55 (s, 1H), 3.90 (s, 3H), 3.84 (s, 3H), 1.97 (s, 3H). MS (ES) m/z 415 (M + H). |
| 69 | 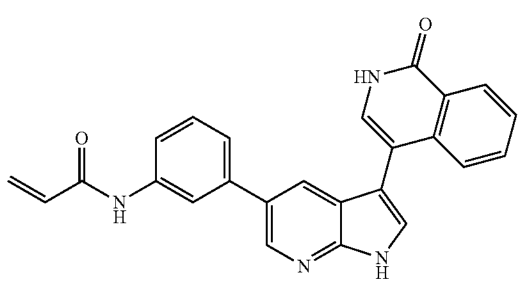 [SMILES: C=CC(=O)Nc1cccc(-c2cnc3[nH]cc(-c4c[nH]c(=O)c5ccccc45)c3c2)c1] | N-(3-(3-(1-oxo-1,2-dihydroisoquinolin-4-yl)-1H-pyrrolo[2,3-b]pyridin-5-yl)phenyl)acrylamide | No NMR. MS (ES) m/z 407 (M + H). |

TABLE 1-continued

Compound Examples

| Ex. # | Structure | Name | Spectral Data |
|---|---|---|---|
| 70 | 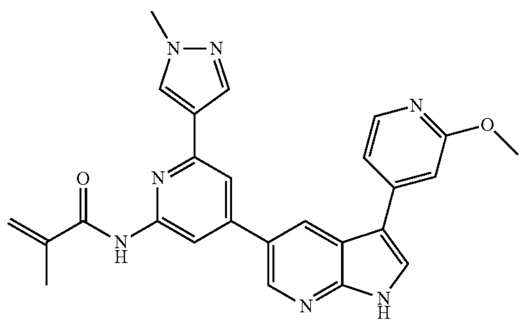 [SMILES: C=C(C)C(=O)Nc1cc(-c2cnc3[nH]cc(-c4ccnc(OC)c4)c3c2)cc(-c2cnn(C)c2)n1] | N-(4-(3-(2-methoxypyridin-4-yl)-1H-pyrrolo[2,3-b]pyridin-5-yl)-6-(1-methyl-1H-pyrazol-4-yl)pyridin-2-yl)methacrylamide | $^1$H NMR (400 MHz, MeOD) δ ppm, 8.71 (m, 2H), 8.34 (d, J = 1.2 Hz, 1H), 8.29 (s, 1H), 8.18 (m, 2H), 8.04 (s, 1H), 7.78 (d, J = 1.6 Hz, 1H), 7.44 (d, J = 1.6 Hz, 1H), 7.21 (d, J = 1.2 Hz, 1H), 5.97 (s, 1H), 5.64 (d, J = 1.2 Hz, 1H), 3.99 (d, J = 1.6 Hz, 6H), 2.14 (m, 3H). MS (ES) m/z 466 (M + H). |
| 71 | 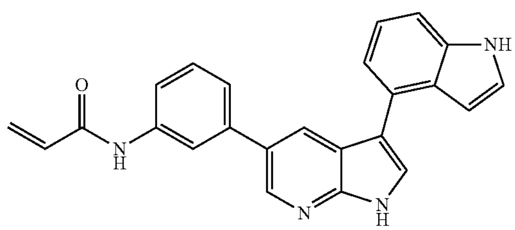 [SMILES: C=CC(=O)Nc1cccc(-c2cnc3[nH]cc(-c4cccc5[nH]ccc45)c3c2)c1] | N-(3-(3-(1H-indol-4-yl)-1H-pyrrolo[2,3-b]pyridin-5-yl)phenyl)acrylamide | MS (ES) m/z 379 (M + H). |
| 72 | 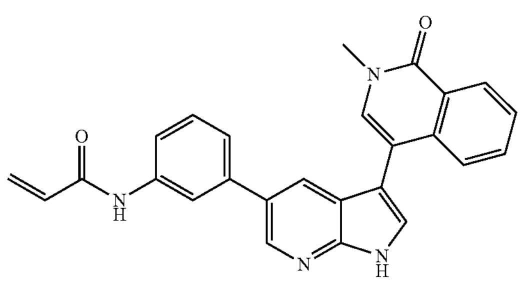 [SMILES: C=CC(=O)Nc1cccc(-c2cnc3[nH]cc(-c4cn(C)c(=O)c5ccccc45)c3c2)c1] | N-(3-(3-(2-methyl-1-oxo-1,2-dihydroisoquinolin-4-yl)-1H-pyrrolo[2,3-b]pyridin-5-yl)phenyl)acrylamide | $^1$H NMR (400 MHz, DMSO-d$_6$) δ ppm, 12.07 (s, 1H), 10.19 (s, 1H), 8.57 (s, 1H), 8.35 (d, J = 8.61 Hz, 1H), 7.88 (s, 2H), 7.72-7.55 (m, 6H), 7.38 (br. s, 2H), 6.46-6.38 (m, 1H), 6.25 (d, J = 18.78 Hz, 1H), 5.75 (d, J = 9.78 Hz, 1H), 3.59 (s, 3H). ). MS (ES) m/z 421 (M + H). |
| 73 | 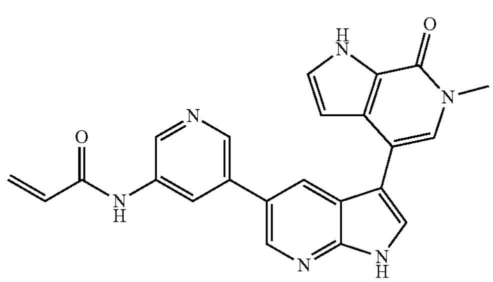 [SMILES: C=CC(=O)Nc1cncc(-c2cnc3[nH]cc(-c4cn(C)c(=O)c5[nH]ccc45)c3c2)c1] | N-(5-(3-(6-methyl-7-oxo-6,7-dihydro-1H-pyrrolo[2,3-c]pyridin-4-yl)-1H-pyrrolo[2,3-b]pyridin-5-yl)pyridin-3-yl)acrylamide | $^1$H NMR (400 MHz, DMSO-d$_6$) δ ppm, 12.13 (s, 1H), 11.97 (s, 1H), 10.24 (s, 1H), 8.54 (s, 1H), 8.21 (s, 1H), 7.94 (s, 1H), 7.75 (s, 1H), 7.71 (br. s, 1H), 7.48-7.41 (m, 3H), 7.33 (s, 1H), 6.48-6.44 (m, 1H), 6.41 (br. s, 1H), 6.27 (d, J = 16.44 Hz, 1H), 5.77 (d, J = 9.78 Hz, 1H), 3.62 (s, 3H). MS (ES) m/z 410 (M + H). |

TABLE 1-continued

Compound Examples

| Ex. # | Structure | Name | Spectral Data |
|---|---|---|---|
| 74 | 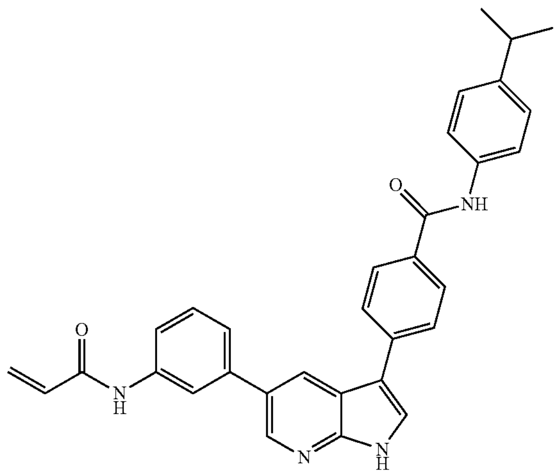 [SMILES: C=CC(=O)Nc1cccc(-c2cnc3[nH]cc(-c4ccc(C(=O)Nc5ccc(C(C)C)cc5)cc4)c3c2)c1] | 4-(5-(3-acrylamidophenyl)-1H-pyrrolo[2,3-b]pyridin-3-yl)-N-(4-isopropylphenyl)benzamide | $^1$H NMR (400 MHz, DMSO-$d_6$) δ ppm, 12.22 (s, 1H), 10.28 (s, 1H), 10.19 (s, 1H), 8.56 (s, 1H), 8.48 (s, 1H), 8.12 (s, 1H), 8.06 (d, J = 7.43 Hz, 2H), 8.02 (s, 1H), 7.95 (d, J = 7.43 Hz, 2H), 7.72-7.71 (m, 3H), 7.51-7.47 (m, 2H), 7.23 (d, J = 7.82 Hz, 2H), 6.51-6.44 (m, 1H), 6.29 (d, J = 17.61 Hz, 1H), 5.79 (d, J = 10.96 Hz, 1H), 2.88-2.86 (m, 1H), 1.21 (d, J = 7.05 Hz, 6H). MS (ES) m/z 501 (M + H). |
| 75 | 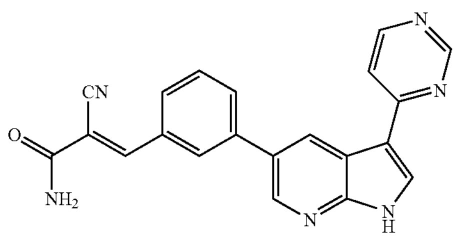 [SMILES: N#C/C(=C\c1cccc(-c2cnc3[nH]cc(-c4ccncn4)c3c2)c1)C(N)=O] | (E)-2-cyano-3-(3-(3-(pyrimidin-4-yl)-1H-pyrrolo[2,3-b]pyridin-5-yl)phenyl)acrylamide | MS (ES) m/z 368 (M + H). |
| 76 | 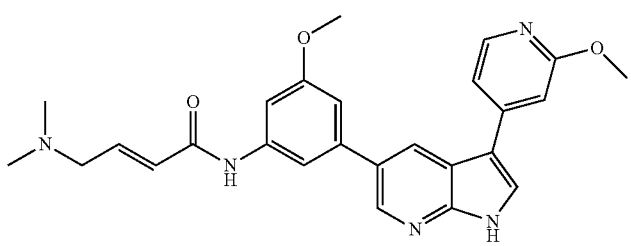 | (E)-4-(dimethylamino)-N-(3-methoxy-5-(3-(2-methoxypyridin-4-yl)-1H-pyrrolo[2,3-b]pyridin-5-yl)phenyl)but-2-enamide | $^1$H NMR (400 MHz, DMSO-d6) δ ppm, 12.33 (s, 1H), 10.19 (s, 1H), 8.55 (d, J = 2.0 Hz, 1H), 8.44 (d, J = 2.0 Hz, 1H), 8.25 (s, 1H), 7.46 (m, 3H), 7.19 (s, 1H), 6.75 (m, 1H), 8.29 (m, 1H), 3.90 (s, 3H), 3.84 (s, 3H), 3.06 (d, J = 5.2 Hz, 2H), 2.33 (m, 6H). MS (ES) m/z 458 (M + H). |
| 77 | 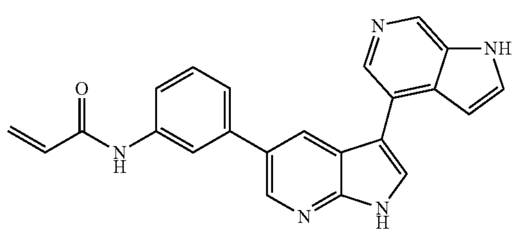 [SMILES: C=CC(=O)Nc1cccc(-c2cnc3[nH]cc(-c4cncc5[nH]ccc45)c3c2)c1] | N-(3-(3-(1H-pyrrolo[2,3-c]pyridin-4-yl)-1H-pyrrolo[2,3-b]pyridin-5-yl)phenyl)acrylamide | $^1$H NMR (400 MHz, DMSO-$d_6$) δ ppm, 12.14 (s, 1H), 11.72 (s, 1H), 10.24 (s, 1H), 8.72 (s, 1H), 8.59 (s, 1H), 8.41 (s, 1H), 8.26 (s, 1H), 7.95 (s, 1H), 7.72 (br. s, 1H), 7.65 (s, 1H), 7.45-7.43 (m, 3H), 6.65 (s, 1H), 6.42 (d, J = 10.17 Hz, 1H), 6.30 (br. s, 1H), 5.76 (d, J = 10.17 Hz, 1H). MS (ES) m/z 380 (M + H). |
| 78 | 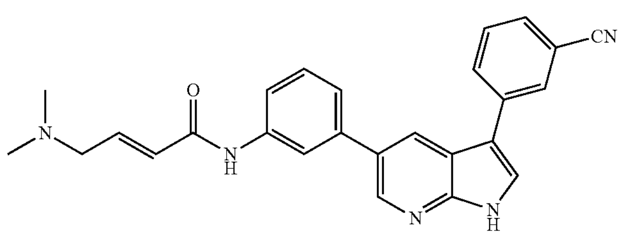 [SMILES: CN(C)C/C=C/C(=O)Nc1cccc(-c2cnc3[nH]cc(-c4cccc(C#N)c4)c3c2)c1] | (E)-N-(3-(3-(3-cyanophenyl)-1H-pyrrolo[2,3-b]pyridin-5-yl)phenyl)-4-(dimethylamino)but-2-enamide | $^1$H NMR (400 MHz, DMSO-$d_6$) δ ppm, 12.20 (s, 1H), 10.16 (s, 1H), 8.53 (s, 1H), 8.47 (s, 1H), 8.24 (s, 1H), 8.16 (d, J = 7.44 Hz, 1H), 8.12 (s, 1H), 7.71-7.65 (m, 3H), 7.46-7.44 (m, 2H), 674 (br. s, 1H), 6.30 (d, J = 15.65 Hz, 1H), 3.07 (d, J = 5.48 Hz, 2H), 2.18 (s, 6H). MS (ES) m/z 422 (M + H). |

TABLE 1-continued

Compound Examples

| Ex. # | Structure | Name | Spectral Data |
|---|---|---|---|
| 79 | 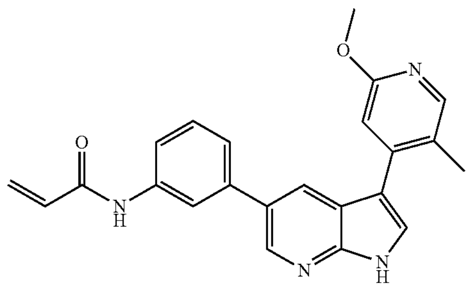 [SMILES: C=CC(=O)Nc1cccc(-c2cnc3[nH]cc(-c4cc(OC)ncc4C)c3c2)c1] | N-(3-(3-(2-methoxy-5-methylpyridin-4-yl)-1H-pyrrolo[2,3-b]pyridin-5-yl)phenyl)acrylamide | $^1$H NMR (400 MHz, MeOD) δ ppm, 8.57 (s, 1H), 8.16 (s, 1H), 8.09 (s, 1H), 7.98 (s, 1H), 7.67 (m, 2H), 7.49 (m, 2H), 6.94 (s, 1H), 6.46 (m, 2H), 5.81 (d, J = 10.0 Hz, 1H), 3.95 (s, 3H), 2.33 (s, 3H). MS (ES) m/z 385 (M + H). |
| 80 | 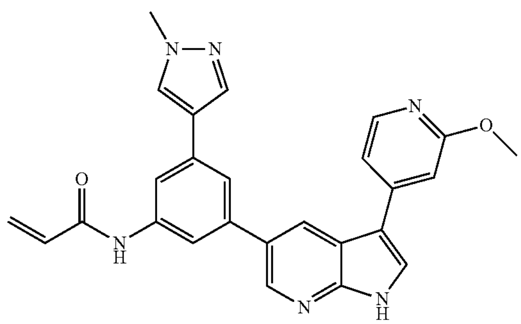 [SMILES: C=CC(=O)Nc1cc(-c2cnc3[nH]cc(-c4ccnc(OC)c4)c3c2)cc(-c2cnn(C)c2)c1] | N-(3-(3-(2-methoxypyridin-4-yl)-1H-pyrrolo[2,3-b]pyridin-5-yl)-5-(1-methyl-1H-pyrazol-4-yl)phenyl)acrylamide | $^1$H NMR (400 MHz, MeOD) δ ppm, 8.70 (dd, J = 2.0 Hz, J = 7.2 Hz, 2H), 8.41 (s, 1H), 8.28 (s, 1H), 8.19 (d, J = 5.6 Hz, 1H), 8.15 (s, 1H), 8.03 (s, 1H), 7.77 (d, J = 1.2 Hz, 1H), 7.43 (dd, J = 1.6 Hz, J = 4.0 Hz, 1H), 7.21 (s, 1H), 6.60 (m, 1H), 6.50 (m, 1H), 5.86 (dd, J = 1.6 Hz, J = 8.4 Hz, 1H), 3.99 (m, 6H). MS (ES) m/z 452 (M + H). |
| 81 | 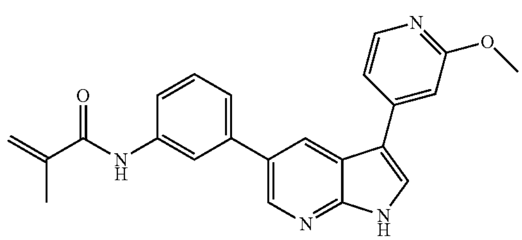 [SMILES: C=C(C)C(=O)Nc1cccc(-c2cnc3[nH]cc(-c4ccnc(OC)c4)c3c2)c1] | N-(3-(3-(2-methoxypyridin-4-yl)-1H-pyrrolo[2,3-b]pyridin-5-yl)phenyl)methacrylamide | $^1$H NMR (400 MHz, DMSO-$d_6$) δ ppm, 12.33 (s, 1H), 9.90 (s, 1H), 8.56 (s, 1H), 8.46 (s, 1H), 8.25 (s, 1H), 8.19 (d, J = 5.08 Hz, 1H), 8.00 (s, 1H), 7.80 (d, J = 8.22 Hz, 1H), 7.50-7.45 (m, 3H), 7.20 (s, 1H), 5.86 (s, 1H), 5.56 (s, 1H), 3.90 (s, 3H), 1.98 (s, 3H). MS (ES) m/z 385 (M + H). |
| 82 | 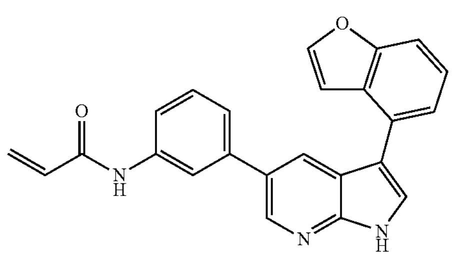 [SMILES: C=CC(=O)Nc1cccc(-c2cnc3[nH]cc(-c4cccc5occc45)c3c2)c1] | N-(3-(3-(benzofuran-4-yl)-1H-pyrrolo[2,3-b]pyridin-5-yl)phenyl)acrylamide | No NMR. MS (ES) m/z 380 (M + H). |
| 83 | 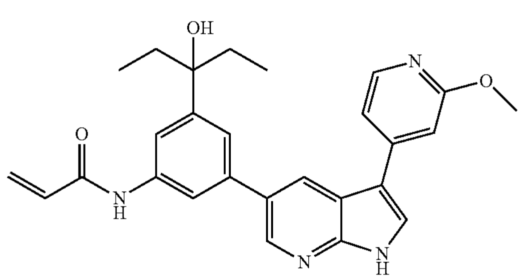 [SMILES: C=CC(=O)Nc1cc(-c2cnc3[nH]cc(-c4ccnc(OC)c4)c3c2)cc(C(O)(CC)CC)c1] | N-(3-(3-hydroxypentan-3-yl)-5-(3-(2-methoxypyridin-4-yl)-1H-pyrrolo[2,3-b]pyridin-5-yl)phenyl)acrylamide | $^1$H NMR (400 MHz, DMSO-d6) δ ppm, 12.33 (s, 1H), 10.25 (s, 1H), 8.54 (s, 1H), 8.41 (d, J = 1.2 Hz, 1H), 8.20 (m, 2H), 7.94 (s, 1H), 7.67 (s, 1H), 7.44 (d, J = 4.0 Hz, 2H), 7.18 (s, 1H), 6.44 (m, 1H), 6.29 (m, 1H), 5.76 (d, J = 10.4 Hz, 1H), 4.68 (s, 1H) 3.90 (s, 3H), 1.80 (m, 4H), 0.71 (m, 6H). MS (ES) m/z 457 (M + H). |

TABLE 1-continued

Compound Examples

| Ex. # | Structure | Name | Spectral Data |
|---|---|---|---|
| 84 | | (E)-4-(dimethylamino)-N-(3-(3-(pyridin-3-yl)-1H-pyrrolo[2,3-b]pyridin-5-yl)phenyl)but-2-enamide | $^1$H NMR (400 MHz, DMSO-$d_6$) δ ppm, 12.36 (s, 1H), 10.36 (s, 1H), 9.02 (s, 1H), 8.56 (d, J = 8.22 Hz, 1H), 8.47 (d, J = 4.69 Hz, 1H), 8.43 (d, J = 8.61 Hz, 1H), 8.20 (d, J = 8.22 Hz, 1H), 8.07 (s, 1H), 7.77-7.71 (m, 1H), 7.64-7.59 (m, 1H), 7.48-7.43 (m, 3H), 6.77-6.73 (m, 1H), 6.37 (d, J = 13.70 Hz, 1H), 3.06 (d, J = 5.48 Hz, 2H), 2.18 (s, 6H). MS (ES) m/z 398 (M + H). |
| 85 | | N-(3-(3-(pyridin-3-yl)-1H-pyrrolo[2,3-b]pyridin-5-yl)phenyl)methacrylamide | $^1$H NMR (400 MHz, DMSO-$d_6$) δ ppm, 12.17 (s, 1H), 9.85 (s, 1H), 8.56 (s, 1H), 8.48 (d, J = 5.09 Hz, 1H), 8.43 (s, 1H), 8.19 (d, J = 7.82 Hz, 1H), 8.07 (s, 1H), 8.00 (s, 1H), 7.79 (d, J = 8.61 Hz, 1H), 7.52-7.41 (m, 3H), 5.85 (s, 1H), 5.54 (s, 1H), 1.98 (s, 3H). MS (ES) m/z 355 (M + H). |
| 86 | | N-(3-(3-(2-(cyclopropylmethyl)-1-oxo-1,2-dihydroisoquinolin-4-yl)-1H-pyrrolo[2,3-b]pyridin-5-yl)phenyl)acrylamide | $^1$H NMR (400 MHz, DMSO-$d_6$) δ ppm, 12.06 (s, 1H), 10.16 (s, 1H), 8.58 (s, 1H), 8.38 (d, J = 8.21 Hz, 1H), 7.91 (s, 2H), 7.74 (s, 1H), 7.71-7.62 (m, 4H), 7.58-7.54 (m, 1H), 7.40-7.39 (m, 2H), 6.44-6.37 (m, 1H), 6.25 (d, J = 16.43 Hz, 1H), 5.75 (d, J = 10.57 Hz, 1H), 3.93 (d, J = 6.65 Hz, 2H), 1.38-1.30 (m, 1H), 0.51-0.44 (m, 4H). MS (ES) m/z 461 (M + H). |
| 87 | | (E)-2-cyano-N-(3-(3-(2-methoxypyridin-4-yl)-1H-pyrrolo[2,3-b]pyridin-5-yl)phenyl)-4-methylpent-2-enamide | $^1$H NMR (400 MHz, CDCl$_3$) δ ppm, 9.30 (s, 1H), 8.60 (m, 1H), 8.41 (d, J = 2.0 Hz, 1H), 8.25 (d, J = 5.2 Hz, 1H), 7.73 (m, 1H), 7.63 (m, 1H), 7.50 (m, 2H), 7.39 (d, J = 6.8 Hz, 1H), 7.20 (m, 1H), 7.07 (s, 1H), 4.47 (t, J = 3.6 Hz, 1H), 4.00 (m, 3H), 3.88 (d, J = 3.2 Hz, 1H), 3.63 (s, 1H). MS (ES) m/z 438 (M + H). |
| 88 | | N-(3-(3-(6-(cyclopropylmethyl)-7-oxo-6,7-dihydro-1H-pyrrolo[2,3-c]pyridin-4-yl)-1H-pyrrolo[2,3-b]pyridin-5-yl)phenyl)acrylamide | $^1$H NMR (400 MHz, DMSO-$d_6$) δ ppm, 12.09 (s, 1H), 11.96 (s, 1H), 10.21 (s, 1H), 8.55 (s, 1H), 8.22 (s, 1H), 8.00 (s, 1H), 7.76 (s, 1H), 7.66 (d, J = 6.26 Hz, 1H), 7.50 (s, 1H), 7.44-7.39 (m, 2H), 7.34 (s, 1H), 6.48-6.41 (m, 2H), 6.27 (d, J = 16.82 Hz, 1H), 5.76 (d, J = 11.74 Hz, 1H), 3.95 (d, J = 7.05 Hz, 2H), 1.37-1.26 (m, 1H), 0.52-0.46 (m, 4H). MS (ES) m/z 450 (M + H). |

TABLE 1-continued

Compound Examples

| Ex. # | Structure | Name | Spectral Data |
|---|---|---|---|
| 89 | 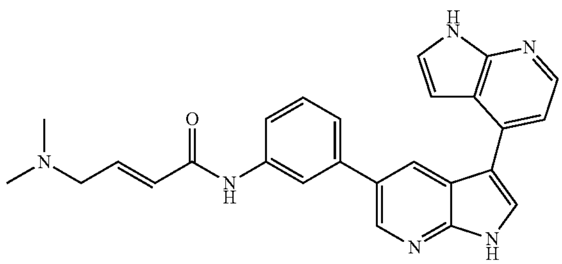 [SMILES: CN(C)C/C=C/C(=O)Nc1cccc(-c2cnc3[nH]cc(-c4ccnc5[nH]ccc45)c3c2)c1] | (E)-N-(3-(1H,1'H-[3,4'-bipyrrolo[2,3-b]pyridin]-5-yl)phenyl)-4-(dimethylamino)but-2-enamide | MS (ES) m/z 437 (M + H). |
| 90 | 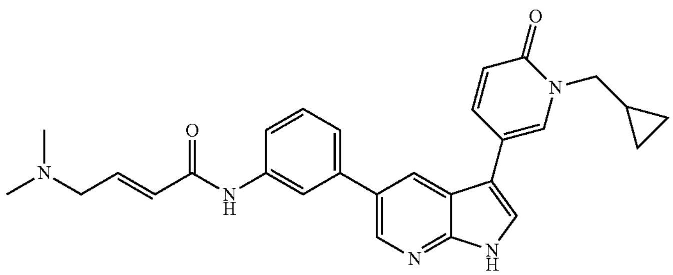 [SMILES: CN(C)C/C=C/C(=O)Nc1cccc(-c2cnc3[nH]cc(-c4ccc(=O)n(CC5CC5)c4)c3c2)c1] | (E)-N-(3-(3-(1-(cyclopropylmethyl)-6-oxo-1,6-dihydropyridin-3-yl)-1H-pyrrolo[2,3-b]pyridin-5-yl)phenyl)-4-(dimethylamino)but-2-enamide | MS (ES) m/z 468 (M + H). |
| 91 | 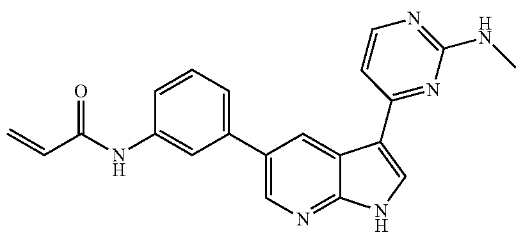 [SMILES: C=CC(=O)Nc1cccc(-c2cnc3[nH]cc(-c4ccnc(NC)n4)c3c2)c1] | N-(3-(3-(2-(methylamino)pyrimidin-4-yl)-1H-pyrrolo[2,3-b]pyridin-5-yl)phenyl)acrylamide | $^1$H NMR (400 MHz, DMSO-d$_6$) δ ppm, 12.30 (s, 1H), 10.26 (s, 1H), 8.54 (s, 1H), 8.43 (s, 1H), 8.20 (s, 1H), 7.45 (br. s, 2H), 7.09 (d, J = 5.48 Hz, 1H), 6.95 (br. s, 1H), 6.52-6.45 (m, 1H), 6.29 (d, J = 16.82 Hz, 1H), 5.79 (d, J = 10.17 Hz, 1H), 2.93 (br. s, 3H). MS (ES) m/z 371 (M + H). |
| 92 | 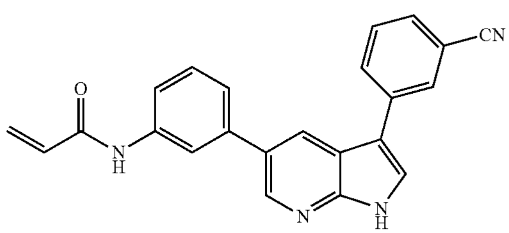 [SMILES: C=CC(=O)Nc1cccc(-c2cnc3[nH]cc(-c4cccc(C#N)c4)c3c2)c1] | N-(3-(3-(3-cyanophenyl)-1H-pyrrolo[2,3-b]pyridin-5-yl)phenyl)acrylamide | $^1$H NMR (400 MHz, DMSO-d$_6$) δ ppm, 12.20 (s, 1H), 10.25 (s, 1H), 8.54 (s, 1H), 8.48 (s, 1H), 8.24 (s, 1H), 8.17 (d, J = 7.43 Hz, 1H), 8.13 (s, 1H), 7.96 (s, 1H), 7.75 (d, J = 7.82 Hz, 1H), 7.71-7.63 (m, 2H), 7.52-7.44 (m, 2H), 6.51-6.44 (m, 1H), 6.29 (d, J = 17.21 Hz, 1H), 5.78 (d, J = 11.74 Hz, 1H). MS (ES) m/z 365 (M + H). |
| 93 | 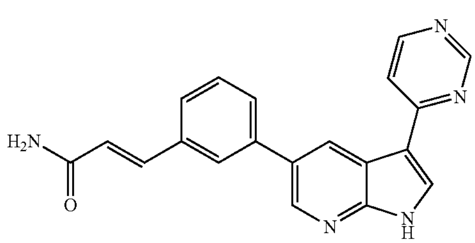 [SMILES: NC(=O)/C=C/c1cccc(-c2cnc3[nH]cc(-c4ccncn4)c3c2)c1] | (E)-3-(3-(3-(pyrimidin-4-yl)-1H-pyrrolo[2,3-b]pyridin-5-yl)phenyl)acrylamide | $^1$H NMR (400 MHz, DMSO-d6) δ ppm, 12.53 (s, 1H), 9.16 (s, 1H), 9.03 (s, 1H), 8.65 (m, 3H), 8.02 (d, J = 5.08 Hz, 1H), 7.91 (s, 1H), 7.75 (d, J = 7.43 Hz, 1H), 7.57 (m, 4H), 7.12 (s, 1H), 6.75 (d, J = 15.65 Hz, 1H). MS (ES) m/z 342 (M + H). |
| 94 | 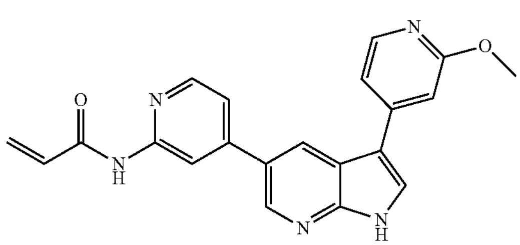 | N-(4-(3-(2-methoxypyridin-4-yl)-1H-pyrrolo[2,3-b]pyridin-5-yl)pyridin-2-yl)acrylamide | MW (calc) 371.40 |

TABLE 1-continued

Compound Examples

| Ex. # | Structure | Name | Spectral Data |
|---|---|---|---|
| 95 | 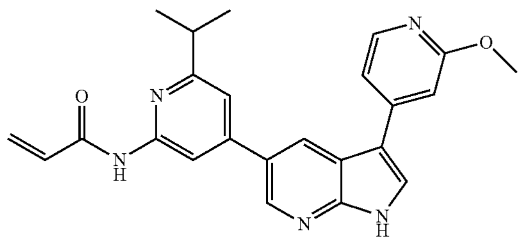 | N-(6-isopropyl-4-(3-(2-methoxypyridin-4-yl)-1H-pyrrolo[2,3-b]pyridin-5-yl)pyridin-2-yl)acrylamide | MW (calc) 413.48 |
| 96 | 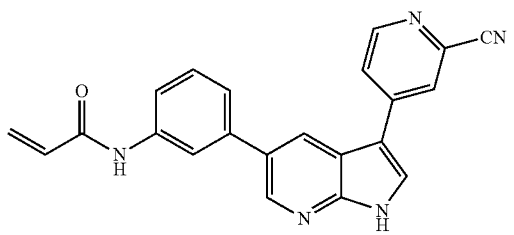 [SMILES: C=CC(=O)Nc1cccc(-c2cnc3[nH]cc(-c4ccnc(C#N)c4)c3c2)c1] | N-(3-(3-(2-cyanopyridin-4-yl)-1H-pyrrolo[2,3-b]pyridin-5-yl)phenyl)acrylamide | MW (calc) 365.40 |
| 97 | 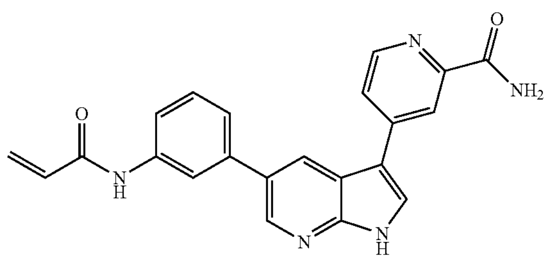 [SMILES: C=CC(=O)Nc1cccc(-c2cnc3[nH]cc(-c4ccnc(C(N)=O)c4)c3c2)c1] | 4-(5-(3-acrylamidophenyl)-1H-pyrrolo[2,3-b]pyridin-3-yl)picolinamide | MW (calc) 383.41 |
| 98 | 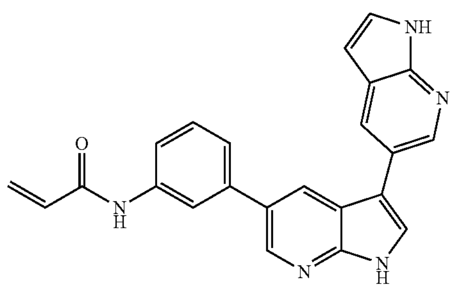 [SMILES: C=CC(=O)Nc1cccc(-c2cnc3[nH]cc(-c4cnc5[nH]ccc5c4)c3c2)c1] | N-(3-(1H,1'H-[3,5'-bipyrrolo[2,3-b]pyridin]-5-yl)phenyl)acrylamide | MW (calc) 379.42 |

The following compounds in Table 2 can generally be made using the methods described above. It is expected that these compounds when made will have activity similar to those that have been prepared.

TABLE 2

| Structure | Name |
|---|---|
| 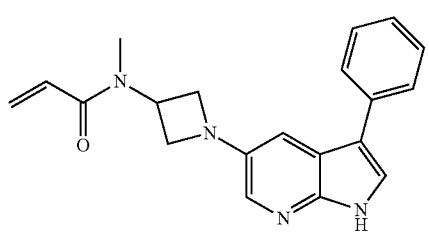 [SMILES: C=CC(=O)N(C)C1CN(c2cnc3[nH]cc(-c4ccccc4)c3c2)C1] | N-methyl-N-(1-(3-phenyl-1H-pyrrolo[2,3-b]pyridin-5-yl)azetidin-3-yl)acrylamide |

TABLE 2-continued

| Structure | Name |
|---|---|
| 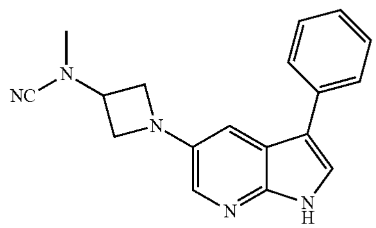 [SMILES: CN(C#N)C1CN(c2cnc3[nH]cc(-c4ccccc4)c3c2)C1] | N-methyl-N-(1-(3-phenyl-1H-pyrrolo[2,3-b]pyridin-5-yl)azetidin-3-yl)cyanamide |
| 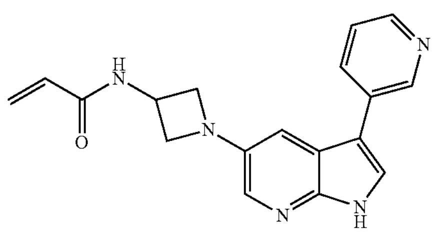 [SMILES: C=CC(=O)NC1CN(c2cnc3[nH]cc(-c4cccnc4)c3c2)C1] | N-(1-(3-(pyridin-3-yl)-1H-pyrrolo[2,3-b]pyridin-5-yl)azetidin-3-yl)acrylamide |
| 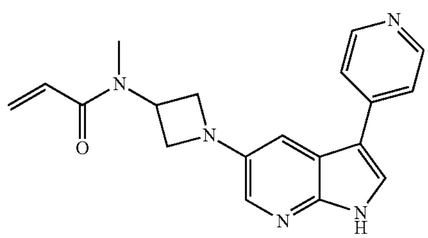 [SMILES: C=CC(=O)N(C)C1CN(c2cnc3[nH]cc(-c4ccncc4)c3c2)C1] | N-methyl-N-(1-(3-(pyridin-4-yl)-1H-pyrrolo[2,3-b]pyridin-5-yl)azetidin-3-yl)acrylamide |
| 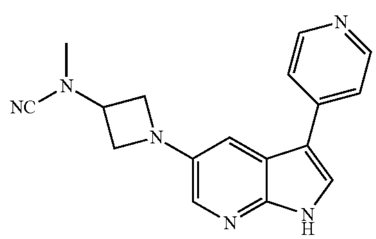 [SMILES: CN(C#N)C1CN(c2cnc3[nH]cc(-c4ccncc4)c3c2)C1] | N-methyl-N-(1-(3-(pyridin-4-yl)-1H-pyrrolo[2,3-b]pyridin-5-yl)azetidin-3-yl)cyanamide |
| 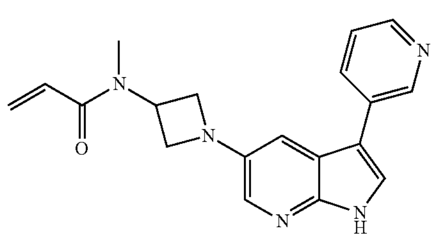 [SMILES: C=CC(=O)N(C)C1CN(c2cnc3[nH]cc(-c4cccnc4)c3c2)C1] | N-methyl-N-(1-(3-(pyridin-3-yl)-1H-pyrrolo[2,3-b]pyridin-5-yl)azetidin-3-yl)acrylamide |
| 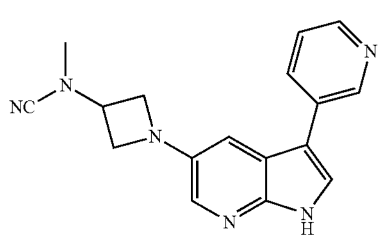 [SMILES: CN(C#N)C1CN(c2cnc3[nH]cc(-c4cccnc4)c3c2)C1] | N-methyl-N-(1-(3-(pyridin-3-yl)-1H-pyrrolo[2,3-b]pyridin-5-yl)azetidin-3-yl)cyanamide |

TABLE 2-continued

| Structure | Name |
|---|---|
| 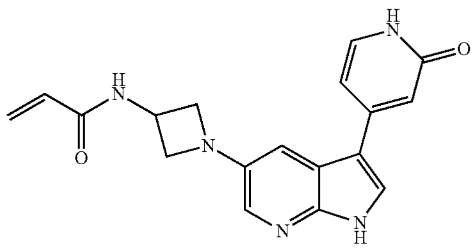 [SMILES: C=CC(=O)NC1CN(c2cnc3[nH]cc(-c4cc[nH]c(=O)c4)c3c2)C1] | N-(1-(3-(2-oxo-1,2-dihydropyridin-4-yl)-1H-pyrrolo[2,3-b]pyridin-5-yl)azetidin-3-yl)acrylamide |
| 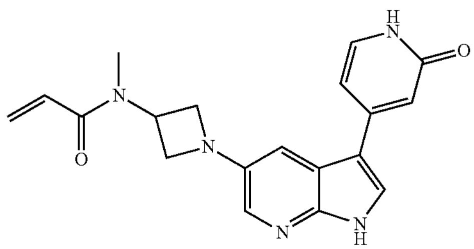 [SMILES: C=CC(=O)N(C)C1CN(c2cnc3[nH]cc(-c4cc[nH]c(=O)c4)c3c2)C1] | N-methyl-N-(1-(3-(2-oxo-1,2-dihydropyridin-4-yl)-1H-pyrrolo[2,3-b]pyridin-5-yl)azetidin-3-yl)acrylamide |
| 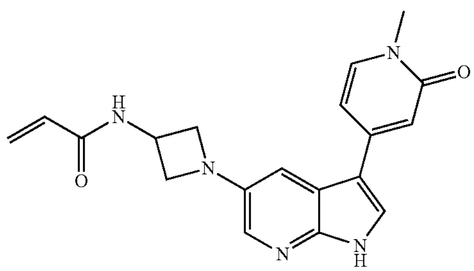 [SMILES: C=CC(=O)NC1CN(c2cnc3[nH]cc(-c4ccn(C)c(=O)c4)c3c2)C1] | N-(1-(3-(1-methyl-2-oxo-1,2-dihydropyridin-4-yl)-1H-pyrrolo[2,3-b]pyridin-5-yl)azetidin-3-yl)acrylamide |
| 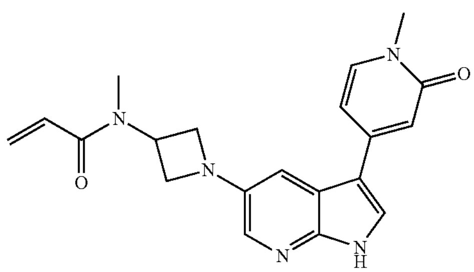 [SMILES: C=CC(=O)N(C)C1CN(c2cnc3[nH]cc(-c4ccn(C)c(=O)c4)c3c2)C1] | N-methyl-N-(1-(3-(1-methyl-2-oxo-1,2-dihydropyridin-4-yl)-1H-pyrrolo[2,3-b]pyridin-5-yl)azetidin-3-yl)acrylamide |
| 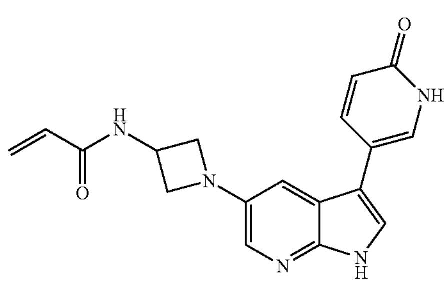 [SMILES: C=CC(=O)NC1CN(c2cnc3[nH]cc(-c4ccc(=O)[nH]c4)c3c2)C1] | N-(1-(3-(6-oxo-1,6-dihydropyridin-3-yl)-1H-pyrrolo[2,3-b]pyridin-5-yl)azetidin-3-yl)acrylamide |
| 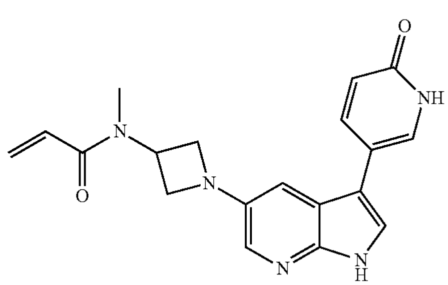 [SMILES: C=CC(=O)N(C)C1CN(c2cnc3[nH]cc(-c4ccc(=O)[nH]c4)c3c2)C1] | N-methyl-N-(1-(3-(6-oxo-1,6-dihydropyridin-3-yl)-1H-pyrrolo[2,3-b]pyridin-5-yl)azetidin-3-yl)acrylamide |

TABLE 2-continued

| Structure | Name |
|---|---|
| 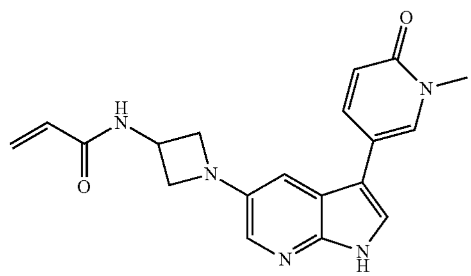 [SMILES: C=CC(=O)NC1CN(c2cnc3[nH]cc(-c4ccc(=O)n(C)c4)c3c2)C1] | N-(1-(3-(1-methyl-6-oxo-1,6-dihydropyridin-3-yl)-1H-pyrrolo[2,3-b]pyridin-5-yl)azetidin-3-yl)acrylamide |
| 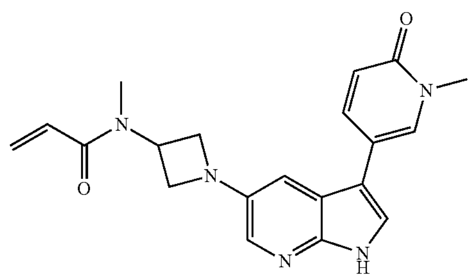 [SMILES: C=CC(=O)N(C)C1CN(c2cnc3[nH]cc(-c4ccc(=O)n(C)c4)c3c2)C1] | N-methyl-N-(1-(3-(1-methyl-6-oxo-1,6-dihydropyridin-3-yl)-1H-pyrrolo[2,3-b]pyridin-5-yl)azetidin-3-yl)acrylamide |
| 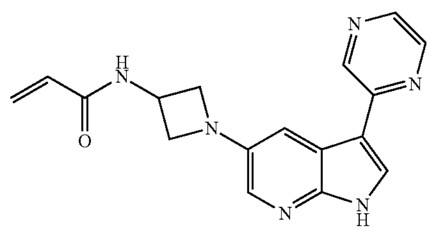 [SMILES: C=CC(=O)NC1CN(c2cnc3[nH]cc(-c4cnccn4)c3c2)C1] | N-(1-(3-(pyrazin-2-yl)-1H-pyrrolo[2,3-b]pyridin-5-yl)azetidin-3-yl)acrylamide |
| 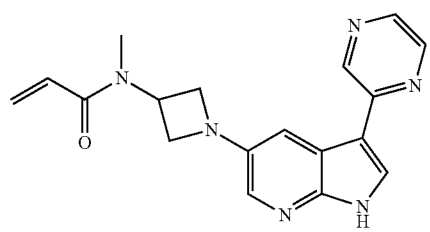 [SMILES: C=CC(=O)N(C)C1CN(c2cnc3[nH]cc(-c4cnccn4)c3c2)C1] | N-methyl-N-(1-(3-(pyrazin-2-yl)-1H-pyrrolo[2,3-b]pyridin-5-yl)azetidin-3-yl)acrylamide |
| 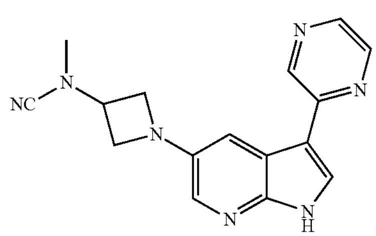 [SMILES: CN(C#N)C1CN(c2cnc3[nH]cc(-c4cnccn4)c3c2)C1] | N-methyl-N-(1-(3-(pyrazin-2-yl)-1H-pyrrolo[2,3-b]pyridin-5-yl)azetidin-3-yl)cyanlamide |
| 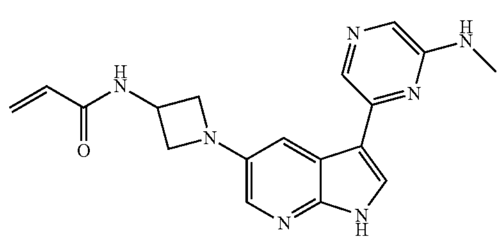 [SMILES: C=CC(=O)NC1CN(c2cnc3[nH]cc(-c4cncc(NC)n4)c3c2)C1] | N-(1-(3-(6-(methylamino)pyrazin-2-yl)-1H-pyrrolo[2,3-b]pyridin-5-yl)azetidin-3-yl)acrylamide |

TABLE 2-continued

| Structure | Name |
|---|---|
| 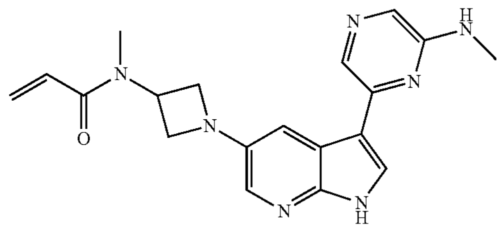 [SMILES: C=CC(=O)N(C)C1CN(c2cnc3[nH]cc(-c4cncc(NC)n4)c3c2)C1] | N-methyl-N-(1-(3-(6-(methylamino)pyrazin-2-yl)-1H-pyrrolo[2,3-b]pyridin-5-yl)azetidin-3-yl)acrylamide |
| 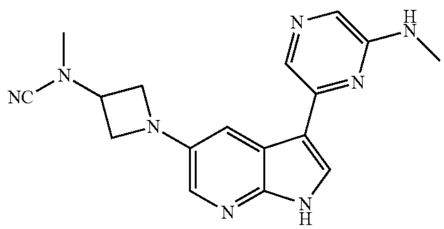 [SMILES: CNc1cncc(-c2c[nH]c3ncc(N4CC(N(C)C#N)C4)cc23)n1] | N-methyl-N-(1-(3-(6-(methylamino)pyrazin-2-yl)-1H-pyrrolo[2,3-b]pyridin-5-yl)azetidin-3-yl)cyanamide |
| 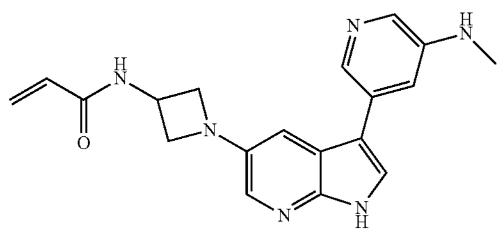 [SMILES: C=CC(=O)NC1CN(c2cnc3[nH]cc(-c4cncc(NC)c4)c3c2)C1] | N-(1-(3-(5-(methylamino)pyrazin-3-yl)-1H-pyrrolo[2,3-b]pyridin-5-yl)azetidin-3-yl)acrylamide |
| 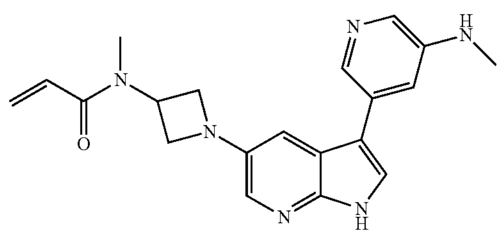 [SMILES: C=CC(=O)N(C)C1CN(c2cnc3[nH]cc(-c4cncc(NC)c4)c3c2)C1] | N-methyl-N-(1-(3-(5-(methylamino)pyridin-3-yl)-1H-pyrrolo[2,3-b]pyridin-5-yl)azetidin-3-yl)acrylamide |
| 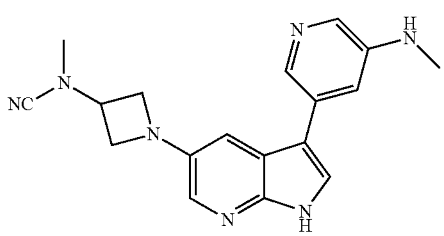 [SMILES: CNc1cncc(-c2c[nH]c3ncc(N4CC(N(C)C#N)C4)cc23)c1] | N-methyl-N-(1-(3-(5-(methylamino)pyridin-3-yl)-1H-pyrrolo[2,3-b]pyridin-5-yl)azetidin-3-yl)cyanamide |
| 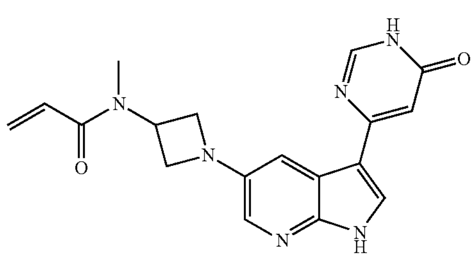 [SMILES: C=CC(=O)N(C)C1CN(c2cnc3[nH]cc(-c4cc(=O)[nH]cn4)c3c2)C1] | N-methyl-N-(1-(3-(6-oxo-1,6-dihydropyrimidin-4-yl)-1H-pyrrolo[2,3-b]pyridin-5-yl)azetidin-3-yl)acrylamide |

TABLE 2-continued

| Structure | Name |
|---|---|
| 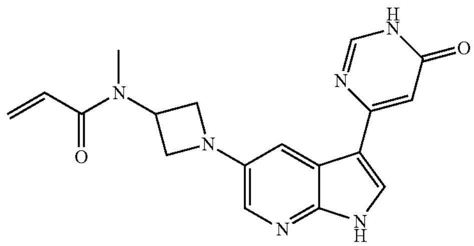 [SMILES: C=CC(=O)N(C)C1CN(c2cnc3[nH]cc(-c4cc(=O)[nH]cn4)c3c2)C1] | N-methyl-N-(1-(3-(6-oxo-1,6-dihydropyrimidin-4-yl)-1H-pyrrolo[2,3-b]pyridin-5-yl)azetidin-3-yl)acrylamide |
| 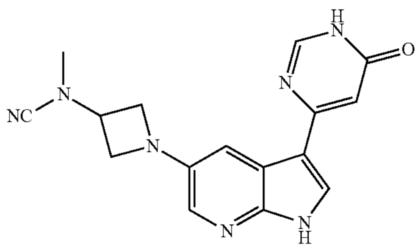 [SMILES: CN(C#N)C1CN(c2cnc3[nH]cc(-c4cc(=O)[nH]cn4)c3c2)C1] | N-methyl-N-(1-(3-(6-oxo-1,6-dihydropyrimidin-4-yl)-1H-pyrrolo[2,3-b]pyridin-5-yl)azetidin-3-yl)cyanamide |
| 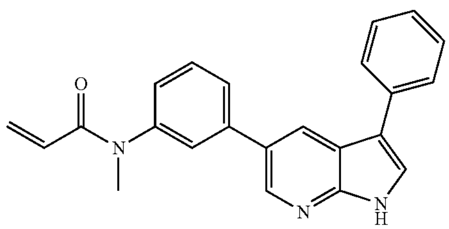 [SMILES: C=CC(=O)N(C)c1cccc(-c2cnc3[nH]cc(-c4ccccc4)c3c2)c1] | N-methyl-N-(3-(3-phenyl-1H-pyrrolo[2,3-b]pyridin-5-yl)phenyl)acrylamide |
| 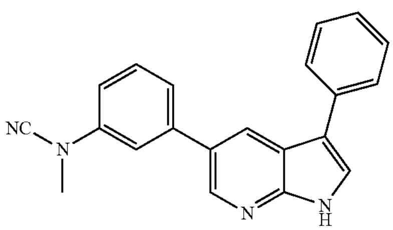 [SMILES: CN(C#N)c1cccc(-c2cnc3[nH]cc(-c4ccccc4)c3c2)c1] | N-methyl-N-(3-(3-phenyl-1H-pyrrolo[2,3-b]pyridin-5-yl)phenyl)cyanamide |
| 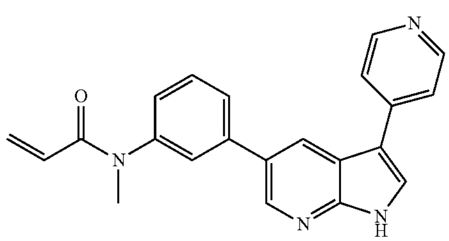 [SMILES: C=CC(=O)N(C)c1cccc(-c2cnc3[nH]cc(-c4ccncc4)c3c2)c1] | N-methyl-N-(3-(3-(pyridin-4-yl)-1H-pyrrolo[2,3-b]pyridin-5-yl)phenyl)acrylamide |
| 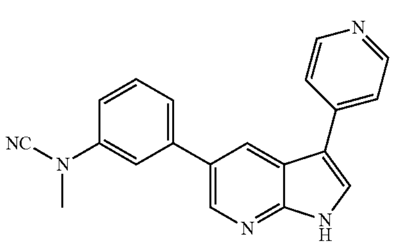 [SMILES: CN(C#N)c1cccc(-c2cnc3[nH]cc(-c4ccncc4)c3c2)c1] | N-methyl-N-(3-(3-(pyridin-4-yl)-1H-pyrrolo[2,3-b]pyridin-5-yl)phenyl)cyanamide |

TABLE 2-continued

| Structure | Name |
|---|---|
| 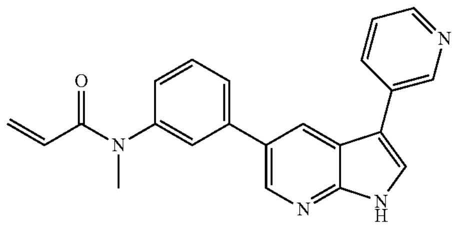 [SMILES: C=CC(=O)N(C)c1cccc(-c2cnc3[nH]cc(-c4cccnc4)c3c2)c1] | N-methyl-N-(3-(3-(pyridin-3-yl)-1H-pyrrolo[2,3-b]pyridin-5-yl)phenyl)acrylamide |
| 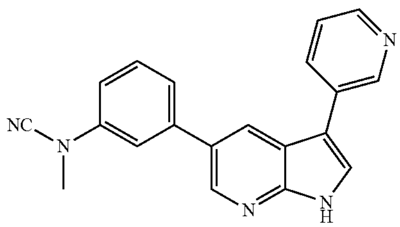 [SMILES: CN(C#N)c1cccc(-c2cnc3[nH]cc(-c4cccnc4)c3c2)c1] | N-methyl-N-(3-(3-(pyridin-3-yl)-1H-pyrrolo[2,3-b]pyridin-5-yl)phenyl)cyanamide |
| | O=C(C=C)NC1=CC(C2=CN=C(NC=C3C4=CC(NC=C4)=O)C3=C2)=CC=C1 |
| 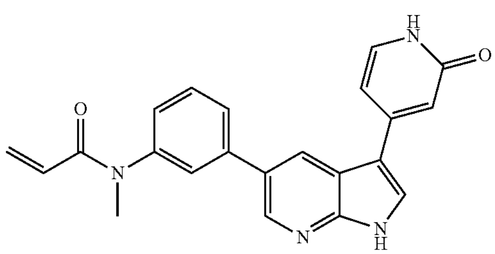 [SMILES: C=CC(=O)N(C)c1cccc(-c2cnc3[nH]cc(-c4cc[nH]c(=O)c4)c3c2)c1] | N-methyl-N-(3-(3-(2-oxo-1,2-dihydropyridin-4-yl)-1H-pyrrolo[2,3-b]pyridin-5-yl)phenyl)acrylamide |
| 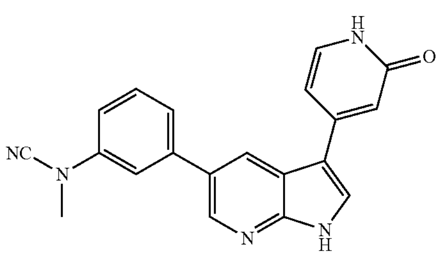 [SMILES: CN(C#N)c1cccc(-c2cnc3[nH]cc(-c4cc[nH]c(=O)c4)c3c2)c1] | N-methyl-N-(3-(3-(2-oxo-1,2-dihydropyridin-4-yl)-1H-pyrrolo[2,3-b]pyridin-5-yl)phenyl)cyanamide |
| 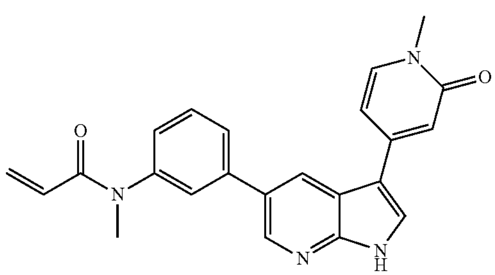 [SMILES: C=CC(=O)N(C)c1cccc(-c2cnc3[nH]cc(-c4ccn(C)c(=O)c4)c3c2)c1] | N-methyl-N-(3-(3-(1-methyl-2-oxo-1,2-dihydropyridin-4-yl)-1H-pyrrolo[2,3-b]pyridin-5-yl)phenyl)acrylamide |

TABLE 2-continued

| Structure | Name |
|---|---|
| 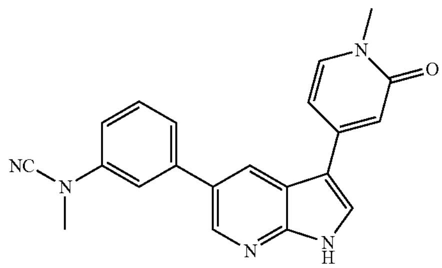 [SMILES: CN(C#N)c1cccc(-c2cnc3[nH]cc(-c4ccn(C)c(=O)c4)c3c2)c1] | N-methyl-N-(3-(3-(1-methyl-2-oxo-1,2-dihydropyridin-4-yl)-1H-pyrrolo[2,3-b]pyridin-5-yl)phenyl)cyanamide |
| 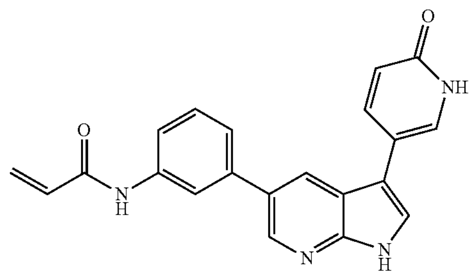 [SMILES: C=CC(=O)Nc1cccc(-c2cnc3[nH]cc(-c4ccc(=O)[nH]c4)c3c2)c1] | N-(3-(3-(6-oxo-1,6-dihydropyridin-3-yl)-1H-pyrrolo[2,3-b]pyridin-5-yl)phenyl)acrylamide |
| 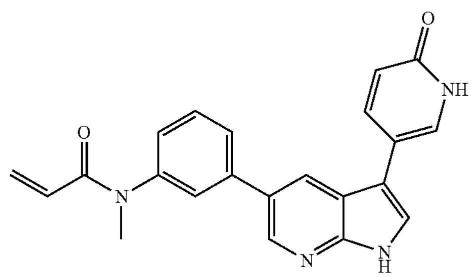 [SMILES: C=CC(=O)N(C)c1cccc(-c2cnc3[nH]cc(-c4ccc(=O)[nH]c4)c3c2)c1] | N-methyl-N-(3-(3-(6-oxo-1,6-dihydropyridin-3-yl)-1H-pyrrolo[2,3-b]pyridin-5-yl)phenyl)acrylamide |
| 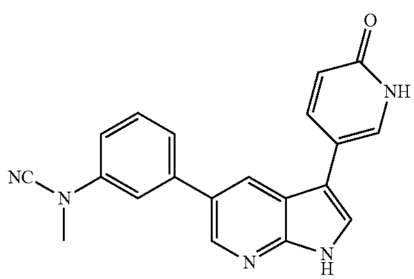 [SMILES: CN(C#N)c1cccc(-c2cnc3[nH]cc(-c4ccc(=O)[nH]c4)c3c2)c1] | N-methyl-N-(3-(3-(6-oxo-1,6-dihydropyridin-3-yl)-1H-pyrrolo[2,3-b]pyridin-5-yl)phenyl)cyanamide |
| 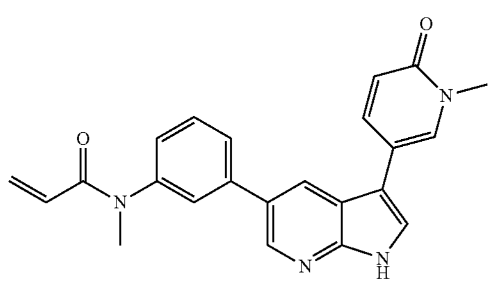 [SMILES: C=CC(=O)N(C)c1cccc(-c2cnc3[nH]cc(-c4ccc(=O)n(C)c4)c3c2)c1] | N-methyl-N-(3-(3-(1-methyl-6-oxo-1,6-dihydropyridin-3-yl)-1H-pyrrolo[2,3-b]pyridin-5-yl)phenyl)acrylamide |

TABLE 2-continued

| Structure | Name |
|---|---|
| 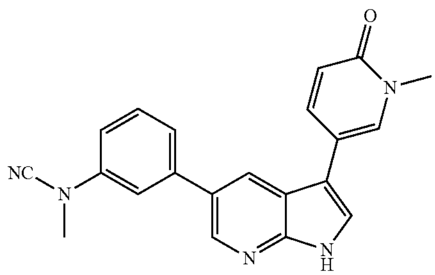 [SMILES: CN(C#N)c1cccc(-c2cnc3[nH]cc(-c4ccc(=O)n(C)c4)c3c2)c1] | N-methyl-N-(3-(3-(1-methyl-6-oxo-1,6-dihydropyridin-3-yl)-1H-pyrrolo[2,3-b]pyridin-5-yl)phenyl)cyanamide |
| 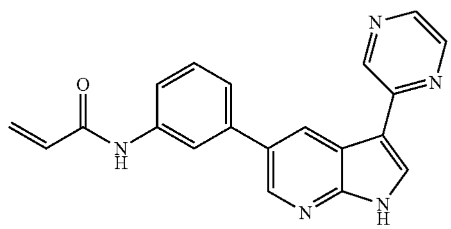 [SMILES: C=CC(=O)Nc1cccc(-c2cnc3[nH]cc(-c4cnccn4)c3c2)c1] | N-(3-(3-(pyrazin-2-yl)-1H-pyrrolo[2,3-b]pyridin-5-yl)phenyl)acrylamide |
| 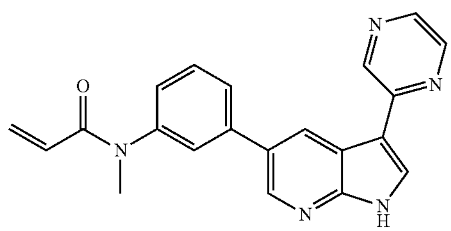 [SMILES: C=CC(=O)N(C)c1cccc(-c2cnc3[nH]cc(-c4cnccn4)c3c2)c1] | N-methyl-N-(3-(3-(pyrazin-2-yl)-1H-pyrrolo[2,3-b]pyridin-5-yl)phenyl)acrylamide |
| 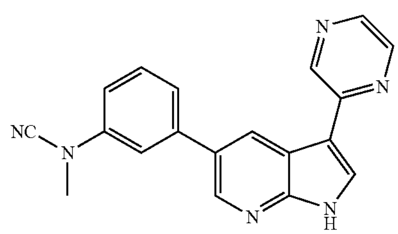 [SMILES: CN(C#N)c1cccc(-c2cnc3[nH]cc(-c4cnccn4)c3c2)c1] | N-methyl-N-(3-(3-(pyrazin-2-yl)-1H-pyrrolo[2,3-b]pyridin-5-yl)phenyl)cyanamide |
| 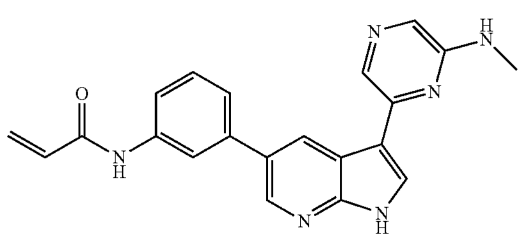 [SMILES: C=CC(=O)Nc1cccc(-c2cnc3[nH]cc(-c4cncc(NC)n4)c3c2)c1] | N-(3-(3-(6-(methylamino)pyrazin-2-yl)-1H-pyrrolo[2,3-b]pyridin-5-yl)phenyl)acrylamide |
| 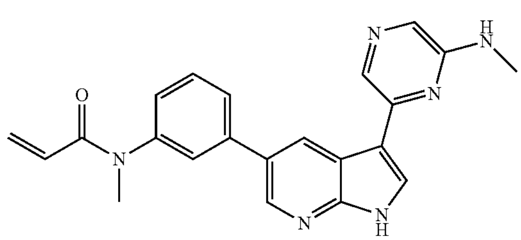 [SMILES: C=CC(=O)N(C)c1cccc(-c2cnc3[nH]cc(-c4cncc(NC)n4)c3c2)c1] | N-methyl-N-(3-(3-(6-(methylamino)pyrazin-2-yl)-1H-pyrrolo[2,3-b]pyridin-5-yl)phenyl)acrylamide |

TABLE 2-continued

| Structure | Name |
|---|---|
| 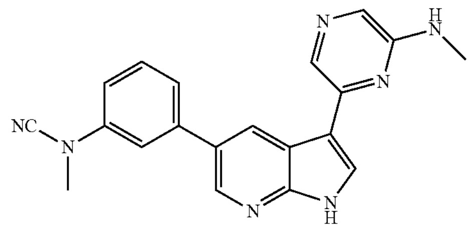 [SMILES: CNc1cncc(-c2c[nH]c3ncc(-c4cccc(N(C)C#N)c4)cc23)n1] | N-methyl-N-(3-(3-(6-(methylamino)pyrazin-2-yl)-1H-pyrrolo[2,3-b]pyridin-5-yl)phenyl)cyanamide |
| 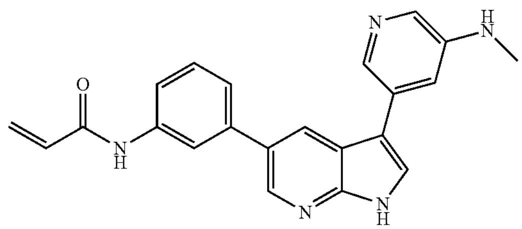 [SMILES: C=CC(=O)Nc1cccc(-c2cnc3[nH]cc(-c4cncc(NC)c4)c3c2)c1] | N-(3-(3-(5-(methylamino)pyridin-3-yl)-1H-pyrrolo[2,3-b]pyridin-5-yl)phenyl)acrylamide |
| 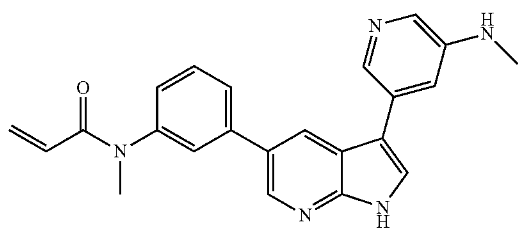 [SMILES: C=CC(=O)N(C)c1cccc(-c2cnc3[nH]cc(-c4cncc(NC)c4)c3c2)c1] | N-methyl-N-(3-(3-(5-(methylamino)pyridin-3-yl)-1H-pyrrolo[2,3-b]pyridin-5-yl)phenyl)acrylamide |
| 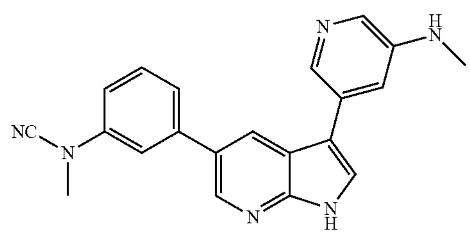 [SMILES: CNc1cncc(-c2c[nH]c3ncc(-c4cccc(N(C)C#N)c4)cc23)c1] | N-methyl-N-(3-(3-(5-(methylamino)pyridin-3-yl)-1H-pyrrolo[2,3-b]pyridin-5-yl)phenyl)cyanamide |
| 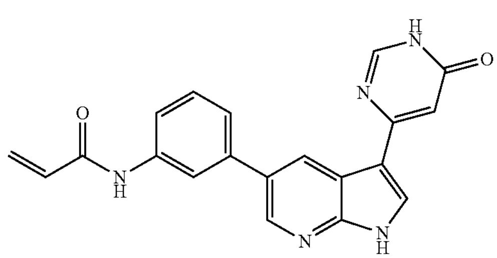 [SMILES: C=CC(=O)Nc1cccc(-c2cnc3[nH]cc(-c4cc(=O)[nH]cn4)c3c2)c1] | N-(3-(3-(6-oxo-1,6-dihydropyrimidin-4-yl)-1H-pyrrolo[2,3-b]pyridin-5-yl)phenyl)acrylamide |
| 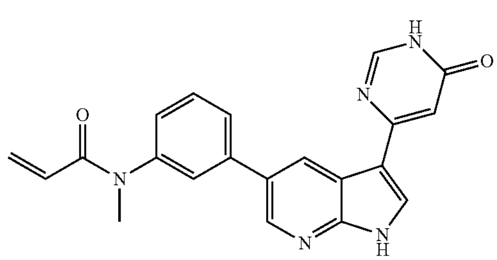 [SMILES: C=CC(=O)N(C)c1cccc(-c2cnc3[nH]cc(-c4cc(=O)[nH]cn4)c3c2)c1] | N-methyl-N-(3-(3-(6-oxo-1,6-dihydropyrimidin-4-yl)-1H-pyrrolo[2,3-b]pyridin-5-yl)phenyl)acrylamide |

TABLE 2-continued

| Structure | Name |
|---|---|
| 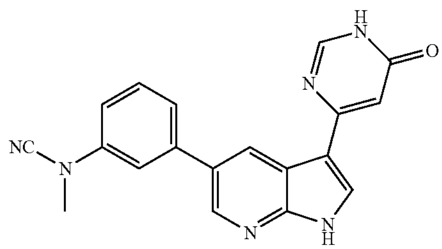 [SMILES: CN(C#N)c1cccc(-c2cnc3[nH]cc(-c4cc(=O)[nH]cn4)c3c2)c1] | N-methyl-N-(3-(3-(6-oxo-1,6-dihydropyrimidin-4-yl)-1H-pyrrolo[2,3-b]pyridin-5-yl)phenyl)cyanamide |
| 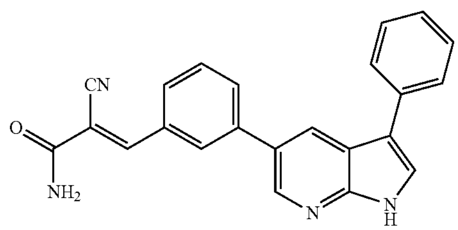 [SMILES: N#C/C(=C\c1cccc(-c2cnc3[nH]cc(-c4ccccc4)c3c2)c1)C(N)=O] | (E)-2-cyano-3-(3-(3-phenyl-1H-pyrrolo[2,3-b]pyridin-5-yl)phenyl)acrylamide |
| 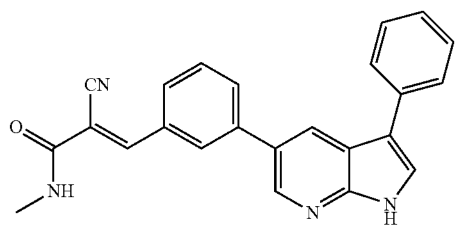 [SMILES: CNC(=O)/C(C#N)=C/c1cccc(-c2cnc3[nH]cc(-c4ccccc4)c3c2)c1] | (E)-2-cyano-N-methyl-3-(3-(3-phenyl-1H-pyrrolo[2,3-b]pyridin-5-yl)phenyl)acrylamide |
| 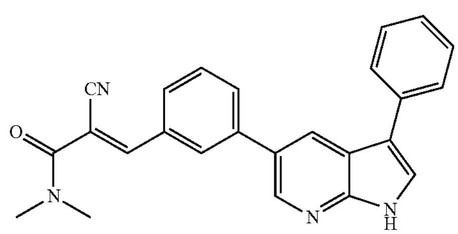 [SMILES: CN(C)C(=O)/C(C#N)=C/c1cccc(-c2cnc3[nH]cc(-c4ccccc4)c3c2)c1] | (E)-2-cyano-N,N-dimethyl-3-(3-(3-phenyl-1H-pyrrolo[2,3-b]pyridin-5-yl)phenyl)acrylamide |
| 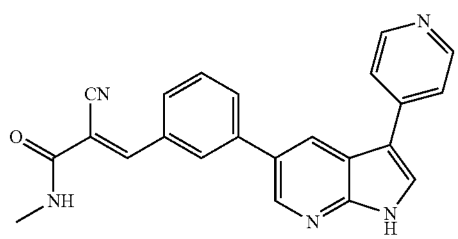 [SMILES: CNC(=O)/C(C#N)=C/c1cccc(-c2cnc3[nH]cc(-c4ccncc4)c3c2)c1] | (E)-2-cyano-N-methyl-3-(3-(3-(pyridin-4-yl)-1H-pyrrolo[2,3-b]pyridin-5-yl)phenyl)acrylamide |
| 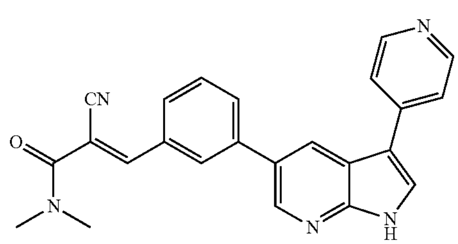 [SMILES: CN(C)C(=O)/C(C#N)=C/c1cccc(-c2cnc3[nH]cc(-c4ccncc4)c3c2)c1] | (E)-2-cyano-N,N-dimethyl-3-(3-(3-(pyridin-4-yl)-1H-pyrrolo[2,3-b]pyridin-5-yl)phenyl)acrylamide |

TABLE 2-continued

| Structure | Name |
|---|---|
| 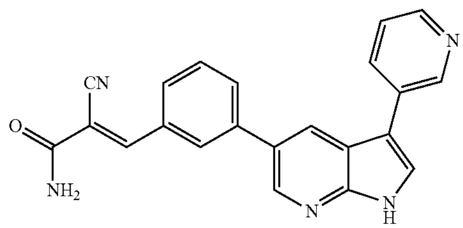 [SMILES: N#C/C(=C\c1cccc(-c2cnc3[nH]cc(-c4cccnc4)c3c2)c1)C(N)=O] | (E)-2-cyano-3-(3-(3-(pyridin-3-yl)-1H-pyrrolo[2,3-b]pyridin-5-yl)phenyl)acrylamide |
| 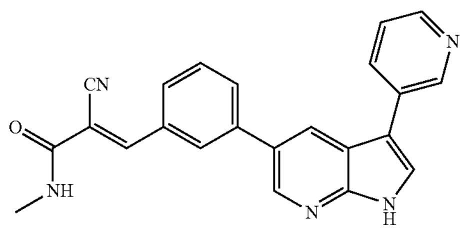 [SMILES: CNC(=O)/C(C#N)=C/c1cccc(-c2cnc3[nH]cc(-c4cccnc4)c3c2)c1] | (E)-2-cyano-N-methyl-3-(3-(3-(pyridin-3-yl)-1H-pyrrolo[2,3-b]pyridin-5-yl)phenyl)acrylamide |
| 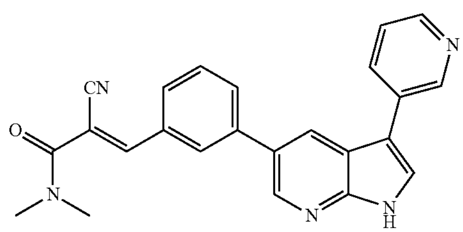 [SMILES: CN(C)C(=O)/C(C#N)=C/c1cccc(-c2cnc3[nH]cc(-c4cccnc4)c3c2)c1] | (E)-2-cyano-N,N-dimethyl-3-(3-(3-(pyridin-3-yl)-1H-pyrrolo[2,3-b]pyridin-5-yl)phenyl)acrylamide |
| 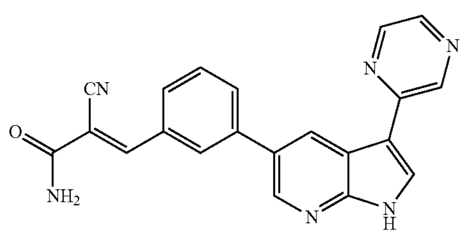 [SMILES: N#C/C(=C\c1cccc(-c2cnc3[nH]cc(-c4cnccn4)c3c2)c1)C(N)=O] | (E)-2-cyano-3-(3-(3-(pyrazin-2-yl)-1H-pyrrolo[2,3-b]pyridin-5-yl)phenyl)acrylamide |
| 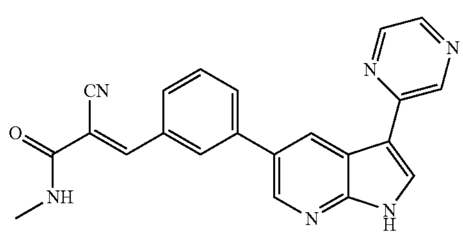 [SMILES: CNC(=O)/C(C#N)=C/c1cccc(-c2cnc3[nH]cc(-c4cnccn4)c3c2)c1] | (E)-2-cyano-N-methyl-3-(3-(3-(pyrazin-2-yl)-1H-pyrrolo[2,3-b]pyridin-5-yl)phenyl)acrylamide |
| 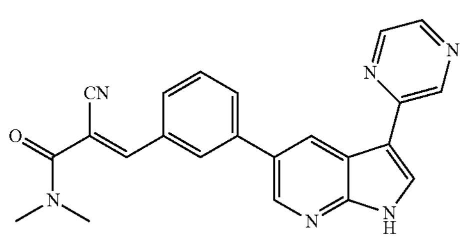 [SMILES: CN(C)C(=O)/C(C#N)=C/c1cccc(-c2cnc3[nH]cc(-c4cnccn4)c3c2)c1] | (E)-2-cyano-N,N-dimethyl-3-(3-(3-(pyrazin-2-yl)-1H-pyrrolo[2,3-b]pyridin-5-yl)phenyl)acrylamide |

TABLE 2-continued

| Structure | Name |
|---|---|
| 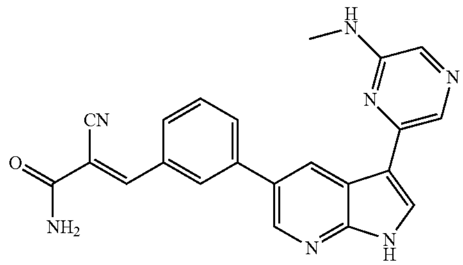 [SMILES: CNc1cncc(-c2c[nH]c3ncc(-c4cccc(/C=C(\C#N)C(N)=O)c4)cc23)n1] | (E)-2-cyano-3-(3-(3-(6-(methylamino)pyrazin-2-yl)-1H-pyrrolo[2,3-b]pyridin-5-yl)phenyl)acrylamide |
| 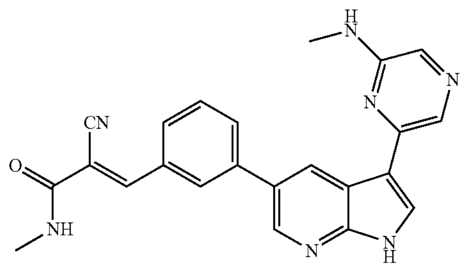 [SMILES: CNC(=O)/C(C#N)=C/c1cccc(-c2cnc3[nH]cc(-c4cncc(NC)n4)c3c2)c1] | (E)-2-cyano-N-methyl-3-(3-(3-(6-(methylamino)pyrazin-2-yl)-1H-pyrrolo[2,3-b]pyridin-5-yl)phenyl)acrylamide |
| 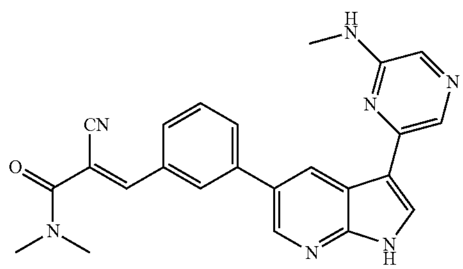 [SMILES: CNc1cncc(-c2c[nH]c3ncc(-c4cccc(/C=C(\C#N)C(=O)N(C)C)c4)cc23)n1] | (E)-2-cyano-N,N-dimethyl-3-(3-(3-(6-(methylamino)pyrazin-2-yl)-1H-pyrrolo[2,3-b]pyridin-5-yl)phenyl)acrylamide |
| 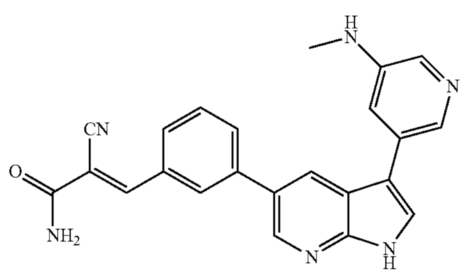 [SMILES: CNc1cncc(-c2c[nH]c3ncc(-c4cccc(/C=C(\C#N)C(N)=O)c4)cc23)c1] | (E)-2-cyano-3-(3-(3-(5-(methylamino)pyridin-3-yl)-1H-pyrrolo[2,3-b]pyridin-5-yl)phenyl)acrylamide |
| 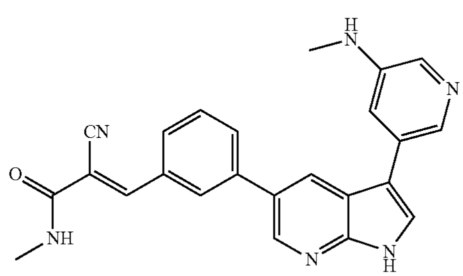 [SMILES: CNC(=O)/C(C#N)=C/c1cccc(-c2cnc3[nH]cc(-c4cncc(NC)c4)c3c2)c1] | (E)-2-cyano-N-methyl-3-(3-(3-(5-(methylamino)pyridin-3-yl)-1H-pyrrolo[2,3-b]pyridin-5-yl)phenyl)acrylamide |

TABLE 2-continued

| Structure | Name |
| --- | --- |
| 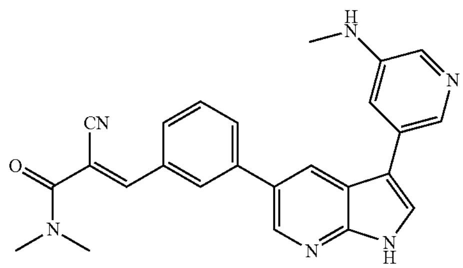 [SMILES: CNc1cncc(-c2c[nH]c3ncc(-c4cccc(/C=C(\C#N)C(=O)N(C)C)c4)cc23)c1] | (E)-2-cyano-N,N-dimethyl-3-(3-(3-(5-(methylamino)pyridin-3-yl)-1H-pyrrolo[2,3-b]pyridin-5-yl)phenyl)acrylamide |
| 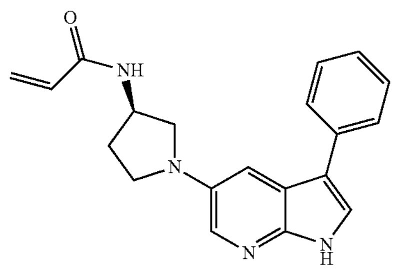 [SMILES: C=CC(=O)N[C@@H]1CCN(c2cnc3[nH]cc(-c4ccccc4)c3c2)C1] | (R)-N-(1-(3-phenyl-1H-pyrrolo[2,3-b]pyridin-5-yl)pyrrolidin-3-yl)acrylamide |
| 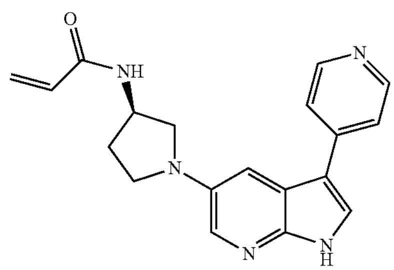 [SMILES: C=CC(=O)N[C@@H]1CCN(c2cnc3[nH]cc(-c4ccncc4)c3c2)C1] | (R)-N-(1-(3-(pyridin-4-yl)-1H-pyrrolo[2,3-b]pyridin-5-yl)pyrrolidin-3-yl)acrylamide |
| 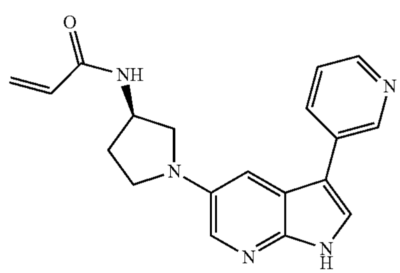 [SMILES: C=CC(=O)N[C@@H]1CCN(c2cnc3[nH]cc(-c4cccnc4)c3c2)C1] | (R)-N-(1-(3-(pyridin-3-yl)-1H-pyrrolo[2,3-b]pyridin-5-yl)pyrrolidin-3-yl)acrylamide |
| 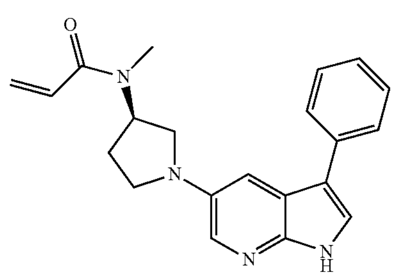 [SMILES: C=CC(=O)N(C)[C@@H]1CCN(c2cnc3[nH]cc(-c4ccccc4)c3c2)C1] | (R)-N-methyl-N-(1-(3-phenyl-1H-pyrrolo[2,3-b]pyridin-5-yl)pyrrolidin-3-yl)acrylamide |

TABLE 2-continued

| Structure | Name |
|---|---|
| 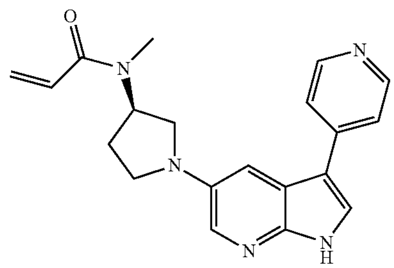 [SMILES: C=CC(=O)N(C)[C@@H]1CCN(c2cnc3[nH]cc(-c4ccncc4)c3c2)C1] | (R)-N-methyl-N-(1-(3-(pyridin-4-yl)-1H-pyrrolo[2,3-b]pyridin-5-yl)pyrrolidin-3-yl)acrylamide |
| 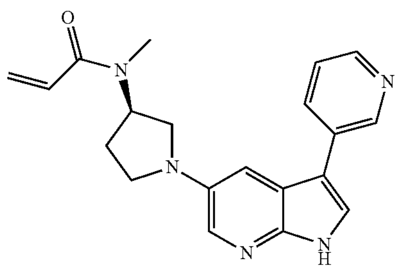 [SMILES: C=CC(=O)N(C)[C@@H]1CCN(c2cnc3[nH]cc(-c4cccnc4)c3c2)C1] | (R)-N-methyl-N-(1-(3-(pyridin-3-yl)-1H-pyrrolo[2,3-b]pyridin-5-yl)pyrrolidin-3-yl)acrylamide |
| 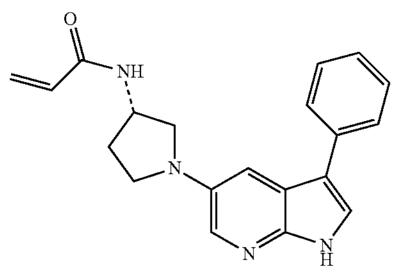 [SMILES: C=CC(=O)N[C@H]1CCN(c2cnc3[nH]cc(-c4ccccc4)c3c2)C1] | (S)-N-(1-(3-phenyl-1H-pyrrolo[2,3-b]pyridin-5-yl)pyrrolidin-3-yl)acrylamide |
| 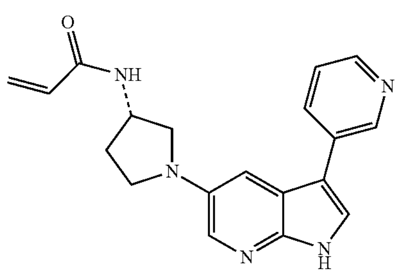 [SMILES: C=CC(=O)N[C@H]1CCN(c2cnc3[nH]cc(-c4cccnc4)c3c2)C1] | (S)-N-(1-(3-(pyridin-3-yl)-1H-pyrrolo[2,3-b]pyridin-5-yl)pyrrolidin-3-yl)acrylamide |
| 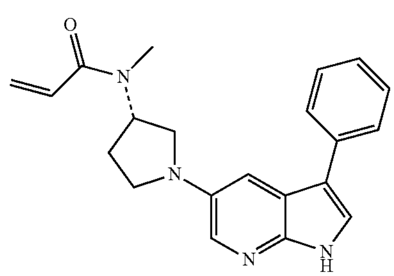 [SMILES: C=CC(=O)N(C)[C@H]1CCN(c2cnc3[nH]cc(-c4ccccc4)c3c2)C1] | (S)-N-methyl-N-(1-(3-phenyl-1H-pyrrolo[2,3-b]pyridin-5-yl)pyrrolidin-3-yl)acrylamide |

TABLE 2-continued

| Structure | Name |
|---|---|
| 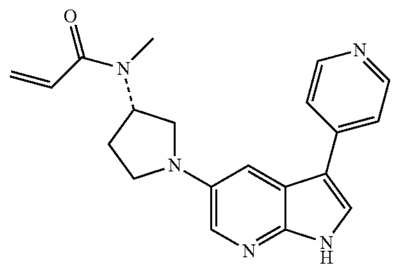 [SMILES: C=CC(=O)N(C)[C@H]1CCN(c2cnc3[nH]cc(-c4ccncc4)c3c2)C1] | (S)-N-methyl-N-(1-(3-(pyridin-4-yl)-1H-pyrrolo[2,3-b]pyridin-5-yl)pyrrolidin-3-yl)acrylamide |
| 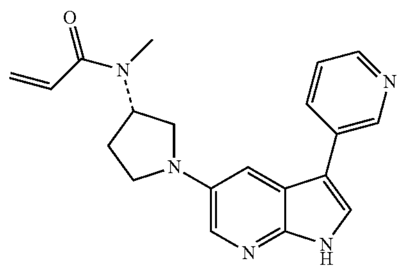 [SMILES: C=CC(=O)N(C)[C@H]1CCN(c2cnc3[nH]cc(-c4cccnc4)c3c2)C1] | (S)-N-methyl-N-(1-(3-(pyridin-3-yl)-1H-pyrrolo[2,3-b]pyridin-5-yl)pyrrolidin-3-yl)acrylamide |
| 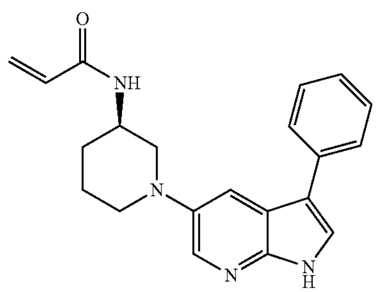 [SMILES: C=CC(=O)N[C@@H]1CCCN(c2cnc3[nH]cc(-c4ccccc4)c3c2)C1] | (R)-N-(1-(3-phenyl-1H-pyrrolo[2,3-b]pyridin-5-yl)piperidin-3-yl)acrylamide |
| 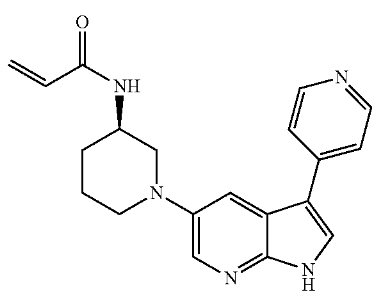 [SMILES: C=CC(=O)N[C@@H]1CCCN(c2cnc3[nH]cc(-c4ccncc4)c3c2)C1] | (R)-N-(1-(3-(pyridin-4-yl)-1H-pyrrolo[2,3-b]pyridin-5-yl)piperidin-3-yl)acrylamide |
| 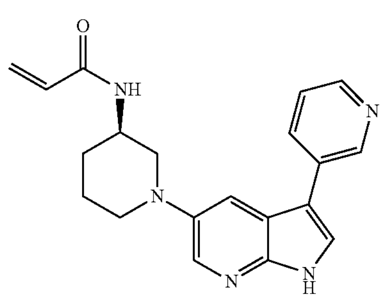 [SMILES: C=CC(=O)N[C@@H]1CCCN(c2cnc3[nH]cc(-c4cccnc4)c3c2)C1] | (R)-N-(1-(3-(pyridin-3-yl)-1H-pyrrolo[2,3-b]pyridin-5-yl)piperidin-3-yl)acrylamide |

TABLE 2-continued

| Structure | Name |
|---|---|
| 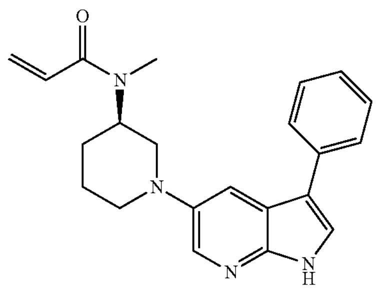 [SMILES: C=CC(=O)N(C)[C@@H]1CCCN(c2cnc3[nH]cc(-c4ccccc4)c3c2)C1] | (R)-N-methyl-N-(1-(3-phenyl-1H-pyrrolo[2,3-b]pyridin-5-yl)piperidin-3-yl)acrylamide |
| 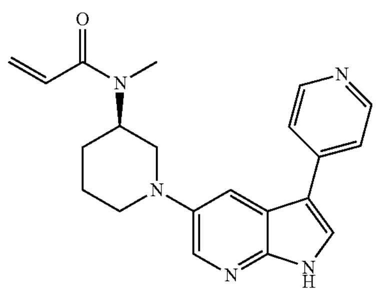 [SMILES: C=CC(=O)N(C)[C@@H]1CCCN(c2cnc3[nH]cc(-c4ccncc4)c3c2)C1] | (R)-N-methyl-N-(1-(3-(pyridin-4-yl)-1H-pyrrolo[2,3-b]pyridin-5-yl)piperidin-3-yl)acrylamide |
| 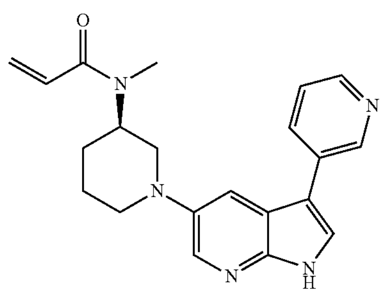 [SMILES: C=CC(=O)N(C)[C@@H]1CCCN(c2cnc3[nH]cc(-c4cccnc4)c3c2)C1] | (R)-N-methyl-N-(1-(3-(pyridin-3-yl)-1H-pyrrolo[2,3-b]pyridin-5-yl)piperidin-3-yl)acrylamide |
| 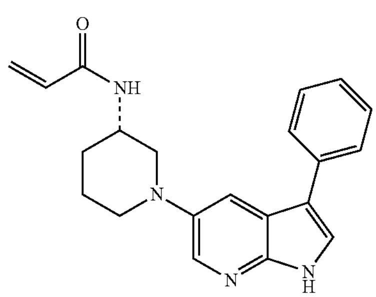 [SMILES: C=CC(=O)N[C@H]1CCCN(c2cnc3[nH]cc(-c4ccccc4)c3c2)C1] | (S)-N-(1-(3-phenyl-1H-pyrrolo[2,3-b]pyridin-5-yl)piperidin-3-yl)acrylamide |
| 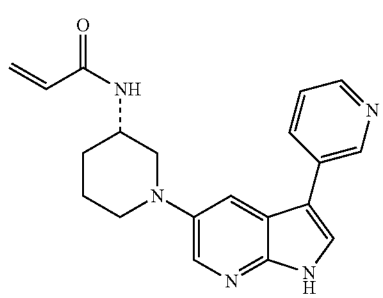 [SMILES: C=CC(=O)N[C@H]1CCCN(c2cnc3[nH]cc(-c4cccnc4)c3c2)C1] | (S)-N-(1-(3-(pyridin-3-yl)-1H-pyrrolo[2,3-b]pyridin-5-yl)piperidin-3-yl)acrylamide |

TABLE 2-continued

| Structure | Name |
|---|---|
| 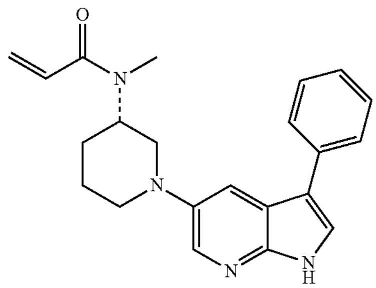 [SMILES: C=CC(=O)N(C)[C@H]1CCCN(c2cnc3[nH]cc(-c4ccccc4)c3c2)C1] | (S)-N-methyl-N-(1-(3-phenyl-1H-pyrrolo[2,3-b]pyridin-5-yl)piperidin-3-yl)acrylamide |
| 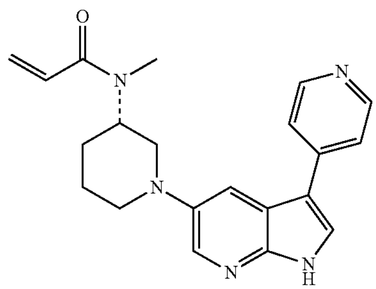 [SMILES: C=CC(=O)N(C)[C@H]1CCCN(c2cnc3[nH]cc(-c4ccncc4)c3c2)C1] | (S)-N-methyl-N-(1-(3-(pyridin-4-yl)-1H-pyrrolo[2,3-b]pyridin-5-yl)piperidin-3-yl)acrylamide |
| 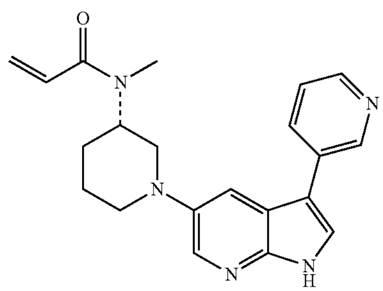 [SMILES: C=CC(=O)N(C)[C@H]1CCCN(c2cnc3[nH]cc(-c4cccnc4)c3c2)C1] | (S)-N-methyl-N-(1-(3-(pyridin-3-yl)-1H-pyrrolo[2,3-b]pyridin-5-yl)piperidin-3-yl)acrylamide |
| 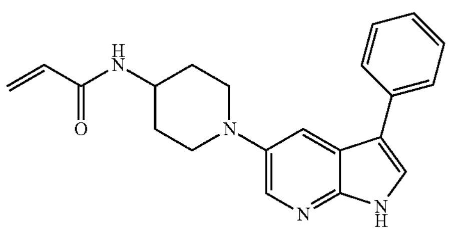 [SMILES: C=CC(=O)NC1CCN(c2cnc3[nH]cc(-c4ccccc4)c3c2)CC1] | N-(1-(3-phenyl-1H-pyrrolo[2,3-b]pyridin-5-yl)piperidin-4-yl)acrylamide |
| 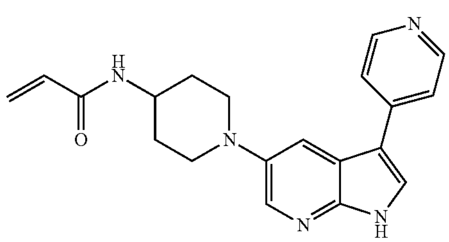 [SMILES: C=CC(=O)NC1CCN(c2cnc3[nH]cc(-c4ccncc4)c3c2)CC1] | N-(1-(3-(pyridin-4-yl)-1H-pyrrolo[2,3-b]pyridin-5-yl)piperidin-4-yl)acrylamide |
| 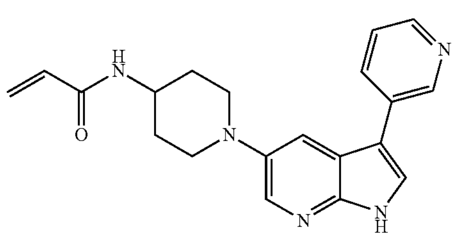 [SMILES: C=CC(=O)NC1CCN(c2cnc3[nH]cc(-c4cccnc4)c3c2)CC1] | N-(1-(3-(pyridin-3-yl)-1H-pyrrolo[2,3-b]pyridin-5-yl)piperidin-4-yl)acrylamide |

TABLE 2-continued

| Structure | Name |
|---|---|
| 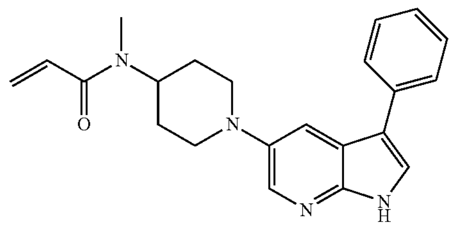 [SMILES: C=CC(=O)N(C)C1CCN(c2cnc3[nH]cc(-c4ccccc4)c3c2)CC1] | N-methyl-N-(1-(3-phenyl-1H-pyrrolo[2,3-b]pyridin-5-yl)piperidin-4-yl)acrylamide |
| 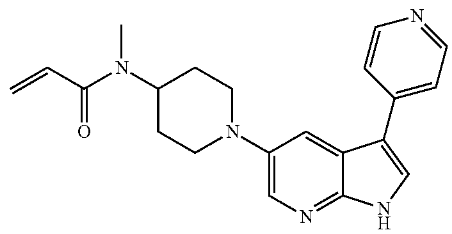 [SMILES: C=CC(=O)N(C)C1CCN(c2cnc3[nH]cc(-c4ccncc4)c3c2)CC1] | N-methyl-N-(1-(3-(pyridin-4-yl)-1H-pyrrolo[2,3-b]pyridin-5-yl)piperidin-4-yl)acrylamide |
| 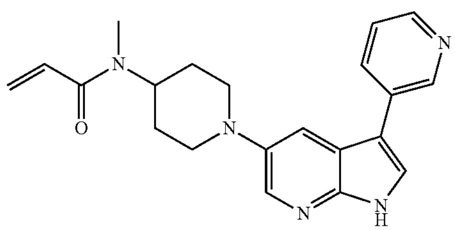 [SMILES: C=CC(=O)N(C)C1CCN(c2cnc3[nH]cc(-c4cccnc4)c3c2)CC1] | N-methyl-N-(1-(3-(pyridin-3-yl)-1H-pyrrolo[2,3-b]pyridin-5-yl)piperidin-4-yl)acrylamide |
| 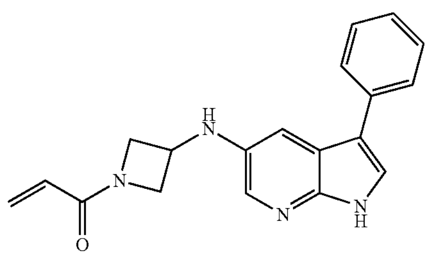 [SMILES: C=CC(=O)N1CC(Nc2cnc3[nH]cc(-c4ccccc4)c3c2)C1] | 1-(3-((3-phenyl-1H-pyrrolo[2,3-b]pyridin-5-yl)amino)azetidin-1-yl)prop-2-en-1-one |
| 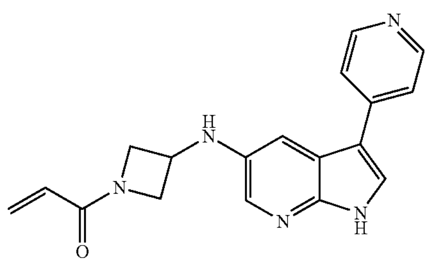 [SMILES: C=CC(=O)N1CC(Nc2cnc3[nH]cc(-c4ccncc4)c3c2)C1] | 1-(3-((3-(pyridin-4-yl)-1H-pyrrolo[2,3-b]pyridin-5-yl)amino)azetidin-1-yl)prop-2-en-1-one |
| 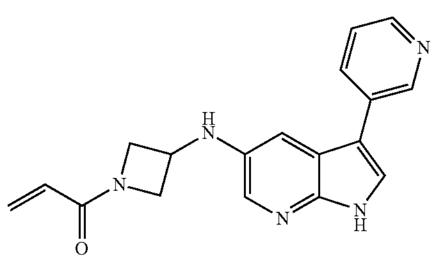 [SMILES: C=CC(=O)N1CC(Nc2cnc3[nH]cc(-c4cccnc4)c3c2)C1] | 1-(3-((3-(pyridin-3-yl)-1H-pyrrolo[2,3-b]pyridin-5-yl)amino)azetidin-1-yl)prop-2-en-1-one |

TABLE 2-continued

| Structure | Name |
|---|---|
| 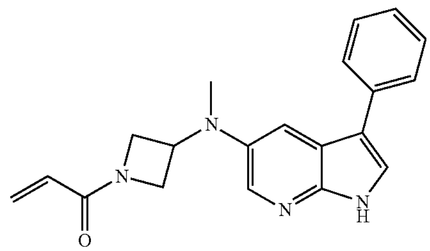 [SMILES: C=CC(=O)N1CC(N(C)c2cnc3[nH]cc(-c4ccccc4)c3c2)C1] | 1-(3-(methyl(3-phenyl-1H-pyrrolo[2,3-b]pyridin-5-yl)amino)azetidin-1-yl)prop-2-en-1-one |
| 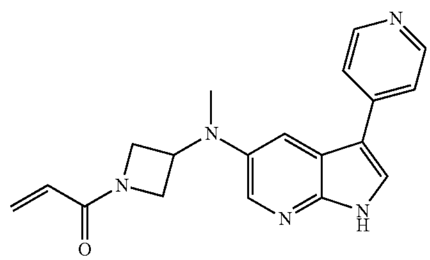 [SMILES: C=CC(=O)N1CC(N(C)c2cnc3[nH]cc(-c4ccncc4)c3c2)C1] | 1-(3-(methyl(3-(pyridin-4-yl)-1H-pyrrolo[2,3-b]pyridin-5-yl)amino)azetidin-1-yl)prop-2-en-1-one |
| 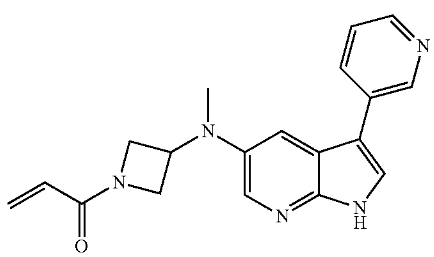 [SMILES: C=CC(=O)N1CC(N(C)c2cnc3[nH]cc(-c4cccnc4)c3c2)C1] | 1-(3-(methyl(3-(pyridin-3-yl)-1H-pyrrolo[2,3-b]pyridin-5-yl)amino)azetidin-1-yl)prop-2-en-1-one |
| 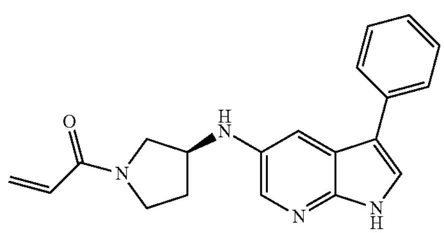 [SMILES: C=CC(=O)N1CC[C@H](Nc2cnc3[nH]cc(-c4ccccc4)c3c2)C1] | (S)-1-(3-((3-phenyl-1H-pyrrolo[2,3-b]pyridin-5-yl)amino)pyrrolidin-1-yl)prop-2-en-1-one |
| 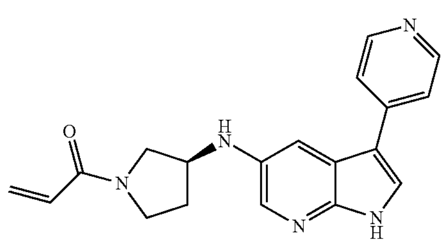 [SMILES: C=CC(=O)N1CC[C@H](Nc2cnc3[nH]cc(-c4ccncc4)c3c2)C1] | (S)-1-(3-((3-(pyridin-4-yl)-1H-pyrrolo[2,3-b]pyridin-5-yl)amino)pyrrolidin-1-yl)prop-2-en-1-one |
| 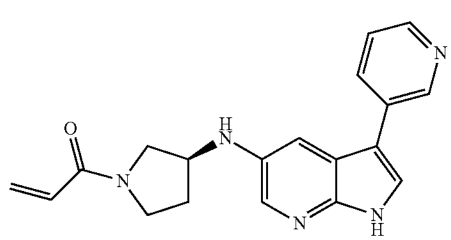 [SMILES: C=CC(=O)N1CC[C@H](Nc2cnc3[nH]cc(-c4cccnc4)c3c2)C1] | (S)-1-(3-((3-(pyridin-3-yl)-1H-pyrrolo[2,3-b]pyridin-5-yl)amino)pyrrolidin-1-yl)prop-2-en-1-one |

TABLE 2-continued

| Structure | Name |
|---|---|
| 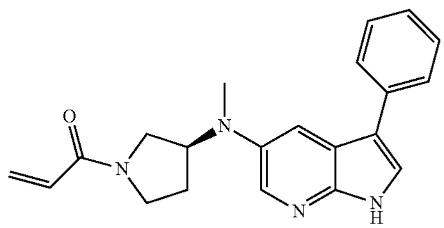 [SMILES: C=CC(=O)N1CC[C@H](N(C)c2cnc3[nH]cc(-c4ccccc4)c3c2)C1] | (S)-1-(3-(methyl(3-phenyl-1H-pyrrolo[2,3-b]pyridin-5-yl)amino)pyrrolidin-1-yl)prop-2-en-1-one |
| | (S)-1-(3-(methyl(3-(pyridin-4-yl)-1H-pyrrolo[2,3-b]pyridin-5-yl)amino)pyrrolidin-1-yl)prop-2-en-1-one |
| | (S)-1-(3-(methyl(3-(pyridin-4-yl)-1H-pyrrolo[2,3-b]pyridin-5-yl)amino)pyrrolidin-1-yl)prop-2-en-1-one |
| 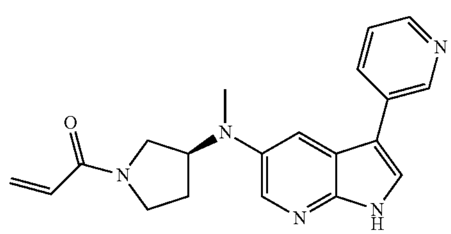 [SMILES: C=CC(=O)N1CC[C@H](N(C)c2cnc3[nH]cc(-c4cccnc4)c3c2)C1] | (S)-1-(3-(methyl(3-(pyridin-3-yl)-1H-pyrrolo[2,3-b]pyridin-5-yl)amino)pyrrolidin-1-yl)prop-2-en-1-one |
| 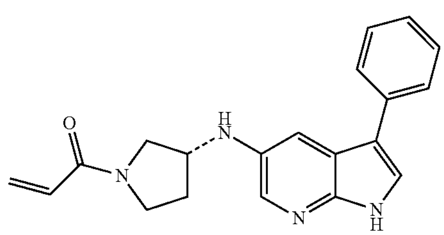 | (R)-1-(3-((3-phenyl-1H-pyrrolo[2,3-b]pyridin-5-yl)amino)pyrrolidin-1-yl)prop-2-en-1-one |
| 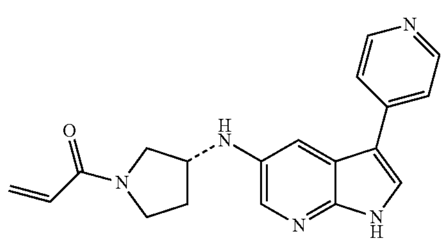 | (R)-1-(3-((3-(pyridin-4-yl)-1H-pyrrolo[2,3-b]pyridin-5-yl)amino)pyrrolidin-1-yl)prop-2-en-1-one |

TABLE 2-continued

| Structure | Name |
|---|---|
| 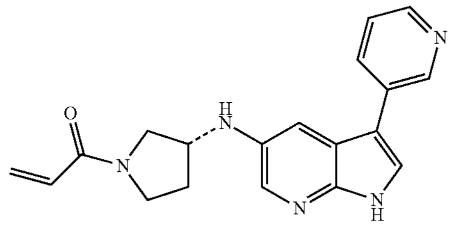 | (R)-1-(3-((3-(pyridin-3-yl)-1H-pyrrolo[2,3-b]pyridin-5-yl)amino)pyrrolidin-1-yl)prop-2-en-1-one |
| 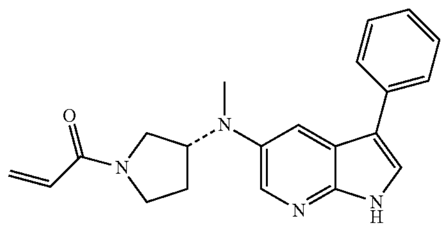 | (R)-1-(3-(methyl(3-phenyl-1H-pyrrolo[2,3-b]pyridin-5-yl)amino)pyrrolidin-1-yl)prop-2-en-1-one |
| 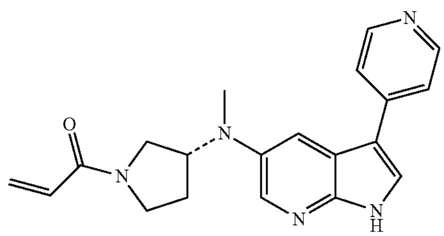 | (R)-1-(3-(methyl(3-(pyridin-4-yl)-1H-pyrrolo[2,3-b]pyridin-5-yl)amino)pyrrolidin-1-yl)prop-2-en-1-one |
| 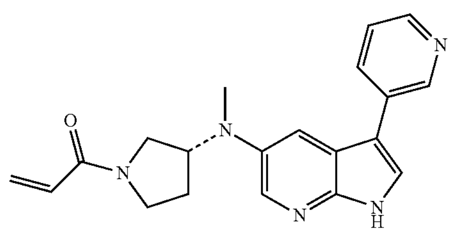 | (R)-1-(3-(methyl(3-(pyridin-3-yl)-1H-pyrrolo[2,3-b]pyridin-5-yl)amino)pyrrolidin-1-yl)prop-2-en-1-one |
| 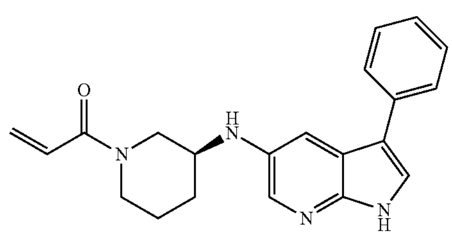 [SMILES: C=CC(=O)N1CCC[C@H](Nc2cnc3[nH]cc(-c4ccccc4)c3c2)C1] | (S)-1-(3-((3-phenyl-1H-pyrrolo[2,3-b]pyridin-5-yl)amino)piperidin-1-yl)prop-2-en-1-one |
| 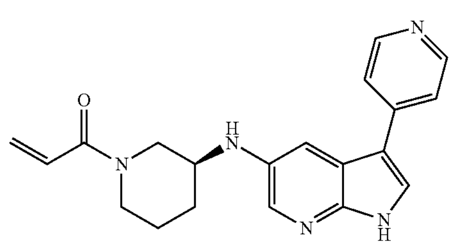 [SMILES: C=CC(=O)N1CCC[C@H](Nc2cnc3[nH]cc(-c4ccncc4)c3c2)C1] | (S)-1-(3-((3-(pyridin-4-yl)-1H-pyrrolo[2,3-b]pyridin-5-yl)amino)piperidin-1-yl)prop-2-en-1-one |

| Structure | Name |
|---|---|
| 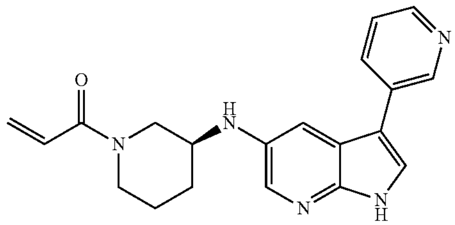 [SMILES: C=CC(=O)N1CCC[C@H](Nc2cnc3[nH]cc(-c4cccnc4)c3c2)C1] | (S)-1-(3-((3-(pyridin-3-yl)-1H-pyrrolo[2,3-b]pyridin-5-yl)amino)piperidin-1-yl)prop-2-en-1-one |
| 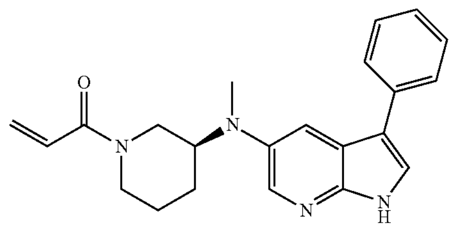 [SMILES: C=CC(=O)N1CCC[C@H](N(C)c2cnc3[nH]cc(-c4ccccc4)c3c2)C1] | (S)-1-(3-(methyl(3-phenyl-1H-pyrrolo[2,3-b]pyridin-5-yl)amino)piperidin-1-yl)prop-2-en-1-one |
| 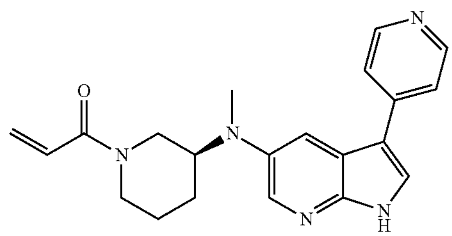 [SMILES: C=CC(=O)N1CCC[C@H](N(C)c2cnc3[nH]cc(-c4ccncc4)c3c2)C1] | (S)-1-(3-(methyl(3-(pyridin-4-yl)-1H-pyrrolo[2,3-b]pyridin-5-yl)amino)piperidin-1-yl)prop-2-en-1-one |
| 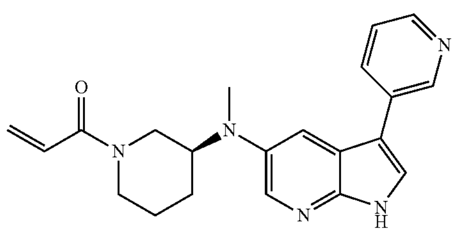 [SMILES: C=CC(=O)N1CCC[C@H](N(C)c2cnc3[nH]cc(-c4cccnc4)c3c2)C1] | (S)-1-(3-(methyl(3-(pyridin-3-yl)-1H-pyrrolo[2,3-b]pyridin-5-yl)amino)piperidin-1-yl)prop-2-en-1-one |
| 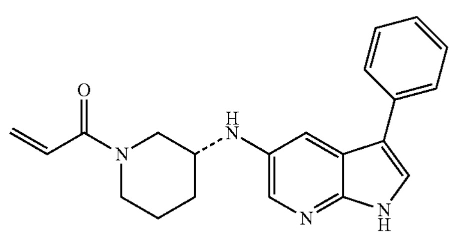 | (R)-1-(3-((3-phenyl-1H-pyrrolo[2,3-b]pyridin-5-yl)amino)piperidin-1-yl)prop-2-en-1-one |
| 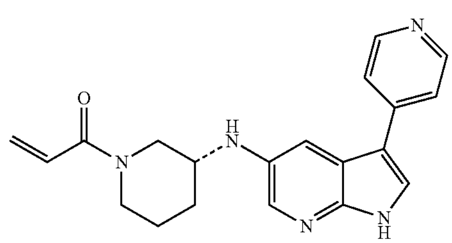 | (R)-1-(3-((3-(pyridin-4-yl)-1H-pyrrolo[2,3-b]pyridin-5-yl)amino)piperidin-1-yl)prop-2-en-1-one |

TABLE 2-continued

| Structure | Name |
|---|---|
| 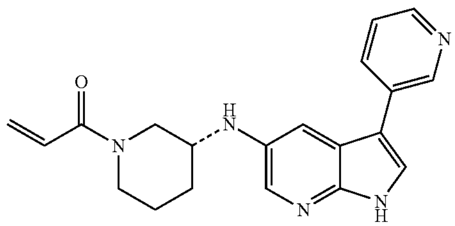 | (R)-1-(3-((3-(pyridin-3-yl)-1H-pyrrolo[2,3-b]pyridin-5-yl)amino)piperidin-1-yl)prop-2-en-1-one |
| 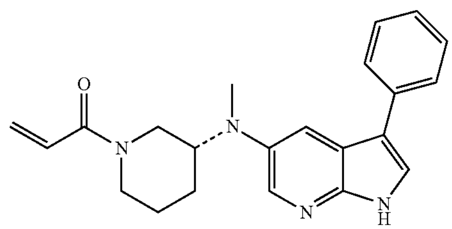 | (R)-1-(3-(methyl(3-phenyl-1H-pyrrolo[2,3-b]pyridin-5-yl)amino)piperidin-1-yl)prop-2-en-1-one |
| 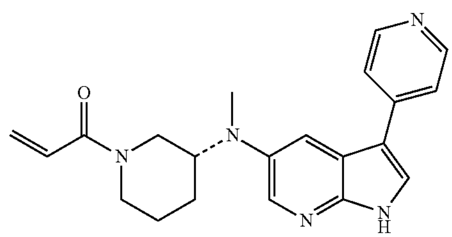 | (R)-1-(3-(methyl(3-(pyridin-4-yl)-1H-pyrrolo[2,3-b]pyridin-5-yl)amino)piperidin-1-yl)prop-2-en-1-one |
| 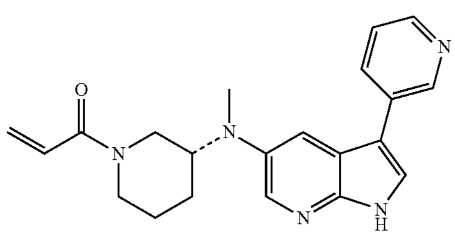 | (R)-1-(3-(methyl(3-(pyridin-3-yl)-1H-pyrrolo[2,3-b]pyridin-5-yl)amino)piperidin-1-yl)prop-2-en-1-one |
| 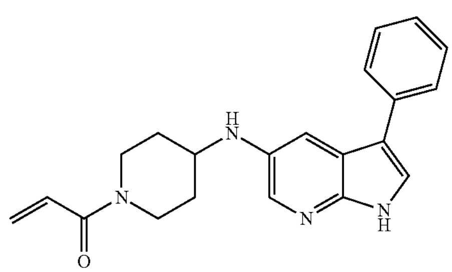 [SMILES: C=CC(=O)N1CCC(Nc2cnc3[nH]cc(-c4ccccc4)c3c2)CC1] | 1-(4-((3-phenyl-1H-pyrrolo[2,3-b]pyridin-5-yl)amino)piperidin-1-yl)prop-2-en-1-one |
| 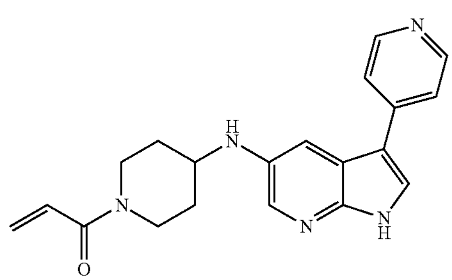 [SMILES: C=CC(=O)N1CCC(Nc2cnc3[nH]cc(-c4ccncc4)c3c2)CC1] | 1-(4-((3-(pyridin-4-yl)-1H-pyrrolo[2,3-b]pyridin-5-yl)amino)piperidin-1-yl)prop-2-en-1-one |

TABLE 2-continued

| Structure | Name |
|---|---|
| 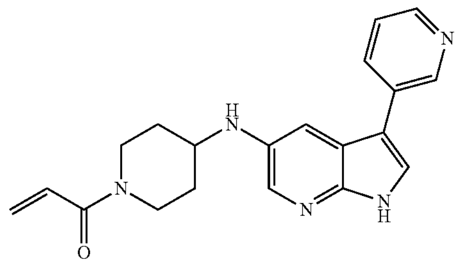 [SMILES: C=CC(=O)N1CCC(Nc2cnc3[nH]cc(-c4cccnc4)c3c2)CC1] | 1-(4-((3-(pyridin-3-yl)-1H-pyrrolo[2,3-b]pyridin-5-yl)amino)piperidin-1-yl)prop-2-en-1-one |
| 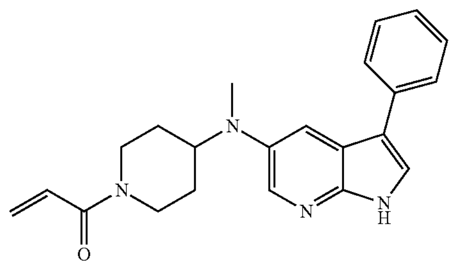 [SMILES: C=CC(=O)N1CCC(N(C)c2cnc3[nH]cc(-c4ccccc4)c3c2)CC1] | 1-(4-(methyl(3-phenyl-1H-pyrrolo[2,3-b]pyridin-5-yl)amino)piperidin-1-yl)prop-2-en-1-one |
| 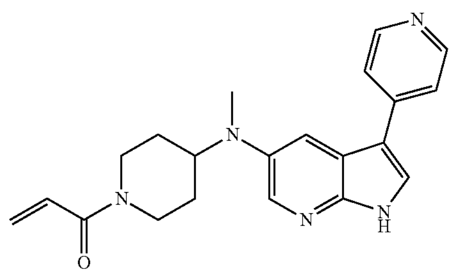 [SMILES: C=CC(=O)N1CCC(N(C)c2cnc3[nH]cc(-c4ccncc4)c3c2)CC1] | 1-(4-(methyl(3-(pyridin-4-yl)-1H-pyrrolo[2,3-b]pyridin-5-yl)amino)piperidin-1-yl)prop-2-en-1-one |
| 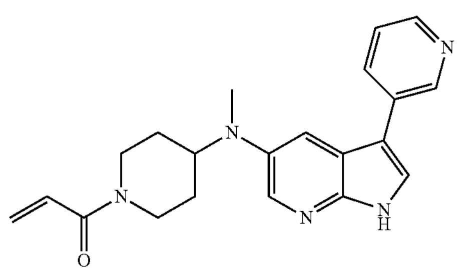 [SMILES: C=CC(=O)N1CCC(N(C)c2cnc3[nH]cc(-c4cccnc4)c3c2)CC1] | 1-(4-(methyl(3-(pyridin-3-yl)-1H-pyrrolo[2,3-b]pyridin-5-yl)amino)piperidin-1-yl)prop-2-en-1-one |
| 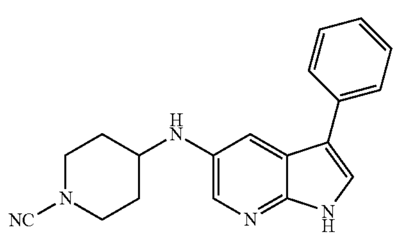 [SMILES: N#CN1CCC(Nc2cnc3[nH]cc(-c4ccccc4)c3c2)CC1] | 4-((3-phenyl-1H-pyrrolo[2,3-b]pyridin-5-yl)amino)piperidine-1-carbonitrile |
| 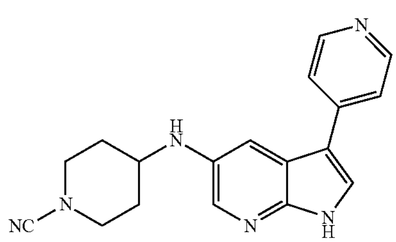 [SMILES: N#CN1CCC(Nc2cnc3[nH]cc(-c4ccncc4)c3c2)CC1] | 4-((3-(pyridin-4-yl)-1H-pyrrolo[2,3-b]pyridin-5-yl)amino)piperidine-1-carbonitrile |

TABLE 2-continued

| Structure | Name |
|---|---|
| 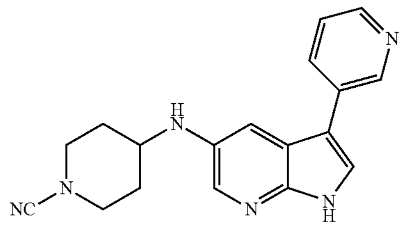 [SMILES: N#CN1CCC(Nc2cnc3[nH]cc(-c4cccnc4)c3c2)CC1] | 4-((3-(pyridin-3-yl)-1H-pyrrolo[2,3-b]pyridin-5-yl)amino)piperidine-1-carbonitrile |
| 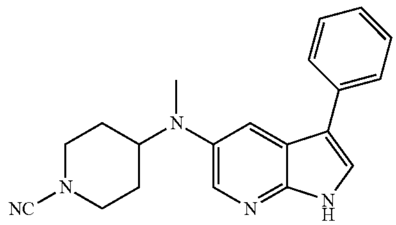 [SMILES: CN(c1cnc2[nH]cc(-c3ccccc3)c2c1)C1CCN(C#N)CC1] | 4-(methyl(3-phenyl-1H-pyrrolo[2,3-b]pyridin-5-yl)amino)piperidine-1-carbonitrile |
| 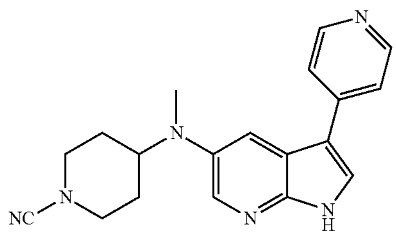 [SMILES: CN(c1cnc2[nH]cc(-c3ccncc3)c2c1)C1CCN(C#N)CC1] | 4-(methyl(3-(pyridin-4-yl)-1H-pyrrolo[2,3-b]pyridin-5-yl)amino)piperidine-1-carbonitrile |
| 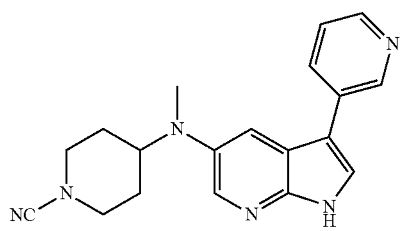 [SMILES: CN(c1cnc2[nH]cc(-c3cccnc3)c2c1)C1CCN(C#N)CC1] | 4-(methyl(3-(pyridin-3-yl)-1H-pyrrolo[2,3-b]pyridin-5-yl)amino)piperidine-1-carbonitrile |
| 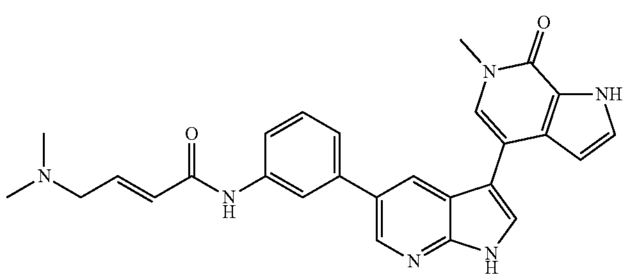 [SMILES: CN(C)C/C=C/C(=O)Nc1cccc(-c2cnc3[nH]cc(-c4cn(C)c(=O)c5[nH]ccc45)c3c2)c1] | (E)-4-(dimethylamino)-N-(3-(3-(6-methyl-7-oxo-6,7-dihydro-1H-pyrrolo[2,3-c]pyridin-4-yl)-1H-pyrrolo[2,3-b]pyridin-5-yl)phenyl)but-2-enamide |
| 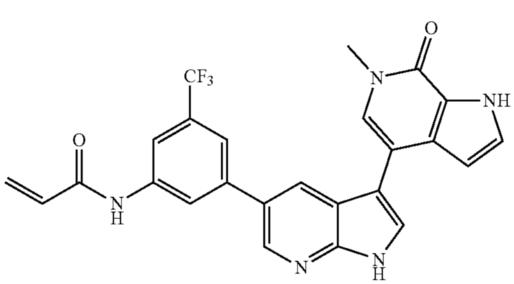 [SMILES: C=CC(=O)Nc1cc(-c2cnc3[nH]cc(-c4cn(C)c(=O)c5[nH]ccc45)c3c2)cc(C(F)(F)F)c1] | N-(3-(3-(6-methyl-7-oxo-6,7-dihydro-1H-pyrrolo[2,3-c]pyridin-4-yl)-1H-pyrrolo[2,3-b]pyridin-5-yl)-5-(trifluoromethyl)phenyl)acrylamide |

TABLE 2-continued

| Structure | Name |
|---|---|
| 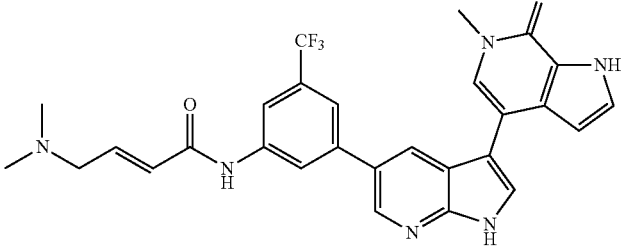 | (E)-4-(dimethylamino)-N-(3-(3-(6-methyl-7-oxo-6,7-dihydro-1H-pyrrolo[2,3-c]pyridin-4-yl)-1H-pyrrolo[2,3-b]pyridin-5-yl)-5-(trifluoromethyl)phenyl)but-2-enamide |
| 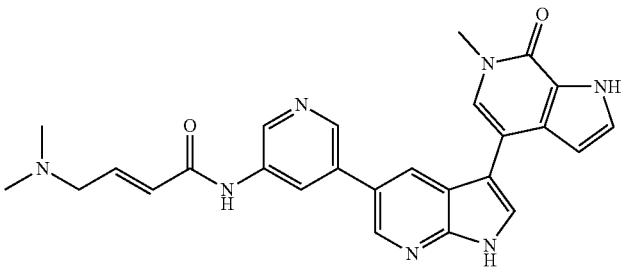 [SMILES: CN(C)C/C=C/C(=O)Nc1cncc(-c2cnc3[nH]cc(-c4cn(C)c(=O)c5[nH]ccc45)c3c2)c1] | (E)-4-(dimethylamino)-N-(5-(3-(6-methyl-7-oxo-6,7-dihydro-1H-pyrrolo[2,3-c]pyridin-4-yl)-1H-pyrrolo[2,3-b]pyridin-5-yl)pyridin-3-yl)but-2-enamide |
| 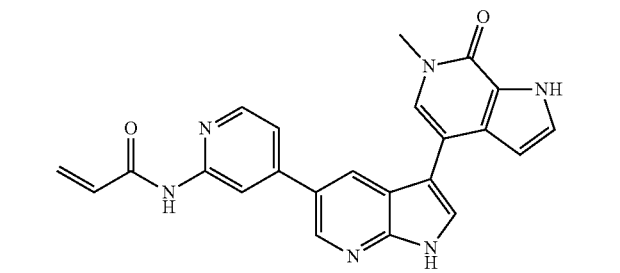 [SMILES: C=CC(=O)Nc1cc(-c2cnc3[nH]cc(-c4cn(C)c(=O)c5[nH]ccc45)c3c2)ccn1] | N-(4-(3-(6-methyl-7-oxo-6,7-dihydro-1H-pyrrolo[2,3-c]pyridin-4-yl)-1H-pyrrolo[2,3-b]pyridin-5-yl)pyridin-2-yl)acrylamide |
| 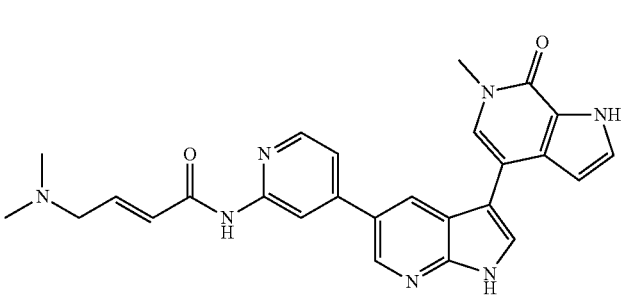 [SMILES: CN(C)C/C=C/C(=O)Nc1cc(-c2cnc3[nH]cc(-c4cn(C)c(=O)c5[nH]ccc45)c3c2)ccn1] | (E)-4-(dimethylamino)-N-(4-(3-(6-methyl-7-oxo-6,7-dihydro-1H-pyrrolo[2,3-c]pyridin-4-yl)-1H-pyrrolo[2,3-b]pyridin-5-yl)pyridin-2-yl)but-2-enamide |
| 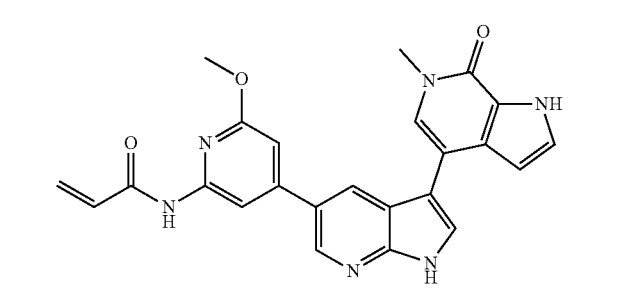 [SMILES: C=CC(=O)Nc1cc(-c2cnc3[nH]cc(-c4cn(C)c(=O)c5[nH]ccc45)c3c2)cc(OC)n1] | N-(6-methoxy-4-(3-(6-methyl-7-oxo-6,7-dihydro-1H-pyrrolo[2,3-c]pyridin-4-yl)-1H-pyrrolo[2,3-b]pyridin-5-yl)pyridin-2-yl)acrylamide |

TABLE 2-continued

| Structure | Name |
|---|---|
| 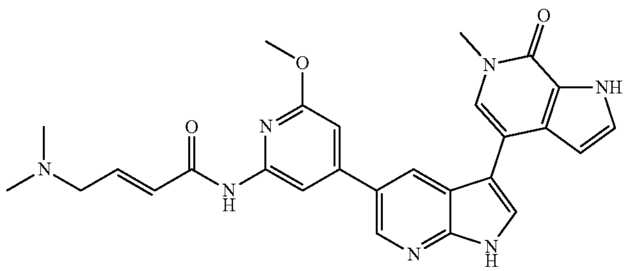 [SMILES: COc1cc(-c2cnc3[nH]cc(-c4cn(C)c(=O)c5[nH]ccc45)c3c2)cc(NC(=O)/C=C/CN(C)C)n1] | (E)-4-(dimethylamino)-N-(6-methoxy-4-(3-(6-methyl-7-oxo-6,7-dihydro-1H-pyrrolo[2,3-c]pyridin-4-yl)-1H-pyrrolo[2,3-b]pyridin-5-yl)pyridin-2-yl)but-2-enamide |
| 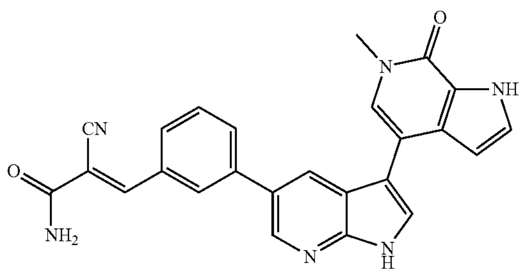 [SMILES: Cn1cc(-c2c[nH]c3ncc(-c4cccc(/C=C(\C#N)C(N)=O)c4)cc23)c2cc[nH]c2c1=O] | (E)-2-cyano-3-(3-(3-(6-methyl-7-oxo-6,7-dihydro-1H-pyrrolo[2,3-c]pyridin-4-yl)-1H-pyrrolo[2,3-b]pyridin-5-yl)phenyl)acrylamide |
| 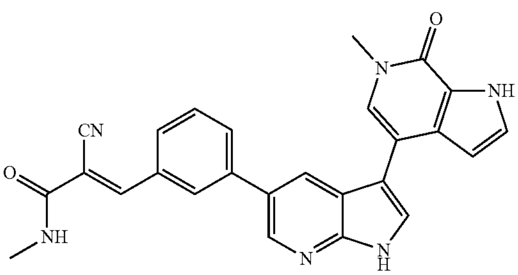 [SMILES: CNC(=O)/C(C#N)=C/c1cccc(-c2cnc3[nH]cc(-c4cn(C)c(=O)c5[nH]ccc45)c3c2)c1] | (E)-2-cyano-N-methyl-3-(3-(3-(6-methyl-7-oxo-6,7-dihydro-1H-pyrrolo[2,3-c]pyridin-4-yl)-1H-pyrrolo[2,3-b]pyridin-5-yl)phenyl)acrylamide |
| 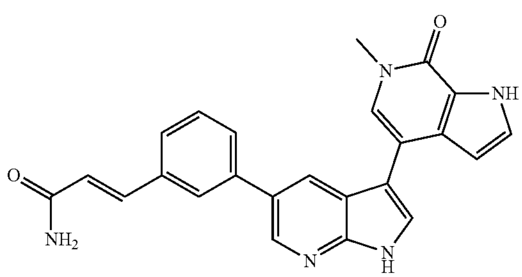 [SMILES: Cn1cc(-c2c[nH]c3ncc(-c4cccc(/C=C/C(N)=O)c4)cc23)c2cc[nH]c2c1=O] | (E)-3-(3-(3-(6-methyl-7-oxo-6,7-dihydro-1H-pyrrolo[2,3-c]pyridin-4-yl)-1H-pyrrolo[2,3-b]pyridin-5-yl)phenyl)acrylamide |
| 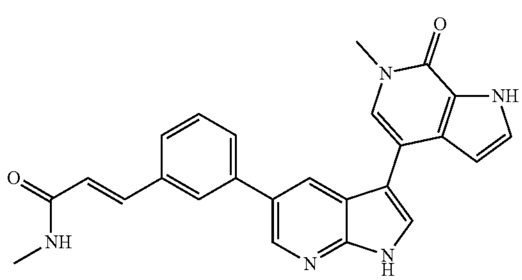 [SMILES: CNC(=O)/C=C/c1cccc(-c2cnc3[nH]cc(-c4cn(C)c(=O)c5[nH]ccc45)c3c2)c1] | (E)-N-methyl-3-(3-(3-(6-methyl-7-oxo-6,7-dihydro-1H-pyrrolo[2,3-c]pyridin-4-yl)-1H-pyrrolo[2,3-b]pyridin-5-yl)phenyl)acrylamide |
| 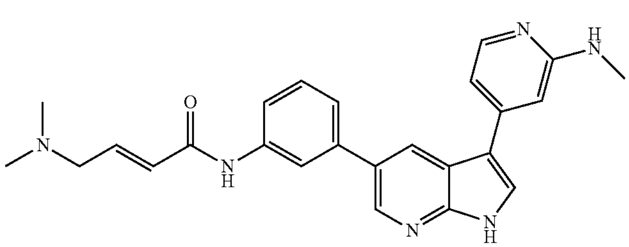 | (E)-4-(dimethylamino)-N-(3-(3-(2-(methylamino)pyridin-4-yl)-1H-pyrrolo[2,3-b]pyridin-5-yl)phenyl)but-2-enamide |

TABLE 2-continued

| Structure | Name |
|---|---|
| 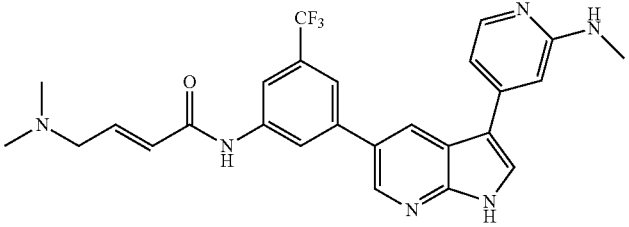 | (E)-4-(dimethylamino)-N-(3-(3-(2-(methylamino)pyridin-4-yl)-1H-pyrrolo[2,3-b]pyridin-5-yl)-5-(trifluoromethyl)phenyl)but-2-enamide |
| 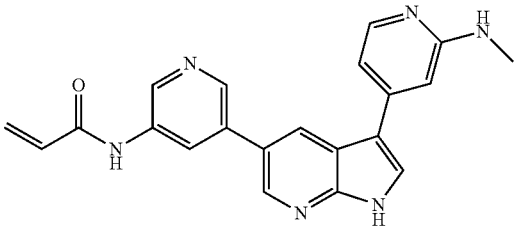 [SMILES: C=CC(=O)Nc1cncc(-c2cnc3[nH]cc(-c4ccnc(NC)c4)c3c2)c1] | N-(5-(3-(2-(methylamino)pyridin-4-yl)-1H-pyrrolo[2,3-b]pyridin-5-yl)pyridin-3-yl)acrylamide |
| 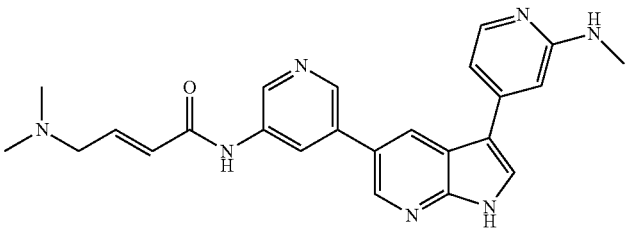 | (E)-4-(dimethylamino)-N-(5-(3-(2-(methylamino)pyridin-4-yl)-1H-pyrrolo[2,3-b]pyridin-5-yl)pyridin-3-yl)but-2-enamide |
| 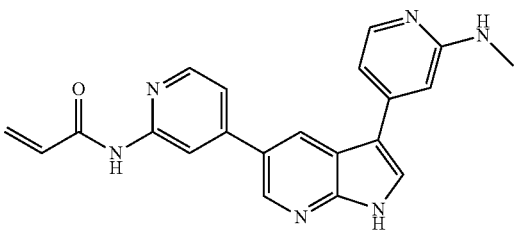 [SMILES: C=CC(=O)Nc1cc(-c2cnc3[nH]cc(-c4ccnc(NC)c4)c3c2)ccn1] | N-(4-(3-(2-(methylamino)pyridin-4-yl)-1H-pyrrolo[2,3-b]pyridin-5-yl)pyridin-2-yl)acrylamide |
| 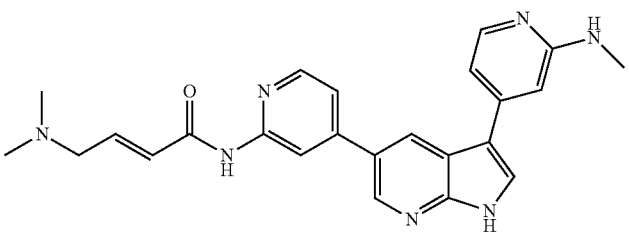 | (E)-4-(dimethylamino)-N-(4-(3-(2-(methylamino)pyridin-4-yl)-1H-pyrrolo[2,3-b]pyridin-5-yl)pyridin-2-yl)but-2-enamide |
| 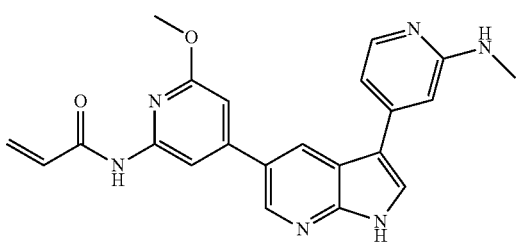 [SMILES: C=CC(=O)Nc1cc(-c2cnc3[nH]cc(-c4ccnc(NC)c4)c3c2)cc(OC)n1] | N-(6-methoxy-4-(3-(2-(methylamino)pyridin-4-yl)-1H-pyrrolo[2,3-b]pyridin-5-yl)pyridin-2-yl)acrylamide |

| Structure | Name |
|---|---|
| 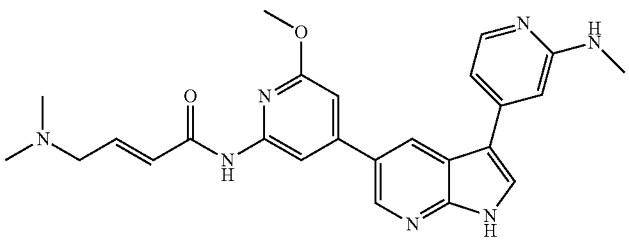 | (E)-4-(dimethylamino)-N-(6-methoxy-4-(3-(2-(methylamino)pyridin-4-yl)-1H-pyrrolo[2,3-b]pyridin-5-yl)pyridin-2-yl)but-2-enamide |
| 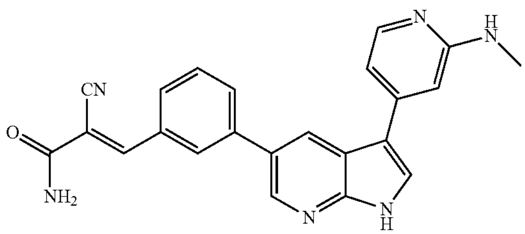 [SMILES: CNc1cc(-c2c[nH]c3ncc(-c4cccc(/C=C(\C#N)C(N)=O)c4)cc23)ccn1] | (E)-2-cyano-3-(3-(3-(2-(methylamino)pyridin-4-yl)-1H-pyrrolo[2,3-b]pyridin-5-yl)phenyl)acrylamide |
| 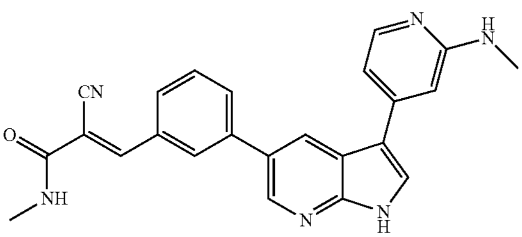 [SMILES: CNC(=O)/C(C#N)=C/c1cccc(-c2cnc3[nH]cc(-c4ccnc(NC)c4)c3c2)c1] | (E)-2-cyano-N-methyl-3-(3-(3-(2-(methylamino)pyridin-4-yl)-1H-pyrrolo[2,3-b]pyridin-5-yl)phenyl)acrylamide |
| 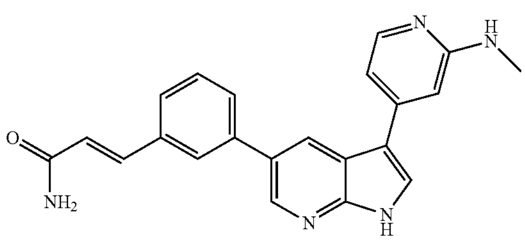 [SMILES: CNc1cc(-c2c[nH]c3ncc(-c4cccc(/C=C/C(N)=O)c4)cc23)ccn1] | (E)-3-(3-(3-(2-(methylamino)pyridin-4-yl)-1H-pyrrolo[2,3-b]pyridin-5-yl)phenyl)acrylamide |
| 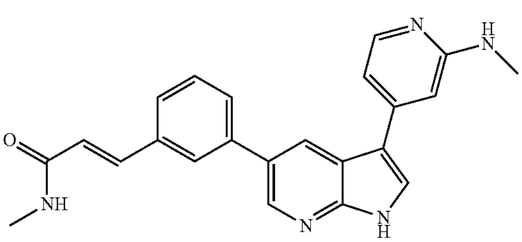 [SMILES: CNC(=O)/C=C/c1cccc(-c2cnc3[nH]cc(-c4ccnc(NC)c4)c3c2)c1] | (E)-N-methyl-3-(3-(3-(2-(methylamino)pyridin-4-yl)-1H-pyrrolo[2,3-b]pyridin-5-yl)phenyl)acrylamide |
| 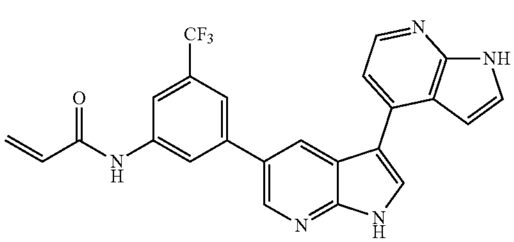 [SMILES: C=CC(=O)Nc1cc(-c2cnc3[nH]cc(-c4ccnc5[nH]ccc45)c3c2)cc(C(F)(F)F)c1] | N-(3-1H,1'H-[3,4'-bipyrrolo[2,3-b]pyridin]-5-yl)-5-(trifluoromethyl)phenyl)acrylamide |

TABLE 2-continued

| Structure | Name |
|---|---|
| 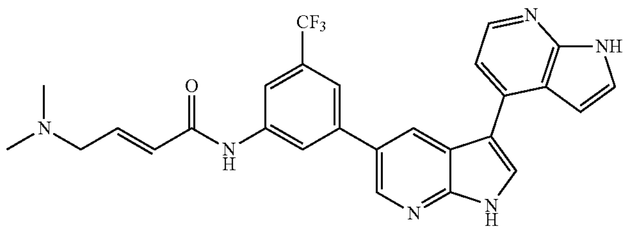 [SMILES: CN(C)C/C=C/C(=O)Nc1cc(-c2cnc3[nH]cc(-c4ccnc5[nH]ccc45)c3c2)cc(C(F)(F)F)c1] | (E)-N-(3-(1H,1'H-[3,4'-bipyrrolo[2,3-b]pyridin]-5-yl)-5-(trifluoromethyl)phenyl)-4-(dimethylamino)but-2-enamide |
| 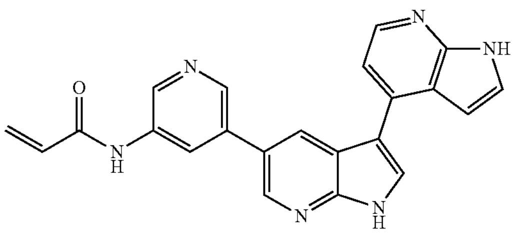 [SMILES: C=CC(=O)Nc1cncc(-c2cnc3[nH]cc(-c4ccnc5[nH]ccc45)c3c2)c1] | N-(5-1H,1'H-[3,4'-bipyrrolo[2,3-b]pyridin]-5-yl)pyridin-3-yl)acrylamide |
| 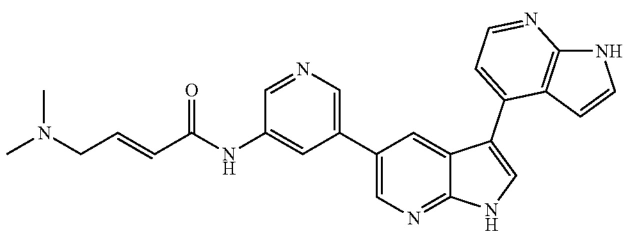 [SMILES: CN(C)C/C=C/C(=O)Nc1cncc(-c2cnc3[nH]cc(-c4ccnc5[nH]ccc45)c3c2)c1] | (E)-N-(5-(1H,1'H-[3,4'-bipyrrolo[2,3-b]pyridin]-5-yl)pyridin-3-yl)-4-(dimethylamino)but-2-enamide |
| 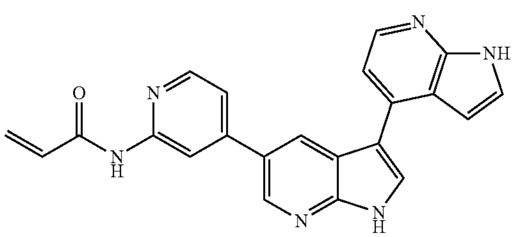 [SMILES: C=CC(=O)Nc1cc(-c2cnc3[nH]cc(-c4ccnc5[nH]ccc45)c3c2)ccn1] | N-(4-(1H,1'H-[3,4'-bipyrrolo[2,3-b]pyridin]-5-yl)pyridin-2-yl)acrylamide |
| 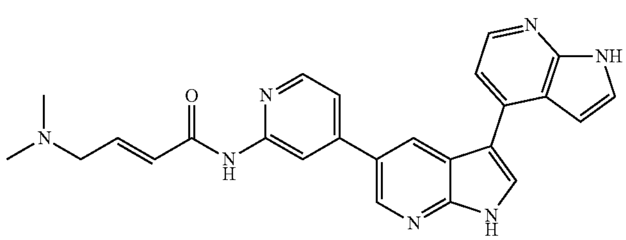 [SMILES: CN(C)C/C=C/C(=O)Nc1cc(-c2cnc3[nH]cc(-c4ccnc5[nH]ccc45)c3c2)ccn1] | (E)-N-(4-(1H,1'H-[3,4'-bipyrrolo[2,3-b]pyridin]-5-yl)pyridin-2-yl)-4-(dimethylamino)but-2-enamide |
| 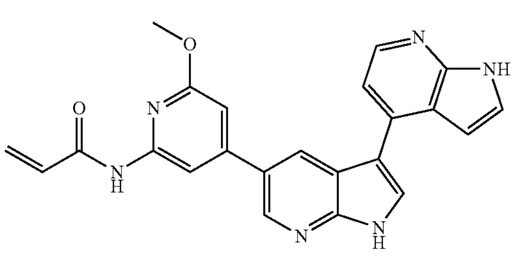 [SMILES: C=CC(=O)Nc1cc(-c2cnc3[nH]cc(-c4ccnc5[nH]ccc45)c3c2)cc(OC)n1] | N-(4-(1H,1'H-[3,4'-bipyrrolo[2,3-b]pyridin]-5-yl)-6-methoxypyridin-2-yl)acrylamide |

TABLE 2-continued

| Structure | Name |
|---|---|
| 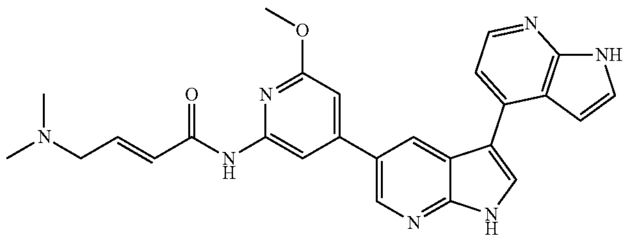 [SMILES: COc1cc(-c2cnc3[nH]cc(-c4ccnc5[nH]ccc45)c3c2)cc(NC(=O)/C=C/CN(C)C)n1] | (E)-N-(4-(1H,1'H-[3,4'-bipyrrolo[2,3-b]pyridin]-5-yl)-6-methoxypyridin-2-yl)-4-(dimethylamino)but-2-enamide |
| 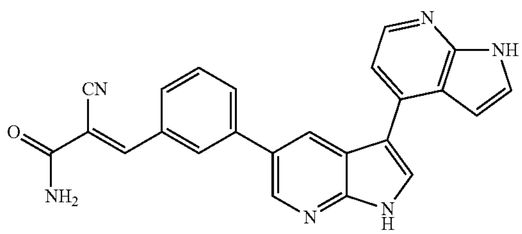 [SMILES: N#C/C(=C\c1cccc(-c2cnc3[nH]cc(-c4ccnc5[nH]ccc45)c3c2)c1)C(N)=O] | (E)-3-(3-(1H,1'H-[3,4'-bipyrrolo[2,3-b]pyridin]-5-yl)phenyl)-2-cyanoacrylamide |
| 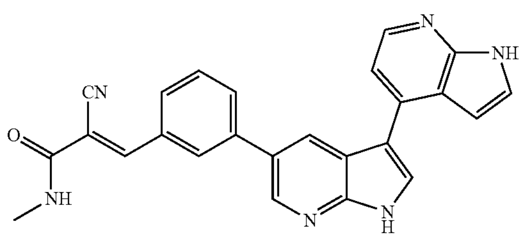 [SMILES: CNC(=O)/C(C#N)=C/c1cccc(-c2cnc3[nH]cc(-c4ccnc5[nH]ccc45)c3c2)c1] | (E)-3-(3-(1H,1'H-[3,4'-bipyrrolo[2,3-b]pyridin]-5-yl)phenyl)-2-cyano-N-methylacrylamide |
| 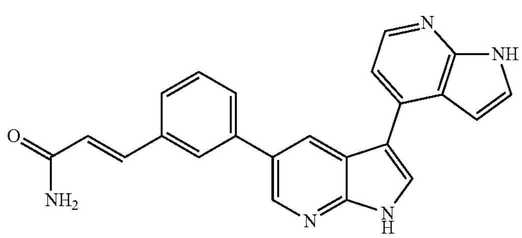 [SMILES: NC(=O)/C=C/c1cccc(-c2cnc3[nH]cc(-c4ccnc5[nH]ccc45)c3c2)c1] | (E)-3-(3-(1H,1'H-[3,4'-bipyrrolo[2,3-b]pyridin]-5-yl)phenyl)acrylamide |
| 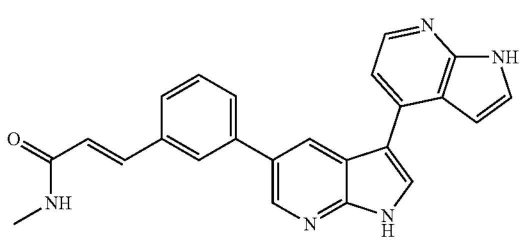 [SMILES: CNC(=O)/C=C/c1cccc(-c2cnc3[nH]cc(-c4ccnc5[nH]ccc45)c3c2)c1] | (E)-3-(3-(1H,1'H-[3,4'-bipyrrolo[2,3-b]pyridin]-5-yl)phenyl)-N-methylacrylamide |
| 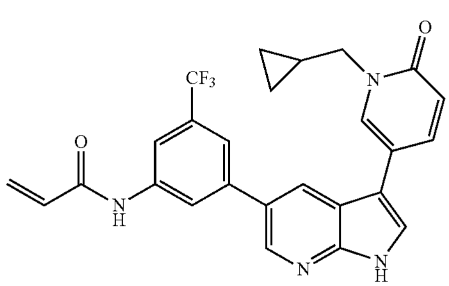 [SMILES: C=CC(=O)Nc1cc(-c2cnc3[nH]cc(-c4ccc(=O)n(CC5CC5)c4)c3c2)cc(C(F)(F)F)c1] | N-(3-(3-(1-(cyclopropylmethyl)-6-oxo-1,6-dihydropyridin-3-yl)-1H-pyrrolo[2,3-b]pyridin-5-yl)-5-(trifluoromethyl)phenyl)acrylamide |

TABLE 2-continued

| Structure | Name |
|---|---|
| 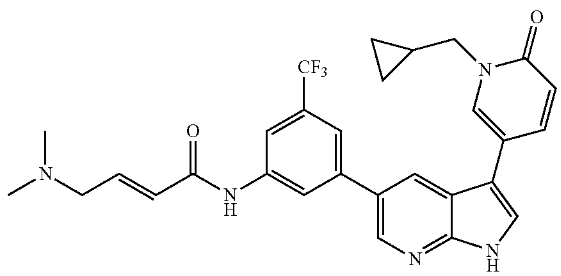 [SMILES: CN(C)C/C=C/C(=O)Nc1cc(-c2cnc3[nH]cc(-c4ccc(=O)n(CC5CC5)c4)c3c2)cc(C(F)(F)F)c1] | (E)-N-(3-(3-(1-(cyclopropylmethyl)-6-oxo-1,6-dihydropyridin-3-yl)-1H-pyrrolo[2,3-b]pyridin-5-yl)-5-(trifluoromethyl)phenyl)-4-(dimethylamino)but-2-enamide |
| 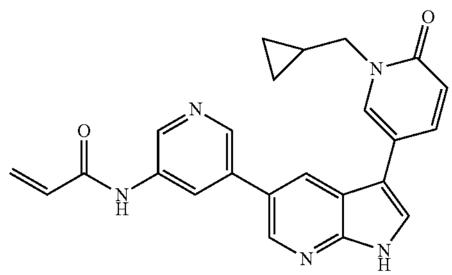 [SMILES: C=CC(=O)Nc1cncc(-c2cnc3[nH]cc(-c4ccc(=O)n(CC5CC5)c4)c3c2)c1] | N-(5-(3-(1-(cyclopropylmethyl)-6-oxo-1,6-dihydropyridin-3-yl)-1H-pyrrolo[2,3-b]pyridin-5-yl)pyridin-3-yl)acrylamide |
| 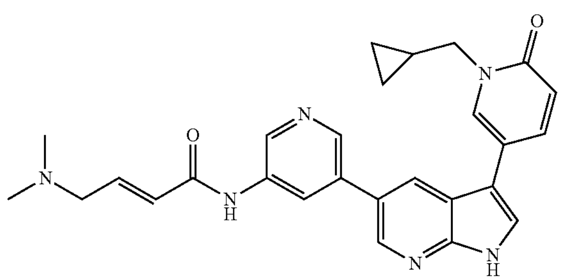 [SMILES: CN(C)C/C=C/C(=O)Nc1cncc(-c2cnc3[nH]cc(-c4ccc(=O)n(CC5CC5)c4)c3c2)c1] | (E)-N-(5-(3-(1-(cyclopropylmethyl)-6-oxo-1,6-dihydropyridin-3-yl)-1H-pyrrolo[2,3-b]pyridin-5-yl)pyridin-3-yl)-4-(dimethylamino)but-2-enamide |
| 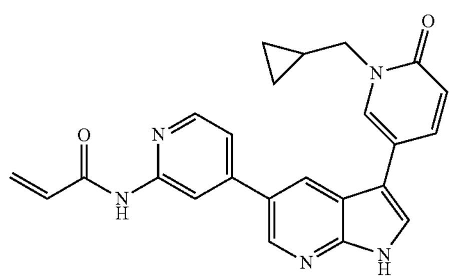 [SMILES: C=CC(=O)Nc1cc(-c2cnc3[nH]cc(-c4ccc(=O)n(CC5CC5)c4)c3c2)ccn1] | N-(4-(3-(1-(cyclopropylmethyl)-6-oxo-1,6-dihydropyridin-3-yl)-1H-pyrrolo[2,3-b]pyridin-5-yl)pyridin-2-yl)acrylamide |
| 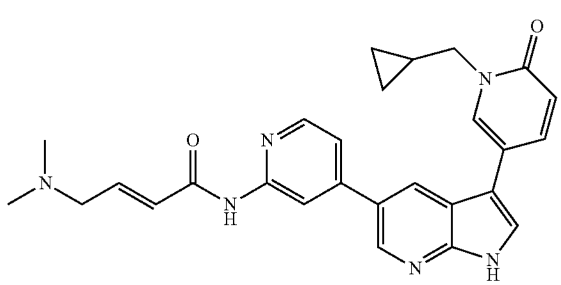 [SMILES: CN(C)C/C=C/C(=O)Nc1cc(-c2cnc3[nH]cc(-c4ccc(=O)n(CC5CC5)c4)c3c2)ccn1] | (E)-N-(4-(3-(1-(cyclopropylmethyl)-6-oxo-1,6-dihydropyridin-3-yl)-1H-pyrrolo[2,3-b]pyridin-5-yl)pyridin-2-yl)-4-(dimethylamino)but-2-enamide |

TABLE 2-continued

| Structure | Name |
|---|---|
| 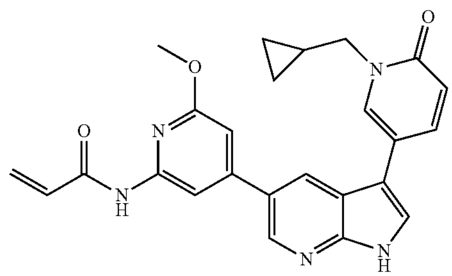 [SMILES: C=CC(=O)Nc1cc(-c2cnc3[nH]cc(-c4ccc(=O)n(CC5CC5)c4)c3c2)cc(OC)n1] | N-(4-(3-(1-(cyclopropylmethyl)-6-oxo-1,6-dihydropyridin-3-yl)-1H-pyrrolo[2,3-b]pyridin-5-yl)-6-methoxypyridin-2-yl)acrylamide |
| 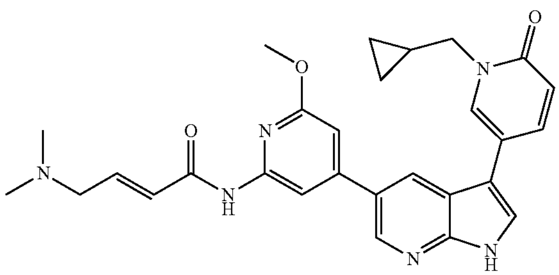 [SMILES: COc1cc(-c2cnc3[nH]cc(-c4ccc(=O)n(CC5CC5)c4)c3c2)cc(NC(=O)/C=C/CN(C)C)n1] | (E)-N-(4-(3-(1-(cyclopropylmethyl)-6-oxo-1,6-dihydropyridin-3-yl)-1H-pyrrolo[2,3-b]pyridin-5-yl)-6-methoxypyridin-2-yl)-4-(dimethylamino)but-2-enamide |
| 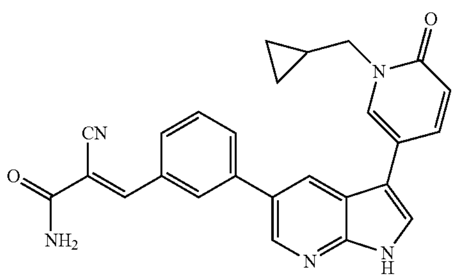 [SMILES: N#C/C(=C\c1cccc(-c2cnc3[nH]cc(-c4ccc(=O)n(CC5CC5)c4)c3c2)c1)C(N)=O] | (E)-2-cyano-3-(3-(3-(1-(cyclopropylmethyl)-6-oxo-1,6-dihydropyridin-3-yl)-1H-pyrrolo[2,3-b]pyridin-5-yl)phenyl)acrylamide |
| 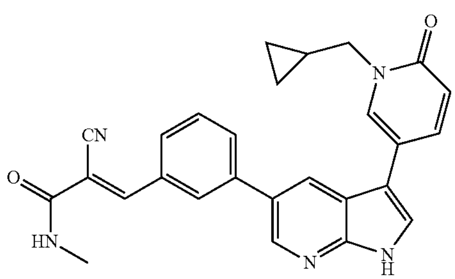 [SMILES: CNC(=O)/C(C#N)=C/c1cccc(-c2cnc3[nH]cc(-c4ccc(=O)n(CC5CC5)c4)c3c2)c1] | (E)-2-cyano-3-(3-(3-(1-(cyclopropylmethyl)-6-oxo-1,6-dihydropyridin-3-yl)-1H-pyrrolo[2,3-b]pyridin-5-yl)phenyl)-N-methylacrylamide |
| 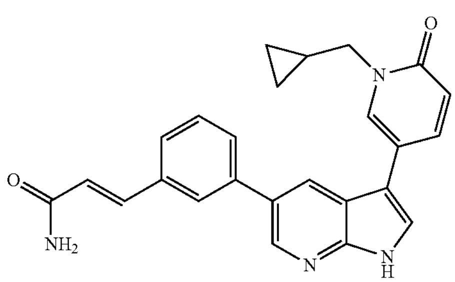 [SMILES: NC(=O)/C=C/c1cccc(-c2cnc3[nH]cc(-c4ccc(=O)n(CC5CC5)c4)c3c2)c1] | (E)-3-(3-(3-(1-(cyclopropylmethyl)-6-oxo-1,6-dihydropyridin-3-yl)-1H-pyrrolo[2,3-b]pyridin-5-yl)phenyl)acrylamide |

TABLE 2-continued

| Structure | Name |
|---|---|
| 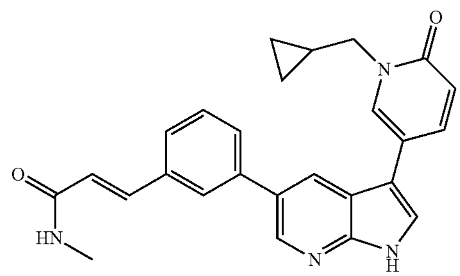 [SMILES: CNC(=O)/C=C/c1cccc(-c2cnc3[nH]cc(-c4ccc(=O)n(CC5CC5)c4)c3c2)c1] | (E)-3-(3-(3-(1-(cyclopropylmethyl)-6-oxo-1,6-dihydropyridin-3-yl)-1H-pyrrolo[2,3-b]pyridin-5-yl)phenyl)-N-methylacrylamide |
| 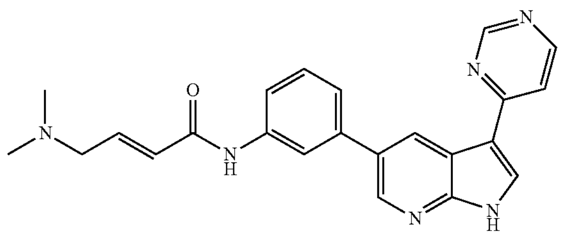 [SMILES: CN(C)C/C=C/C(=O)Nc1cccc(-c2cnc3[nH]cc(-c4ccncn4)c3c2)c1] | (E)-4-(dimethylamino)-N-(3-(3-(pyrimidin-4-yl)-1H-pyrrolo[2,3-b]pyridin-5-yl)phenyl)but-2-enamide |
| 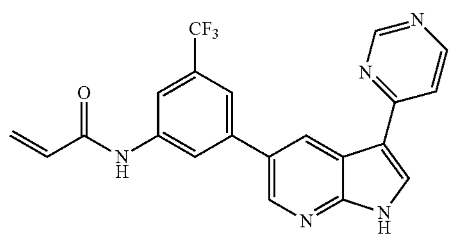 [SMILES: C=CC(=O)Nc1cc(-c2cnc3[nH]cc(-c4ccncn4)c3c2)cc(C(F)(F)F)c1] | N-(3-(3-(pyrimidin-4-yl)-1HH-pyrrolo[2,3-b]pyridin-5-yl)-5-(trifluoromethyl)phenyl)acrylamide |
| 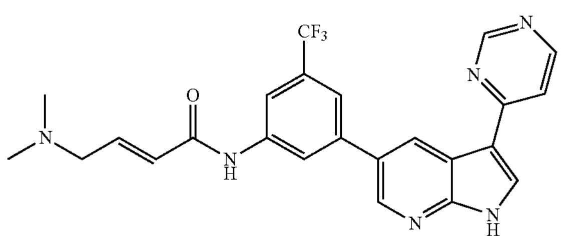 [SMILES: CN(C)C/C=C/C(=O)Nc1cc(-c2cnc3[nH]cc(-c4ccncn4)c3c2)cc(C(F)(F)F)c1] | (E)-4-(dimethylamino)-N-(3-(3-(pyrimidin-4-yl)-1H-pyrrolo[2,3-b]pyridin-5-yl)-5-(trifluoromethyl)phenyl)but-2-enamide |
| 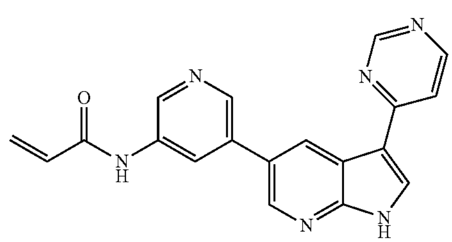 [SMILES: C=CC(=O)Nc1cncc(-c2cnc3[nH]cc(-c4ccncn4)c3c2)c1] | N-(5-(3-(pyrimidin-4-yl)-1H-pyrrolo[2,3-b]pyridin-5-yl)pyridin-3-yl)acrylamide |
| 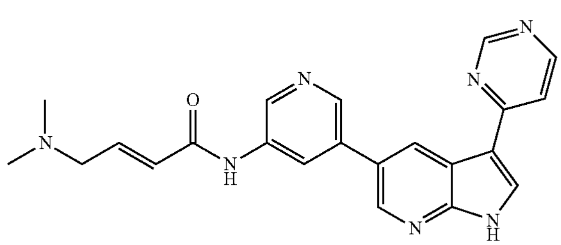 [SMILES: CN(C)C/C=C/C(=O)Nc1cncc(-c2cnc3[nH]cc(-c4ccncn4)c3c2)c1] | (E)-4-(dimethylamino)-N-(5-(3-(pyrimidin-4-yl)-1H-pyrrolo[2,3-b]pyridin-5-yl)pyridin-3-yl)but-2-enamide |

TABLE 2-continued

| Structure | Name |
|---|---|
| 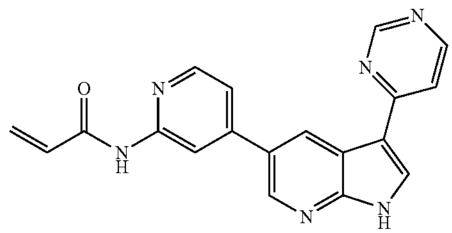 [SMILES: C=CC(=O)Nc1cc(-c2cnc3[nH]cc(-c4ccncn4)c3c2)ccn1] | N-(4-(3-(pyrimidin-4-yl)-1H-pyrrolo[2,3-b]pyridin-5-yl)pyridin-2-yl)acrylamide |
| 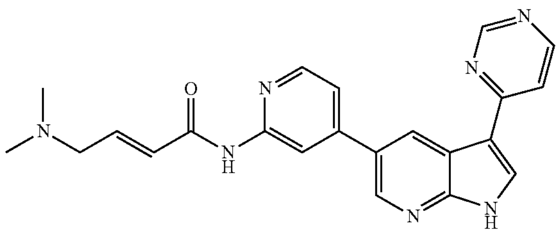 [SMILES: CN(C)C/C=C/C(=O)Nc1cc(-c2cnc3[nH]cc(-c4ccncn4)c3c2)ccn1] | (E)-4-(dimethylamino)-N-(4-(3-(pyrimidin-4-yl)-1H-pyrrolo[2,3-b]pyridin-5-yl)pyridin-2-yl)but-2-enamide |
| 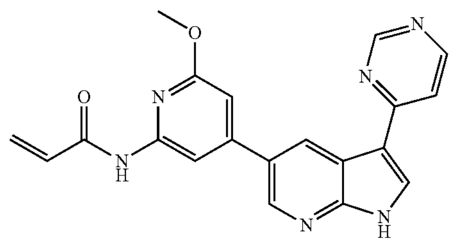 [SMILES: C=CC(=O)Nc1cc(-c2cnc3[nH]cc(-c4ccncn4)c3c2)cc(OC)n1] | N-(6-methoxy-4-(3-(pyrimidin-4-yl)-1H-pyrrolo[2,3-b]pyridin-5-yl)pyridin-2-yl)acrylamide |
| 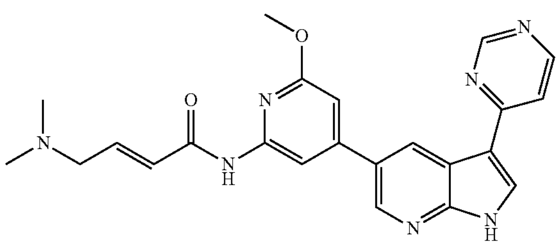 [SMILES: COc1cc(-c2cnc3[nH]cc(-c4ccncn4)c3c2)cc(NC(=O)/C=C/CN(C)C)n1] | (E)-4-(dimethylamino)-N-(6-methoxy-4-(3-(pyrimidin-4-yl)-1H-pyrrolo[2,3-b]pyridin-5-yl)pyridin-2-yl)but-2-enamide |
| 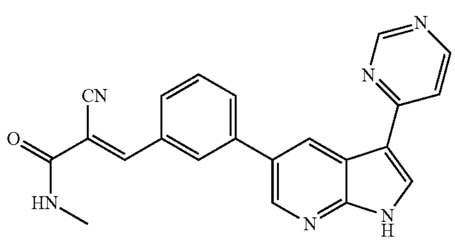 [SMILES: CNC(=O)/C(C#N)=C/c1cccc(-c2cnc3[nH]cc(-c4ccncn4)c3c2)c1] | (E)-2-cyano-N-methyl-3-(3-(3-(pyrimidin-4-yl)-1H-pyrrolo[2,3-b]pyridin-5-yl)phenyl)acrylamide |
| 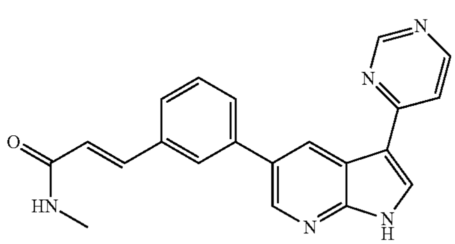 [SMILES: CNC(=O)/C=C/c1cccc(-c2cnc3[nH]cc(-c4ccncn4)c3c2)c1] | (E)-N-methyl-3-(3-(3-(pyrimidin-4-yl)-1H-pyrrolo[2,3-b]pyridin-5-yl)phenyl)acrylamide |

| Structure | Name |
|---|---|
| 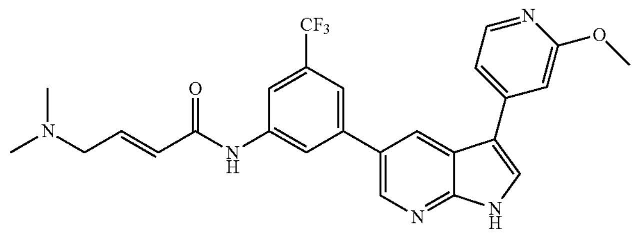 | (E)-4-(dimethylamino)-N-(3-(3-(2-methoxypyridin-4-yl)-1H-pyrrolo[2,3-b]pyridin-5-yl)-5-(trifluoromethyl)phenyl)but-2-enamide |
| 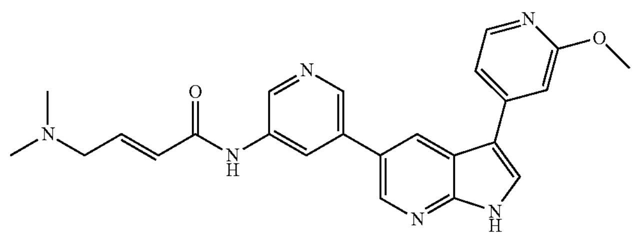 | (E)-4-(dimethylamino)-N-(5-(3-(2-methoxypyridin-4-yl)-1H-pyrrolo[2,3-b]pyridin-5-yl)pyridin-3-yl)but-2-enamide |
| 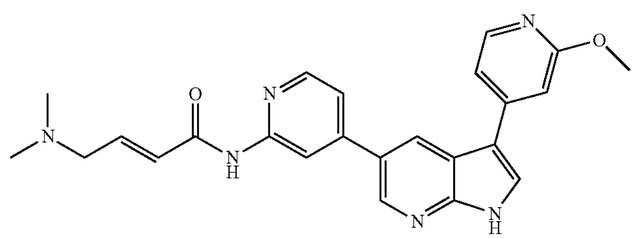 | (E)-4-(dimethylamino)-N-(4-(3-(2-methoxypyridin-4-yl)-1H-pyrrolo[2,3-b]pyridin-5-yl)pyridin-2-yl)but-2-enamide |
| 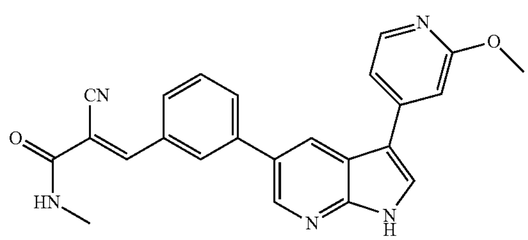 [SMILES: CNC(=O)/C(C#N)=C/c1cccc(-c2cnc3[nH]cc(-c4ccnc(OC)c4)c3c2)c1] | (E)-2-cyano-3-(3-(3-(2-methoxypyridin-4-yl)-1H-pyrrolo[2,3-b]pyridin-5-yl)phenyl)-N-methylacrylamide |
| 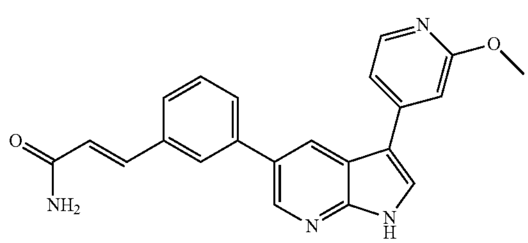 [SMILES: COc1cc(-c2c[nH]c3ncc(-c4cccc(/C=C/C(N)=O)c4)cc23)ccn1] | (E)-3-(3-(3-(2-methoxypyridin-4-yl)-1H-pyrrolo[2,3-b]pyridin-5-yl)phenyl)acrylamide |
| 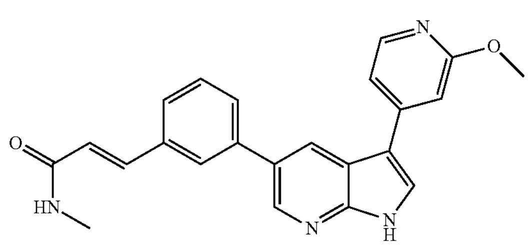 [SMILES: CNC(=O)/C=C/c1cccc(-c2cnc3[nH]cc(-c4ccnc(OC)c4)c3c2)c1] | (E)-3-(3-(3-(2-methoxypyridin-4-yl)-1H-pyrrolo[2,3-b]pyridin-5-yl)phenyl)-N-methylacrylamide |

TABLE 2-continued

| Structure | Name |
| --- | --- |
| 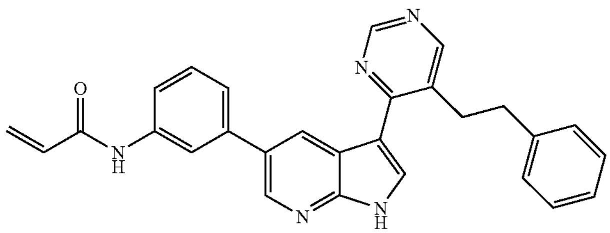 [SMILES: C=CC(=O)Nc1cccc(-c2cnc3[nH]cc(-c4ncncc4CCc4ccccc4)c3c2)c1] | N-(3-(3-(5-phenethylpyrimidin-4-yl)-1H-pyrrolo[2,3-b]pyridin-5-yl)phenyl)acrylamide |
| 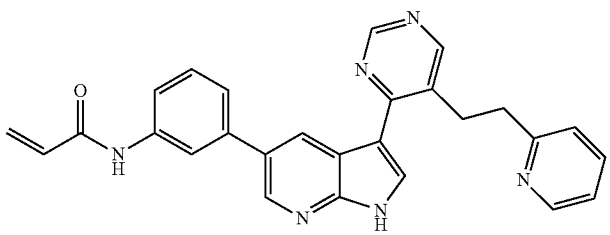 [SMILES: C=CC(=O)Nc1cccc(-c2cnc3[nH]cc(-c4ncncc4CCc4ccccn4)c3c2)c1] | N-(3-(3-(5-(2-(pyridin-2-yl)ethyl)pyrimidin-4-yl)-1H-pyrrolo[2,3-b]pyridin-5-yl)phenyl)acrylamide |
| 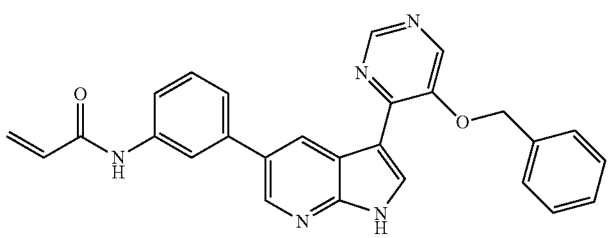 [SMILES: C=CC(=O)Nc1cccc(-c2cnc3[nH]cc(-c4ncncc4OCc4ccccc4)c3c2)c1] | N-(3-(3-(5-(benzyloxy)pyrimidin-4-yl)-1H-pyrrolo[2,3-b]pyridin-5-yl)phenyl)acrylamide |
| 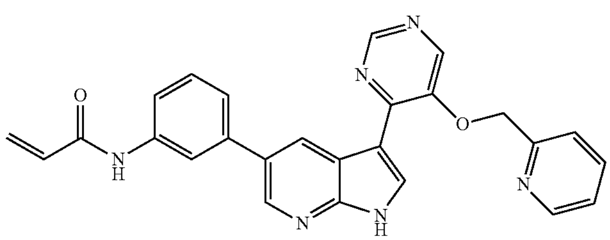 [SMILES: C=CC(=O)Nc1cccc(-c2cnc3[nH]cc(-c4ncncc4OCc4ccccn4)c3c2)c1] | N-(3-(3-(5-(pyridin-2-ylmethoxy)pyrimidin-4-yl)-1H-pyrrolo[2,3-b]pyridin-5-yl)phenyl)acrylamide |
| 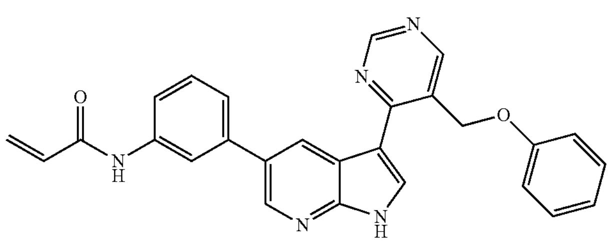 [SMILES: C=CC(=O)Nc1cccc(-c2cnc3[nH]cc(-c4ncncc4COc4ccccc4)c3c2)c1] | N-(3-(3-(5-(phenoxymethyl)pyrimidin-4-yl)-1H-pyrrolo[2,3-b]pyridin-5-yl)phenyl)acrylamide |
| 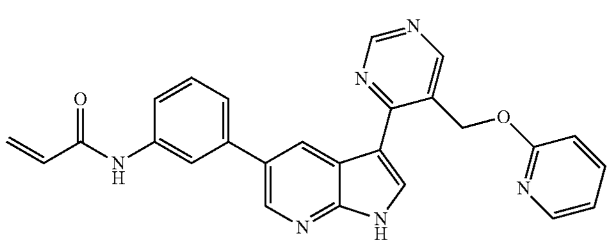 [SMILES: C=CC(=O)Nc1cccc(-c2cnc3[nH]cc(-c4ncncc4COc4ccccn4)c3c2)c1] | N-(3-(3-(5-((pyridin-2-yloxy)methyl)pyrimidin-4-yl)-1H-pyrrolo[2,3-b]pyridin-5-yl)phenyl)acrylamide |

TABLE 2-continued

| Structure | Name |
|---|---|
| 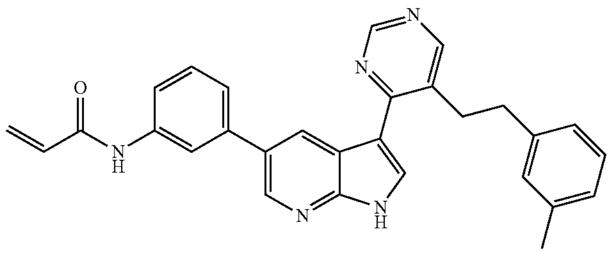 [SMILES: C=CC(=O)Nc1cccc(-c2cnc3[nH]cc(-c4ncncc4CCc4cccc(C)c4)c3c2)c1] | N-(3-(3-(5-(3-methylphenethyl)pyrimidin-4-yl)-1H-pyrrolo[2,3-b]pyridin-5-yl)phenyl)acrylamide |
| 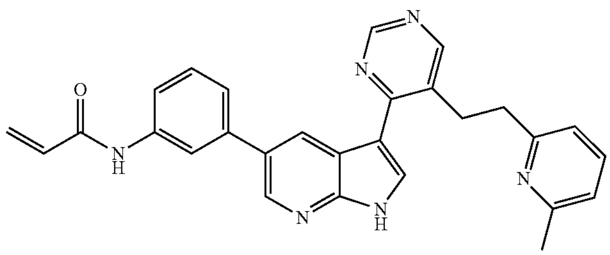 [SMILES: C=CC(=O)Nc1cccc(-c2cnc3[nH]cc(-c4ncncc4CCc4cccc(C)n4)c3c2)c1] | N-(3-(3-(5-(2-(6-methylpyridin-2-yl)ethyl)pyrimidin-4-yl)-1H-pyrrolo[2,3-b]pyridin-5-yl)phenyl)acrylamide |
| 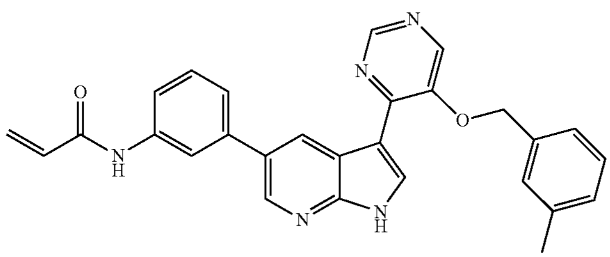 [SMILES: C=CC(=O)Nc1cccc(-c2cnc3[nH]cc(-c4ncncc4OCc4cccc(C)c4)c3c2)c1] | N-(3-(3-(5-((3-methylbenzyl)oxy)pyrimidin-4-yl)-1H-pyrrolo[2,3-b]pyridin-5-yl)phenyl)acrylamide |
| 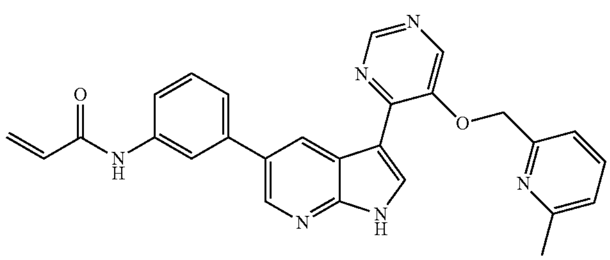 [SMILES: C=CC(=O)Nc1cccc(-c2cnc3[nH]cc(-c4ncncc4OCc4cccc(C)n4)c3c2)c1] | N-(3-(3-(5-((6-methylpyridin-2-yl)methoxy)pyrimidin-4-yl)-1H-pyrrolo[2,3-b]pyridin-5-yl)phenyl)acrylamide |
| 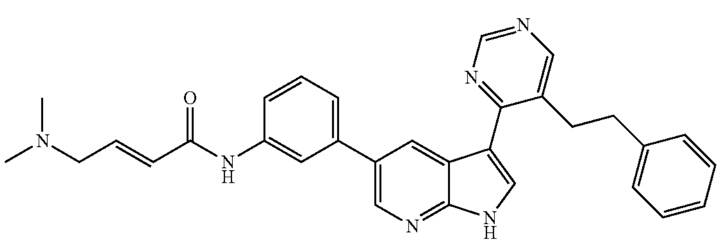 [SMILES: CN(C)C/C=C/C(=O)Nc1cccc(-c2cnc3[nH]cc(-c4ncncc4CCc4ccccc4)c3c2)c1] | (E)-4-(dimethylamino)-N-(3-(3-(5-phenethylpyrimidin-4-yl)-1H-pyrrolo[2,3-b]pyridin-5-yl)phenyl)but-2-enamide |
| 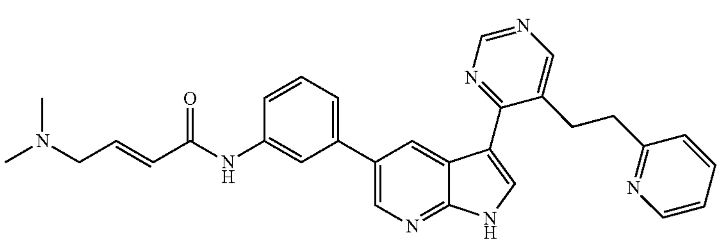 [SMILES: CN(C)C/C=C/C(=O)Nc1cccc(-c2cnc3[nH]cc(-c4ncncc4CCc4ccccn4)c3c2)c1] | (E)-4-(dimethylamino)-N-(3-(3-(5-(2-(pyridin-2-yl)ethyl)pyrimidin-4-yl)-1H-pyrrolo[2,3-b]pyridin-5-yl)phenyl)but-2-enamide |

TABLE 2-continued

| Structure | Name |
|---|---|
| 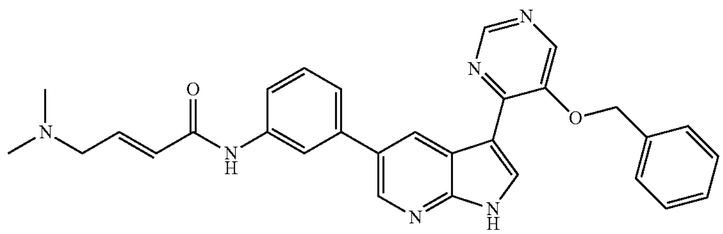 [SMILES: CN(C)C/C=C/C(=O)Nc1cccc(-c2cnc3[nH]cc(-c4ncncc4OCc4ccccc4)c3c2)c1] | (E)-N-(3-(3-(5-(benzyloxy)pyrimidin-4-yl)-1H-pyrrolo[2,3-b]pyridin-5-yl)phenyl)-4-(dimethylamino)but-2-enamide |
| 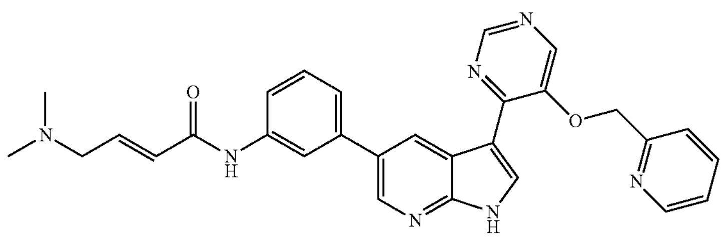 [SMILES: CN(C)C/C=C/C(=O)Nc1cccc(-c2cnc3[nH]cc(-c4ncncc4OCc4ccccn4)c3c2)c1] | (E)-4-(dimethylamino)-N-(3-(3-(5-(pyridin-2-ylmethoxy)pyrimidin-4-yl)-1H-pyrrolo[2,3-b]pyridin-5-yl)phenyl)but-2-enamide |
| | N-(3-(3-(5-(3-cyclopropylpropyl)pyrimidin-4-yl)-1H-pyrrolo[2,3-b]pyridin-5-yl)phenyl)acrylamide |
| | N-(3-(3-(5-(3-cyclopropylpropyl)pyrimidin-4-yl)-1H-pyrrolo[2,3-b]pyridin-5-yl)phenyl)acrylamide |
| | N-(3-(3-(5-(3-cyclopropylpropyl)-2-methoxypyridin-4-yl)-1H-pyrrolo[2,3-b]pyridin-5-yl)phenyl)acrylamide |
| | N-(3-(3-(5-(3-cyclopropylpropyl)-2-methoxypyridin-4-yl)-1H-pyrrolo[2,3-b]pyridin-5-yl)phenyl)acrylamide |

TABLE 2-continued

| Structure | Name |
|---|---|
| 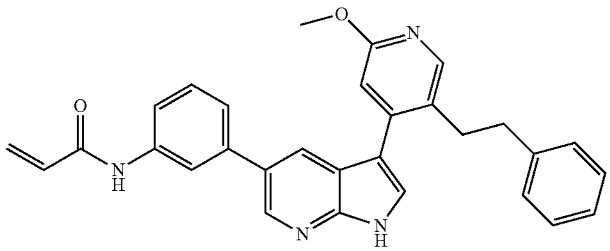 [SMILES: C=CC(=O)Nc1cccc(-c2cnc3[nH]cc(-c4cc(OC)ncc4CCc4ccccc4)c3c2)c1] | N-(3-(3-(2-methoxy-5-phenethylpyridin-4-yl)-1H-pyrrolo[2,3-b]pyridin-5-yl)phenyl)acrylamide |
| 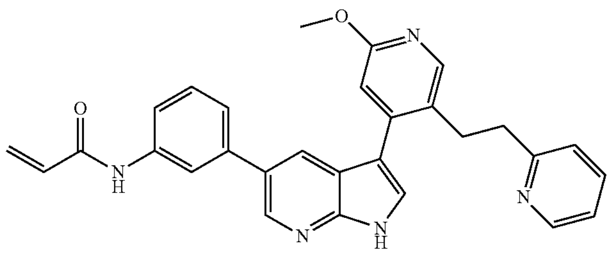 [SMILES: C=CC(=O)Nc1cccc(-c2cnc3[nH]cc(-c4cc(OC)ncc4CCc4ccccn4)c3c2)c1] | N-(3-(3-(2-methoxy-5-(2-(pyridin-2-yl)ethyl)pyridin-4-yl)-1H-pyrrolo[2,3-b]pyridin-5-yl)phenyl)acrylamide |
| 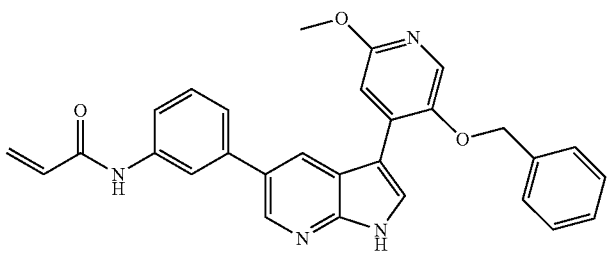 [SMILES: C=CC(=O)Nc1cccc(-c2cnc3[nH]cc(-c4cc(OC)ncc4OCc4ccccc4)c3c2)c1] | N-(3-(3-(5-(benzyloxy)-2-methoxypyridin-4-yl)-1H-pyrrolo[2,3-b]pyridin-5-yl)phenyl)acrylamide |
| 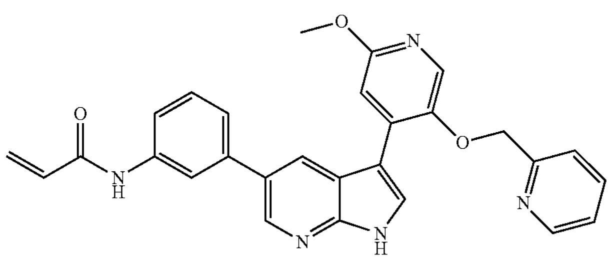 [SMILES: C=CC(=O)Nc1cccc(-c2cnc3[nH]cc(-c4cc(OC)ncc4OCc4ccccn4)c3c2)c1] | N-(3-(3-(2-methoxy-5-(pyridin-2-ylmethoxy)pyridin-4-yl)-1H-pyrrolo[2,3-b]pyridin-5-yl)phenyl)acrylamide |
| 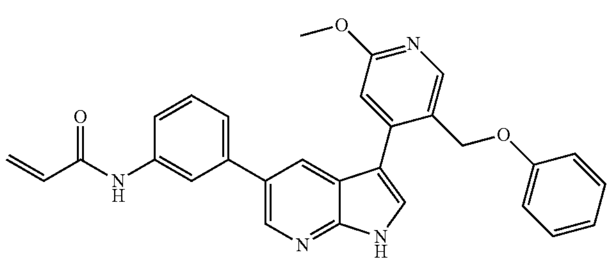 [SMILES: C=CC(=O)Nc1cccc(-c2cnc3[nH]cc(-c4cc(OC)ncc4COc4ccccc4)c3c2)c1] | N-(3-(3-(2-methoxy-5-(phenoxymethyl)pyridin-4-yl)-1H-pyrrolo[2,3-b]pyridin-5-yl)phenyl)acrylamide |
| 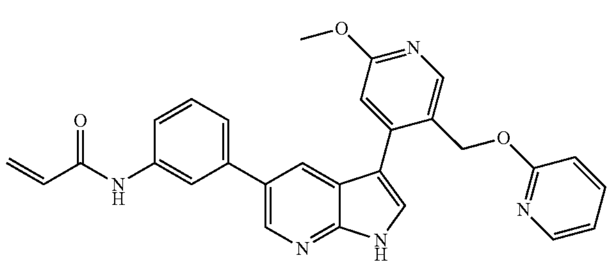 [SMILES: C=CC(=O)Nc1cccc(-c2cnc3[nH]cc(-c4cc(OC)ncc4COc4ccccn4)c3c2)c1] | N-(3-(3-(2-methoxy-5-((pyridin-2-yloxy)methyl)pyridin-4-yl)-1H-pyrrolo[2,3-b]pyridin-5-yl)phenyl)acrylamide |

TABLE 2-continued

| Structure | Name |
|---|---|
| 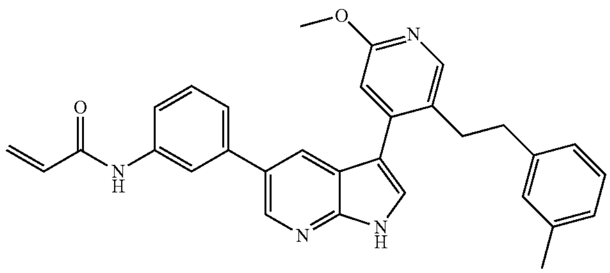 [SMILES: C=CC(=O)Nc1cccc(-c2cnc3[nH]cc(-c4cc(OC)ncc4CCc4cccc(C)c4)c3c2)c1] | N-(3-(3-(2-methoxy-5-(3-methylphenethyl)pyridin-4-yl)-1H-pyrrolo[2,3-b]pyridin-5-yl)phenyl)acrylamide |
| 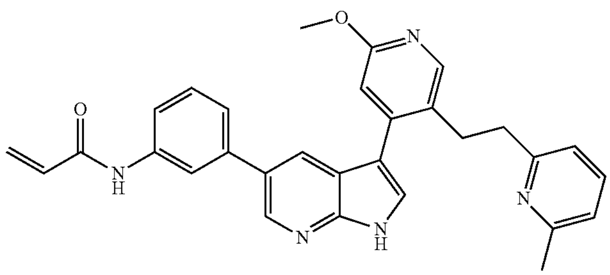 [SMILES: C=CC(=O)Nc1cccc(-c2cnc3[nH]cc(-c4cc(OC)ncc4CCc4cccc(C)n4)c3c2)c1] | N-(3-(3-(2-methoxy-5-(2-(6-methylpyridin-2-yl)ethyl)pyridin-4-yl)-1H-pyrrolo[2,3-b]pyridin-5-yl)phenyl)acrylamide |
| 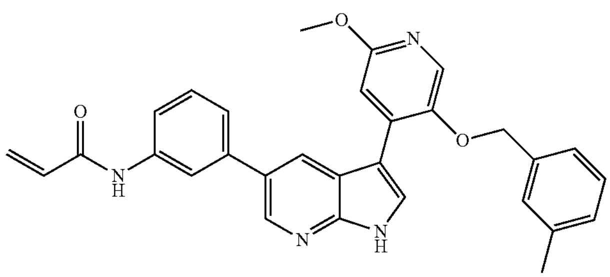 [SMILES: C=CC(=O)Nc1cccc(-c2cnc3[nH]cc(-c4cc(OC)ncc4OCc4cccc(C)c4)c3c2)c1] | N-(3-(3-(2-methoxy-5-((3-methylbenzyl)oxy)pyridin-4-yl)-1H-pyrrolo[2,3-b]pyridin-5-yl)phenyl)acrylamide |
| 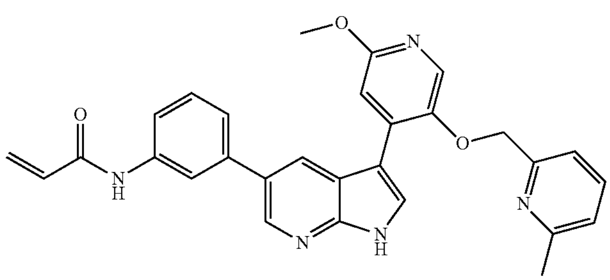 [SMILES: C=CC(=O)Nc1cccc(-c2cnc3[nH]cc(-c4cc(OC)ncc4OCc4cccc(C)n4)c3c2)c1] | N-(3-(3-(2-methoxy-5-((6-methylpyridin-2-yl)methoxy)pyridin-4-yl)-1H-pyrrolo[2,3-b]pyridin-5-yl)phenyl)acrylamide |
| 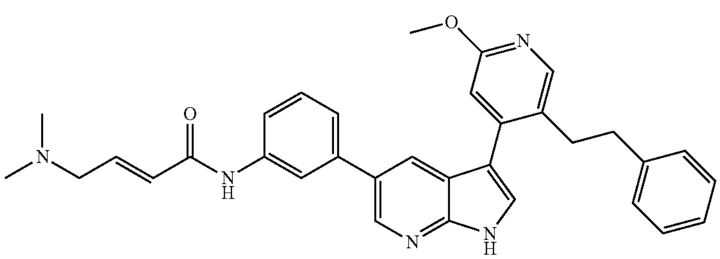 [SMILES: COc1cc(-c2c[nH]c3ncc(-c4cccc(NC(=O)/C=C/CN(C)C)c4)cc23)c(CCc2ccccc2)cn1] | (E)-4-(dimethylamino)-N-(3-(3-(2-methoxy-5-phenethylpyridin-4-yl)-1H-pyrrolo[2,3-b]pyridin-5-yl)phenyl)but-2-enamide |
| 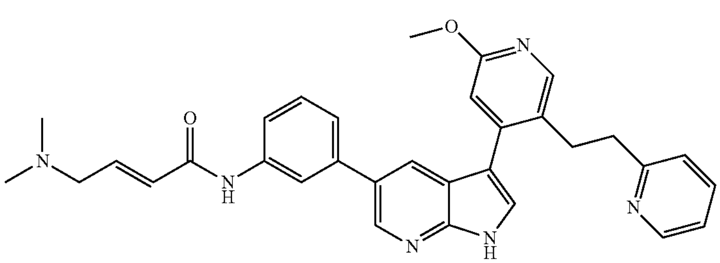 [SMILES: COc1cc(-c2c[nH]c3ncc(-c4cccc(NC(=O)/C=C/CN(C)C)c4)cc23)c(CCc2ccccn2)cn1] | (E)-4-(dimethylamino)-N-(3-(3-(2-methoxy-5-(2-(pyridin-2-yl)ethyl)pyridin-4-yl)-1H-pyrrolo[2,3-b]pyridin-5-yl)phenyl)but-2-enamide |

TABLE 2-continued

| Structure | Name |
| --- | --- |
| 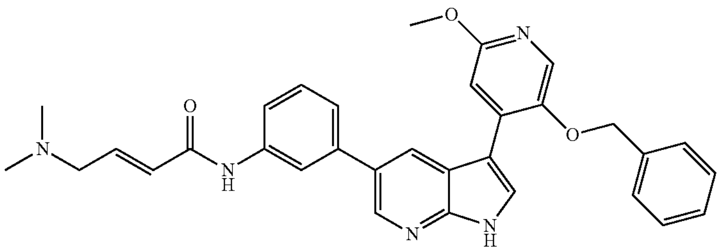 [SMILES: COc1cc(-c2c[nH]c3ncc(-c4cccc(NC(=O)/C=C/CN(C)C)c4)cc23)c(OCc2ccccc2)cn1] | (E)-N-(3-(3-(5-(benzyloxy)-2-methoxypyridin-4-yl)-1H-pyrrolo[2,3-b]pyridin-5-yl)phenyl)-4-(dimethylamino)but-2-enamide |
| 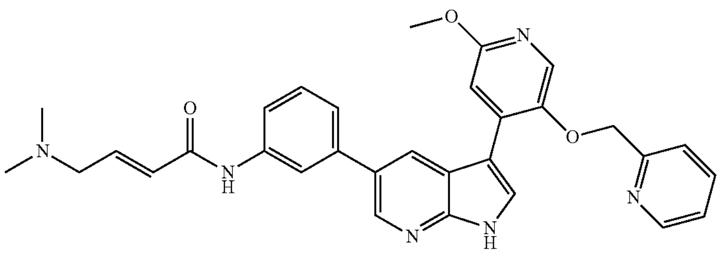 [SMILES: COc1cc(-c2c[nH]c3ncc(-c4cccc(NC(=O)/C=C/CN(C)C)c4)cc23)c(OCc2ccccn2)cn1] | (E)-4-(dimethylamino)-N-(3-(3-(2-methoxy-5-(pyridin-2-ylmethoxy)pyridin-4-yl)-1H-pyrrolo[2,3-b]pyridin-5-yl)phenyl)but-2-enamide |
| 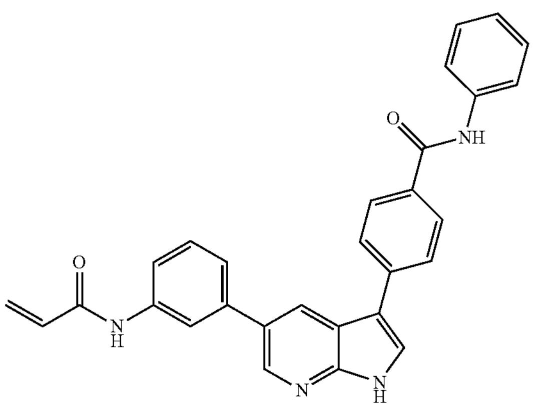 [SMILES: C=CC(=O)Nc1cccc(-c2cnc3[nH]cc(-c4ccc(C(=O)Nc5ccccc5)cc4)c3c2)c1] | 4-(5-(3-acrylamidophenyl)-1H-pyrrolo[2,3-b]pyridin-3-yl)-N-phenylbenzamide |
| 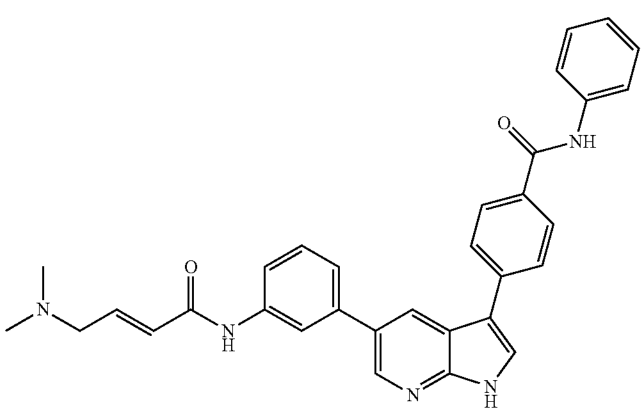 [SMILES: CN(C)C/C=C/C(=O)Nc1cccc(-c2cnc3[nH]cc(-c4ccc(C(=O)Nc5ccccc5)cc4)c3c2)c1] | (E)-4-(5-(3-(4-(dimethylamino)but-2-enamido)phenyl)-1H-pyrrolo[2,3-b]pyridin-3-yl)-N-phenylbenzamide |

TABLE 2-continued
| Structure | Name |
|---|---|
| 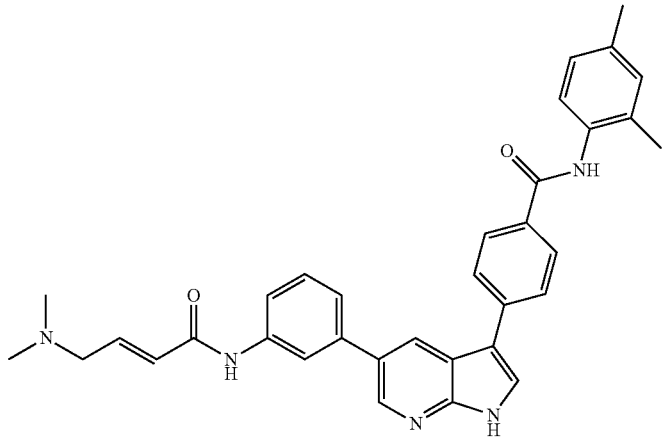 | (E)-4-(5-(3-(4-(dimethylamino)but-2-enamido)phenyl)-1H-pyrrolo[2,3-b]pyridin-3-yl)-N-(2,4-dimethylphenyl)benzamide |
| 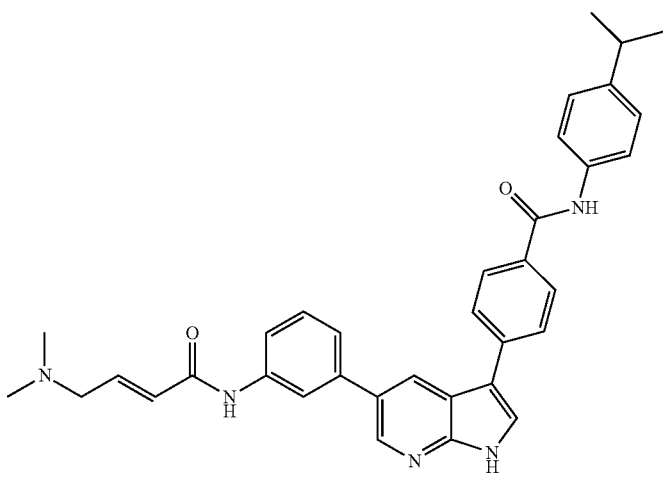 [SMILES: CC(C)c1ccc(NC(=O)c2ccc(-c3c[nH]c4ncc(-c5cccc(NC(=O)/C=C/CN(C)C)c5)cc34)cc2)cc1] | (E)-4-(5-(3-(4-(dimethylamino)but-2-enamido)phenyl)-1H-pyrrolo[2,3-b]pyridin-3-yl)-N-(4-isopropylphenyl)benzamide |
| 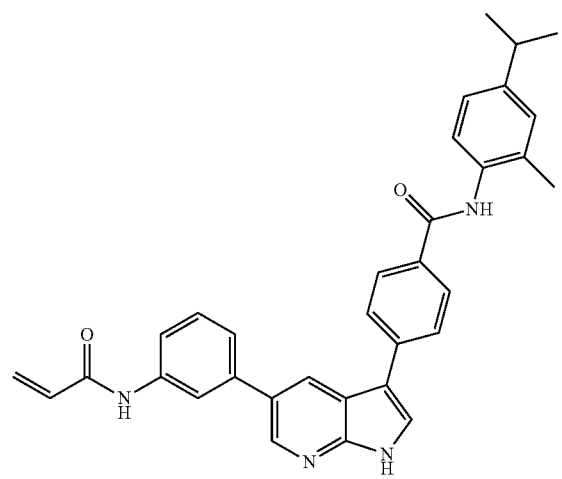 [SMILES: C=CC(=O)Nc1cccc(-c2cnc3[nH]cc(-c4ccc(C(=O)Nc5ccc(C(C)C)cc5C)cc4)c3c2)c1] | 4-(5-(3-acrylamidophenyl)-1H-pyrrolo[2,3-b]pyridin-3-yl)-N-(4-isopropyl-2-methylphenyl)benzamide |

TABLE 2-continued

| Structure | Name |
|---|---|
| 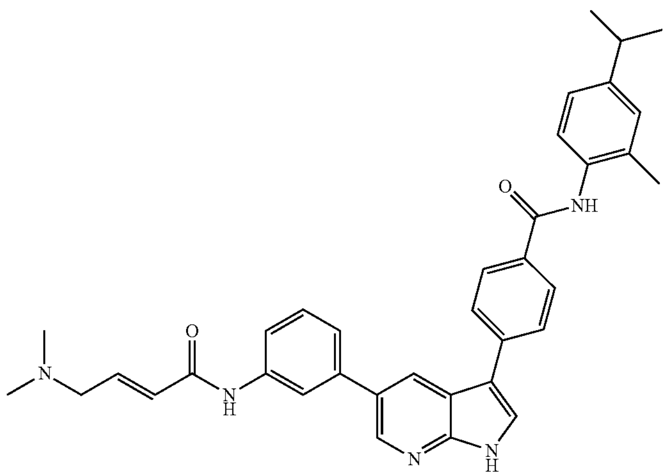 [SMILES: Cc1cc(C(C)C)ccc1NC(=O)c1ccc(-c2c[nH]c3ncc(-c4cccc(NC(=O)/C=C/CN(C)C)c4)cc23)cc1] | (E)-4-(5-(3-(4-(dimethylamino)but-2-enamido)phenyl)-1H-pyrrolo[2,3-b]pyridin-3-yl)-N-(4-isopropyl-2-methylphenyl)benzamide |
| 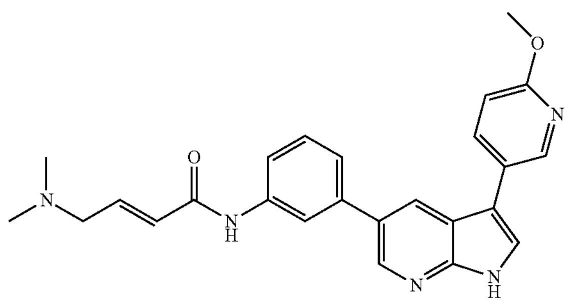 [SMILES: COc1ccc(-c2c[nH]c3ncc(-c4cccc(NC(=O)/C=C/CN(C)C)c4)cc23)cn1] | (E)-4-(dimethylamino)-N-(3-(3-(6-methoxypyridin-3-yl)-1H-pyrrolo[2,3-b]pyridin-5-yl)phenyl)but-2-enamide |
| 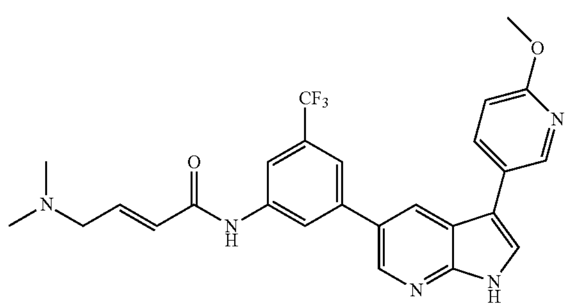 [SMILES: COc1ccc(-c2c[nH]c3ncc(-c4cc(NC(=O)/C=C/CN(C)C)cc(C(F)(F)F)c4)cc23)cn1] | (E)-4-(dimethylamino)-N-(3-(3-(6-methoxypyridin-3-yl)-1H-pyrrolo[2,3-b]pyridin-5-yl)-5-(trifluoromethyl)phenyl)but-2-enamide |
| 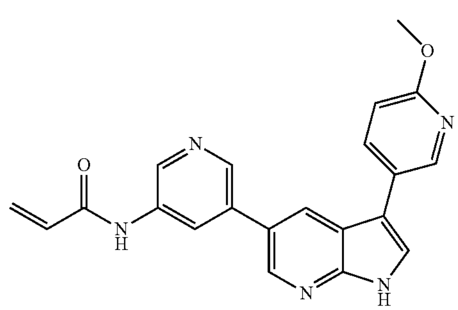 [SMILES: C=CC(=O)Nc1cncc(-c2cnc3[nH]cc(-c4ccc(OC)nc4)c3c2)c1] | N-(5-(3-(6-methoxypyridin-3-yl)-1H-pyrrolo[2,3-b]pyridin-5-yl)pyridin-3-yl)acrylamide |

| Structure | Name |
|---|---|
| 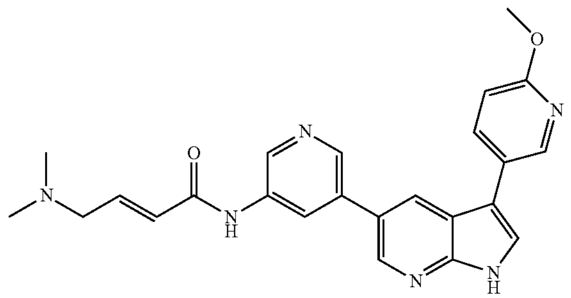 [SMILES: COc1ccc(-c2c[nH]c3ncc(-c4cncc(NC(=O)/C=C/CN(C)C)c4)cc23)cn1] | (E)-4-(dimethylamino)-N-(5-(3-(6-methoxypyridin-3-yl)-1H-pyrrolo[2,3-b]pyridin-5-yl)pyridin-3-yl)but-2-enamide |
| 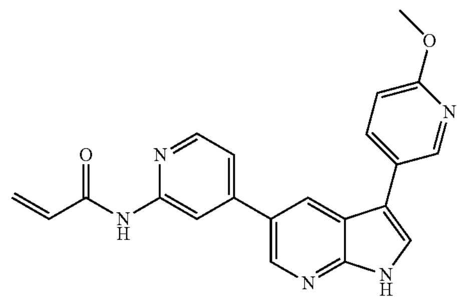 [SMILES: C=CC(=O)Nc1cc(-c2cnc3[nH]cc(-c4ccc(OC)nc4)c3c2)ccn1] | N-(4-(3-(6-methoxypyridin-3-yl)-1H-pyrrolo[2,3-b]pyridin-5-yl)pyridin-2-yl)acrylamide |
| 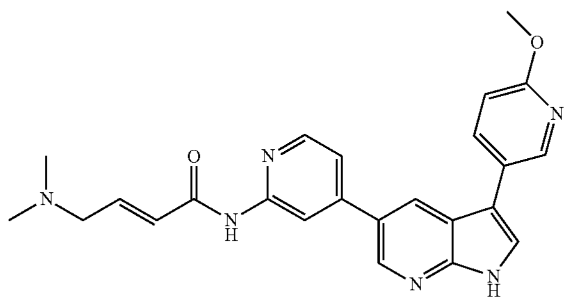 [SMILES: COc1ccc(-c2c[nH]c3ncc(-c4ccnc(NC(=O)/C=C/CN(C)C)c4)cc23)cn1] | (E)-4-(dimethylamino)-N-(4-(3-(6-methoxypyridin-3-yl)-1H-pyrrolo[2,3-b]pyridin-5-yl)pyridin-2-yl)but-2-enamide |
| 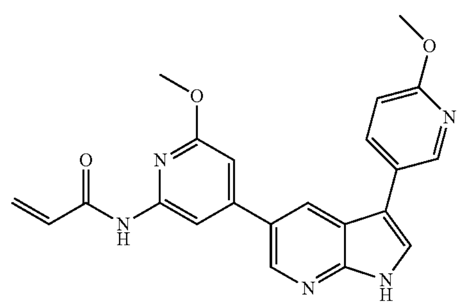 [SMILES: C=CC(=O)Nc1cc(-c2cnc3[nH]cc(-c4ccc(OC)nc4)c3c2)cc(OC)n1] | N-(6-methoxy-4-(3-(6-methoxypyridin-3-yl)-1H-pyrrolo[2,3-b]pyridin-5-yl)pyridin-2-yl)acrylamide |
| 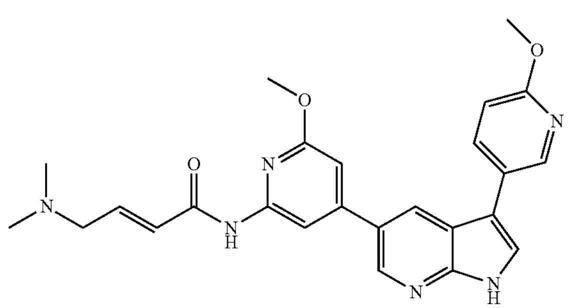 | (E)-4-(dimethylamino)-N-(6-methoxy-4-(3-(6-methoxypyridin-3-yl)-1H-pyrrolo[2,3-b]pyridin-5-yl)pyridin-2-yl)but-2-enamide |

TABLE 2-continued

| Structure | Name |
|---|---|
| 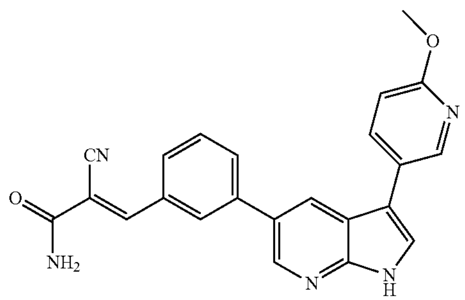 [SMILES: COc1ccc(-c2c[nH]c3ncc(-c4cccc(/C=C(\C#N)C(N)=O)c4)cc23)cn1] | (E)-2-cyano-3-(3-(3-(6-methoxypyridin-3-yl)-1H-pyrrolo[2,3-b]pyridin-5-yl)phenyl)acrylamide |
| 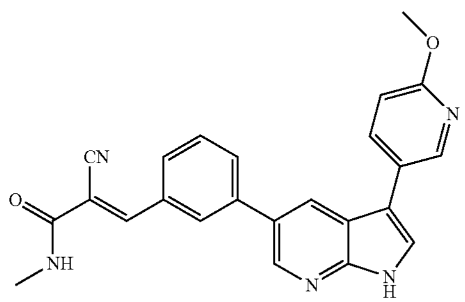 [SMILES: CNC(=O)/C(C#N)=C/c1cccc(-c2cnc3[nH]cc(-c4ccc(OC)nc4)c3c2)c1] | (E)-2-cyano-3-(3-(3-(6-methoxypyridin-3-yl)-1H-pyrrolo[2,3-b]pyridin-5-yl)phenyl)-N-methylacrylamide |
| 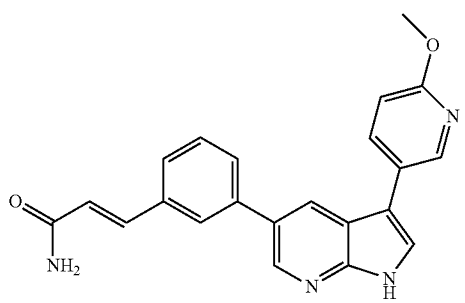 [SMILES: COc1ccc(-c2c[nH]c3ncc(-c4cccc(/C=C/C(N)=O)c4)cc23)cn1] | (E)-3-(3-(3-(6-methoxypyridin-3-yl)-1H-pyrrolo[2,3-b]pyridin-5-yl)phenyl)acrylamide |
| 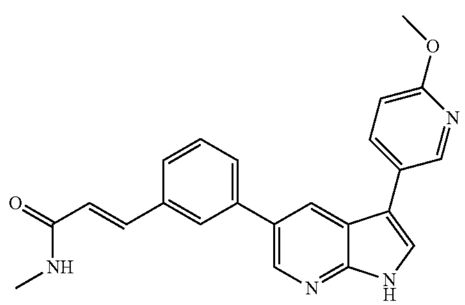 [SMILES: CNC(=O)/C=C/c1cccc(-c2cnc3[nH]cc(-c4ccc(OC)nc4)c3c2)c1] | (E)-3-(3-(3-(6-methoxypyridin-3-yl)-1H-pyrrolo[2,3-b]pyridin-5-yl)phenyl)-N-methylacrylamide |
| 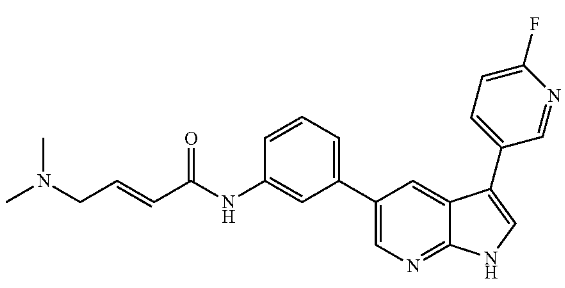 [SMILES: CN(C)C/C=C/C(=O)Nc1cccc(-c2cnc3[nH]cc(-c4ccc(F)nc4)c3c2)c1] | (E)-4-(dimethylamino)-N-(3-(3-(6-fluoropyridin-3-yl)-1H-pyrrolo[2,3-b]pyridin-5-yl)phenyl)but-2-enamide |

TABLE 2-continued

| Structure | Name |
|---|---|
| 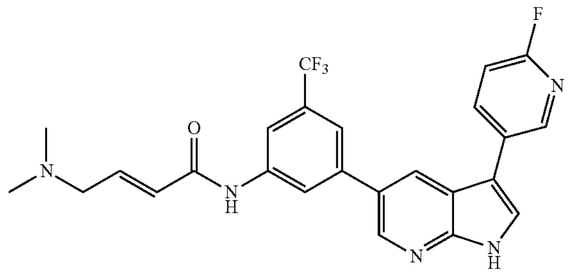 [SMILES: CN(C)C/C=C/C(=O)Nc1cc(-c2cnc3[nH]cc(-c4ccc(F)nc4)c3c2)cc(C(F)(F)F)c1] | (E)-4-(dimethylamino)-N-(3-(3-(6-fluoropyridin-3-yl)-1H-pyrrolo[2,3-b]pyridin-5-yl)-5-(trifluoromethyl)phenyl)but-2-enamide |
| 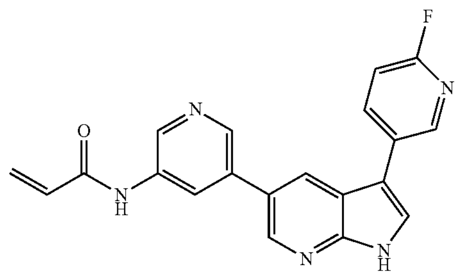 [SMILES: C=CC(=O)Nc1cncc(-c2cnc3[nH]cc(-c4ccc(F)nc4)c3c2)c1] | N-(5-(3-(6-fluoropyridin-3-yl)-1H-pyrrolo[2,3-b]pyridin-5-yl)pyridin-3-yl)acrylamide |
| 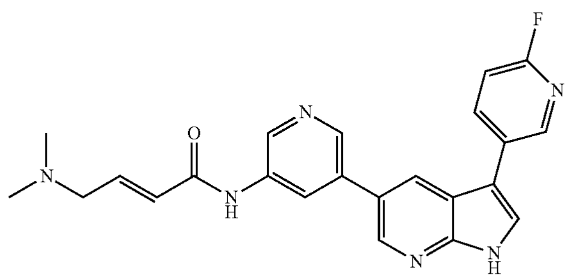 [SMILES: CN(C)C/C=C/C(=O)Nc1cncc(-c2cnc3[nH]cc(-c4ccc(F)nc4)c3c2)c1] | (E)-4-(dimethylamino)-N-(5-(3-(6-fluoropyridin-3-yl)-1H-pyrrolo[2,3-b]pyridin-5-yl)pyridin-3-yl)but-2-enamide |
| 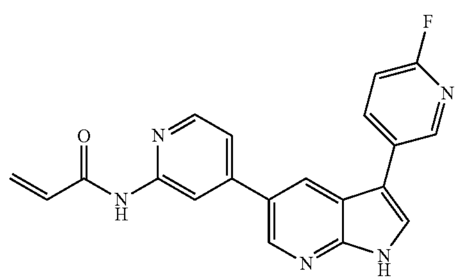 [SMILES: C=CC(=O)Nc1cc(-c2cnc3[nH]cc(-c4ccc(F)nc4)c3c2)ccn1] | N-(4-(3-(6-fluoropyridin-3-yl)-1H-pyrrolo[2,3-b]pyridin-5-yl)pyridin-2-yl)acrylamide |
| 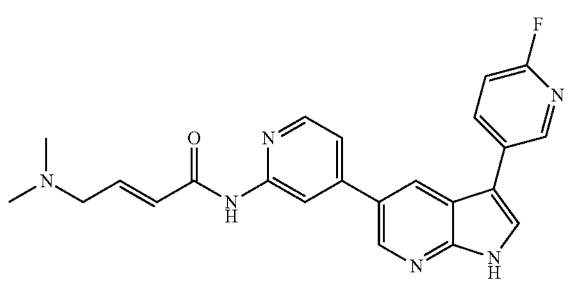 [SMILES: CN(C)C/C=C/C(=O)Nc1cc(-c2cnc3[nH]cc(-c4ccc(F)nc4)c3c2)ccn1] | (E)-4-(dimethylamino)-N-(4-(3-(6-fluoropyridin-3-yl)-1H-pyrrolo[2,3-b]pyridin-5-yl)pyridin-2-yl)but-2-enamide |

TABLE 2-continued

| Structure | Name |
|---|---|
| 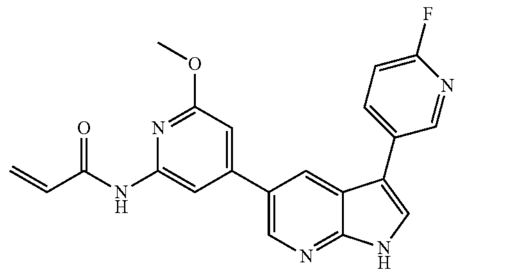 [SMILES: C=CC(=O)Nc1cc(-c2cnc3[nH]cc(-c4ccc(F)nc4)c3c2)cc(OC)n1] | N-(4-(3-(6-fluoropyridin-3-yl)-1H-pyrrolo[2,3-b]pyridin-5-yl)-6-methoxypyridin-2-yl)acrylamide |
| 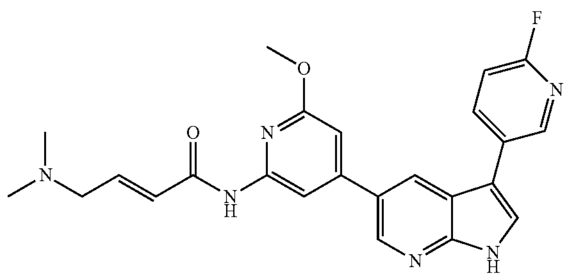 [SMILES: COc1cc(-c2cnc3[nH]cc(-c4ccc(F)nc4)c3c2)cc(NC(=O)/C=C/CN(C)C)n1] | (E)-4-(dimethylamino)-N-(4-(3-(6-fluoropyridin-3-yl)-1H-pyrrolo[2,3-b]pyridin-5-yl)-6-methoxypyridin-2-yl)but-2-enamide |
| 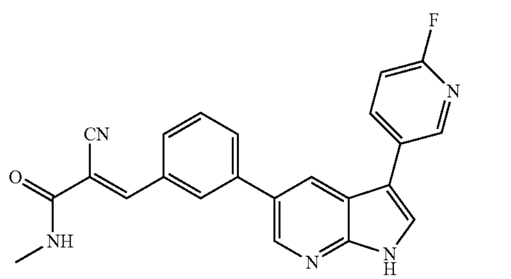 [SMILES: CNC(=O)/C(C#N)=C/c1cccc(-c2cnc3[nH]cc(-c4ccc(F)nc4)c3c2)c1] | (E)-2-cyano-3-(3-(3-(6-fluoropyridin-3-yl)-1H-pyrrolo[2,3-b]pyridin-5-yl)phenyl)-N-methylacrylamide |
| 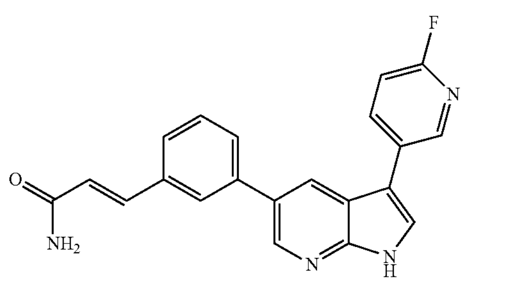 [SMILES: NC(=O)/C=C/c1cccc(-c2cnc3[nH]cc(-c4ccc(F)nc4)c3c2)c1] | (E)-3-(3-(3-(6-fluoropyridin-3-yl)-1H-pyrrolo[2,3-b]pyridin-5-yl)phenyl)acrylamide |
| 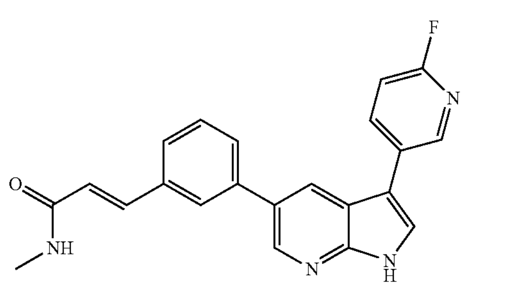 [SMILES: CNC(=O)/C=C/c1cccc(-c2cnc3[nH]cc(-c4ccc(F)nc4)c3c2)c1] | (E)-3-(3-(3-(6-fluoropyridin-3-yl)-1H-pyrrolo[2,3-b]pyridin-5-yl)phenyl)-N-methylacrylamide |

TABLE 2-continued

| Structure | Name |
|---|---|
| 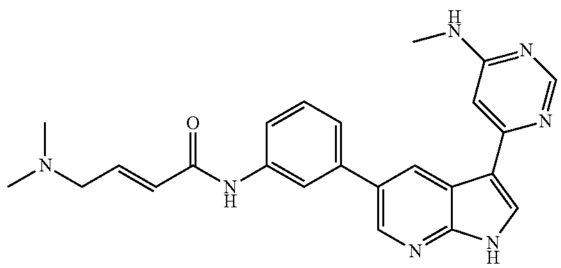 [SMILES: CNc1cc(-c2c[nH]c3ncc(-c4cccc(NC(=O)/C=C/CN(C)C)c4)cc23)ncn1] | (E)-4-(dimethylamino)-N-(3-(3-(6-(methylamino)pyrimidin-4-yl)-1H-pyrrolo[2,3-b]pyridin-5-yl)phenyl)but-2-enamide |
| 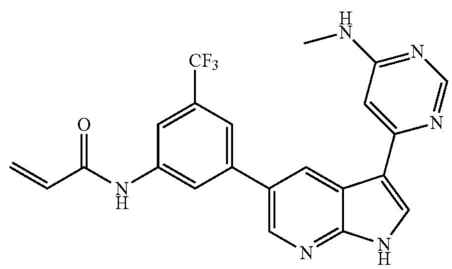 [SMILES: C=CC(=O)Nc1cc(-c2cnc3[nH]cc(-c4cc(NC)ncn4)c3c2)cc(C(F)(F)F)c1] | N-(3-(3-(6-(methylamino)pyrimidin-4-yl)-1H-pyrrolo[2,3-b]pyridin-5-yl)-5-(trifluoromethyl)phenyl)acrylamide |
| 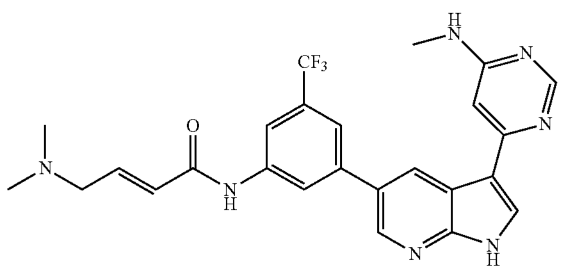 [SMILES: CNc1cc(-c2c[nH]c3ncc(-c4cc(NC(=O)/C=C/CN(C)C)cc(C(F)(F)F)c4)cc23)ncn1] | (E)-4-(dimethylamino)-N-(3-(3-(6-(methylamino)pyrimidin-4-yl)-1H-pyrrolo[2,3-b]pyridin-5-yl)-5-(trifluoromethyl)phenyl)but-2-enamide |
| 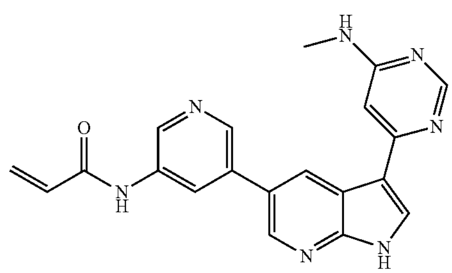 [SMILES: C=CC(=O)Nc1cncc(-c2cnc3[nH]cc(-c4cc(NC)ncn4)c3c2)c1] | N-(5-(3-(6-(methylamino)pyrimidin-4-yl)-1H-pyrrolo[2,3-b]pyridin-5-yl)pyridin-3-yl)-acrylamide |
| 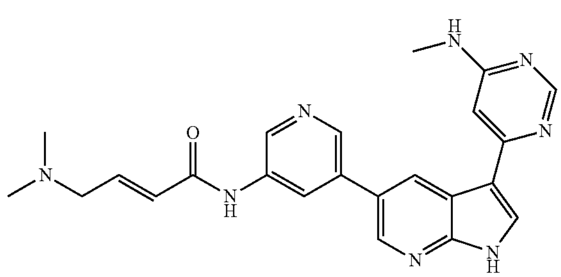 [SMILES: CNc1cc(-c2c[nH]c3ncc(-c4cncc(NC(=O)/C=C/CN(C)C)c4)cc23)ncn1] | (E)-4-(dimethylamino)-N-(5-(3-(6-(methylamino)pyrimidin-4-yl)-1H-pyrrolo[2,3-b]pyridin-5-yl)pyridin-3-yl)but-2-enamide |

TABLE 2-continued

| Structure | Name |
|---|---|
| 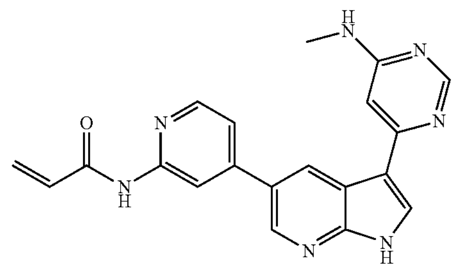 [SMILES: C=CC(=O)Nc1cc(-c2cnc3[nH]cc(-c4cc(NC)ncn4)c3c2)ccn1] | N-(4-(3-(6-(methylamino)pyrimidin-4-yl)-1H-pyrrolo[2,3-b]pyridin-5-yl)pyridin-2-yl)-acrylamide |
| 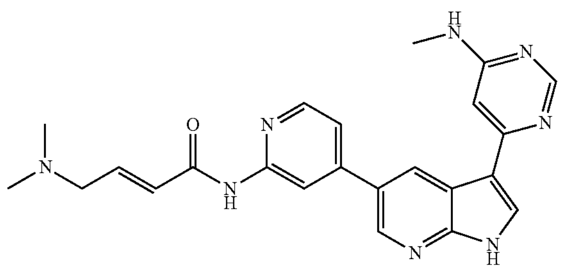 [SMILES: CNc1cc(-c2c[nH]c3ncc(-c4ccnc(NC(=O)/C=C/CN(C)C)c4)cc23)ncn1] | (E)-4-(dimethylamino)-N-(4-(3-(6-(methylamino)pyrimidin-4-yl)-1H-pyrrolo[2,3-b]pyridin-5-yl)pyridin-2-yl)but-2-enamide |
| 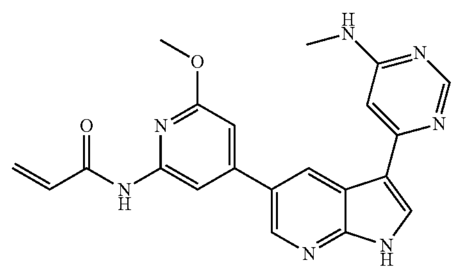 [SMILES: C=CC(=O)Nc1cc(-c2cnc3[nH]cc(-c4cc(NC)ncn4)c3c2)cc(OC)n1] | N-(6-methoxy-4-(3-(6-(methylamino)pyrimidin-4-yl)-1H-pyrrolo[2,3-b]pyridin-5-yl)pyridin-2-yl)-acrylamide |
| 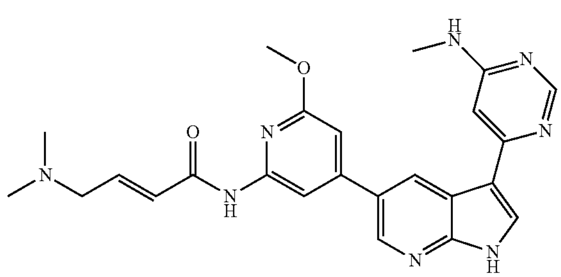 [SMILES: CNc1cc(-c2c[nH]c3ncc(-c4cc(NC(=O)/C=C/CN(C)C)nc(OC)c4)cc23)ncn1] | (E)-4-(dimethylamino)-N-(6-methoxy-4-(3-(6-(methylamino)pyrimidin-4-yl)-1H-pyrrolo[2,3-b]pyridin-5-yl)pyridin-2-yl)but-2-enamide |
| 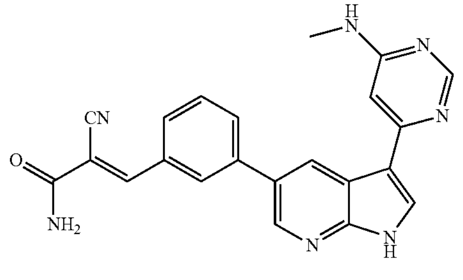 [SMILES: CNc1cc(-c2c[nH]c3ncc(-c4cccc(/C=C(\C#N)C(N)=O)c4)cc23)ncn1] | (E)-2-cyano-3-(3-(3-(6-(methylamino)pyrimidin-4-yl)-1H-pyrrolo[2,3-b]pyridin-5-yl)phenyl)acrylamide |

TABLE 2-continued

| Structure | Name |
|---|---|
| 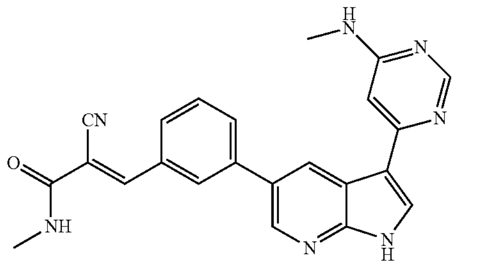 [SMILES: CNC(=O)/C(C#N)=C/c1cccc(-c2cnc3[nH]cc(-c4cc(NC)ncn4)c3c2)c1] | (E)-2-cyano-N-methyl-3-(3-(3-(6-(methylamino)pyrimidin-4-yl)-1H-pyrrolo[2,3-b]pyridin-5-yl)phenyl)acrylamide |
| 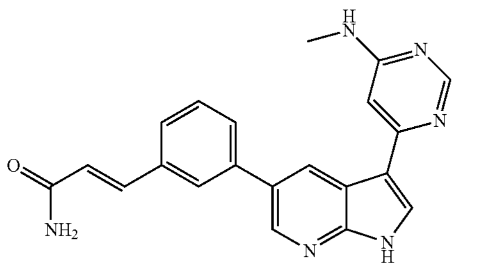 [SMILES: CNc1cc(-c2c[nH]c3ncc(-c4cccc(/C=C/C(N)=O)c4)cc23)ncn1] | (E)-3-(3-(3-(6-(methylamino)pyrimidin-4-yl)-1H-pyrrolo[2,3-b]pyridin-5-yl)phenyl)acrylamide |
| 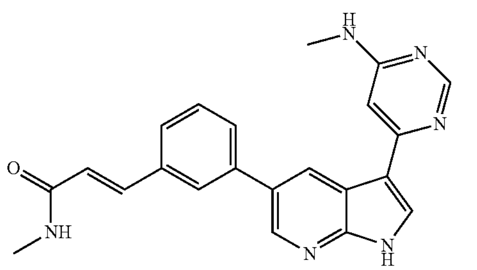 [SMILES: CNC(=O)/C=C/c1cccc(-c2cnc3[nH]cc(-c4cc(NC)ncn4)c3c2)c1] | (E)-N-methyl-3-(3-(3-(6-(methylamino)pyrimidin-4-yl)-1H-pyrrolo[2,3-b]pyridin-5-yl)phenyl)acrylamide |
| 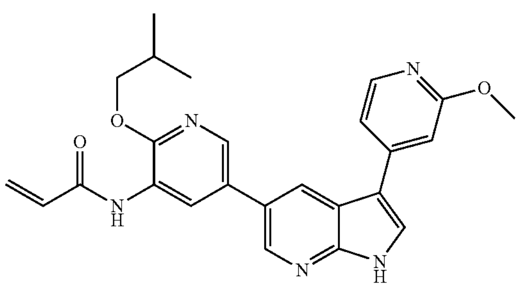 [SMILES: C=CC(=O)Nc1cc(-c2cnc3[nH]cc(-c4ccnc(OC)c4)c3c2)cnc1OCC(C)C] | N-(2-isobutoxy-5-(3-(2-methoxypyridin-4-yl)-1H-pyrrolo[2,3-b]pyridin-5-yl)pyridin-3-yl)acrylamide |
| 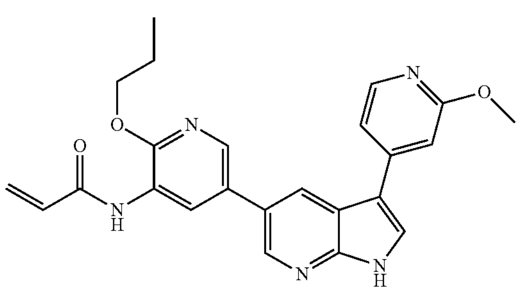 [SMILES: C=CC(=O)Nc1cc(-c2cnc3[nH]cc(-c4ccnc(OC)c4)c3c2)cnc1OCCC] | N-(5-(3-(2-methoxypyridin-4-yl)-1H-pyrrolo[2,3-b]pyridin-5-yl)-2-propoxypyridin-3-yl)acrylamide |

TABLE 2-continued

| Structure | Name |
|---|---|
| 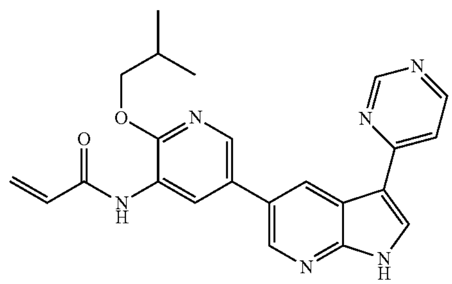 [SMILES: C=CC(=O)Nc1cc(-c2cnc3[nH]cc(-c4ccncn4)c3c2)cnc1OCC(C)C] | N-(2-isobutoxy-5-(3-(pyrimidin-4-yl)-1H-pyrrolo[2,3-b]pyridin-5-yl)pyridin-3-yl)acrylamide |
| 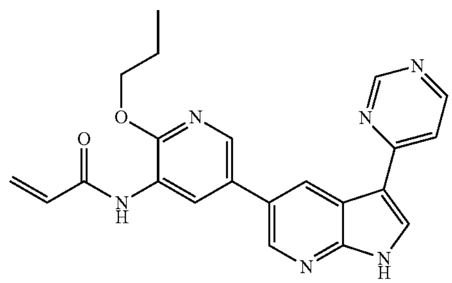 [SMILES: C=CC(=O)Nc1cc(-c2cnc3[nH]cc(-c4ccncn4)c3c2)cnc1OCCC] | N-(2-propoxy-5-(3-(pyrimidin-4-yl)-1H-pyrrolo[2,3-b]pyridin-5-yl)pyridin-3-yl)acrylamide |
| 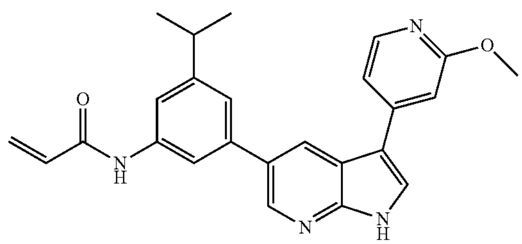 [SMILES: C=CC(=O)Nc1cc(-c2cnc3[nH]cc(-c4ccnc(OC)c4)c3c2)cc(C(C)C)c1] | N-(3-isopropyl-5-(3-(2-methoxypyridin-4-yl)-1H-pyrrolo[2,3-b]pyridin-5-yl)phenyl)acrylamide |
| 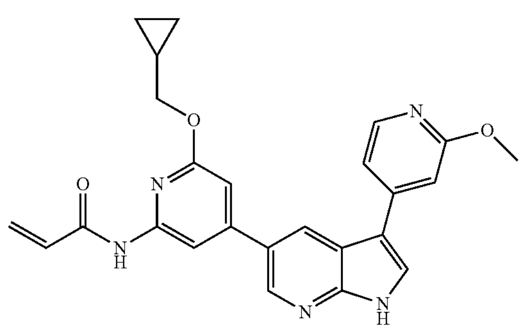 [SMILES: C=CC(=O)Nc1cc(-c2cnc3[nH]cc(-c4ccnc(OC)c4)c3c2)cc(OCC2CC2)n1] | N-(6-(cyclopropylmethoxy)-4-(3-(2-methoxypyridin-4-yl)-1H-pyrrolo[2,3-b]pyridin-5-yl)pyridin-2-yl)acrylamide |
| 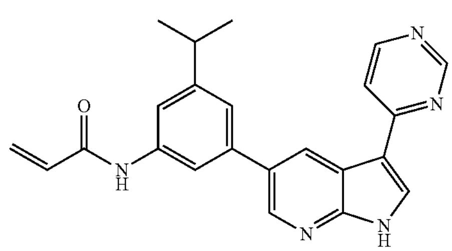 [SMILES: C=CC(=O)Nc1cc(-c2cnc3[nH]cc(-c4ccncn4)c3c2)cc(C(C)C)c1] | N-(3-isopropyl-5-(3-(pyrimidin-4-yl)-1H-pyrrolo[2,3-b]pyridin-5-yl)phenyl)acrylamide |

TABLE 2-continued

| Structure | Name |
|---|---|
| 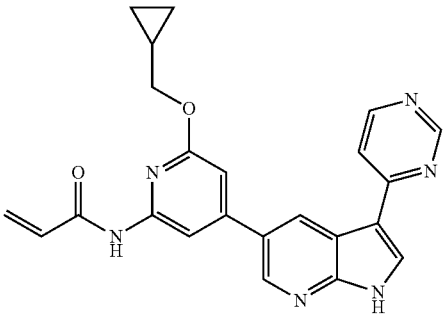 [SMILES: C=CC(=O)Nc1cc(-c2cnc3[nH]cc(-c4ccncn4)c3c2)cc(OCC2CC2)n1] | N-(6-(cyclopropylmethoxy)-4-(3-(pyrimidin-4-yl)-1H-pyrrolo[2,3-b]pyridin-5-yl)pyridin-2-yl)acrylamide |
| 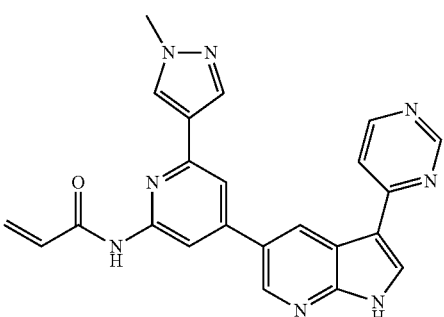 | N-(6-(1-methyl-1H-pyrazol-4-yl)-4-(3-(pyrimidin-4-yl)-1H-pyrrolo[2,3-b]pyridin-5-yl)pyridin-2-yl)acrylamide |
| 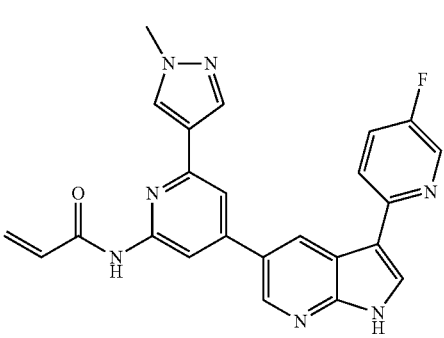 [SMILES: C=CC(=O)Nc1cc(-c2cnc3[nH]cc(-c4ccc(F)cn4)c3c2)cc(-c2cnn(C)c2)n1] | N-(4-(3-(6-fluoropyridin-3-yl)-1H-pyrrolo[2,3-b]pyridin-5-yl)-6-(1-methyl-1H-pyrazol-4-yl)pyridin-2-yl)acrylamide |
| 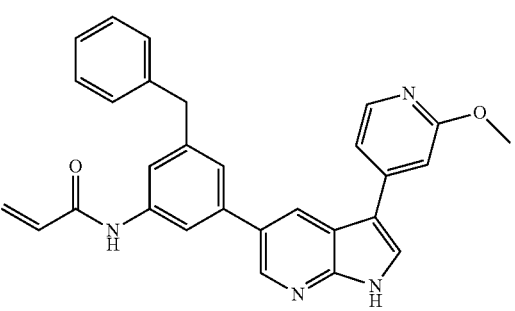 [SMILES: C=CC(=O)Nc1cc(Cc2ccccc2)cc(-c2cnc3[nH]cc(-c4ccnc(OC)c4)c3c2)c1] | N-(3-benzyl-5-(3-(2-methoxypyridin-4-yl)-1H-pyrrolo[2,3-b]pyridin-5-yl)phenyl)acrylamide |
| 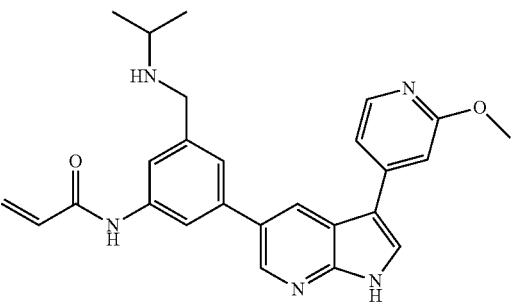 [SMILES: C=CC(=O)Nc1cc(CNC(C)C)cc(-c2cnc3[nH]cc(-c4ccnc(OC)c4)c3c2)c1] | N-(3-((isopropylamino)methyl)-5-(3-(2-methoxypyridin-4-yl)-1H-pyrrolo[2,3-b]pyridin-5-yl)phenyl)acrylamide |

TABLE 2-continued

| Structure | Name |
|---|---|
| 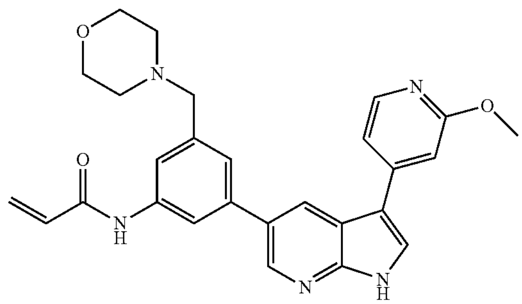 [SMILES: C=CC(=O)Nc1cc(CN2CCOCC2)cc(-c2cnc3[nH]cc(-c4ccnc(OC)c4)c3c2)c1] | N-(3-(3-(2-methoxypyridin-4-yl)-1H-pyrrolo[2,3-b]pyridin-5-yl)-5-(morpholinomethyl)phenyl)acrylamide |
| 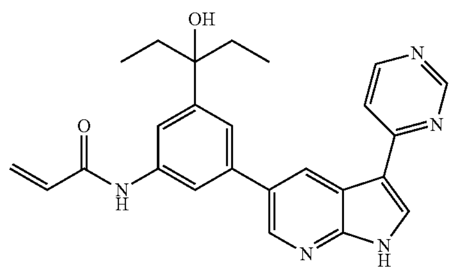 [SMILES: C=CC(=O)Nc1cc(-c2cnc3[nH]cc(-c4ccncn4)c3c2)cc(C(O)(CC)CC)c1] | N-(3-(3-hydroxypentan-3-yl)-5-(3-(pyrimidin-4-yl)-1H-pyrrolo[2,3-b]pyridin-5-yl)phenyl)acrylamide |
| 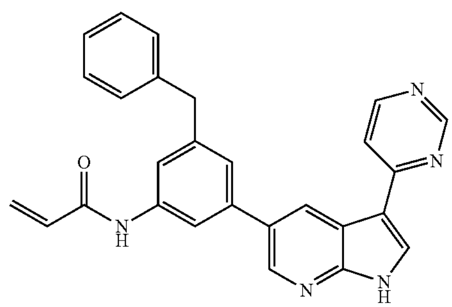 [SMILES: C=CC(=O)Nc1cc(Cc2ccccc2)cc(-c2cnc3[nH]cc(-c4ccncn4)c3c2)c1] | N-(3-benzyl-5-(3-(pyrimidin-4-yl)-1H-pyrrolo[2,3-b]pyridin-5-yl)phenyl)acrylamide |
| 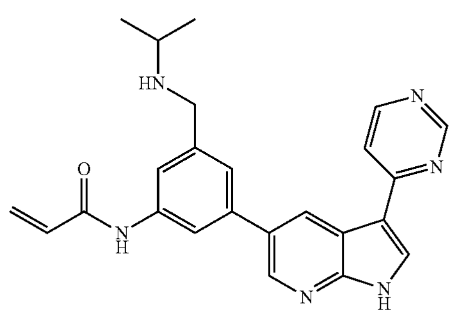 [SMILES: C=CC(=O)Nc1cc(CNC(C)C)cc(-c2cnc3[nH]cc(-c4ccncn4)c3c2)c1] | N-(3-((isopropylamino)methyl)-5-(3-(pyrimidin-4-yl)-1H-pyrrolo[2,3-b]pyridin-5-yl)phenyl)acrylamide |
| 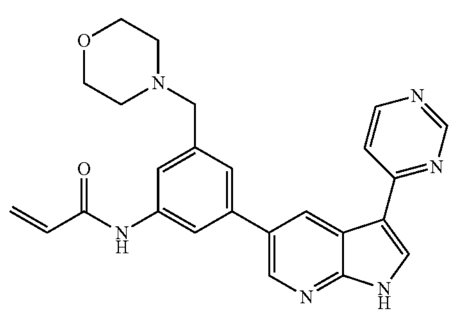 [SMILES: C=CC(=O)Nc1cc(CN2CCOCC2)cc(-c2cnc3[nH]cc(-c4ccncn4)c3c2)c1] | N-(3-(morpholinomethyl)-5-(3-(pyrimidin-4-yl)-1H-pyrrolo[2,3-b]pyridin-5-yl)phenyl)acrylamide |

TABLE 2-continued

| Structure | Name |
|---|---|
| 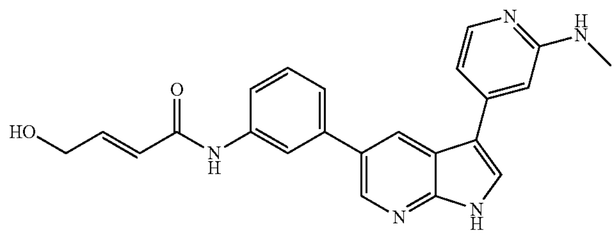 [SMILES: CNc1cc(-c2c[nH]c3ncc(-c4cccc(NC(=O)/C=C/CO)c4)cc23)ccn1] | (E)-4-hydroxy-N-(3-(3-(2-(methylamino)pyridin-4-yl)-1H-pyrrolo[2,3-b]pyridin-5-yl)phenyl)but-2-enamide |
| 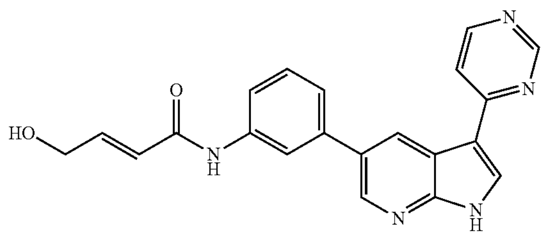 [SMILES: O=C(/C=C/CO)Nc1cccc(-c2cnc3[nH]cc(-c4ccncn4)c3c2)c1] | (E)-4-hydroxy-N-(3-(3-(pyrimidin-4-yl)-1H-pyrrolo[2,3-b]pyridin-5-yl)phenyl)but-2-enamide |
| 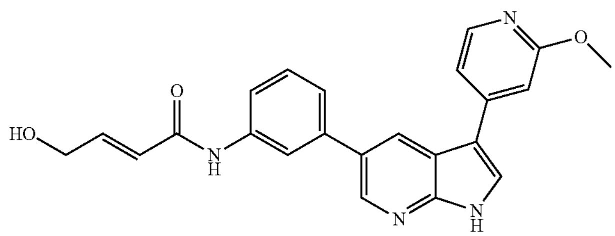 [SMILES: COc1cc(-c2c[nH]c3ncc(-c4cccc(NC(=O)/C=C/CO)c4)cc23)ccn1] | (E)-4-hydroxy-N-(3-(3-(2-methoxypyridin-4-yl)-1H-pyrrolo[2,3-b]pyridin-5-yl)phenyl)but-2-enamide |
| 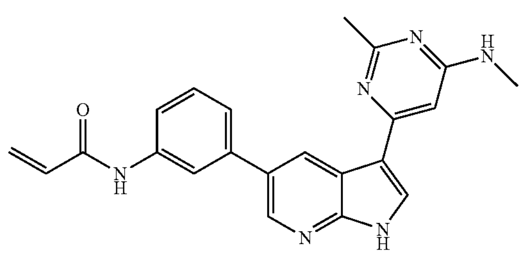 [SMILES: C=CC(=O)Nc1cccc(-c2cnc3[nH]cc(-c4cc(NC)nc(C)n4)c3c2)c1] | N-(3-(3-(2-methyl-6-(methylamino)pyrimidin-4-yl)-1H-pyrrolo[2,3-b]pyridin-5-yl)phenyl)acrylamide |
| 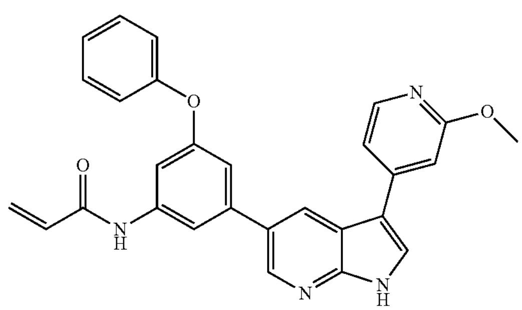 [SMILES: C=CC(=O)Nc1cc(Oc2ccccc2)cc(-c2cnc3[nH]cc(-c4ccnc(OC)c4)c3c2)c1] | N-(3-(3-(2-methoxypyridin-4-yl)-1H-pyrrolo[2,3-b]pyridin-5-yl)-5-phenoxyphenyl)acrylamide |
| 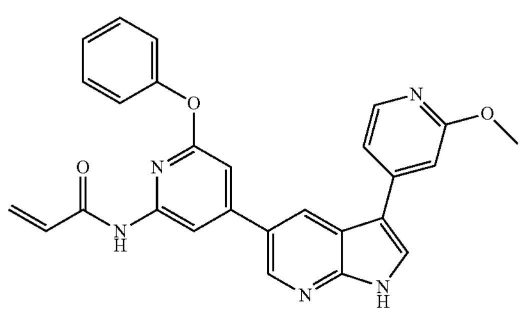 [SMILES: C=CC(=O)Nc1cc(-c2cnc3[nH]cc(-c4ccnc(OC)c4)c3c2)cc(Oc2ccccc2)n1] | N-(4-(3-(2-methoxypyridin-4-yl)-1H-pyrrolo[2,3-b]pyridin-5-yl)-6-phenoxypyridin-2-yl)acrylamide |

TABLE 2-continued

| Structure | Name |
|---|---|
| 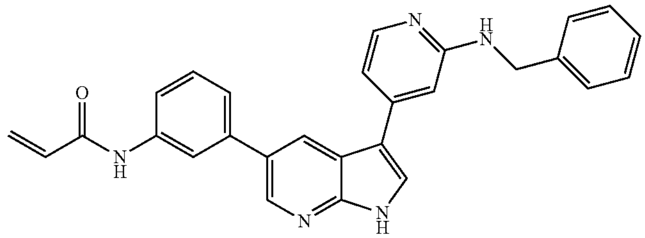 [SMILES: C=CC(=O)Nc1cccc(-c2cnc3[nH]cc(-c4ccnc(NCc5ccccc5)c4)c3c2)c1] | N-(3-(3-(2-(benzylamino)pyridin-4-yl)-1H-pyrrolo[2,3-b]pyridin-5-yl)phenyl)acrylamide |
| 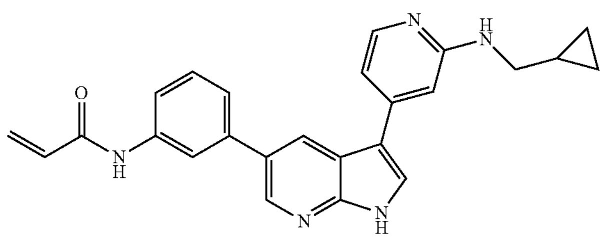 [SMILES: C=CC(=O)Nc1cccc(-c2cnc3[nH]cc(-c4ccnc(NCC5CC5)c4)c3c2)c1] | N-(3-(3-(2-((cyclopropylmethyl)amino)pyridin-4-yl)-1H-pyrrolo[2,3-b]pyridin-5-yl)phenyl)acrylamide |
| 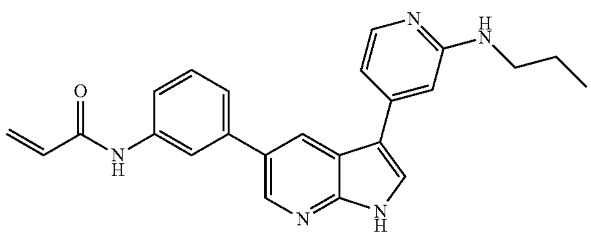 [SMILES: C=CC(=O)Nc1cccc(-c2cnc3[nH]cc(-c4ccnc(NCCC)c4)c3c2)c1] | N-(3-(3-(2-(propylamino)pyridin-4-yl)-1H-pyrrolo[2,3-b]pyridin-5-yl)phenyl)acrylamide |
| 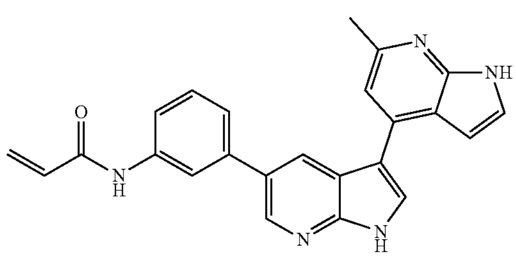 [SMILES: C=CC(=O)Nc1cccc(-c2cnc3[nH]cc(-c4cc(C)nc5[nH]ccc45)c3c2)c1] | N-(3-(6'-methyl-1H,1'H-[3,4'-bipyrrolo[2,3-b]pyridin]-5-yl)phenyl)acrylamide |
| 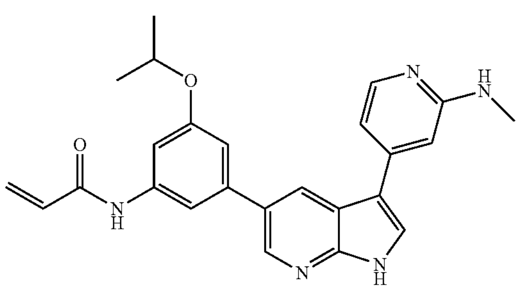 [SMILES: C=CC(=O)Nc1cc(OC(C)C)cc(-c2cnc3[nH]cc(-c4ccnc(NC)c4)c3c2)c1] | N-(3-isopropoxy-5-(3-(2-(methylamino)pyridin-4-yl)-1H-pyrrolo[2,3-b]pyridin-5-yl)phenyl)acrylamide |
| 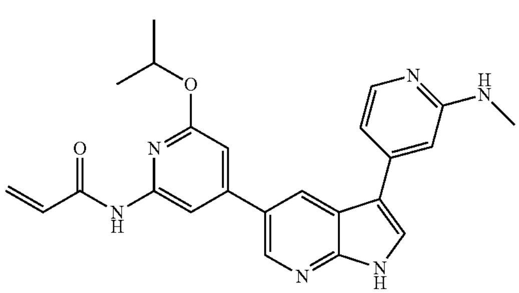 [SMILES: C=CC(=O)Nc1cc(-c2cnc3[nH]cc(-c4ccnc(NC)c4)c3c2)cc(OC(C)C)n1] | N-(6-isopropoxy-4-(3-(2-(methylamino)pyridin-4-yl)-1H-pyrrolo[2,3-b]pyridin-5-yl)-pyridin-2-yl)acrylamide |

TABLE 2-continued

| Structure | Name |
|---|---|
| 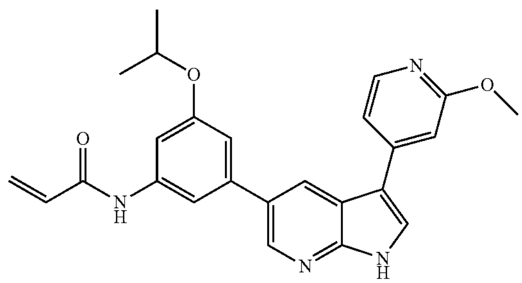 [SMILES: C=CC(=O)Nc1cc(OC(C)C)cc(-c2cnc3[nH]cc(-c4ccnc(OC)c4)c3c2)c1] | N-(3-isopropoxy-5-(3-(2-methoxypyridin-4-yl)-1H-pyrrolo[2,3-b]pyridin-5-yl)phenyl)acrylamide |
| 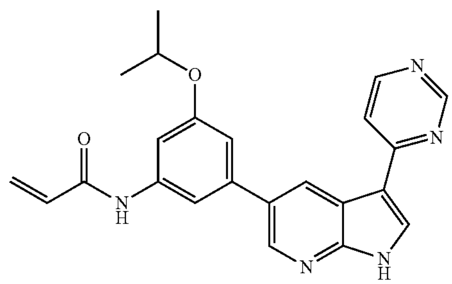 [SMILES: C=CC(=O)Nc1cc(OC(C)C)cc(-c2cnc3[nH]cc(-c4ccncn4)c3c2)c1] | N-(3-isopropoxy-5-(3-(pyrimidin-4-yl)-1H-pyrrolo[2,3-b]pyridin-5-yl)phenyl)acrylamide |
| 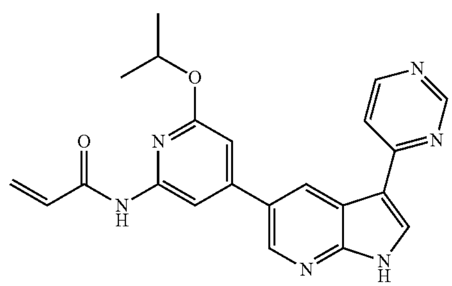 [SMILES: C=CC(=O)Nc1cc(-c2cnc3[nH]cc(-c4ccncn4)c3c2)cc(OC(C)C)n1] | N-(6-isopropoxy-4-(3-(pyrimidin-4-yl)-1H-pyrrolo[2,3-b]pyridin-5-yl)pyridin-2-yl)acrylamide |
| 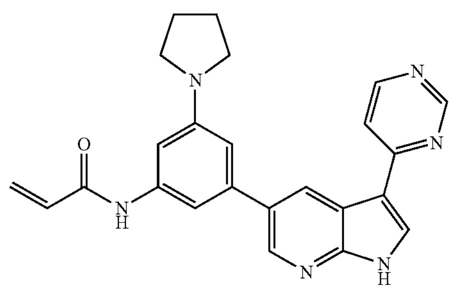 [SMILES: C=CC(=O)Nc1cc(-c2cnc3[nH]cc(-c4ccncn4)c3c2)cc(N2CCCC2)c1] | N-(3-(3-(pyrimidin-4-yl)-1H-pyrrolo[2,3-b]pyridin-5-yl)-5-(pyrrolidin-1-yl)phenyl)acrylamide |
| 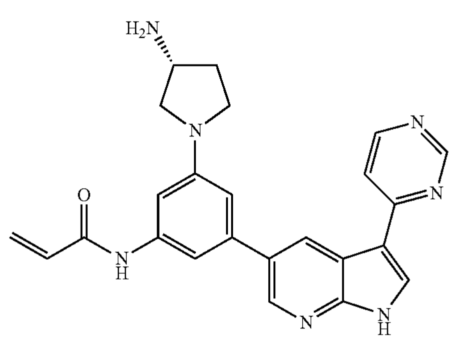 [SMILES: C=CC(=O)Nc1cc(-c2cnc3[nH]cc(-c4ccncn4)c3c2)cc(N2CC[C@@H](N)C2)c1] | (R)-N-(3-(3-aminopyrrolidin-1-yl)-5-(3-(pyrimidin-4-yl)-1H-pyrrolo[2,3-b]pyridin-5-yl)phenyl)acrylamide |

TABLE 2-continued

| Structure | Name |
|---|---|
| 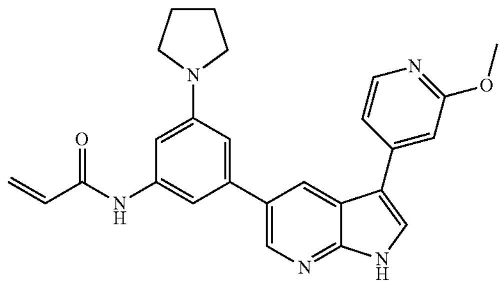 [SMILES: C=CC(=O)Nc1cc(-c2cnc3[nH]cc(-c4ccnc(OC)c4)c3c2)cc(N2CCCC2)c1] | N-(3-(3-(2-methoxypyridin-4-yl)-1H-pyrrolo[2,3-b]pyridin-5-yl)-5-(pyrrolidin-1-yl)phenyl)acrylamide |
| 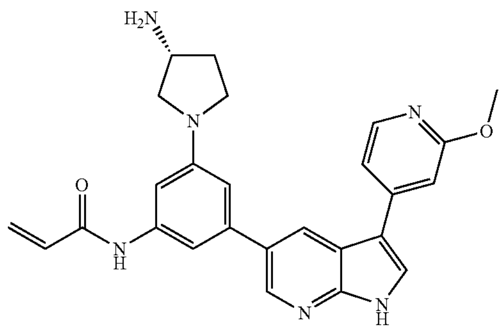 [SMILES: C=CC(=O)Nc1cc(-c2cnc3[nH]cc(-c4ccnc(OC)c4)c3c2)cc(N2CC[C@@H](N)C2)c1] | (R)-N-(3-(3-aminopyrrolidin-1-yl)-5-(3-(2-methoxypyridin-4-yl)-1H-pyrrolo[2,3-b]pyridin-5-yl)phenyl)acrylamide |
| 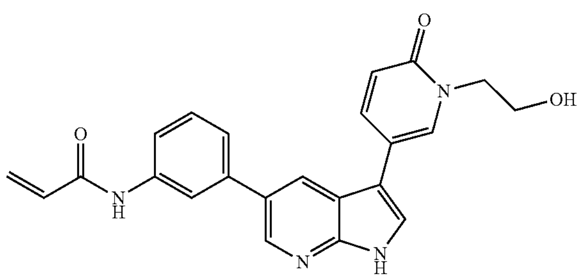 [SMILES: C=CC(=O)Nc1cccc(-c2cnc3[nH]cc(-c4ccc(=O)n(CCO)c4)c3c2)c1] | N-(3-(3-(1-(2-hydroxyethyl)-6-oxo-1,6-dihydropyridin-3-yl)-1H-pyrrolo[2,3-b]pyridin-5-yl)phenyl)acrylamide |
| 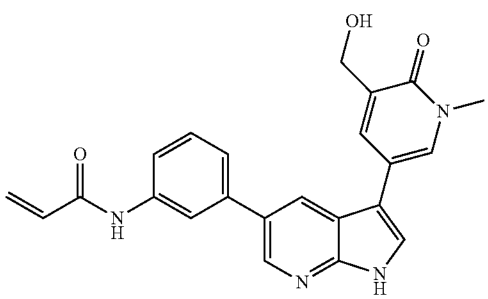 [SMILES: C=CC(=O)Nc1cccc(-c2cnc3[nH]cc(-c4cc(CO)c(=O)n(C)c4)c3c2)c1] | N-(3-(3-(5-(hydroxymethyl)-1-methyl-6-oxo-1,6-dihydropyridin-3-yl)-1H-pyrrolo[2,3-b]pyridin-5-yl)phenyl)acrylamide |
| 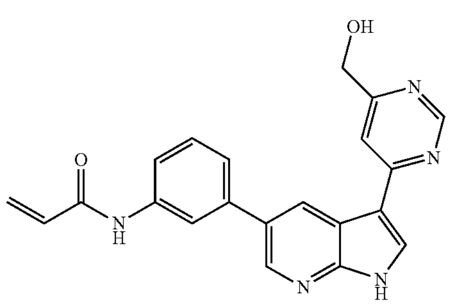 [SMILES: C=CC(=O)Nc1cccc(-c2cnc3[nH]cc(-c4cc(CO)ncn4)c3c2)c1] | N-(3-(3-(6-(hydroxymethyl)pyrimidin-4-yl)-1H-pyrrolo[2,3-b]pyridin-5-yl)phenyl)acrylamide |

| Structure | Name |
|---|---|
| 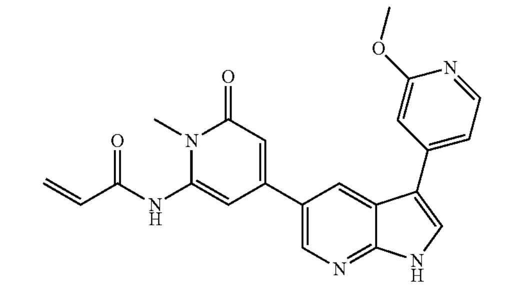 [SMILES: C=CC(=O)Nc1cc(-c2cnc3[nH]cc(-c4ccnc(OC)c4)c3c2)cc(=O)n1C] | N-(4-(3-(2-methoxypyridin-4-yl)-1H-pyrrolo[2,3-b]pyridin-5-yl)-1-methyl-6-oxo-1,6-dihydropyridin-2-yl)acrylamide |
| 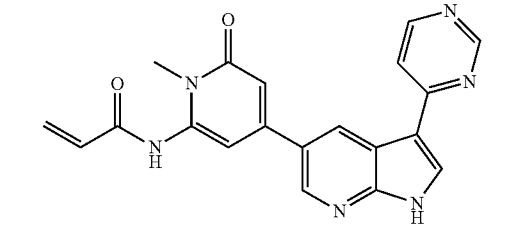 [SMILES: C=CC(=O)Nc1cc(-c2cnc3[nH]cc(-c4ccncn4)c3c2)cc(=O)n1C] | N-(1-methyl-6-oxo-4-(3-(pyrimidin-4-yl)-1H-pyrrolo[2,3-b]pyridin-5-yl)-1,6-dihydropyridin-2-yl)acrylamide |
| 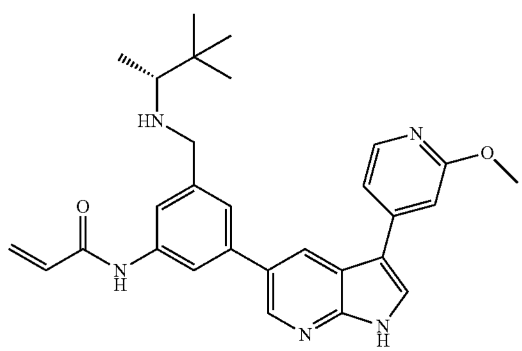 [SMILES: C=CC(=O)Nc1cc(CN[C@H](C)C(C)(C)C)cc(-c2cnc3[nH]cc(-c4ccnc(OC)c4)c3c2)c1] | (R)-N-(3-(((3,3-dimethylbutan-2-yl)amino)methyl)-5-(3-(2-methoxypyridin-4-yl)-1H-pyrrolo[2,3-b]pyridin-5-yl)phenyl)acrylamide |
| 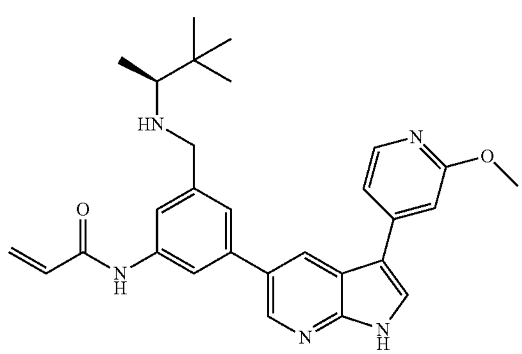 [SMILES: C=CC(=O)Nc1cc(CN[C@@H](C)C(C)(C)C)cc(-c2cnc3[nH]cc(-c4ccnc(OC)c4)c3c2)c1] | (S)-N-(3-(((3,3-dimethylbutan-2-yl)amino)methyl)-5-(3-(2-methoxypyridin-4-yl)-1H-pyrrolo[2,3-b]pyridin-5-yl)phenyl)acrylamide |
| 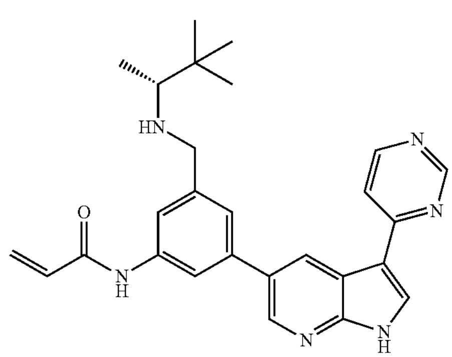 [SMILES: C=CC(=O)Nc1cc(CN[C@H](C)C(C)(C)C)cc(-c2cnc3[nH]cc(-c4ccncn4)c3c2)c1] | (R)-N-(3-(((3,3-dimethylbutan-2-yl)amino)methyl)-5-(3-(pyrimidin-4-yl)-1H-pyrrolo[2,3-b]pyridin-5-yl)phenyl)acrylamide |

TABLE 2-continued

| Structure | Name |
|---|---|
| 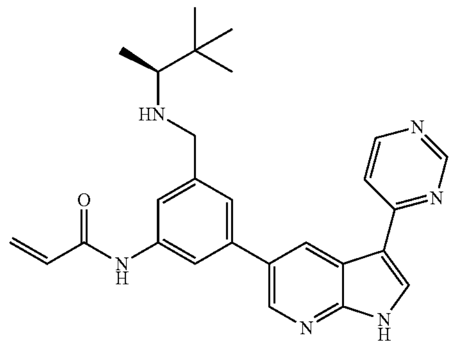 [SMILES: C=CC(=O)Nc1cc(CN[C@@H](C)C(C)(C)C)cc(-c2cnc3[nH]cc(-c4ccncn4)c3c2)c1] | (S)-N-(3-(((3,3-dimethylbutan-2-yl)amino)methyl)-5-(3-(pyrimidin-4-yl)-1H-pyrrolo[2,3-b]pyridin-5-yl)phenyl)acrylamide |
| 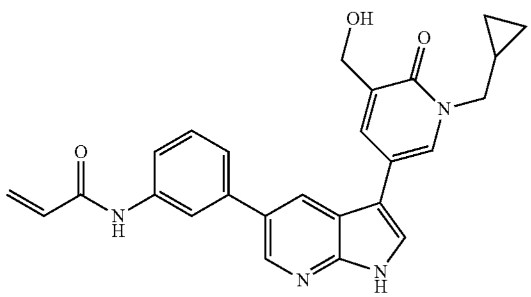 [SMILES: C=CC(=O)Nc1cccc(-c2cnc3[nH]cc(-c4cc(CO)c(=O)n(CC5CC5)c4)c3c2)c1] | N-(3-(3-(1-(cyclopropylmethyl)-5-(hydroxymethyl)-6-oxo-1,6-dihydropyridin-3-yl)-1H-pyrrolo[2,3-b]pyridin-5-yl)phenyl)acrylamide |
| 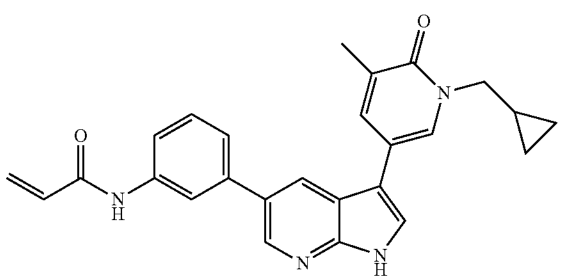 [SMILES: C=CC(=O)Nc1cccc(-c2cnc3[nH]cc(-c4cc(C)c(=O)n(CC5CC5)c4)c3c2)c1] | N-(3-(3-(1-(cyclopropylmethyl)-5-methyl-6-oxo-1,6-dihydropyridin-3-yl)-1H-pyrrolo[2,3-b]pyridin-5-yl)phenyl)acrylamide |
| 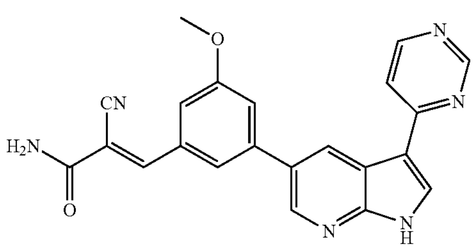 [SMILES: COc1cc(/C=C(\C#N)C(N)=O)cc(-c2cnc3[nH]cc(-c4ccncn4)c3c2)c1] | (E)-2-cyano-3-(3-methoxy-5-(3-(pyrimidin-4-yl)-1H-pyrrolo[2,3-b]pyridin-5-yl)phenyl)acrylamide |
| 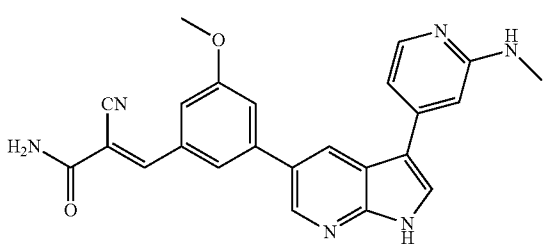 [SMILES: CNc1cc(-c2c[nH]c3ncc(-c4cc(/C=C(\C#N)C(N)=O)cc(OC)c4)cc23)ccn1] | (E)-2-cyano-3-(3-methoxy-5-(3-(2-(methylamino)pyridin-4-yl)-1H-pyrrolo[2,3-b]pyridin-5-yl)phenyl)acrylamide |

TABLE 2-continued

| Structure | Name |
|---|---|
| 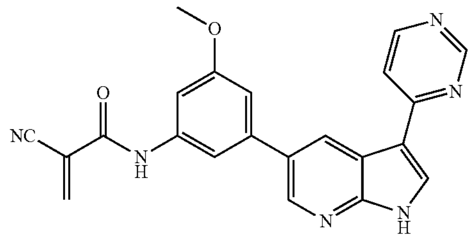 [SMILES: C=C(C#N)C(=O)Nc1cc(OC)cc(-c2cnc3[nH]cc(-c4ccncn4)c3c2)c1] | 2-cyano-N-(3-methoxy-5-(3-(pyrimidin-4-yl)-1H-pyrrolo[2,3-b]pyridin-5-yl)phenyl)acrylamide |
| 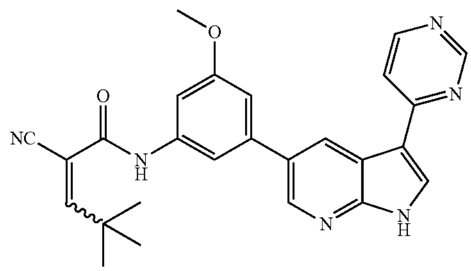 [SMILES: COc1cc(NC(=O)C(C#N)=CC(C)(C)C)cc(-c2cnc3[nH]cc(-c4ccncn4)c3c2)c1] | 2-cyano-N-(3-methoxy-5-(3-(pyrimidin-4-yl)-1H-pyrrolo[2,3-b]pyridin-5-yl)phenyl)-4,4-dimethylpent-2-enamide |
| 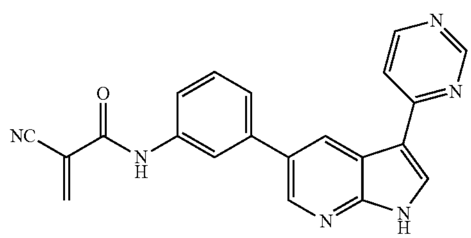 [SMILES: C=C(C#N)C(=O)Nc1cccc(-c2cnc3[nH]cc(-c4ccncn4)c3c2)c1] | 2-cyano-N-(3-(3-(pyrimidin-4-yl)-1H-pyrrolo[2,3-b]pyridin-5-yl)phenyl)acrylamide |
| 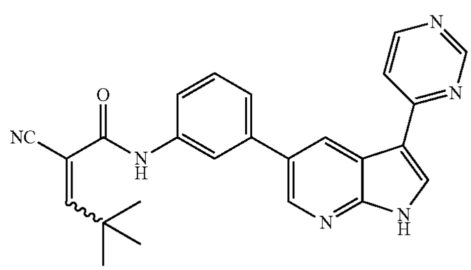 [SMILES: CC(C)(C)C=C(C#N)C(=O)Nc1cccc(-c2cnc3[nH]cc(-c4ccncn4)c3c2)c1] | 2-cyano-4,4-dimethyl-N-(3-(3-(pyrimidin-4-yl)-1H-pyrrolo[2,3-b]pyridin-5-yl)phenyl)pent-2-enamide |
| 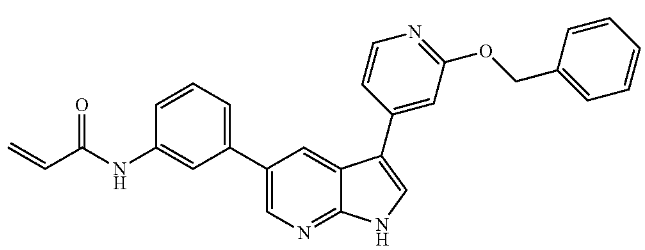 [SMILES: C=CC(=O)Nc1cccc(-c2cnc3[nH]cc(-c4ccnc(OCc5ccccc5)c4)c3c2)c1] | N-(3-(3-(2-(benzyloxy)pyridin-4-yl)-1H-pyrrolo[2,3-b]pyridin-5-yl)phenyl)acrylamide |
| 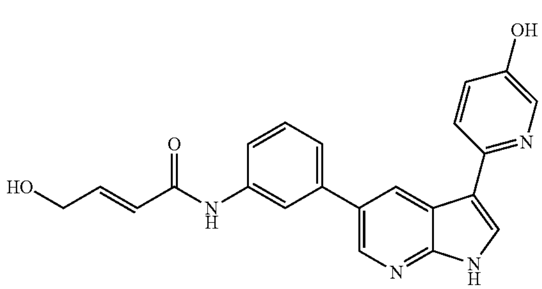 [SMILES: O=C(/C=C/CO)Nc1cccc(-c2cnc3[nH]cc(-c4ccc(O)cn4)c3c2)c1] | (E)-4-hydroxy-N-(3-(3-(5-hydroxypyridin-2-yl)-1H-pyrrolo[2,3-b]pyridin-5-yl)phenyl)but-2-enamide |

TABLE 2-continued

| Structure | Name |
|---|---|
| 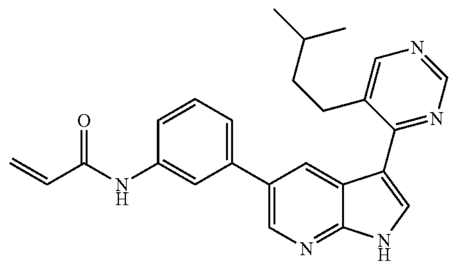 [SMILES: C=CC(=O)Nc1cccc(-c2cnc3[nH]cc(-c4ncncc4CCC(C)C)c3c2)c1] | N-(3-(3-(5-isopentylpyrimidin-4-yl)-1H-pyrrolo[2,3-b]pyridin-5-yl)phenyl)acrylamide |
| 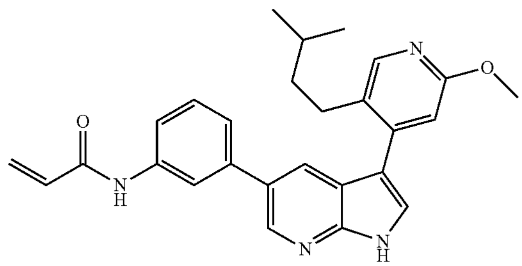 [SMILES: C=CC(=O)Nc1cccc(-c2cnc3[nH]cc(-c4cc(OC)ncc4CCC(C)C)c3c2)c1] | N-(3-(3-(5-isopentyl-2-methoxypyridin-4-yl)-1H-pyrrolo[2,3-b]pyridin-5-yl)phenyl)acrylamide |
| 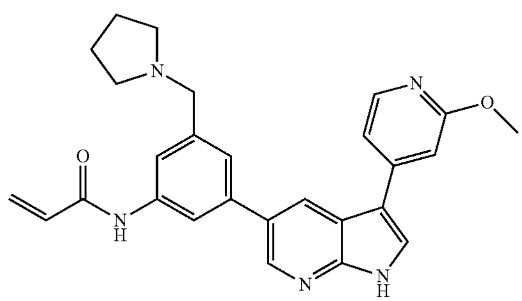 [SMILES: C=CC(=O)Nc1cc(CN2CCCC2)cc(-c2cnc3[nH]cc(-c4ccnc(OC)c4)c3c2)c1] | N-(3-(3-(2-methoxypyridin-4-yl)-1H-pyrrolo[2,3-b]pyridin-5-yl)-5-(pyrrolidin-1-ylmethyl)phenyl)acrylamide |
| 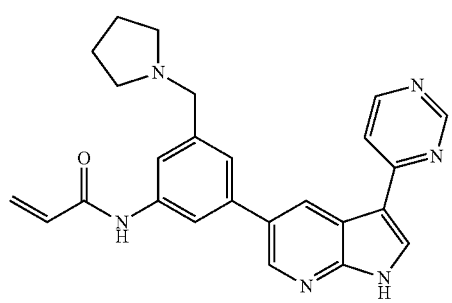 [SMILES: C=CC(=O)Nc1cc(CN2CCCC2)cc(-c2cnc3[nH]cc(-c4ccncn4)c3c2)c1] | N-(3-(3-(pyrimidin-4-yl)-1H-pyrrolo[2,3-b]pyridin-5-yl)-5-(pyrrolidin-1-ylmethyl)phenyl)acrylamide |
| 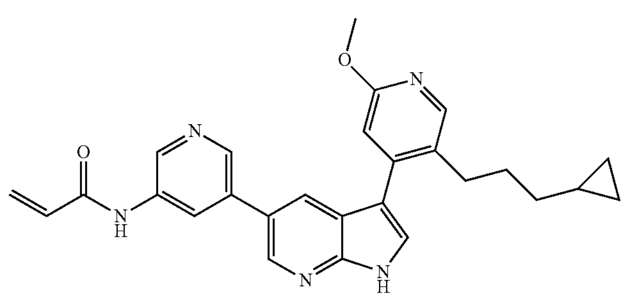 [SMILES: C=CC(=O)Nc1cncc(-c2cnc3[nH]cc(-c4cc(OC)ncc4CCCC4CC4)c3c2)c1] | N-(5-(3-(5-(3-cyclopropylpropyl)-2-methoxypyridin-4-yl)-1H-pyrrolo[2,3-b]pyridin-5-yl)pyridin-3-yl)acrylamide |

TABLE 2-continued

| Structure | Name |
|---|---|
| 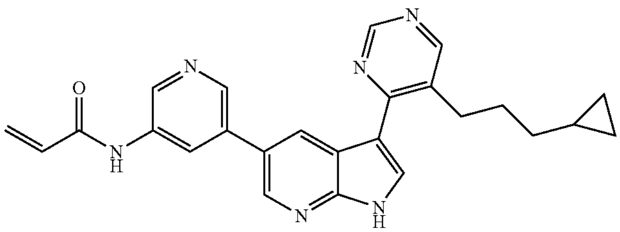 [SMILES: C=CC(=O)Nc1cncc(-c2cnc3[nH]cc(-c4ncncc4CCCC4CC4)c3c2)c1] | N-(5-(3-(5-(3-cyclopropylpropyl)pyrimidin-4-yl)-1H-pyrrolo[2,3-b]pyridin-5-yl)pyridin-3-yl)acrylamide |
| 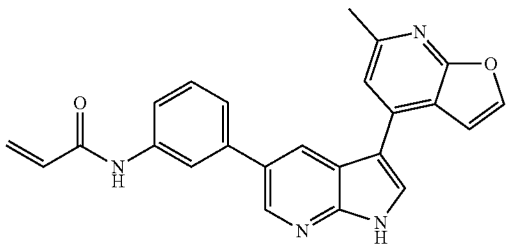 [SMILES: C=CC(=O)Nc1cccc(-c2cnc3[nH]cc(-c4cc(C)nc5occc45)c3c2)c1] | N-(3-(3-(6-methylfuro[2,3-b]pyridin-4-yl)-1H-pyrrolo[2,3-b]pyridin-5-yl)phenyl)acrylamide |
| 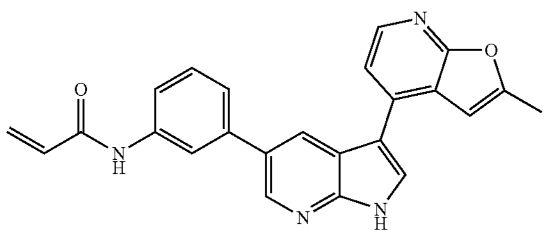 [SMILES: C=CC(=O)Nc1cccc(-c2cnc3[nH]cc(-c4ccnc5oc(C)cc45)c3c2)c1] | N-(3-(3-(2-methylfuro[2,3-b]pyridin-4-yl)-1H-pyrrolo[2,3-b]pyridin-5-yl)phenyl)acrylamide |
| 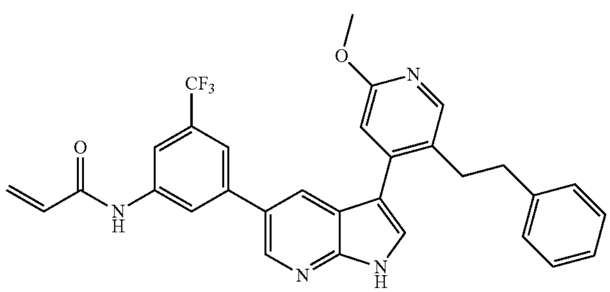 [SMILES: C=CC(=O)Nc1cc(-c2cnc3[nH]cc(-c4cc(OC)ncc4CCc4ccccc4)c3c2)cc(C(F)(F)F)c1] | N-(3-(3-(2-methoxy-5-phenethylpyridin-4-yl)-1H-pyrrolo[2,3-b]pyridin-5-yl)-5-(trifluoromethyl)phenyl)acrylamide |
| 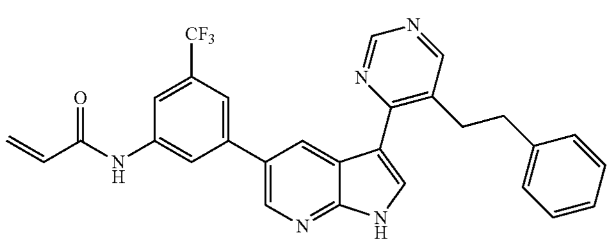 [SMILES: C=CC(=O)Nc1cc(-c2cnc3[nH]cc(-c4ncncc4CCc4ccccc4)c3c2)cc(C(F)(F)F)c1] | N-(3-(3-(5-phenethylpyrimidin-4-yl)-1H-pyrrolo[2,3-b]pyridin-5-yl)-5-(trifluoromethyl)phenyl)acrylamide |
| 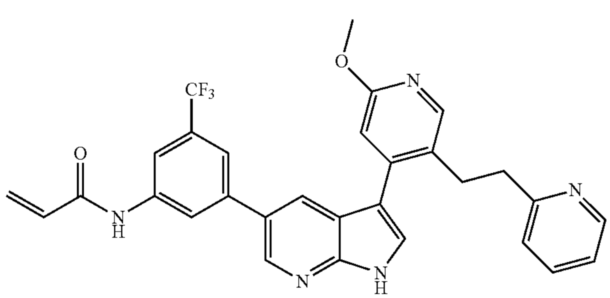 [SMILES: C=CC(=O)Nc1cc(-c2cnc3[nH]cc(-c4cc(OC)ncc4CCc4ccccn4)c3c2)cc(C(F)(F)F)c1] | N-(3-(3-(2-methoxy-5-(2-(pyridin-2-yl)ethyl)pyridin-4-yl)-1H-pyrrolo[2,3-b]pyridin-5-yl)-5-(trifluoromethyl)phenyl)acrylamide |

TABLE 2-continued

| Structure | Name |
|---|---|
| 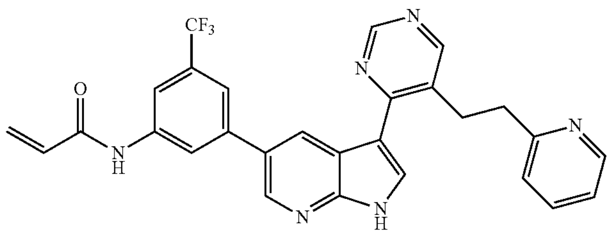 [SMILES: C=CC(=O)Nc1cc(-c2cnc3[nH]cc(-c4ncncc4CCc4ccccn4)c3c2)cc(C(F)(F)F)c1] | N-(3-(3-(5-(2-(pyridin-2-yl)ethyl)pyrimidin-4-yl)-1H-pyrrolo[2,3-b]pyridin-5-yl)-5-(trifluoromethyl)phenyl)acrylamide |
| 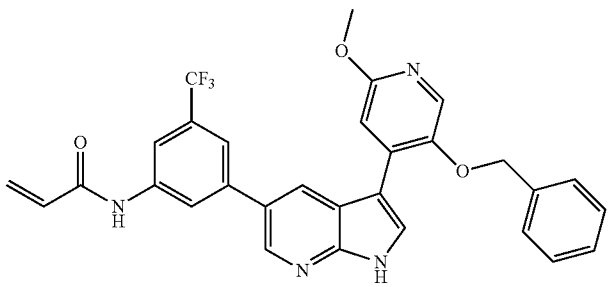 [SMILES: C=CC(=O)Nc1cc(-c2cnc3[nH]cc(-c4cc(OC)ncc4OCc4ccccc4)c3c2)cc(C(F)(F)F)c1] | N-(3-(3-(5-(benzyloxy)-2-methoxypyridin-4-yl)-1H-pyrrolo[2,3-b]pyridin-5-yl)-5-(trifluoromethyl)phenyl)acrylamide |
| 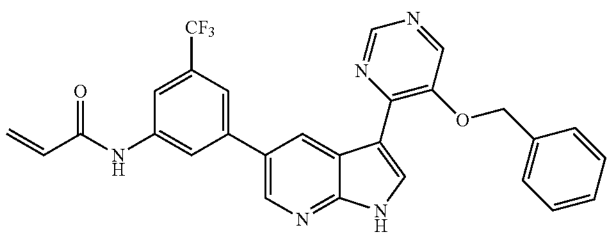 [SMILES: C=CC(=O)Nc1cc(-c2cnc3[nH]cc(-c4ncncc4OCc4ccccc4)c3c2)cc(C(F)(F)F)c1] | N-(3-(3-(5-(benzyloxy)pyrimidin-4-yl)-1H-pyrrolo[2,3-b]pyridin-5-yl)-5-(trifluoromethyl)phenyl)acrylamide |
| 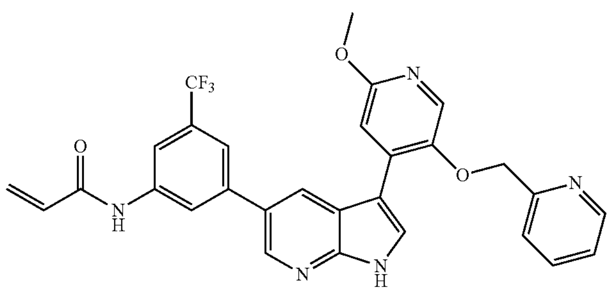 [SMILES: C=CC(=O)Nc1cc(-c2cnc3[nH]cc(-c4cc(OC)ncc4OCc4ccccn4)c3c2)cc(C(F)(F)F)c1] | N-(3-(3-(2-methoxy-5-(pyridin-2-ylmethoxy)pyridin-4-yl)-1H-pyrrolo[2,3-b]pyridin-5-yl)-5-(trifluoromethyl)phenyl)acrylamide |
| 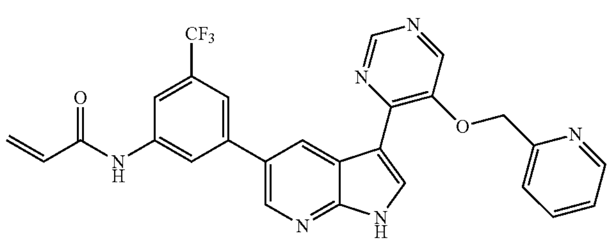 [SMILES: C=CC(=O)Nc1cc(-c2cnc3[nH]cc(-c4ncncc4OCc4ccccn4)c3c2)cc(C(F)(F)F)c1] | N-(3-(3-(5-(pyridin-2-ylmethoxy)pyrimidin-4-yl)-1H-pyrrolo[2,3-b]pyridin-5-yl)-5-(trifluoromethyl)phenyl)acrylamide |
| 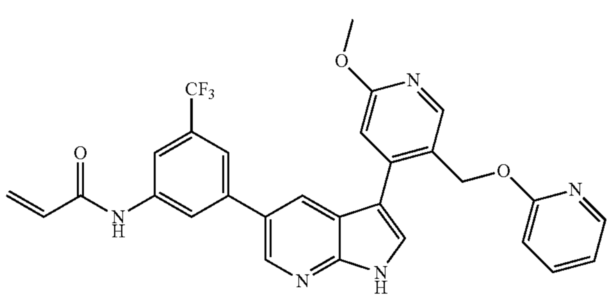 [SMILES: C=CC(=O)Nc1cc(-c2cnc3[nH]cc(-c4cc(OC)ncc4COc4ccccn4)c3c2)cc(C(F)(F)F)c1] | N-(3-(3-(2-methoxy-5-((pyridin-2-yloxy)methyl)pyridin-4-yl)-1H-pyrrolo[2,3-b]pyridin-5-yl)-5-(trifluoromethyl)phenyl)acrylamide |

TABLE 2-continued

| Structure | Name |
|---|---|
| 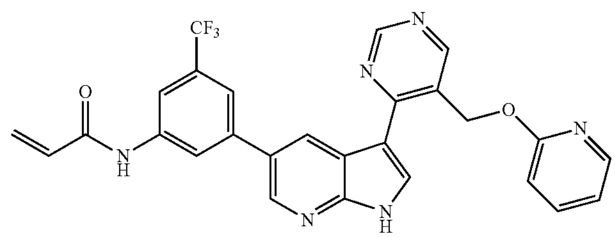 [SMILES: C=CC(=O)Nc1cc(-c2cnc3[nH]cc(-c4ncncc4COc4ccccn4)c3c2)cc(C(F)(F)F)c1] | N-(3-(3-(5-((pyridin-2-yloxy)methyl)pyrimidin-4-yl)-1H-pyrrolo[2,3-b]pyridin-5-yl)-5-(trifluoromethyl)phenyl)acrylamide |
| 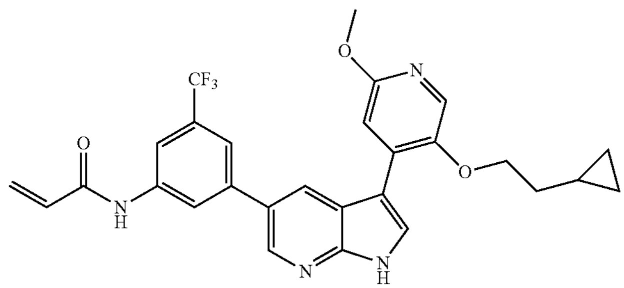 [SMILES: C=CC(=O)Nc1cc(-c2cnc3[nH]cc(-c4cc(OC)ncc4OCCC4CC4)c3c2)cc(C(F)(F)F)c1] | N-(3-(3-(5-(3-cyclopropylpropyl)-2-methoxypyridin-4-yl)-1H-pyrrolo[2,3-b]pyridin-5-yl)-5-(trifluoromethyl)phenyl)acrylamide |
| 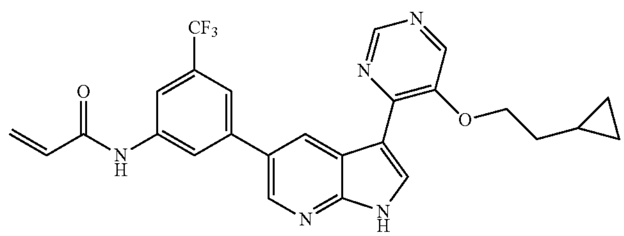 [SMILES: C=CC(=O)Nc1cc(-c2cnc3[nH]cc(-c4ncncc4OCCC4CC4)c3c2)cc(C(F)(F)F)c1] | N-(3-(3-(5-(3-cyclopropylpropyl)pyrimidin-4-yl)-1H-pyrrolo[2,3-b]pyridin-5-yl)-5-(trifluoromethyl)phenyl)acrylamide |
| 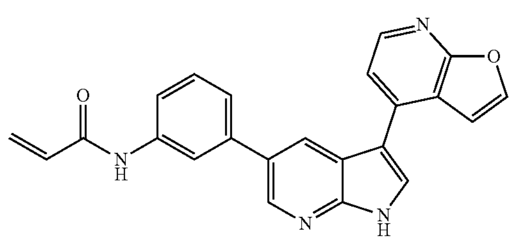 [SMILES: C=CC(=O)Nc1cccc(-c2cnc3[nH]cc(-c4ccnc5occc45)c3c2)c1] | N-(3-(3-(furo[2,3-b]pyridin-4-yl)-1H-pyrrolo[2,3-b]pyridin-5-yl)phenyl)acrylamide |
| 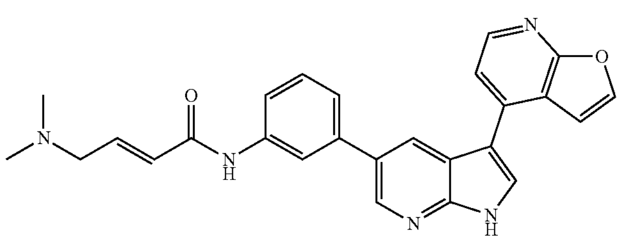 [SMILES: CN(C)C/C=C/C(=O)Nc1cccc(-c2cnc3[nH]cc(-c4ccnc5occc45)c3c2)c1] | (E)-4-(dimethylamino)-N-(3-(3-(furo[2,3-b]pyridin-4-yl)-1H-pyrrolo[2,3-b]pyridin-5-yl)phenyl)but-2-enamide |
| 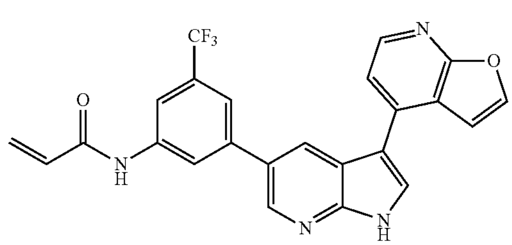 [SMILES: C=CC(=O)Nc1cc(-c2cnc3[nH]cc(-c4ccnc5occc45)c3c2)cc(C(F)(F)F)c1] | N-(3-(3-(furo[2,3-b]pyridin-4-yl)-1H-pyrrolo[2,3-b]pyridin-5-yl)-5-(trifluoromethyl)phenyl)acrylamide |

TABLE 2-continued

| Structure | Name |
|---|---|
| 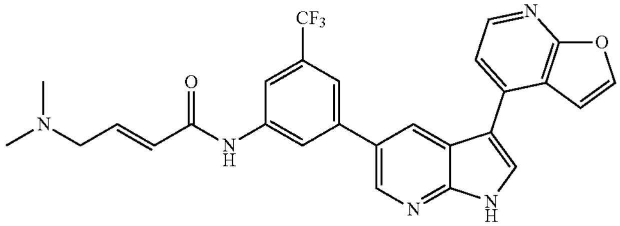 [SMILES: CN(C)C/C=C/C(=O)Nc1cc(-c2cnc3[nH]cc(-c4ccnc5occc45)c3c2)cc(C(F)(F)F)c1] | (E)-4-(dimethylamino)-N-(3-(3-(furo[2,3-b]pyridin-4-yl)-1H-pyrrolo[2,3-b]pyridin-5-yl)-5-(trifluoromethyl)phenyl)but-2-enamide |
| 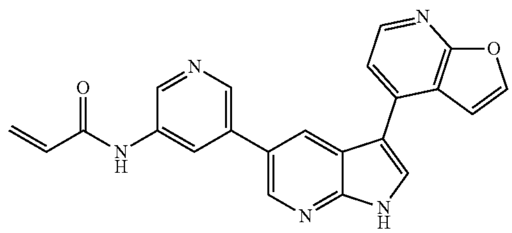 [SMILES: C=CC(=O)Nc1cncc(-c2cnc3[nH]cc(-c4ccnc5occc45)c3c2)c1] | N-(5-(3-(furo[2,3-b]pyridin-4-yl)-1H-pyrrolo[2,3-b]pyridin-5-yl)pyridin-3-yl)acrylamide |
| 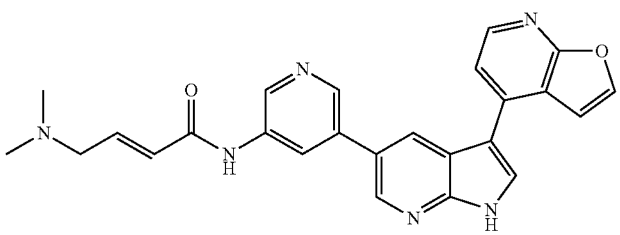 [SMILES: CN(C)C/C=C/C(=O)Nc1cncc(-c2cnc3[nH]cc(-c4ccnc5occc45)c3c2)c1] | (E)-4-(dimethylamino)-N-(5-(3-(furo[2,3-b]pyridin-4-yl)-1H-pyrrolo[2,3-b]pyridin-5-yl)pyridin-3-yl)but-2-enamide |
| 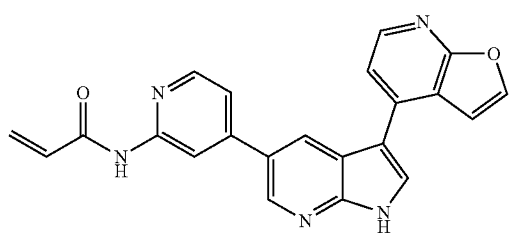 [SMILES: C=CC(=O)Nc1cc(-c2cnc3[nH]cc(-c4ccnc5occc45)c3c2)ccn1] | N-(4-(3-(furo[2,3-b]pyridin-4-yl)-1H-pyrrolo[2,3-b]pyridin-5-yl)pyridin-2-yl)acrylamide |
| 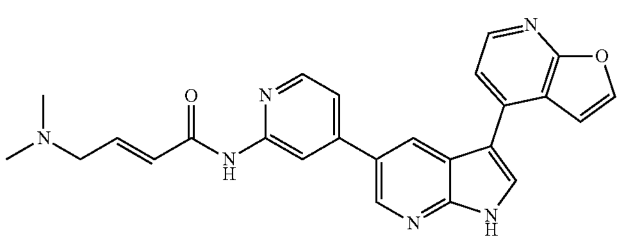 [SMILES: CN(C)C/C=C/C(=O)Nc1cc(-c2cnc3[nH]cc(-c4ccnc5occc45)c3c2)ccn1] | (E)-4-(dimethylamino)-N-(4-(3-(furo[2,3-b]pyridin-4-yl)-1H-pyrrolo[2,3-b]pyridin-5-yl)pyridin-2-yl)but-2-enamide |
| 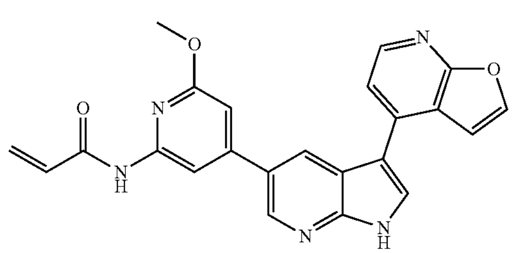 [SMILES: C=CC(=O)Nc1cc(-c2cnc3[nH]cc(-c4ccnc5occc45)c3c2)cc(OC)n1] | N-(4-(3-(furo[2,3-b]pyridin-4-yl)-1H-pyrrolo[2,3-b]pyridin-5-yl)-6-methoxypyridin-2-yl)acrylamide |

TABLE 2-continued

| Structure | Name |
|---|---|
| 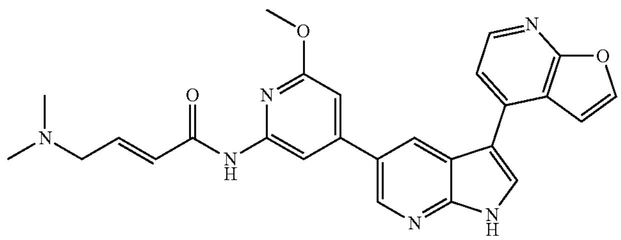 [SMILES: COc1cc(-c2cnc3[nH]cc(-c4ccnc5occc45)c3c2)cc(NC(=O)/C=C/CN(C)C)n1] | (E)-4-(dimethylamino)-N-(4-(3-(furo[2,3-b]pyridin-4-yl)-1H-pyrrolo[2,3-b]pyridin-5-yl)-6-methoxypyridin-2-yl)but-2-enamide |
| 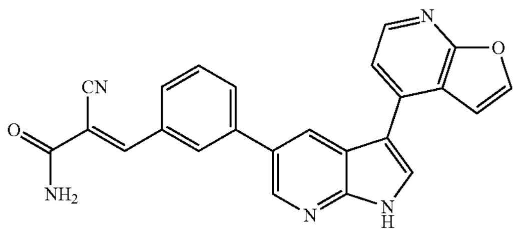 [SMILES: N#C/C(=C\c1cccc(-c2cnc3[nH]cc(-c4ccnc5occc45)c3c2)c1)C(N)=O] | (E)-2-cyano-3-(3-(3-(furo[2,3-b]pyridin-4-yl)-1H-pyrrolo[2,3-b]pyridin-5-yl)phenyl)acrylamide |
| 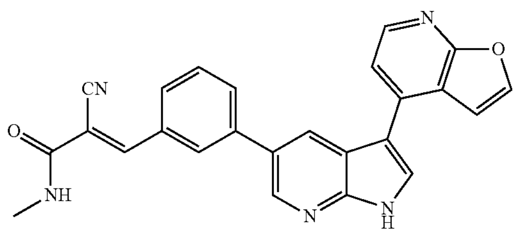 [SMILES: CNC(=O)/C(C#N)=C/c1cccc(-c2cnc3[nH]cc(-c4ccnc5occc45)c3c2)c1] | (E)-2-cyano-3-(3-(3-(furo[2,3-b]pyridin-4-yl)-1H-pyrrolo[2,3-b]pyridin-5-yl)phenyl)-N-methylacrylamide |
| 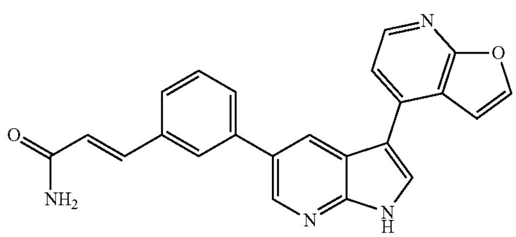 [SMILES: NC(=O)/C=C/c1cccc(-c2cnc3[nH]cc(-c4ccnc5occc45)c3c2)c1] | (E)-3-(3-(3-(furo[2,3-b]pyridin-4-yl)-1H-pyrrolo[2,3-b]pyridin-5-yl)phenyl)acrylamide |
| 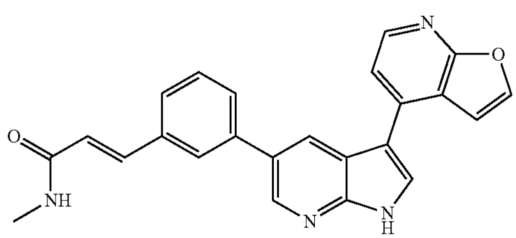 [SMILES: CNC(=O)/C=C/c1cccc(-c2cnc3[nH]cc(-c4ccnc5occc45)c3c2)c1] | (E)-3-(3-(3-(furo[2,3-b]pyridin-4-yl)-1H-pyrrolo[2,3-b]pyridin-5-yl)phenyl)-N-methylacrylamide |
| 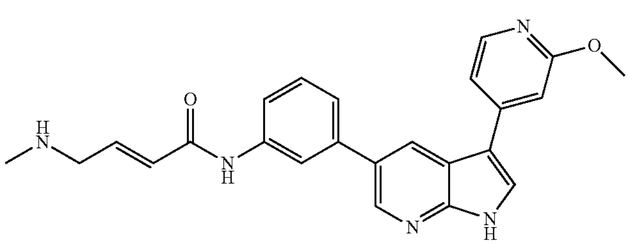 | (E)-N-(3-(3-(2-methoxypyridin-4-yl)-1H-pyrrolo[2,3-b]pyridin-5-yl)phenyl)-4-(methylamino)but-2-enamide |

TABLE 2-continued

| Structure | Name |
|---|---|
| 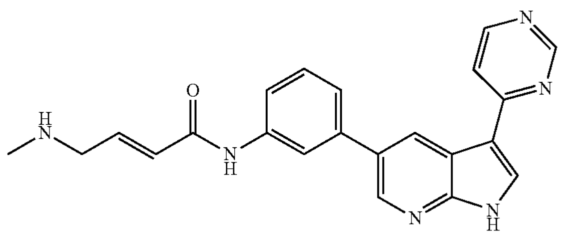 [SMILES: CNC/C=C/C(=O)Nc1cccc(-c2cnc3[nH]cc(-c4ccncn4)c3c2)c1] | (E)-4-(methylamino)-N-(3-(3-(pyrimidin-4-yl)-1H-pyrrolo[2,3-b]pyridin-5-yl)phenyl)but-2-enamide |
| 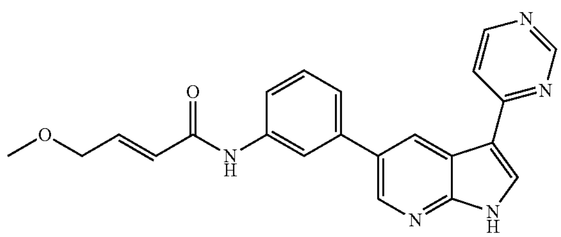 [SMILES: COC/C=C/C(=O)Nc1cccc(-c2cnc3[nH]cc(-c4ccncn4)c3c2)c1] | (E)-4-methoxy-N-(3-(3-(pyrimidin-4-yl)-1H-pyrrolo[2,3-b]pyridin-5-yl)phenyl)but-2-enamide |
| 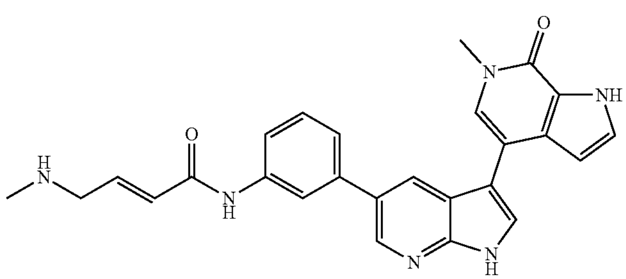 [SMILES: CNC/C=C/C(=O)Nc1cccc(-c2cnc3[nH]cc(-c4cn(C)c(=O)c5[nH]ccc45)c3c2)c1] | (E)-N-(3-(3-(6-methyl-7-oxo-6,7-dihydro-1H-pyrrolo[2,3-c]pyridin-4-yl)-1H-pyrrolo[2,3-b]pyridin-5-yl)phenyl)-4-(methylamino)but-2-enamide |
| 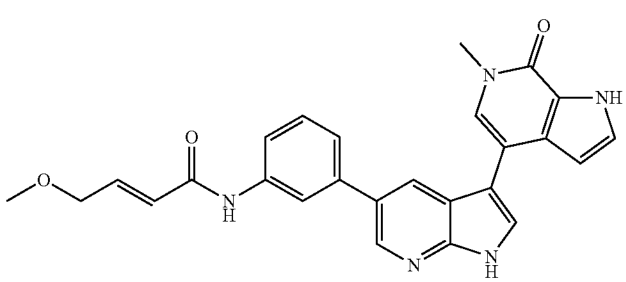 [SMILES: COC/C=C/C(=O)Nc1cccc(-c2cnc3[nH]cc(-c4cn(C)c(=O)c5[nH]ccc45)c3c2)c1] | (E)-4-methoxy-N-(3-(3-(6-methyl-7-oxo-6,7-dihydro-1H-pyrrolo[2,3-c]pyridin-4-yl)-1H-pyrrolo[2,3-b]pyridin-5-yl)phenyl)but-2-enamide |
| 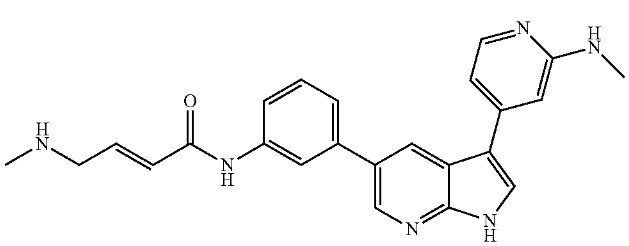 | (E)-4-(methylamino)-N-(3-(3-(2-(methylamino)pyridin-4-yl)-1H-pyrrolo[2,3-b]pyridin-5-yl)phenyl)but-2-enamide |
| 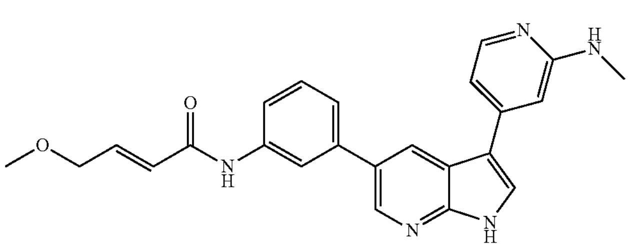 | (E)-4-methoxy-N-(3-(3-(2-(methylamino)pyridin-4-yl)-1H-pyrrolo[2,3-b]pyridin-5-yl)phenyl)but-2-enamide |

TABLE 2-continued

| Structure | Name |
|---|---|
| 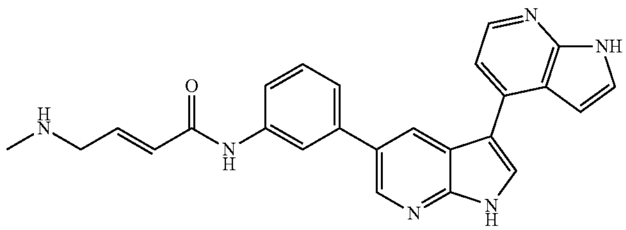 [SMILES: CNC/C=C/C(=O)Nc1cccc(-c2cnc3[nH]cc(-c4ccnc5[nH]ccc45)c3c2)c1] | (E)-N-(3-(1H,1'H-[3,4'-bipyrrolo[2,3-b]pyridin]-5-yl)phenyl)-4-(methylamino)but-2-enamide |
| 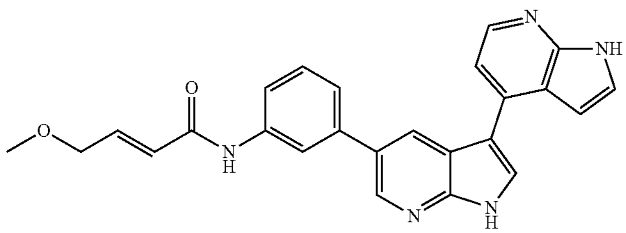 [SMILES: COC/C=C/C(=O)Nc1cccc(-c2cnc3[nH]cc(-c4ccnc5[nH]ccc45)c3c2)c1] | (E)-N-(3-(1H,1'H-[3,4'-bipyrrolo[2,3-b]pyridin]-5-yl)phenyl)-4-(methoxybut-2-enamide |
| 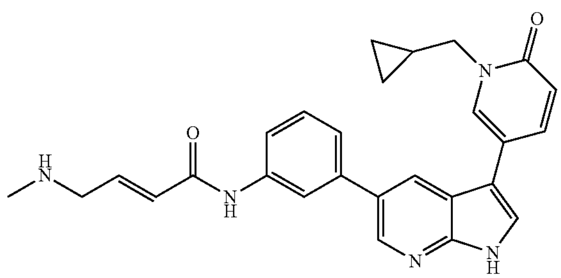 [SMILES: CNC/C=C/C(=O)Nc1cccc(-c2cnc3[nH]cc(-c4ccc(=O)n(CC5CC5)c4)c3c2)c1] | (E)-N-(3-(3-(1-(cyclopropylmethyl)-6-oxo-1,6-dihydropyridin-3-yl)-1H-pyrrolo[2,3-b]pyridin-5-yl)phenyl)-4-(methylamino)but-2-enamide |
| 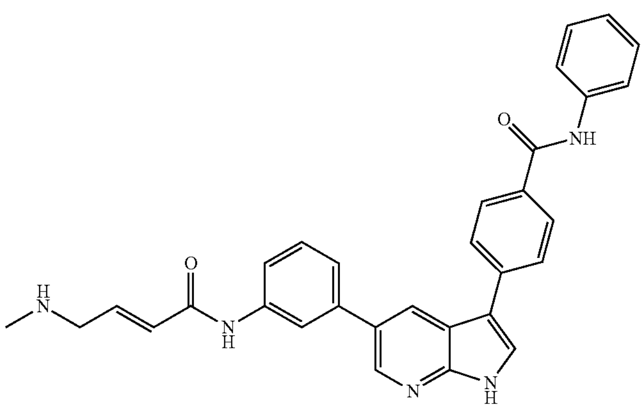 [SMILES: CNC/C=C/C(=O)Nc1cccc(-c2cnc3[nH]cc(-c4ccc(C(=O)Nc5ccccc5)cc4)c3c2)c1] | (E)-4-(5-(3-(4-(methylamino)but-2-enamido)phenyl)-1H-pyrrolo[2,3-b]pyridin-3-yl)-N-phenylbenzamide |
| 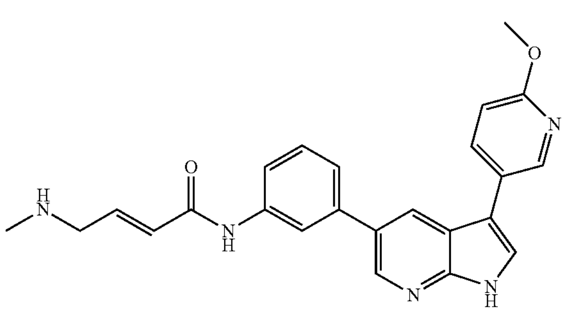 [SMILES: CNC/C=C/C(=O)Nc1cccc(-c2cnc3[nH]cc(-c4ccc(OC)nc4)c3c2)c1] | (E)-N-(3-(3-(6-methoxypyridin-3-yl)-1H-pyrrolo[2,3-b]pyridin-5-yl)phenyl)-4-(methylamino)but-2-enamide |

TABLE 2-continued

| Structure | Name |
|---|---|
| 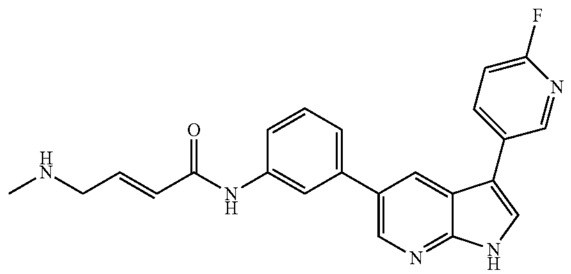 [SMILES: CNC/C=C/C(=O)Nc1cccc(-c2cnc3[nH]cc(-c4ccc(F)nc4)c3c2)c1] | (E)-N-(3-(3-(6-fluoropyridin-3-yl)-1H-pyrrolo[2,3-b]pyridin-5-yl)phenyl)-4-(methylamino)but-2-enamide |
| 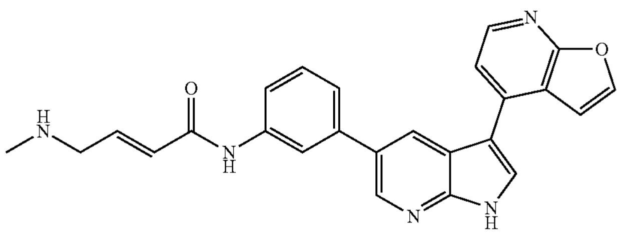 [SMILES: CNC/C=C/C(=O)Nc1cccc(-c2cnc3[nH]cc(-c4ccnc5occc45)c3c2)c1] | (E)-N-(3-(3-(furo[2,3-b]pyridin-4-yl)-1H-pyrrolo[2,3-b]pyridin-5-yl)phenyl)-4-(methylamino)but-2-enamide |
| 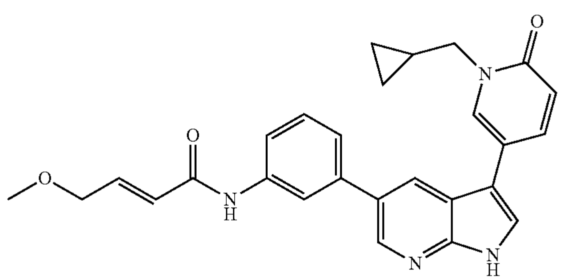 [SMILES: COC/C=C/C(=O)Nc1cccc(-c2cnc3[nH]cc(-c4ccc(=O)n(CC5CC5)c4)c3c2)c1] | (E)-N-(3-(3-(1-(cyclopropylmethyl)-6-oxo-1,6-dihydropyridin-3-yl)-1H-pyrrolo[2,3-b]pyridin-5-yl)phenyl)-4-methoxybut-2-enamide |
| 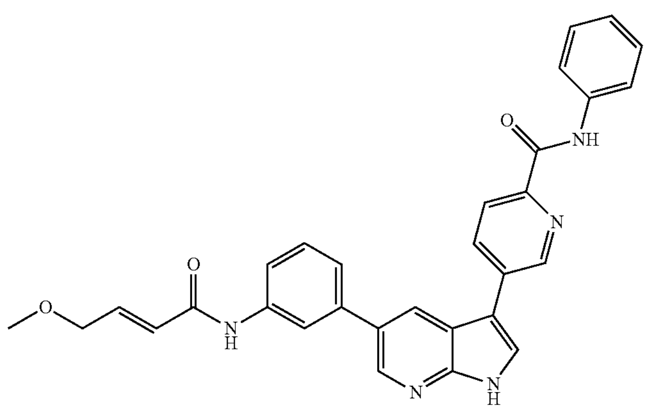 [SMILES: COC/C=C/C(=O)Nc1cccc(-c2cnc3[nH]cc(-c4ccc(C(=O)Nc5ccccc5)nc4)c3c2)c1] | (E)-4-(5-(3-(4-methoxybut-2-enamido)phenyl)-1H-pyrrolo[2,3-b]pyridin-3-yl)-N-phenylbenzamide |
| 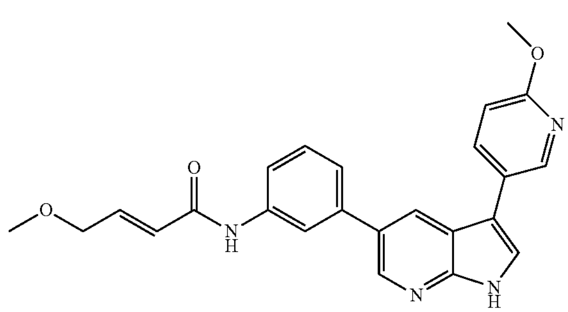 [SMILES: COC/C=C/C(=O)Nc1cccc(-c2cnc3[nH]cc(-c4ccc(OC)nc4)c3c2)c1] | (E)-4-methoxy-N-(3-(3-(6-methoxypyridin-3-yl)-1H-pyrrolo[2,3-b]pyridin-5-yl)phenyl)but-2-enamide |

TABLE 2-continued

| Structure | Name |
|---|---|
| 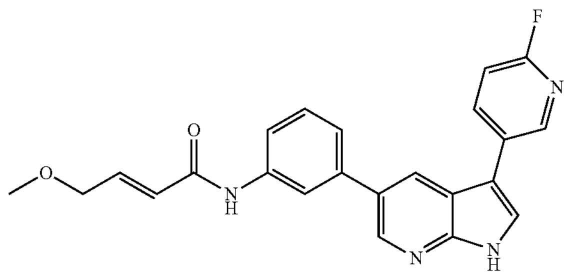 [SMILES: COC/C=C/C(=O)Nc1cccc(-c2cnc3[nH]cc(-c4ccc(F)nc4)c3c2)c1] | (E)-N-(3-(3-(6-fluoropyridin-3-yl)-1H-pyrrolo[2,3-b]pyridin-5-yl)phenyl)-4-methoxybut-2-enamide |
| 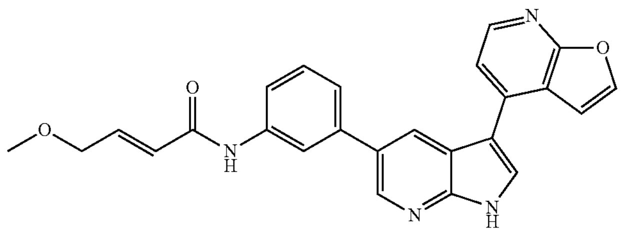 [SMILES: COC/C=C/C(=O)Nc1cccc(-c2cnc3[nH]cc(-c4ccnc5occc45)c3c2)c1] | (E)-N-(3-(3-(furo[2,3-b]pyridin-4-yl)-1H-pyrrolo[2,3-b]pyridin-5-yl)phenyl)-4-methoxybut-2-enamide |
| 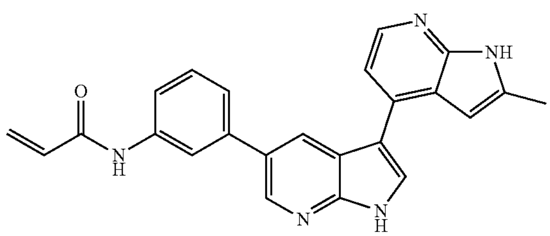 [SMILES: C=CC(=O)Nc1cccc(-c2cnc3[nH]cc(-c4ccnc5[nH]c(C)cc45)c3c2)c1] | N-(3-(2'-methyl-1H,1'H-[3,4'-bipyrrolo[2,3-b]pyridin]-5-yl)phenyl)acrylamide |
| 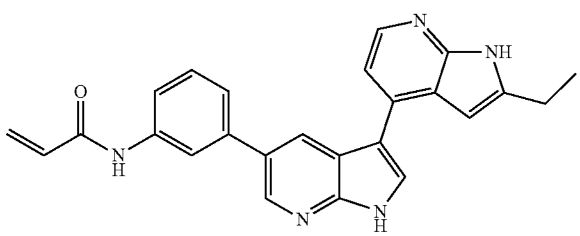 [SMILES: C=CC(=O)Nc1cccc(-c2cnc3[nH]cc(-c4ccnc5[nH]c(CC)cc45)c3c2)c1] | N-(3-(2'-ethyl-1H,1'H-[3,4'-bipyrrolo[2,3-b]pyridin]-5-yl)phenyl)acrylamide |
| 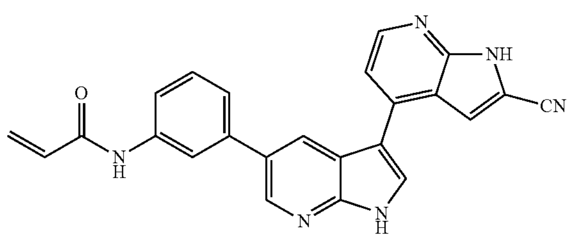 [SMILES: C=CC(=O)Nc1cccc(-c2cnc3[nH]cc(-c4ccnc5[nH]c(C#N)cc45)c3c2)c1] | N-(3-(2'-cyano-1H,1'H-[3,4'-bipyrrolo[2,3-b]pyridin]-5-yl)phenyl)acrylamide |
| 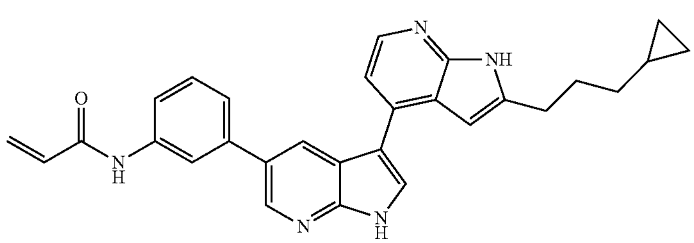 [SMILES: C=CC(=O)Nc1cccc(-c2cnc3[nH]cc(-c4ccnc5[nH]c(CCCC6CC6)cc45)c3c2)c1] | N-(3-(2'-(3-cyclopropylpropyl)-1H,1'H-[3,4'-bipyrrolo[2,3-b]pyridin]-5-yl)phenyl)acrylamide |

TABLE 2-continued

| Structure | Name |
| --- | --- |
| 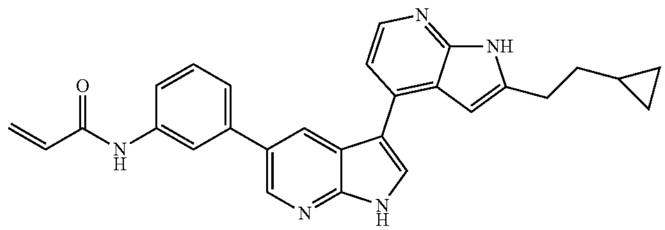 [SMILES: C=CC(=O)Nc1cccc(-c2cnc3[nH]cc(-c4ccnc5[nH]c(CCC6CC6)cc45)c3c2)c1] | N-(3-(2'-(2-cyclopropylethyl)-1H,1'H-[3,4'-bipyrrolo[2,3-b]pyridin]-5-yl)phenyl)acrylamide |
| 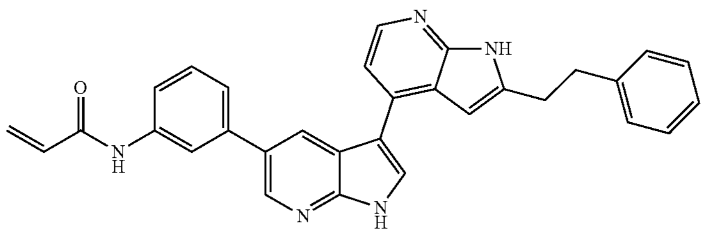 [SMILES: C=CC(=O)Nc1cccc(-c2cnc3[nH]cc(-c4ccnc5[nH]c(CCc6ccccc6)cc45)c3c2)c1] | N-(3-(2'-phenethyl-1H,1'H-[3,4'-bipyrrolo[2,3-b]pyridin]-5-yl)phenyl)acrylamide |
| 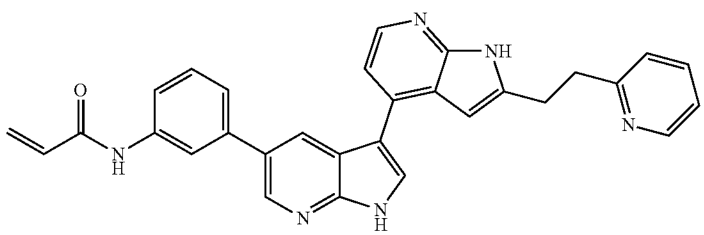 [SMILES: C=CC(=O)Nc1cccc(-c2cnc3[nH]cc(-c4ccnc5[nH]c(CCc6ccccn6)cc45)c3c2)c1] | N-(3-(2'-(2-(pyridin-2-yl)ethyl)-1H,1'H-[3,4'-bipyrrolo[2,3-b]pyridin]-5-yl)phenyl)acrylamide |
| 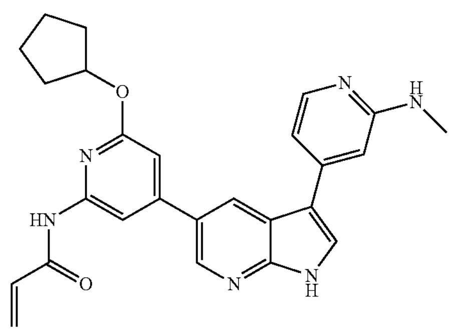 [SMILES: C=CC(=O)Nc1cc(-c2cnc3[nH]cc(-c4ccnc(NC)c4)c3c2)cc(OC2CCCC2)n1] | N-(6-(cyclopentyloxy)-4-(3-(2-(methylamino)pyridin-4-yl)-1H-pyrrolo[2,3-b]pyridin-5-yl)pyridin-2-yl)acrylamide |
| 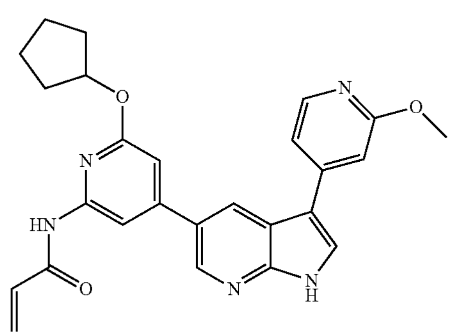 [SMILES: C=CC(=O)Nc1cc(-c2cnc3[nH]cc(-c4ccnc(OC)c4)c3c2)cc(OC2CCCC2)n1] | N-(6-(cyclopentyloxy)-4-(3-(2-methoxypyridin-4-yl)-1H-pyrrolo[2,3-b]pyridin-5-yl)pyridin-2-yl)acrylamide |

TABLE 2-continued

| Structure | Name |
|---|---|
| 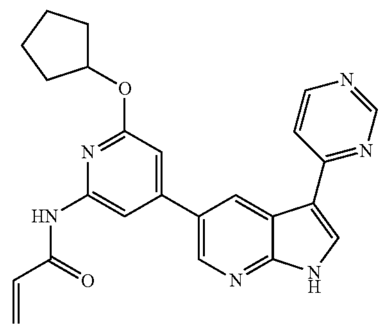 [SMILES: C=CC(=O)Nc1cc(-c2cnc3[nH]cc(-c4ccncn4)c3c2)cc(OC2CCCC2)n1] | N-(6-(cyclopentyloxy)-4-(3-(pyrimidin-4-yl)-1H-pyrrolo[2,3-b]pyridin-5-yl)pyridin-2-yl)acrylamide |
| 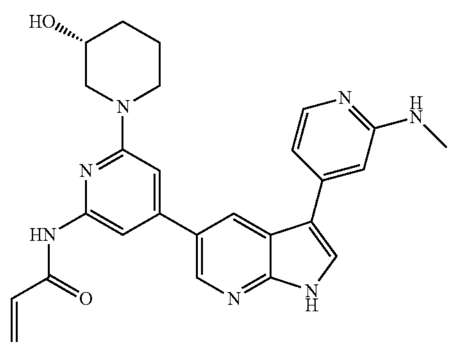 [SMILES: C=CC(=O)Nc1cc(-c2cnc3[nH]cc(-c4ccnc(NC)c4)c3c2)cc(N2CCC[C@@H](O)C2)n1] | (R)-N-(6-(3-hydroxypiperidin-1-yl)-4-(3-(2-(methylamino)pyridin-4-yl)-1H-pyrrolo[2,3-b]pyridin-5-yl)pyridin-2-yl)acrylamide |
| 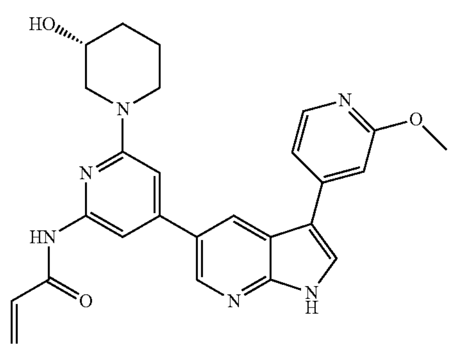 [SMILES: C=CC(=O)Nc1cc(-c2cnc3[nH]cc(-c4ccnc(OC)c4)c3c2)cc(N2CCC[C@@H](O)C2)n1] | (R)-N-(6-(3-hydroxypiperidin-1-yl)-4-(3-(2-methoxypyridin-4-yl)-1H-pyrrolo[2,3-b]pyridin-5-yl)pyridin-2-yl)acrylamide |
| 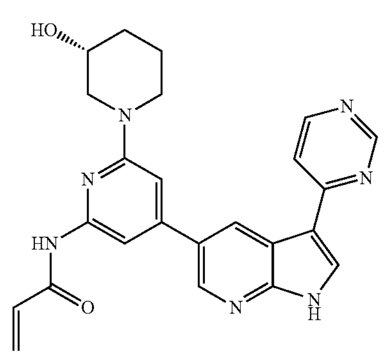 [SMILES: C=CC(=O)Nc1cc(-c2cnc3[nH]cc(-c4ccncn4)c3c2)cc(N2CCC[C@@H](O)C2)n1] | (R)-N-(6-(3-hydroxypiperidin-1-yl)-4-(3-(pyrimidin-4-yl)-1H-pyrrolo[2,3-b]pyridin-5-yl)pyridin-2-yl)acrylamide |

TABLE 2-continued

| Structure | Name |
|---|---|
| | N-(6-(1-methyl-1H-pyrazol-4-yl)-4-(3-(pyrimidin-4-yl)-1H-pyrrolo[2,3-b]pyridin-5-yl)pyridin-2-yl)acrylamide |
| 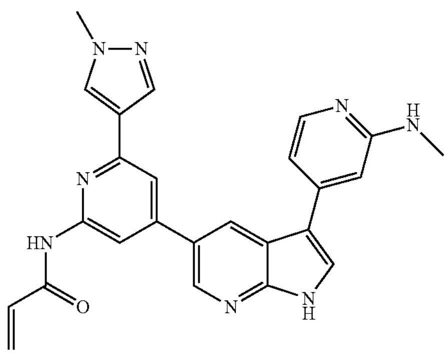 [SMILES: C=CC(=O)Nc1cc(-c2cnc3[nH]cc(-c4ccnc(NC)c4)c3c2)cc(-c2cnn(C)c2)n1] | N-(6-(1-methyl-1H-pyrazol-4-yl)-4-(3-(2-(methylamino)pyridin-4-yl)-1H-pyrrolo[2,3-b]pyridin-5-yl)pyridin-2-yl)acrylamide |
| 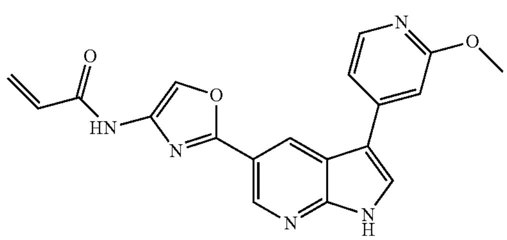 [SMILES: C=CC(=O)Nc1coc(-c2cnc3[nH]cc(-c4ccnc(OC)c4)c3c2)n1] | N-(2-(3-(2-methoxypyridin-4-yl)-1H-pyrrolo[2,3-b]pyridin-5-yl)oxazol-4-yl)acrylamide |
| 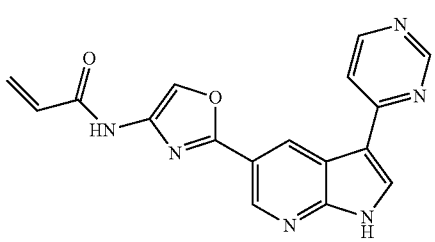 [SMILES: C=CC(=O)Nc1coc(-c2cnc3[nH]cc(-c4ccncn4)c3c2)n1] | N-(2-(3-(pyrimidin-4-yl)-1H-pyrrolo[2,3-b]pyridin-5-yl)oxazol-4-yl)acrylamide |
| 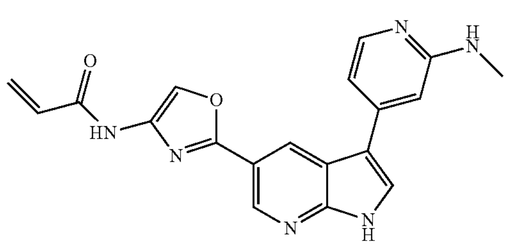 [SMILES: C=CC(=O)Nc1coc(-c2cnc3[nH]cc(-c4ccnc(NC)c4)c3c2)n1] | N-(2-(3-(2-(methylamino)pyridin-4-yl)-1H-pyrrolo[2,3-b]pyridin-5-yl)oxazol-4-yl)acrylamide |

TABLE 2-continued

| Structure | Name |
|---|---|
| 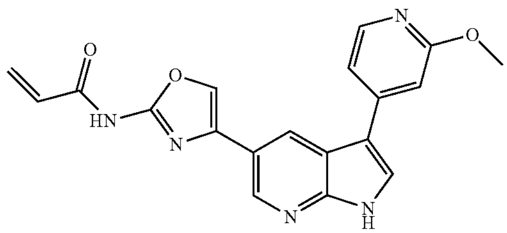 [SMILES: C=CC(=O)Nc1nc(-c2cnc3[nH]cc(-c4ccnc(OC)c4)c3c2)co1] | N-(4-(3-(2-methoxypyridin-4-yl)-1H-pyrrolo[2,3-b]pyridin-5-yl)oxazol-2-yl)acrylamide |
| 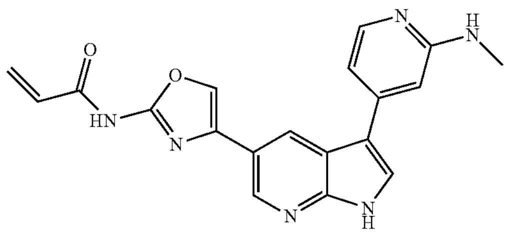 [SMILES: C=CC(=O)Nc1nc(-c2cnc3[nH]cc(-c4ccnc(NC)c4)c3c2)co1] | N-(4-(3-(2-(methylamino)pyridin-4-yl)-1H-pyrrolo[2,3-b]pyridin-5-yl)oxazol-2-yl)acrylamide |
| 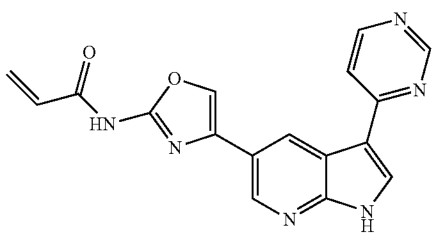 [SMILES: C=CC(=O)Nc1nc(-c2cnc3[nH]cc(-c4ccncn4)c3c2)co1] | N-(4-(3-(pyrimidin-4-yl)-1H-pyrrolo[2,3-b]pyridin-5-yl)oxazol-2-yl)acrylamide |
| 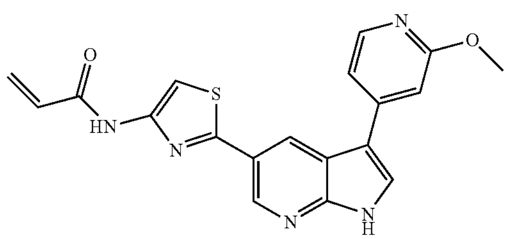 [SMILES: C=CC(=O)Nc1csc(-c2cnc3[nH]cc(-c4ccnc(OC)c4)c3c2)n1] | N-(2-(3-(2-methoxypyridin-4-yl)-1H-pyrrolo[2,3-b]pyridin-5-yl)thiazol-4-yl)acrylamide |
| 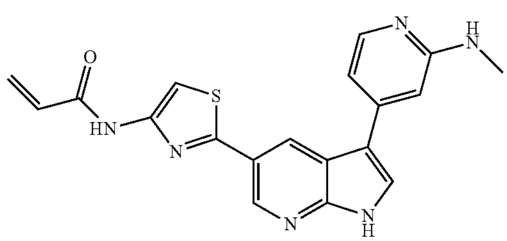 [SMILES: C=CC(=O)Nc1csc(-c2cnc3[nH]cc(-c4ccnc(NC)c4)c3c2)n1] | N-(2-(3-(2-(methylamino)pyridin-4-yl)-1H-pyrrolo[2,3-b]pyridin-5-yl)thiazol-4-yl)acrylamide |
| 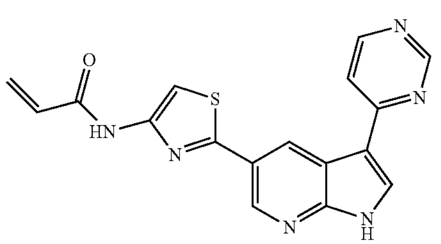 [SMILES: C=CC(=O)Nc1csc(-c2cnc3[nH]cc(-c4ccncn4)c3c2)n1] | N-(2-(3-(pyrimidin-4-yl)-1H-pyrrolo[2,3-b]pyridin-5-yl)thiazol-4-yl)acrylamide |

TABLE 2-continued

| Structure | Name |
|---|---|
| 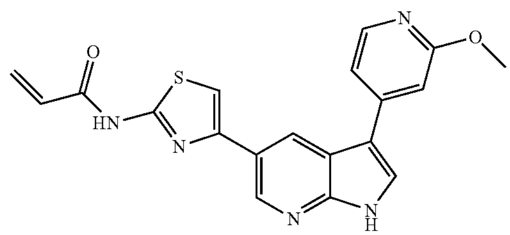 [SMILES: C=CC(=O)Nc1nc(-c2cnc3[nH]cc(-c4ccnc(OC)c4)c3c2)cs1] | N-(4-(3-(2-methoxypyridin-4-yl)-1H-pyrrolo[2,3-b]pyridin-5-yl)thiazol-2-yl)acrylamide |
| 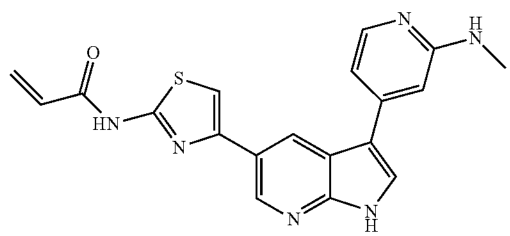 [SMILES: C=CC(=O)Nc1nc(-c2cnc3[nH]cc(-c4ccnc(NC)c4)c3c2)cs1] | N-(4-(3-(2-methylamino)pyridin-4-yl)-1H-pyrrolo[2,3-b]pyridin-5-yl)thiazol-2-yl)acrylamide |
| 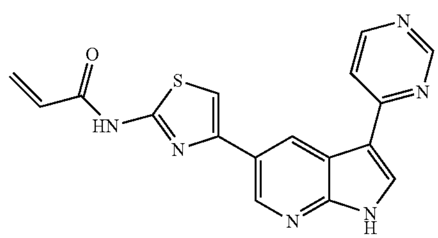 [SMILES: C=CC(=O)Nc1nc(-c2cnc3[nH]cc(-c4ccncn4)c3c2)cs1] | N-(4-(3-(pyrimidin-4-yl)-1H-pyrrolo[2,3-b]pyridin-5-yl)thiazol-2-yl)acrylamide |
| 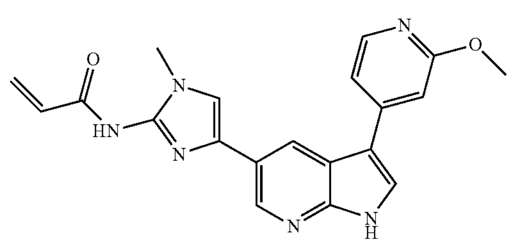 [SMILES: C=CC(=O)Nc1nc(-c2cnc3[nH]cc(-c4ccnc(OC)c4)c3c2)cn1C] | N-(4-(3-(2-methoxypyridin-4-yl)-1H-pyrrolo[2,3-b]pyridin-5-yl)-1-methyl-1H-imidazol-2-yl)acrylamide |
| 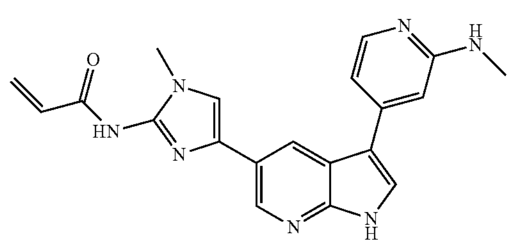 [SMILES: C=CC(=O)Nc1nc(-c2cnc3[nH]cc(-c4ccnc(NC)c4)c3c2)cn1C] | N-(1-methyl-4-(3-(2-(methylamino)pyridin-4-yl)-1H-pyrrolo[2,3-b]pyridin-5-yl)-1H-imidazol-2-yl)acrylamide |
| 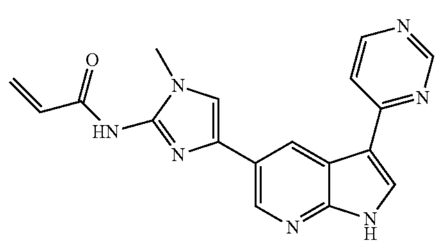 [SMILES: C=CC(=O)Nc1nc(-c2cnc3[nH]cc(-c4ccncn4)c3c2)cn1C] | N-(1-methyl-4-(3-(pyrimidin-4-yl)-1H-pyrrolo[2,3-b]pyridin-5-yl)-1H-imidazol-2-yl)acrylamide |

TABLE 2-continued

| Structure | Name |
|---|---|
| 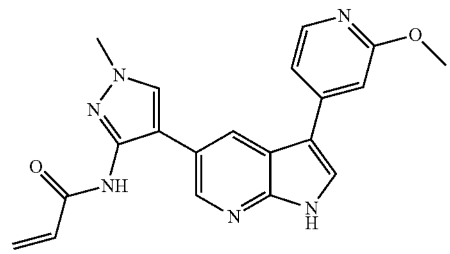 [SMILES: C=CC(=O)Nc1nn(C)cc1-c1cnc2[nH]cc(-c3ccnc(OC)c3)c2c1] | N-(4-(3-(2-methoxypyridin-4-yl)-1H-pyrrolo[2,3-b]pyridin-5-yl)-1-methyl-1H-pyrazol-3-yl)acrylamide |
| 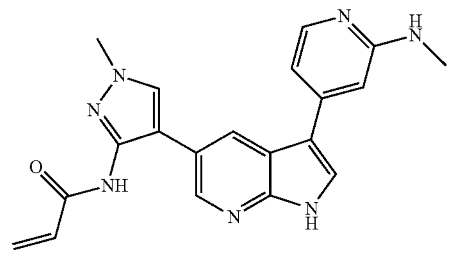 [SMILES: C=CC(=O)Nc1nn(C)cc1-c1cnc2[nH]cc(-c3ccnc(NC)c3)c2c1] | N-(1-methyl-4-(3-(2-(methylamino)pyridin-4-yl)-1H-pyrrolo[2,3-b]pyridin-5-yl)-1H-pyrazol-3-yl)acrylamide |
| 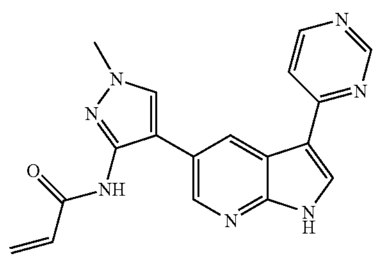 [SMILES: C=CC(=O)Nc1nn(C)cc1-c1cnc2[nH]cc(-c3ccncn3)c2c1] | N-(1-methyl-4-(3-(pyrimidin-4-yl)-1H-pyrrolo[2,3-b]pyridin-5-yl)-1H-pyrazol-3-yl)acrylamide |
| 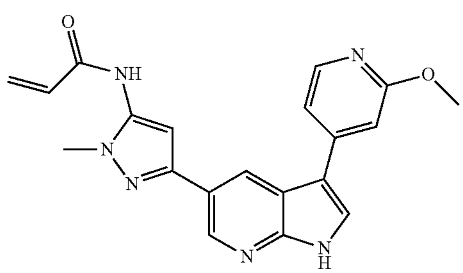 [SMILES: C=CC(=O)Nc1cc(-c2cnc3[nH]cc(-c4ccnc(OC)c4)c3c2)nn1C] | N-(3-(3-(2-methoxypyridin-4-yl)-1H-pyrrolo[2,3-b]pyridin-5-yl)-1-methyl-1H-pyrazol-5-yl)acrylamide |
| 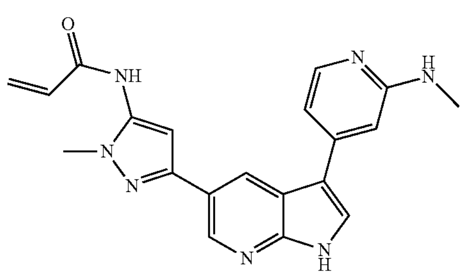 [SMILES: C=CC(=O)Nc1cc(-c2cnc3[nH]cc(-c4ccnc(NC)c4)c3c2)nn1C] | N-(1-methyl-3-(3-(2-(methylamino)pyridin-4-yl)-1H-pyrrolo[2,3-b]pyridin-5-yl)-1H-pyrazol-5-yl)acrylamide |
| 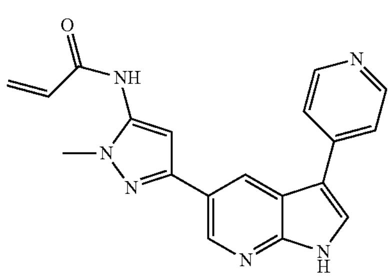 [SMILES: C=CC(=O)Nc1cc(-c2cnc3[nH]cc(-c4ccncc4)c3c2)nn1C] | N-(1-methyl-3-(3-(pyridin-4-yl)-1H-pyrrolo[2,3-b]pyridin-5-yl)-1H-pyrazol-5-yl)acrylamide |

TABLE 2-continued

| Structure | Name |
|---|---|
| 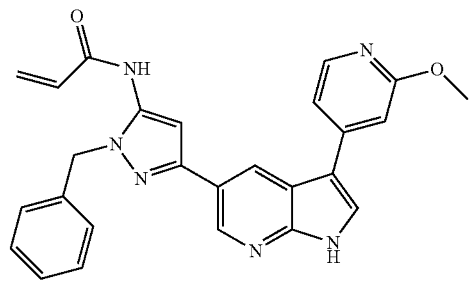 [SMILES: C=CC(=O)Nc1cc(-c2cnc3[nH]cc(-c4ccnc(OC)c4)c3c2)nn1Cc1ccccc1] | N-(1-benzyl-3-(3-(2-methoxypyridin-4-yl)-1H-pyrrolo[2,3-b]pyridin-5-yl)-1H-pyrazol-5-yl)acrylamide |
| 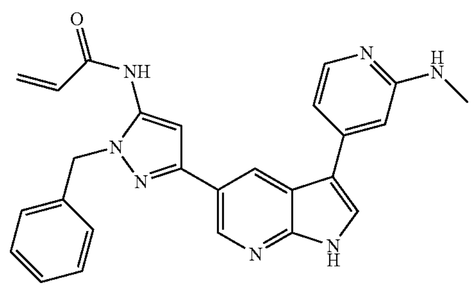 [SMILES: C=CC(=O)Nc1cc(-c2cnc3[nH]cc(-c4ccnc(NC)c4)c3c2)nn1Cc1ccccc1] | N-(1-benzyl-3-(3-(2-(methylamino)pyridin-4-yl)-1H-pyrrolo[2,3-b]pyridin-5-yl)-1H-pyrazol-5-yl)acrylamide |
| 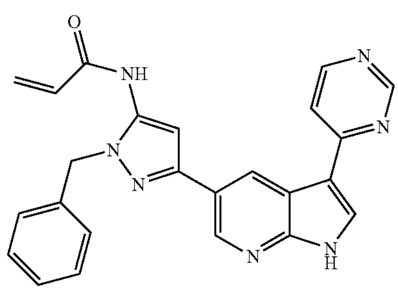 [SMILES: C=CC(=O)Nc1cc(-c2cnc3[nH]cc(-c4ccncn4)c3c2)nn1Cc1ccccc1] | N-(1-benzyl-3-(3-(pyrimidin-4-yl)-1H-pyrrolo[2,3-b]pyridin-5-yl)-1H-pyrazol-5-yl)acrylamide |
| 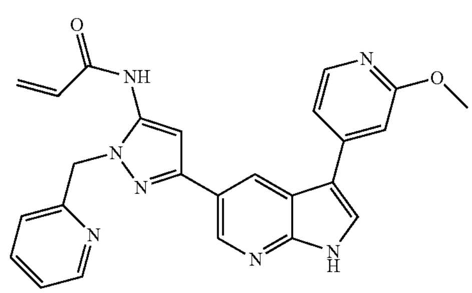 [SMILES: C=CC(=O)Nc1cc(-c2cnc3[nH]cc(-c4ccnc(OC)c4)c3c2)nn1Cc1ccccn1] | N-(3-(3-(2-methoxypyridin-4-yl)-1H-pyrrolo[2,3-b]pyridin-5-yl)-1-(pyridin-2-ylmethyl)-1H-pyrazol-5-yl)acrylamide |
| 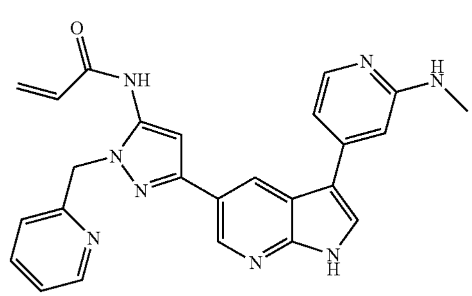 [SMILES: C=CC(=O)Nc1cc(-c2cnc3[nH]cc(-c4ccnc(NC)c4)c3c2)nn1Cc1ccccn1] | N-(3-(3-(2-(methylamino)pyridin-4-yl)-1H-pyrrolo[2,3-b]pyridin-5-yl)-1-(pyridin-2-ylmethyl)-1H-pyrazol-5-yl)acrylamide |

| Structure | Name |
|---|---|
| 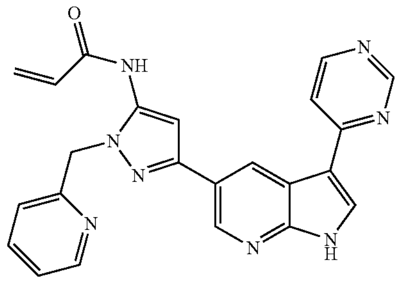 [SMILES: C=CC(=O)Nc1cc(-c2cnc3[nH]cc(-c4ccncn4)c3c2)nn1Cc1ccccn1] | N-(1-pyridin-2-ylmethyl)-3-(3-(pyrimidin-4-yl)-1H-pyrrolo[2,3-b]pyridin-5-yl)-1H-pyrazol-5-yl)acrylamide |
| 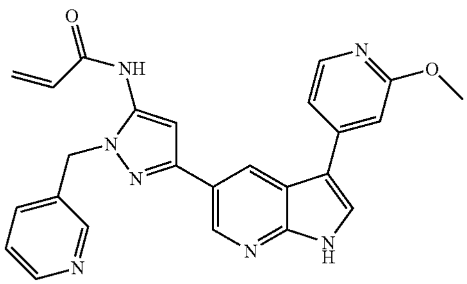 [SMILES: C=CC(=O)Nc1cc(-c2cnc3[nH]cc(-c4ccnc(OC)c4)c3c2)nn1Cc1cccnc1] | N-(3-(3-(2-methoxypyridin-4-yl)-1H-pyrrolo[2,3-b]pyridin-5-yl)-1-(pyridin-3-ylmethyl)-1H-pyrazol-5-yl)acrylamide |
| 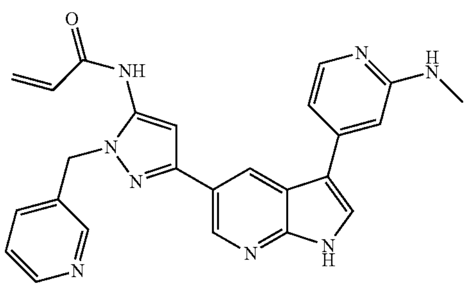 [SMILES: C=CC(=O)Nc1cc(-c2cnc3[nH]cc(-c4ccnc(NC)c4)c3c2)nn1Cc1cccnc1] | N-(3-(3-(2-(methylamino)pyridin-4-yl)-1H-pyrrolo[2,3-b]pyridin-5-yl)-1-(pyridin-3-ylmethyl)-1H-pyrazol-5-yl)acrylamide |
| 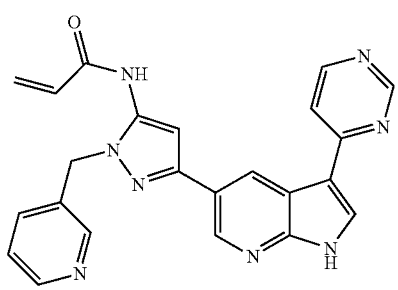 [SMILES: C=CC(=O)Nc1cc(-c2cnc3[nH]cc(-c4ccncn4)c3c2)nn1Cc1cccnc1] | N-(1-(pyridin-3-ylmethyl)-3-(3-(pyrimidin-4-yl)-1H-pyrrolo[2,3-b]pyridin-5-yl)-1H-pyrazol-5-yl)acrylamide |
| 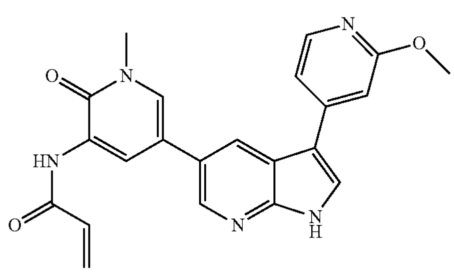 [SMILES: C=CC(=O)Nc1cc(-c2cnc3[nH]cc(-c4ccnc(OC)c4)c3c2)cn(C)c1=O] | N-(5-(3-(2-methoxypyridin-4-yl)-1H-pyrrolo[2,3-b]pyridin-5-yl)-1-methyl-2-oxo-1,2-dihydropyridin-3-yl)acrylamide |

TABLE 2-continued

| Structure | Name |
|---|---|
| 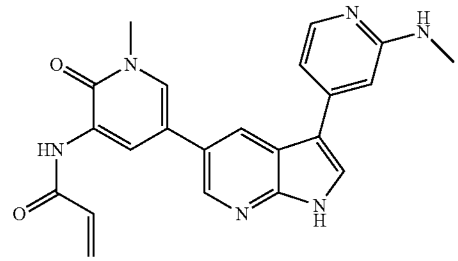 [SMILES: C=CC(=O)Nc1cc(-c2cnc3[nH]cc(-c4ccnc(NC)c4)c3c2)cn(C)c1=O] | N-(1-methyl-5-(3-(2-(methylamino)pyridin-4-yl)-1H-pyrrolo[2,3-b]pyridin-5-yl)-2-oxo-1,2-dihydropyridin-3-yl)acrylamide |
| 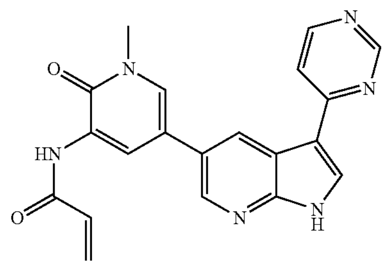 [SMILES: C=CC(=O)Nc1cc(-c2cnc3[nH]cc(-c4ccncn4)c3c2)cn(C)c1=O] | N-(1-methyl-2-oxo-5-(3-(pyrimidin-4-yl)-1H-pyrrolo[2,3-b]pyridin-5-yl)-1,2-dihydropyridin-3-yl)acrylamide |
| 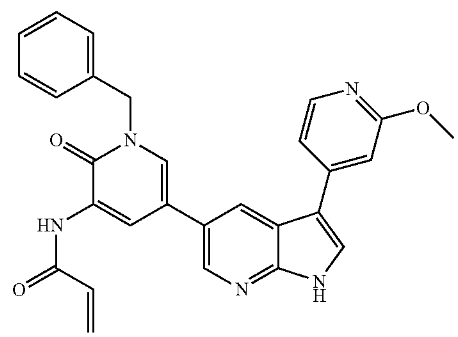 [SMILES: C=CC(=O)Nc1cc(-c2cnc3[nH]cc(-c4ccnc(OC)c4)c3c2)cn(Cc2ccccc2)c1=O] | N-(1-benzyl-5-(3-(2-methoxypyridin-4-yl)-1H-pyrrolo[2,3-b]pyridin-5-yl)-2-oxo-1,2-dihydropyridin-3-yl)acrylamide |
| 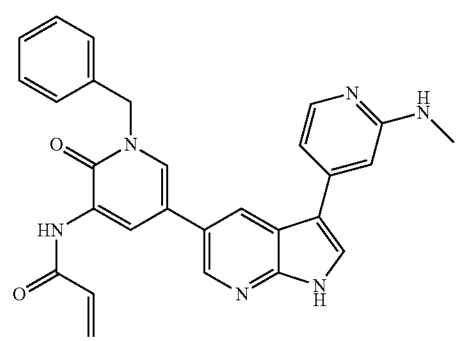 [SMILES: C=CC(=O)Nc1cc(-c2cnc3[nH]cc(-c4ccnc(NC)c4)c3c2)cn(Cc2ccccc2)c1=O] | N-(1-benzyl-5-(3-(2-(methylamino)pyridin-4-yl)-1H-pyrrolo[2,3-b]pyridin-5-yl)-2-oxo-1,2-dihydropyridin-3-yl)acrylamide |
| 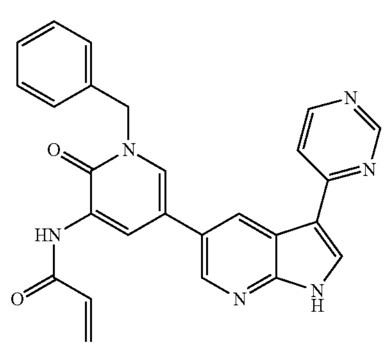 [SMILES: C=CC(=O)Nc1cc(-c2cnc3[nH]cc(-c4ccncn4)c3c2)cn(Cc2ccccc2)c1=O] | N-(1-benzyl-2-oxo-5-(3-(pyrimidin-4-yl)-1H-pyrrolo[2,3-b]pyridin-5-yl)-1,2-dihydropyridin-3-yl)acrylamide |

TABLE 2-continued

| Structure | Name |
|---|---|
| 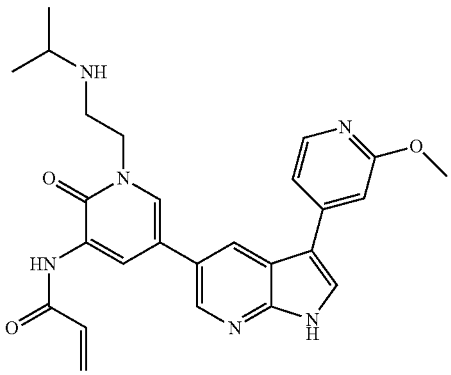 [SMILES: C=CC(=O)Nc1cc(-c2cnc3[nH]cc(-c4ccnc(OC)c4)c3c2)cn(CCNC(C)C)c1=O] | N-(1-(2-(isopropylamino)ethyl)-5-(3-(2-methoxypyridin-4-yl)-1H-pyrrolo[2,3-b]pyridin-5-yl)-2-oxo-1,2-dihydropyridin-3-yl)acrylamide |
| 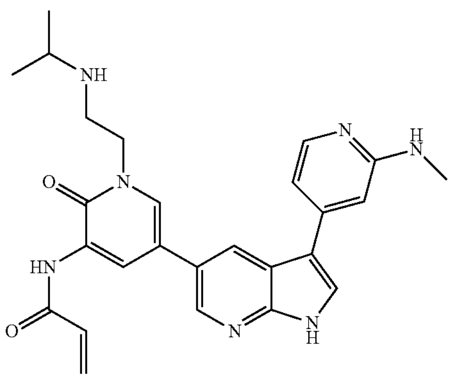 [SMILES: C=CC(=O)Nc1cc(-c2cnc3[nH]cc(-c4ccnc(NC)c4)c3c2)cn(CCNC(C)C)c1=O] | N-(1-(2-(isopropylamino)ethyl)-5-(3-(2-(methylamino)pyridin-4-yl)-1H-pyrrolo[2,3-b]pyridin-5-yl)-2-oxo-1,2-dihydropyridin-3-yl)acrylamide |
| 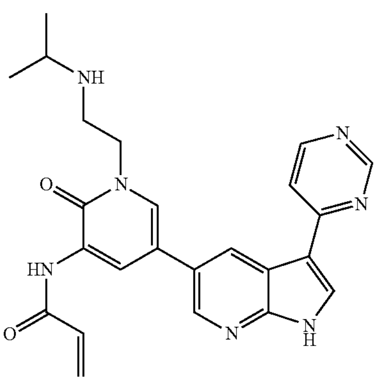 [SMILES: C=CC(=O)Nc1cc(-c2cnc3[nH]cc(-c4ccncn4)c3c2)cn(CCNC(C)C)c1=O] | N-(1-(2-(isopropylamino)ethyl)-2-oxo-5-(3-(pyrimidin-4-yl)-1H-pyrrolo[2,3-b]pyridin-5-yl)-1,2-dihydropyridin-3-yl)acrylamide |
| 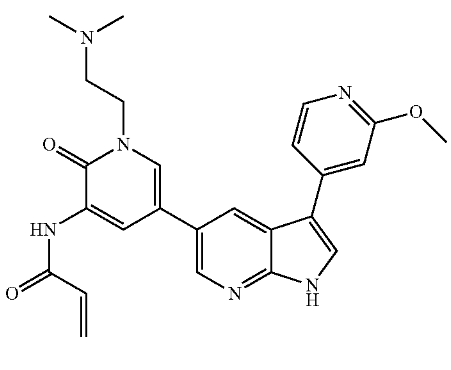 [SMILES: C=CC(=O)Nc1cc(-c2cnc3[nH]cc(-c4ccnc(OC)c4)c3c2)cn(CCN(C)C)c1=O] | N-(1-(2-(dimethylamino)ethyl)-5-(3-(2-methoxypyridin-4-yl)-1H-pyrrolo[2,3-b]pyridin-5-yl)-2-oxo-1,2-dihydropyridin-3-yl)acrylamide |

TABLE 2-continued

| Structure | Name |
|---|---|
| 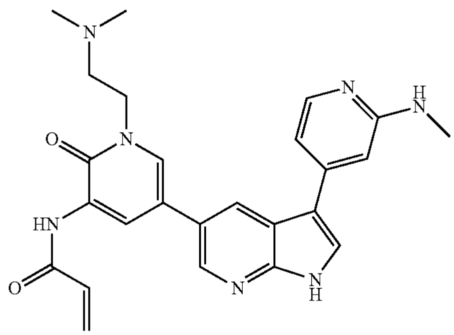 [SMILES: C=CC(=O)Nc1cc(-c2cnc3[nH]cc(-c4ccnc(NC)c4)c3c2)cn(CCN(C)C)c1=O] | N-(1-(2-(dimethylamino)ethyl)-5-(3-(2-(methylamino)pyridin-4-yl)-1H-pyrrolo[2,3-b]pyridin-5-yl)-2-oxo-1,2-dihydropyridin-3-yl)acrylamide |
| 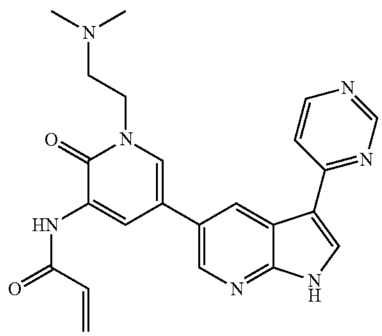 [SMILES: C=CC(=O)Nc1cc(-c2cnc3[nH]cc(-c4ccncn4)c3c2)cn(CCN(C)C)c1=O] | N-(1-(2-(dimethylamino)ethyl)-2-oxo-5-(3-(pyrimidin-4-yl)-1H-pyrrolo[2,3-b]pyridin-5-yl)-1,2-dihydropyridin-3-yl)acrylamide |
| 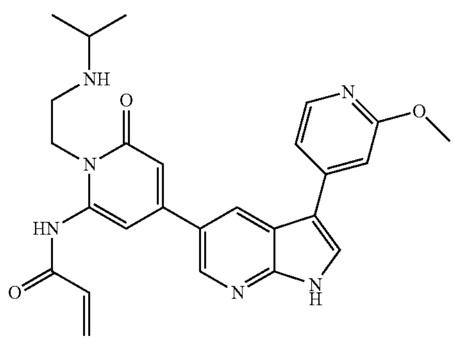 [SMILES: C=CC(=O)Nc1cc(-c2cnc3[nH]cc(-c4ccnc(OC)c4)c3c2)cc(=O)n1CCNC(C)C] | N-(1-(2-(isopropylamino)ethyl)-4-(3-(2-methoxypyridin-4-yl)-1H-pyrrolo[2,3-b]pyridin-5-yl)-6-oxo-1,6-dihydropyridin-2-yl)acrylamide |
| 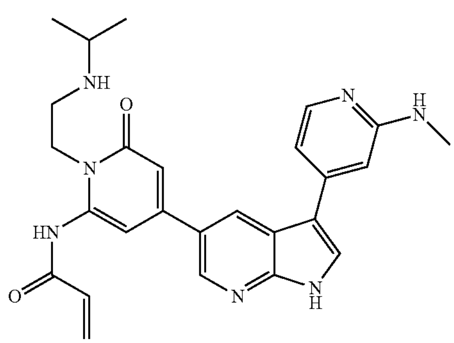 [SMILES: C=CC(=O)Nc1cc(-c2cnc3[nH]cc(-c4ccnc(NC)c4)c3c2)cc(=O)n1CCNC(C)C] | N-(1-(2-(isopropylamino)ethyl)-4-(3-(2-(methylamino)pyridin-4-yl)-1H-pyrrolo[2,3-b]pyridin-5-yl)-6-oxo-1,6-dihydropyridin-2-yl)acrylamide |

TABLE 2-continued

| Structure | Name |
|---|---|
| 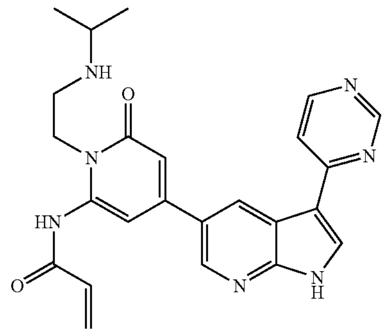 [SMILES: C=CC(=O)Nc1cc(-c2cnc3[nH]cc(-c4ccncn4)c3c2)cc(=O)n1CCNC(C)C] | N-(1-(2-(isopropylamino)ethyl)-6-oxo-4-(3-(pyrimidin-4-yl)-1H-pyrrolo[2,3-b]pyridin-5-yl)-1,6-dihydropyridin-2-yl)acrylamide |
| 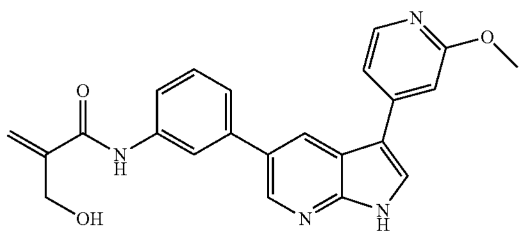 [SMILES: C=C(CO)C(=O)Nc1cccc(-c2cnc3[nH]cc(-c4ccnc(OC)c4)c3c2)c1] | 2-(hydroxymethyl)-N-(3-(3-(2-methoxypyridin-4-yl)-1H-pyrrolo[2,3-b]pyridin-5-yl)phenyl)acrylamide |
| 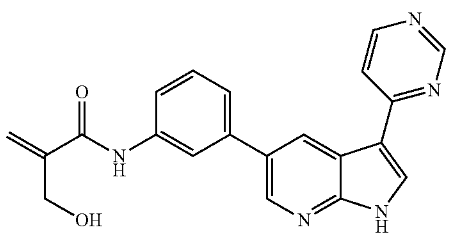 [SMILES: C=C(CO)C(=O)Nc1cccc(-c2cnc3[nH]cc(-c4ccncn4)c3c2)c1] | 2-(hydroxymethyl)-N-(3-(3-(pyrimidin-4-yl)-1H-pyrrolo[2,3-b]pyridin-5-yl)phenyl)acrylamide |
| 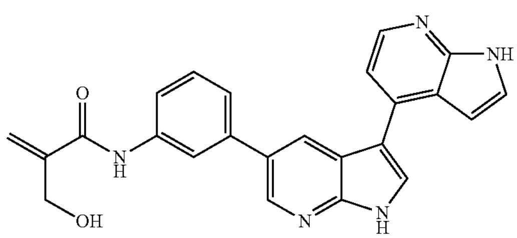 [SMILES: C=C(CO)C(=O)Nc1cccc(-c2cnc3[nH]cc(-c4ccnc5[nH]ccc45)c3c2)c1] | N-(3-(1H,1'H-[3,4'-bipyrrolo[2,3-b]pyridin]-5-yl)phenyl)-2-(hydroxymethyl)acrylamide |
| 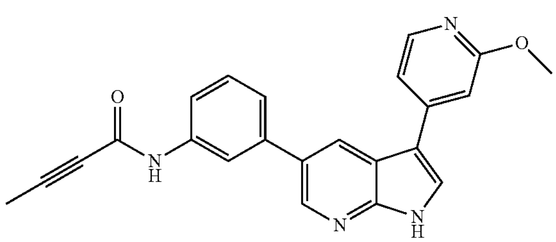 [SMILES: CC#CC(=O)Nc1cccc(-c2cnc3[nH]cc(-c4ccnc(OC)c4)c3c2)c1] | N-(3-(3-(2-methoxypyridin-4-yl)-1H-pyrrolo[2,3-b]pyridin-5-yl)phenyl)but-2-ynamide |
| 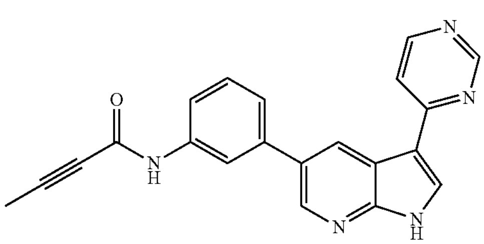 [SMILES: CC#CC(=O)Nc1cccc(-c2cnc3[nH]cc(-c4ccncn4)c3c2)c1] | N-(3-(3-(pyrimidin-4-yl)-1H-pyrrolo[2,3-b]pyridin-5-yl)phenyl)but-2-ynamide |

| Structure | Name |
|---|---|
| 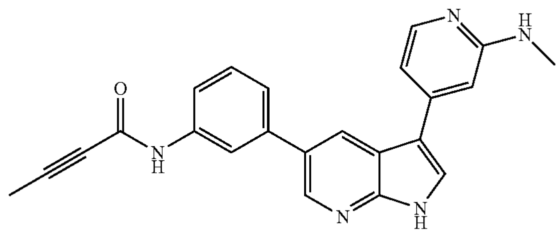 [SMILES: CC#CC(=O)Nc1cccc(-c2cnc3[nH]cc(-c4ccnc(NC)c4)c3c2)c1] | N-(3-(3-(2-(methylamino)pyridin-4-yl)-1H-pyrrolo[2,3-b]pyridin-5-yl)phenyl)but-2-ynamide |
| 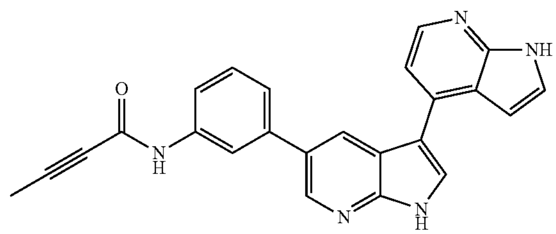 [SMILES: CC#CC(=O)Nc1cccc(-c2cnc3[nH]cc(-c4ccnc5[nH]ccc45)c3c2)c1] | N-(3-(1H,1'H-[3,4'-bipyrrolo[2,3-b]pyridin]-5-yl)phenyl)but-2-ynamide |
| 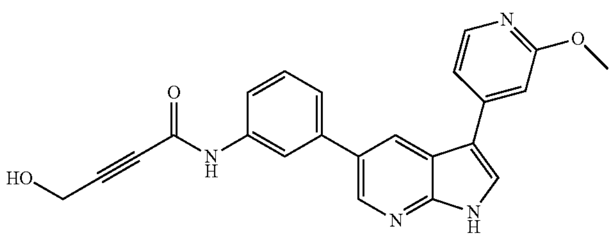 [SMILES: COc1cc(-c2c[nH]c3ncc(-c4cccc(NC(=O)C#CCO)c4)cc23)ccn1] | 4-hydroxy-N-(3-(3-(2-methoxypyridin-4-yl)-1H-pyrrolo[2,3-b]pyridin-5-yl)phenyl)but-2-ynamide |
| 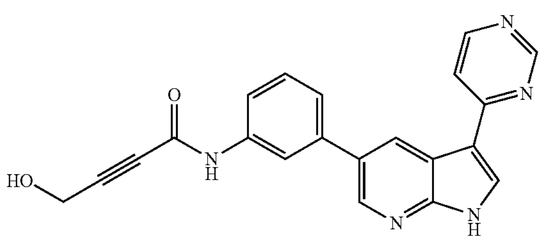 [SMILES: O=C(C#CCO)Nc1cccc(-c2cnc3[nH]cc(-c4ccncn4)c3c2)c1] | 4-hydroxy-N-(3-(3-(pyrimidin-4-yl)-1H-pyrrolo[2,3-b]pyridin-5-yl)phenyl)but-2-ynamide |
| 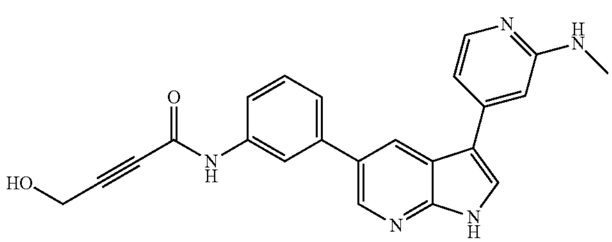 [SMILES: CNc1cc(-c2c[nH]c3ncc(-c4cccc(NC(=O)C#CCO)c4)cc23)ccn1] | 4-hydroxy-N-(3-(3-(2-(methylamino)pyridin-4-yl)-1H-pyrrolo[2,3-b]pyridin-5-yl)phenyl)but-2-ynamide |
| 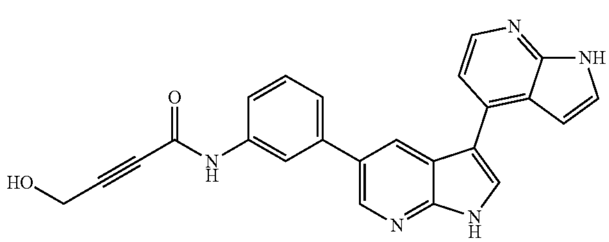 [SMILES: O=C(C#CCO)Nc1cccc(-c2cnc3[nH]cc(-c4ccnc5[nH]ccc45)c3c2)c1] | N-(3-(1H,1'H-[3,4'-bipyrrolo[2,3-b]pyridin]-5-yl)phenyl)-4-hydroxybut-2-ynamide |

| Structure | Name |
|---|---|
| 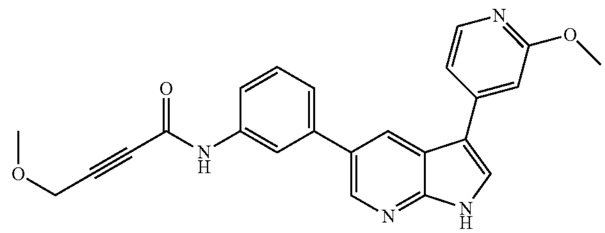 [SMILES: COCC#CC(=O)Nc1cccc(-c2cnc3[nH]cc(-c4ccnc(OC)c4)c3c2)c1] | 4-methoxy-N-(3-(3-(2-methoxypyridin-4-yl)-1H-pyrrolo[2,3-b]pyridin-5-yl)phenyl)but-2-ynamide |
| 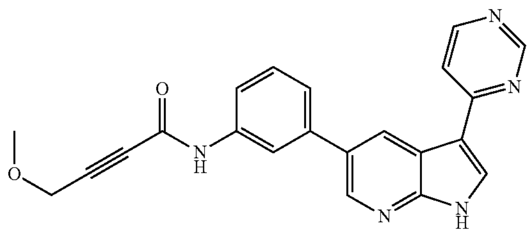 [SMILES: COCC#CC(=O)Nc1cccc(-c2cnc3[nH]cc(-c4ccncn4)c3c2)c1] | 4-methoxy-N-(3-(3-(pyrimidin-4-yl)-1H-pyrrolo[2,3-b]pyridin-5-yl)phenyl)but-2-ynamide |
| 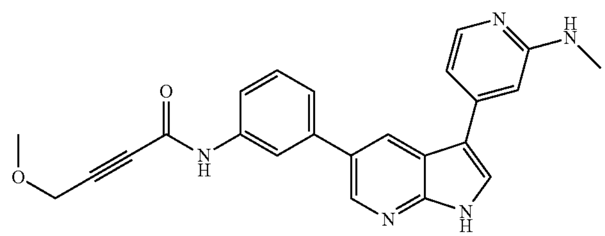 [SMILES: CNc1cc(-c2c[nH]c3ncc(-c4cccc(NC(=O)C#CCOC)c4)cc23)ccn1] | 4-methoxy-N-(3-(3-(2-(methylamino)pyridin-4-yl)-1H-pyrrolo[2,3-b]pyridin-5-yl)phenyl)but-2-ynamide |
| 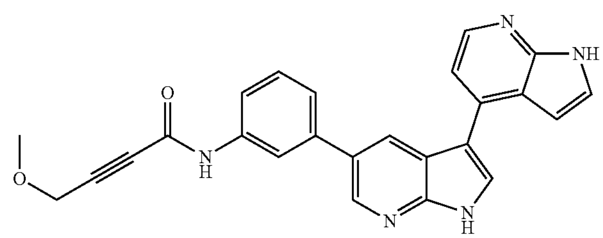 [SMILES: COCC#CC(=O)Nc1cccc(-c2cnc3[nH]cc(-c4ccnc5[nH]ccc45)c3c2)c1] | N-(3-(1H,1'H-[3,4'-bipyrrolo[2,3-b]pyridin]-5-yl)phenyl)-4-methoxybut-2-ynamide |
| 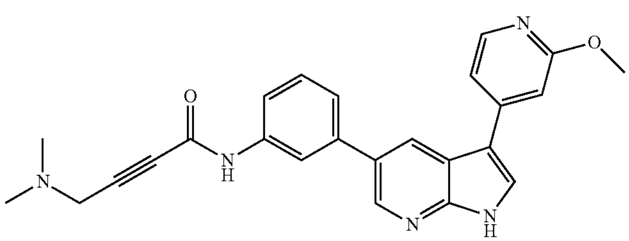 | 4-(dimethylamino)-N-(3-(3-(2-methoxypyridin-4-yl)-1H-pyrrolo[2,3-b]pyridin-5-yl)phenyl)but-2-ynamide |
| 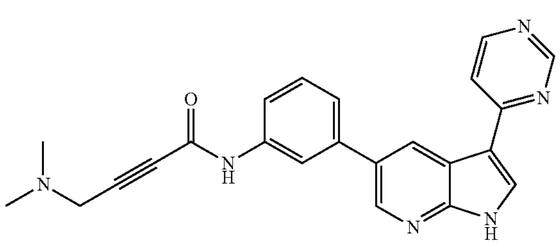 [SMILES: CN(C)CC#CC(=O)Nc1cccc(-c2cnc3[nH]cc(-c4ccncn4)c3c2)c1] | 4-(dimethylamino)-N-(3-(3-(pyrimidin-4-yl)-1H-pyrrolo[2,3-b]pyridin-5-yl)phenyl)but-2-ynamide |

TABLE 2-continued

| Structure | Name |
|---|---|
| 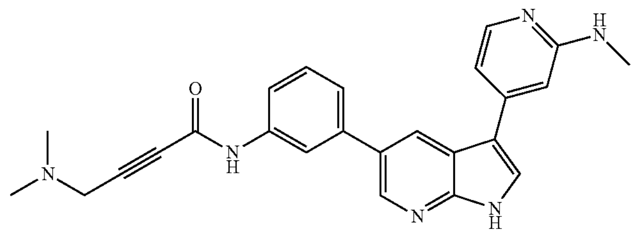 | 4-(dimethylamino)-N-(3-(3-(2-(methylamino)pyridin-4-yl)-1H-pyrrolo[2,3-b]pyridin-5-yl)phenyl)but-2-ynamide |
| 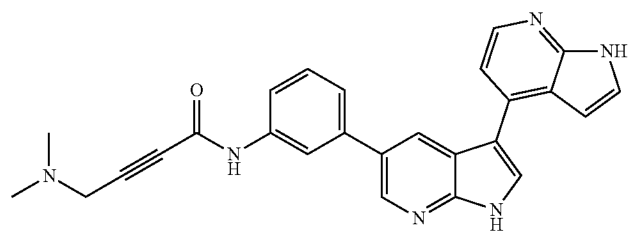 [SMILES: CN(C)CC#CC(=O)Nc1cccc(-c2cnc3[nH]cc(-c4ccnc5[nH]ccc45)c3c2)c1] | N-(3-(1H,1'H-[3,4'-bipyrrolo[2,3-b]pyridin]-5-yl)phenyl)-4-(dimethylamino)but-2-ynamide |
| 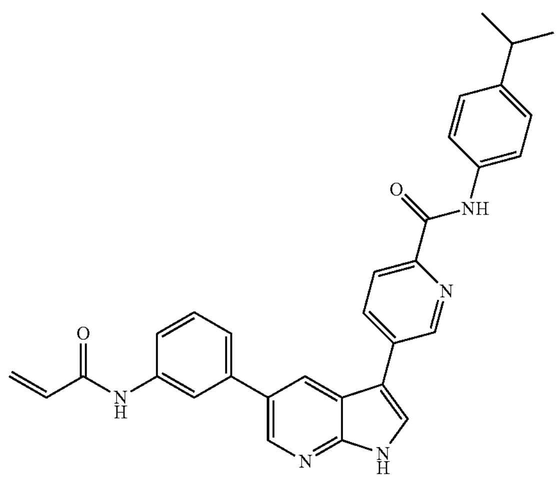 [SMILES: C=CC(=O)Nc1cccc(-c2cnc3[nH]cc(-c4ccc(C(=O)Nc5ccc(C(C)C)cc5)nc4)c3c2)c1] | 5-(5-(3-acrylamidophenyl)-1H-pyrrolo[2,3-b]pyridin-3-yl)-N-(4-isopropylphenyl)picolinamide |
| 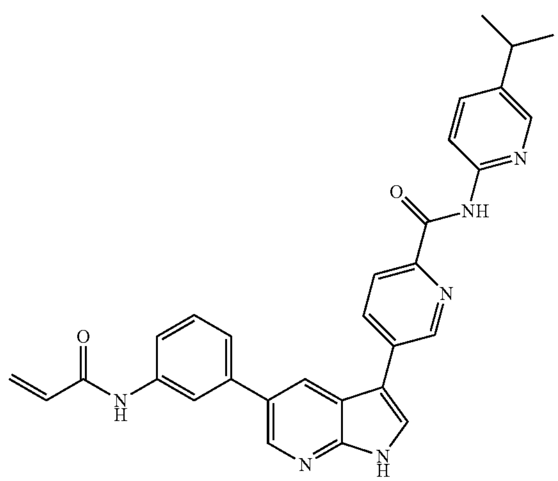 [SMILES: C=CC(=O)Nc1cccc(-c2cnc3[nH]cc(-c4ccc(C(=O)Nc5ccc(C(C)C)cn5)nc4)c3c2)c1] | 5-(5-(3-acrylamidophenyl)-1H-pyrrolo[2,3-b]pyridin-3-yl)-N-(5-isopropylpyridin-2-yl)picolinamide |

TABLE 2-continued

| Structure | Name |
|---|---|
| 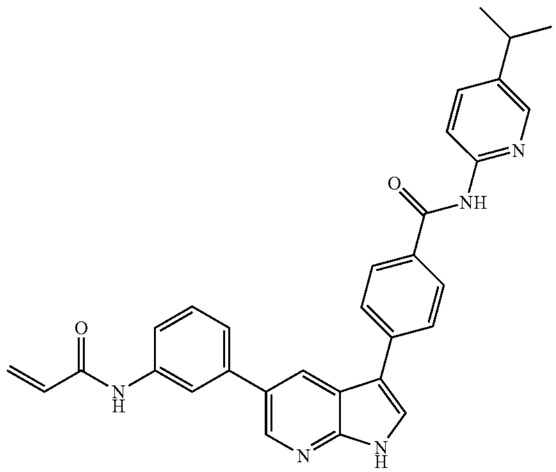 [SMILES: C=CC(=O)Nc1cccc(-c2cnc3[nH]cc(-c4ccc(C(=O)Nc5ccc(C(C)C)cn5)cc4)c3c2)c1] | 4-(5-(3-acrylamidophenyl)-1H-pyrrolo[2,3-b]pyridin-3-yl)-N-(5-isopropylpyridin-2-yl)benzamide |
| 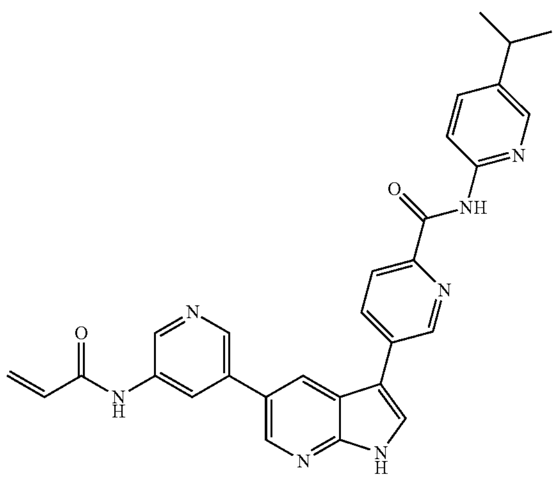 [SMILES: C=CC(=O)Nc1cncc(-c2cnc3[nH]cc(-c4ccc(C(=O)Nc5ccc(C(C)C)cn5)nc4)c3c2)c1] | 5-(5-(5-acrylamidopyridin-3-yl)-1H-pyrrolo[2,3-b]pyridin-3-yl)-N-(5-isopropylpyridin-2-yl)picolinamide |
| 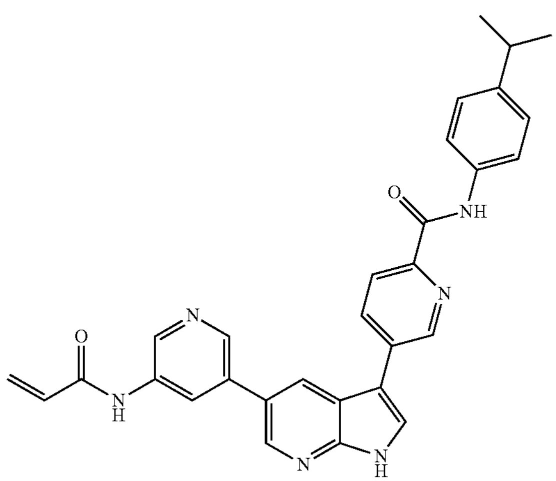 [SMILES: C=CC(=O)Nc1cncc(-c2cnc3[nH]cc(-c4ccc(C(=O)Nc5ccc(C(C)C)cc5)nc4)c3c2)c1] | 5-(5-(5-acrylamidopyridin-3-yl)-1H-pyrrolo[2,3-b]pyridin-3-yl)-N-(4-isopropylphenyl)picolinamide |

TABLE 2-continued

| Structure | Name |
|---|---|
| 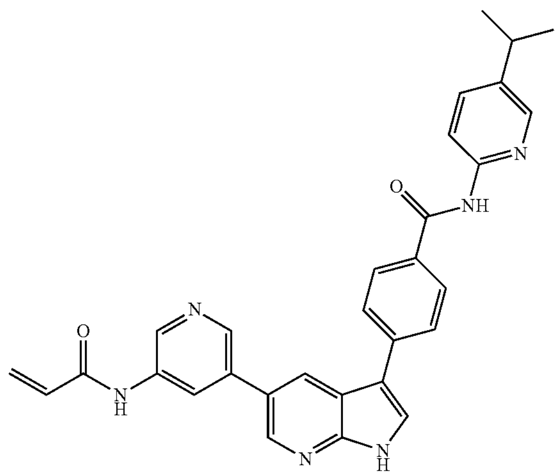 [SMILES: C=CC(=O)Nc1cncc(-c2cnc3[nH]cc(-c4ccc(C(=O)Nc5ccc(C(C)C)cn5)cc4)c3c2)c1] | 4-(5-(5-acrylamidopyridin-3-yl)-1H-pyrrolo[2,3-b]pyridin-3-yl)-N-(5-isopropylpyridin-2-yl)benzamide |
| 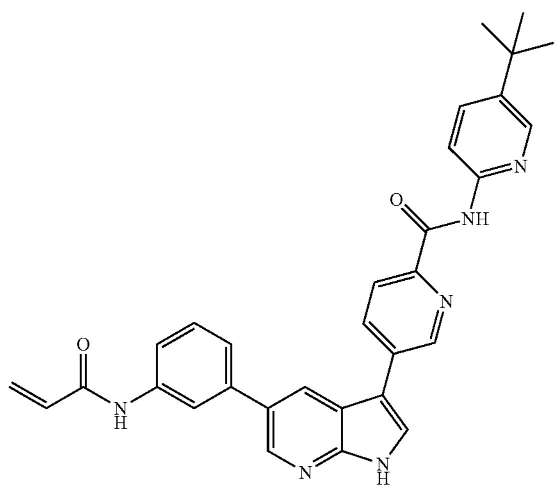 [SMILES: C=CC(=O)Nc1cccc(-c2cnc3[nH]cc(-c4ccc(C(=O)Nc5ccc(C(C)(C)C)cn5)nc4)c3c2)c1] | 5-(5-(3-acrylamidophenyl)-1H-pyrrolo[2,3-b]pyridin-3-yl)-N-(5-(tert-butyl)pyridin-2-yl)picolinamide |
| 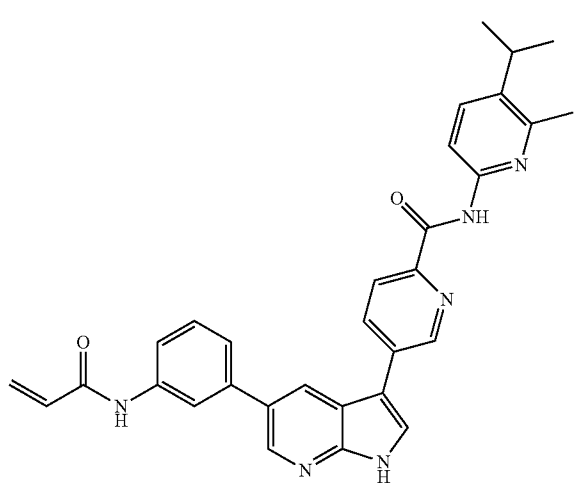 [SMILES: C=CC(=O)Nc1cccc(-c2cnc3[nH]cc(-c4ccc(C(=O)Nc5ccc(C(C)C)c(C)n5)nc4)c3c2)c1] | 5-(5-(3-acrylamidophenyl)-1H-pyrrolo[2,3-b]pyridin-3-yl)-N-(5-isopropyl-6-methylpyridin-2-yl)picolinamide |

TABLE 2-continued

| Structure | Name |
|---|---|
| 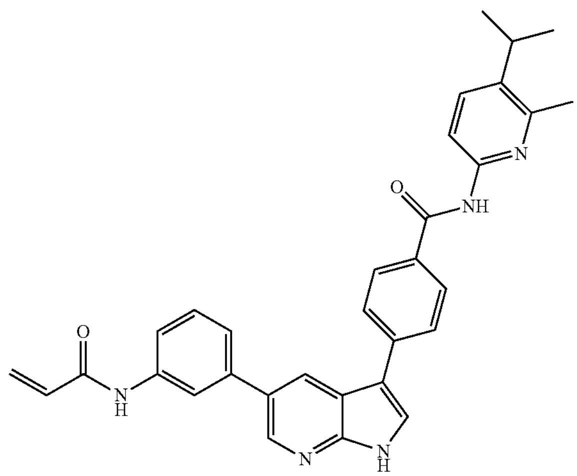 [SMILES: C=CC(=O)Nc1cccc(-c2cnc3[nH]cc(-c4ccc(C(=O)Nc5ccc(C(C)C)c(C)n5)cc4)c3c2)c1] | 4-(5-(3-acrylamidophenyl)-1H-pyrrolo[2,3-b]pyridin-3-yl)-N-(5-isopropyl-6-methylpyridin-2-yl)benzamide |
| 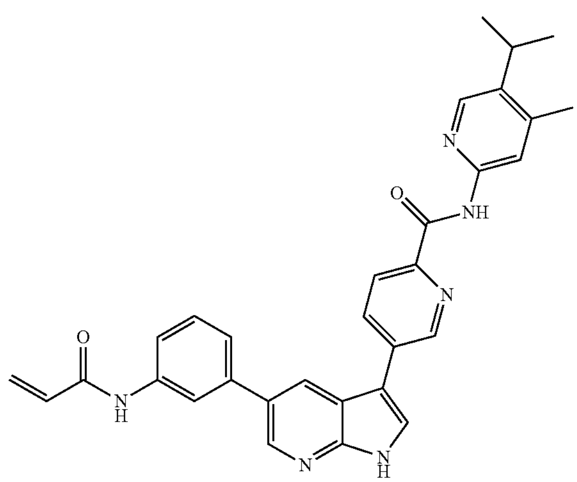 [SMILES: C=CC(=O)Nc1cccc(-c2cnc3[nH]cc(-c4ccc(C(=O)Nc5cc(C)c(C(C)C)cn5)nc4)c3c2)c1] | 5-(5-(3-acrylamidophenyl)-1H-pyrrolo[2,3-b]pyridin-3-yl)-N-(5-isopropyl-4-methylpyridin-2-yl)picolinamide |
| 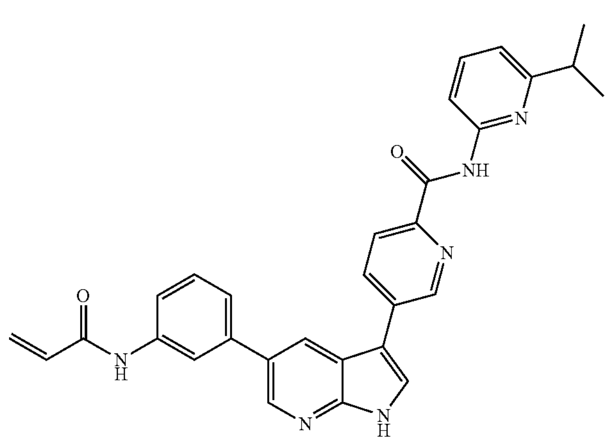 [SMILES: C=CC(=O)Nc1cccc(-c2cnc3[nH]cc(-c4ccc(C(=O)Nc5cccc(C(C)C)n5)nc4)c3c2)c1] | 5-(5-(3-acrylamidophenyl)-1H-pyrrolo[2,3-b]pyridin-3-yl)-N-(6-isopropylpyridin-2-yl)picolinamide |

TABLE 2-continued
| Structure | Name |
|---|---|
| 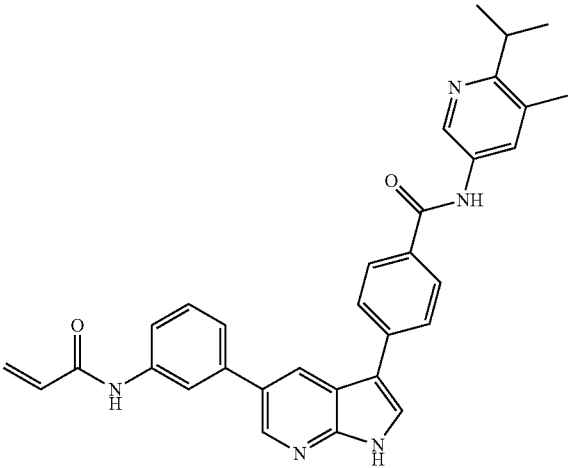 [SMILES: C=CC(=O)Nc1cccc(-c2cnc3[nH]cc(-c4ccc(C(=O)Nc5cnc(C(C)C)c(C)c5)cc4)c3c2)c1] | 4-(5-(3-acrylamidophenyl)-1H-pyrrolo[2,3-b]pyridin-3-yl)-N-(6-isopropyl-5-methylpyridin-3-yl)benzamide |
| 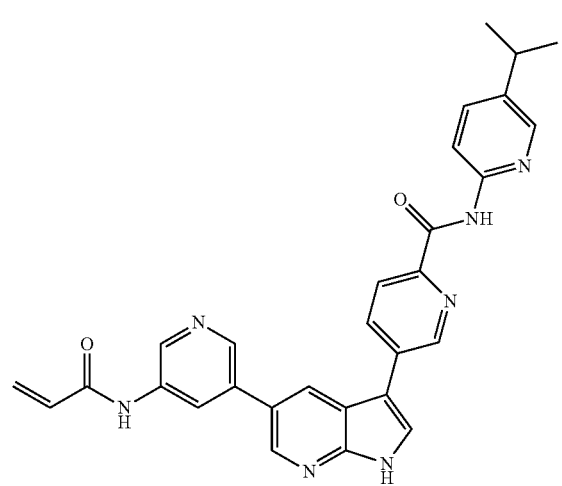 [SMILES: C=CC(=O)Nc1cncc(-c2cnc3[nH]cc(-c4ccc(C(=O)Nc5ccc(C(C)C)cn5)nc4)c3c2)c1] | 5-(5-(5-acrylamidopyridin-3-yl)-1H-pyrrolo[2,3-b]pyridin-3-yl)-N-(6-isopropylpyridin-3-yl)picolinamide |
| 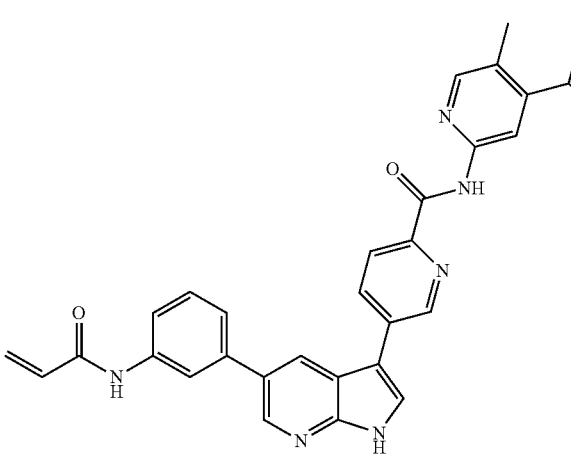 | 5-(5-(3-acrylamidophenyl)-1H-pyrrolo[2,3-b]pyridin-3-yl)-N-(4-isopropyl-5-methylpyridin-2-yl)picolinamide |

TABLE 2-continued

| Structure | Name |
|---|---|
| 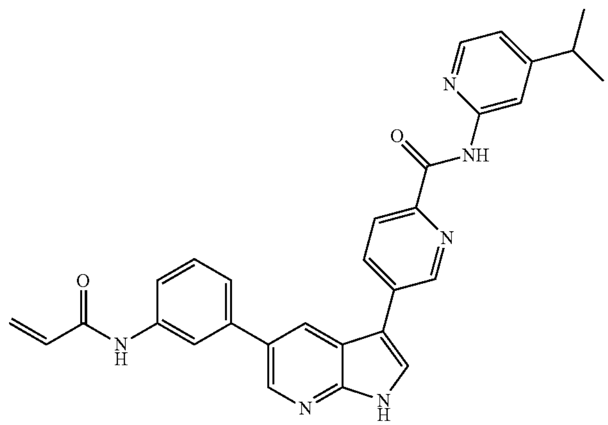 [SMILES: C=CC(=O)Nc1cccc(-c2cnc3[nH]cc(-c4ccc(C(=O)Nc5cc(C(C)C)ccn5)nc4)c3c2)c1] | 5-(5-(3-acrylamidophenyl)-1H-pyrrolo[2,3-b]pyridin-3-yl)-N-(4-isopropylpyridin-2-yl)picolinamide |
| 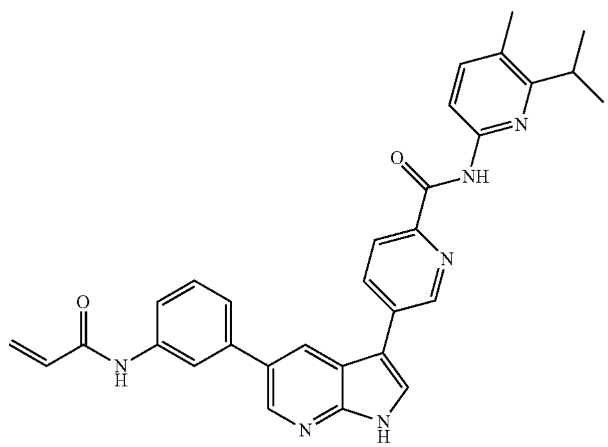 [SMILES: C=CC(=O)Nc1cccc(-c2cnc3[nH]cc(-c4ccc(C(=O)Nc5ccc(C)c(C(C)C)n5)nc4)c3c2)c1] | 5-(5-(3-acrylamidophenyl)-1H-pyrrolo[2,3-b]pyridin-3-yl)-N-(6-isopropyl-5-methylpyridin-2-yl)picolinamide |
| 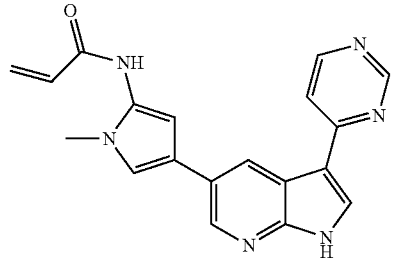 [SMILES: C=CC(=O)Nc1cc(-c2cnc3[nH]cc(-c4ccncn4)c3c2)cn1C] | N-(1-methyl-3-(3-(pyrimidin-4-yl)-1H-pyrrolo[2,3-b]pyridin-5-yl)-1H-pyrazol-5-yl)acrylamide |
| 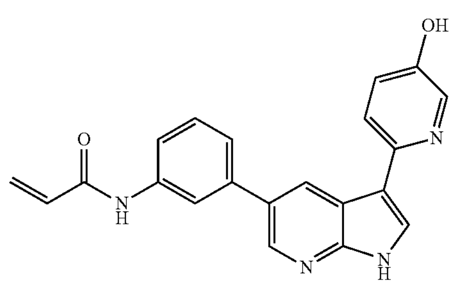 [SMILES: C=CC(=O)Nc1cccc(-c2cnc3[nH]cc(-c4ccc(O)cn4)c3c2)c1] | N-(3-(3-(5-hydroxypyridin-2-yl)-1H-pyrrolo[2,3-b]pyridin-5-yl)phenyl)acrylamide |

| Structure | Name |
|---|---|
| 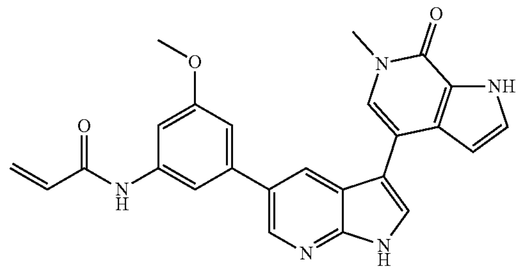 [SMILES: C=CC(=O)Nc1cc(OC)cc(-c2cnc3[nH]cc(-c4cn(C)c(=O)c5[nH]ccc45)c3c2)c1] | N-(3-methoxy-5-(3-(6-methyl-7-oxo-6,7-dihydro-1H-pyrrolo[2,3-c]pyridin-4-yl)-1H-pyrrolo[2,3-b]pyridin-5-yl)phenyl)acrylamide |
| 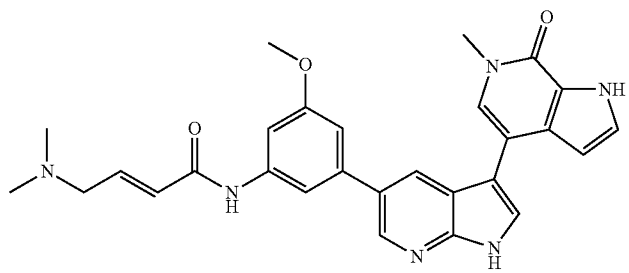 | (E)-4-(dimethylamino)-N-(3-methoxy-5-(3-(6-methyl-7-oxo-6,7-dihydro-1H-pyrrolo[2,3-c]pyridin-4-yl)-1H-pyrrolo[2,3-b]pyridin-5-yl)phenyl)but-2-enamide |
| 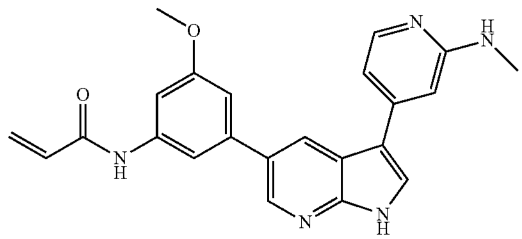 [SMILES: C=CC(=O)Nc1cc(OC)cc(-c2cnc3[nH]cc(-c4ccnc(NC)c4)c3c2)c1] | N-(3-methoxy-5-(3-(2-(methylamino)pyridin-4-yl)-1H-pyrrolo[2,3-b]pyridin-5-yl)phenyl)acrylamide |
| 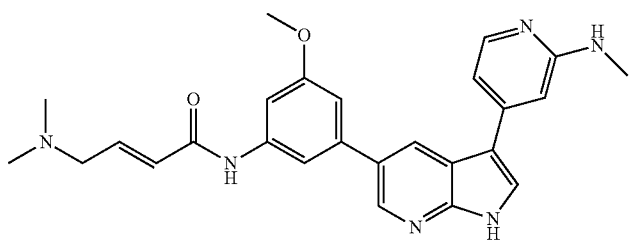 | (E)-4-(dimethylamino)-N-(3-methoxy-5-(3-(2-(methylamino)pyridin-4-yl)-1H-pyrrolo[2,3-b]pyridin-5-yl)phenyl)but-2-enamide |
| 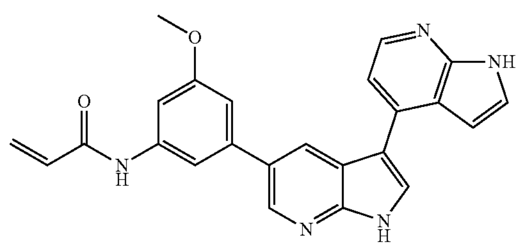 [SMILES: C=CC(=O)Nc1cc(OC)cc(-c2cnc3[nH]cc(-c4ccnc5[nH]ccc45)c3c2)c1] | N-(3-(1H,1'H-[3,4'-bipyrrolo[2,3-b]pyridin]-5-yl)-5-methoxyphenyl)acrylamide |
| 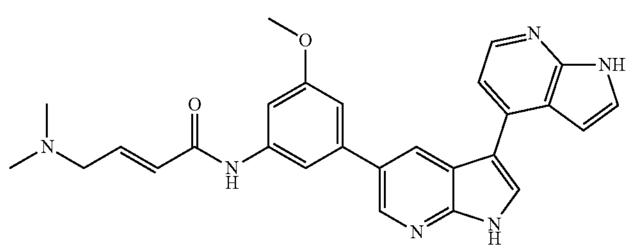 [SMILES: COc1cc(NC(=O)/C=C/CN(C)C)cc(-c2cnc3[nH]cc(-c4ccnc5[nH]ccc45)c3c2)c1] | (E)-N-(3-(1H,1'H-[3,4'-bipyrrolo[2,3-b]pyridin]-5-yl)-5-methoxyphenyl)-4-(dimethylamino)but-2-enamide |

TABLE 2-continued

| Structure | Name |
|---|---|
| 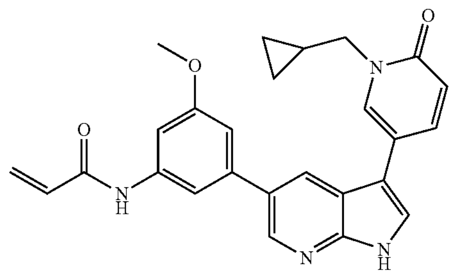 [SMILES: C=CC(=O)Nc1cc(OC)cc(-c2cnc3[nH]cc(-c4ccc(=O)n(CC5CC5)c4)c3c2)c1] | N-(3-(3-(1-(cyclopropylmethyl)-6-oxo-1,6-dihydropyridin-3-yl)-1H-pyrrolo[2,3-b]pyridin-5-yl)-5-methoxyphenyl)acrylamide |
| 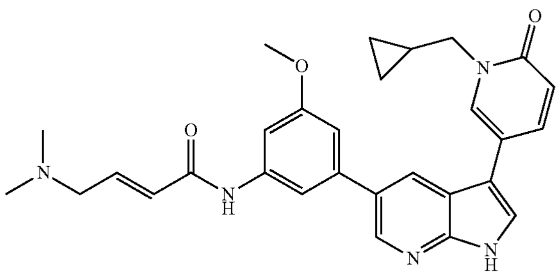 | (E)-N-(3-(3-(1-(cyclopropylmethyl)-6-oxo-1,6-dihydropyridin-3-yl)-1H-pyrrolo[2,3-b]pyridin-5-yl)-5-methoxyphenyl)-4-(dimethylamino)but-2-enamide |
| 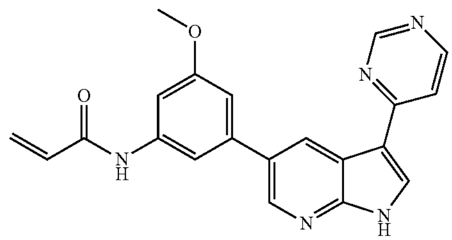 [SMILES: C=CC(=O)Nc1cc(OC)cc(-c2cnc3[nH]cc(-c4ccncn4)c3c2)c1] | N-(3-methoxy-5-(3-(pyrimidin-4-yl)-1H-pyrrolo[2,3-b]pyridin-5-yl)phenyl)acrylamide |
| 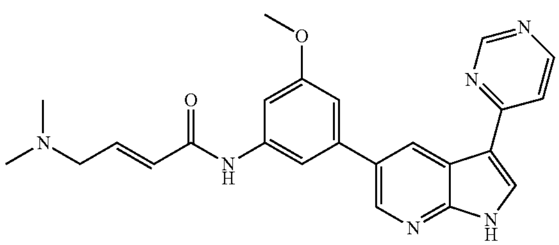 | (E)-4-(dimethylamino)-N-(3-methoxy-5-(3-(pyrimidin-4-yl)-1H-pyrrolo[2,3-b]pyridin-5-yl)phenyl)but-2-enamide |
| 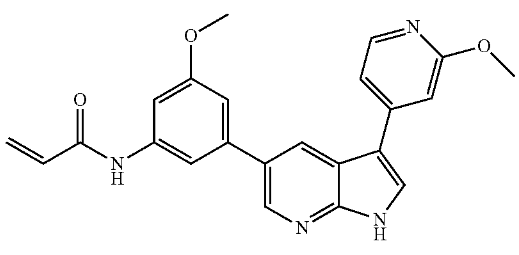 [SMILES: C=CC(=O)Nc1cc(OC)cc(-c2cnc3[nH]cc(-c4ccnc(OC)c4)c3c2)c1] | N-(3-methoxy-5-(3-(2-methoxypyridin-4-yl)-1H-pyrrolo[2,3-b]pyridin-5-yl)phenyl)acrylamide |
| 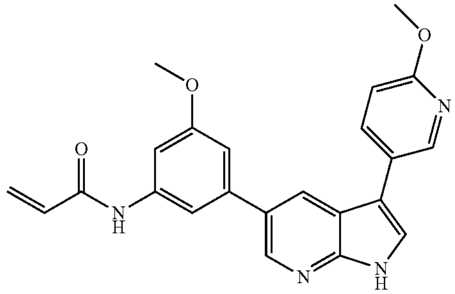 | N-(3-methoxy-5-(3-(6-methoxypyridin-3-yl)-1H-pyrrolo[2,3-b]pyridin-5-yl)phenyl)acrylamide |

TABLE 2-continued

| Structure | Name |
|---|---|
| 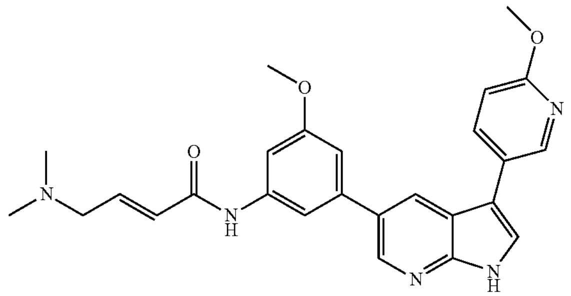 [SMILES: COc1cc(NC(=O)/C=C/CN(C)C)cc(-c2cnc3[nH]cc(-c4ccc(OC)nc4)c3c2)c1] | (E)-4-(dimethylamino)-N-(3-methoxy-5-(3-(6-methoxypyridin-3-yl)-1H-pyrrolo[2,3-b]pyridin-5-yl)phenyl)but-2-enamide |
| 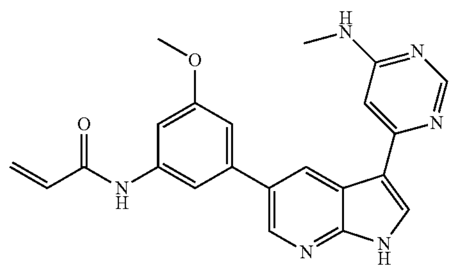 [SMILES: C=CC(=O)Nc1cc(OC)cc(-c2cnc3[nH]cc(-c4cc(NC)ncn4)c3c2)c1] | N-(3-methoxy-5-(3-(6-(methylamino)pyrimidin-4-yl)-1H-pyrrolo[2,3-b]pyridin-5-yl)phenyl)acrylamide |
| 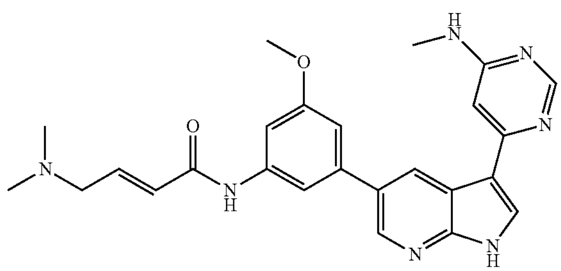 [SMILES: CNc1cc(-c2c[nH]c3ncc(-c4cc(NC(=O)/C=C/CN(C)C)cc(OC)c4)cc23)ncn1] | (E)-4-(dimethylamino)-N-(3-methoxy-5-(3-(6-(methylamino)pyrimidin-4-yl)-1H-pyrrolo[2,3-b]pyridin-5-yl)phenyl)but-2-enamide |
| 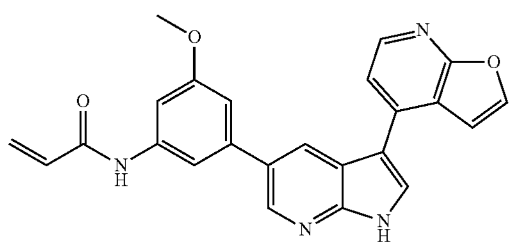 | N-(3-(3-(furo[2,3-b]pyridin-4-yl)-1H-pyrrolo[2,3-b]pyridin-5-yl)-5-methoxyphenyl)acrylamide |
| 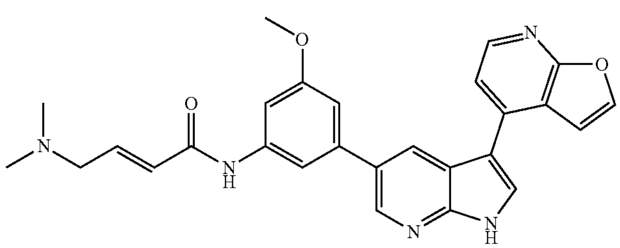 [SMILES: COc1cc(NC(=O)/C=C/CN(C)C)cc(-c2cnc3[nH]cc(-c4ccnc5occc45)c3c2)c1] | (E)-4-(dimethylamino)-N-(3-(3-(furo[2,3-b]pyridin-4-yl)-1H-pyrrolo[2,3-b]pyridin-5-yl)-5-methoxyphenyl)but-2-enamide |
| | (E)-3-(3-(3-(2-(methylamino)pyridin-4-yl)-1H-pyrrolo[2,3-b]pyridin-5-yl)-5-(trifluoromethyl)phenyl)acrylamide |

TABLE 2-continued

| Structure | Name |
|---|---|
| 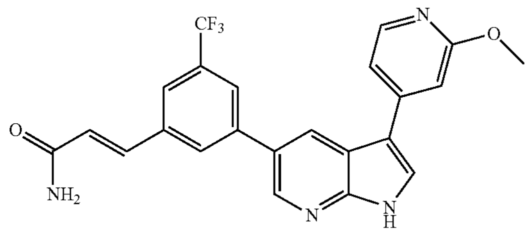 [SMILES: COc1cc(-c2c[nH]c3ncc(-c4cc(/C=C/C(N)=O)cc(C(F)(F)F)c4)cc23)ccn1] | (E)-3-(3-(3-(2-methoxypyridin-4-yl)-1H-pyrrolo[2,3-b]pyridin-5-yl)-5-(trifluoromethyl)phenyl)acrylamide |
| 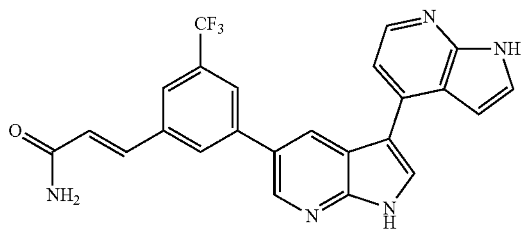 [SMILES: NC(=O)/C=C/c1cc(-c2cnc3[nH]cc(-c4ccnc5[nH]ccc45)c3c2)cc(C(F)(F)F)c1] | (E)-3-(3-(1H,1'H-[3,4'-bipyrrolo[2,3-b]pyridin]-5-yl)-5-(trifluoromethyl)phenyl)acrylamide |
| 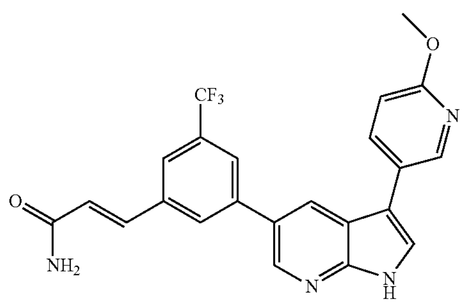 [SMILES: COc1ccc(-c2c[nH]c3ncc(-c4cc(/C=C/C(N)=O)cc(C(F)(F)F)c4)cc23)cn1] | (E)-3-(3-(3-(6-methoxypyridin-3-yl)-1H-pyrrolo[2,3-b]pyridin-5-yl)-5-(trifluoromethyl)phenyl)acrylamide |
| 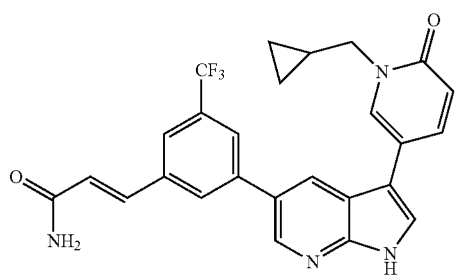 [SMILES: NC(=O)/C=C/c1cc(-c2cnc3[nH]cc(-c4ccc(=O)n(CC5CC5)c4)c3c2)cc(C(F)(F)F)c1] | (E)-3-(3-(3-(1-(cyclopropylmethyl)-6-oxo-1,6-dihydropyridin-3-yl)-1H-pyrrolo[2,3-b]pyridin-5-yl)-5-(trifluoromethyl)phenyl)acrylamide |
| 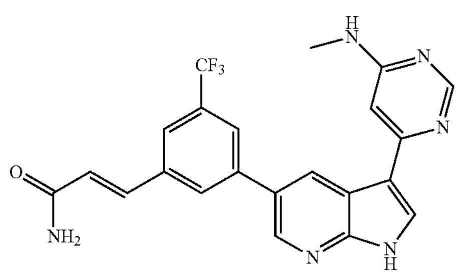 [SMILES: CNc1cc(-c2c[nH]c3ncc(-c4cc(/C=C/C(N)=O)cc(C(F)(F)F)c4)cc23)ncn1] | (E)-3-(3-(3-(6-(methylamino)pyrimidin-4-yl)-1H-pyrrolo[2,3-b]pyridin-5-yl)-5-(trifluoromethyl)phenyl)acrylamide |
| 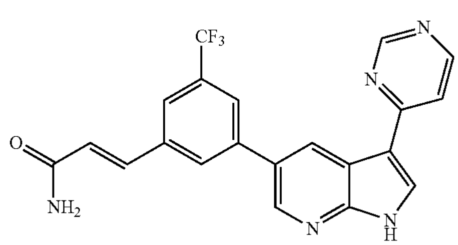 [SMILES: NC(=O)/C=C/c1cc(-c2cnc3[nH]cc(-c4ccncn4)c3c2)cc(C(F)(F)F)c1] | (E)-3-(3-(3-(pyrimidin-4-yl)-1H-pyrrolo[2,3-b]pyridin-5-yl)-5-(trifluoromethyl)phenyl)acrylamide |

TABLE 2-continued

| Structure | Name |
|---|---|
| 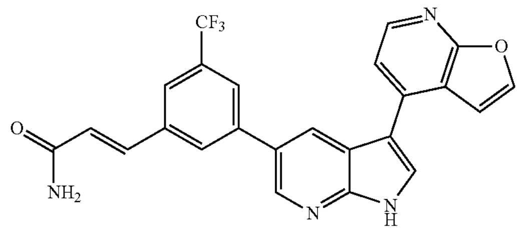 [SMILES: NC(=O)/C=C/c1cc(-c2cnc3[nH]cc(-c4ccnc5occc45)c3c2)cc(C(F)(F)F)c1] | (E)-3-(3-(3-(furo[2,3-b]pyridin-4-yl)-1H-pyrrolo[2,3-b]pyridin-5-yl)-5-(trifluoromethyl)phenyl)acrylamide |
| 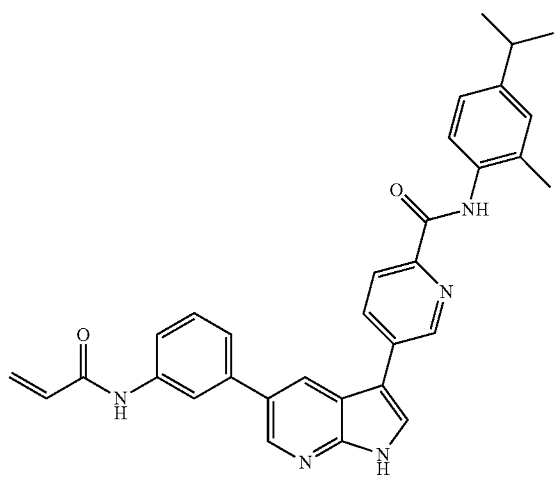 [SMILES: C=CC(=O)Nc1cccc(-c2cnc3[nH]cc(-c4ccc(C(=O)Nc5ccc(C(C)C)cc5C)nc4)c3c2)c1] | 5-(5-(3-acrylamidophenyl)-1H-pyrrolo[2,3-b]pyridin-3-yl)-N-(4-isopropyl-2-methylphenyl)picolinamide |
| 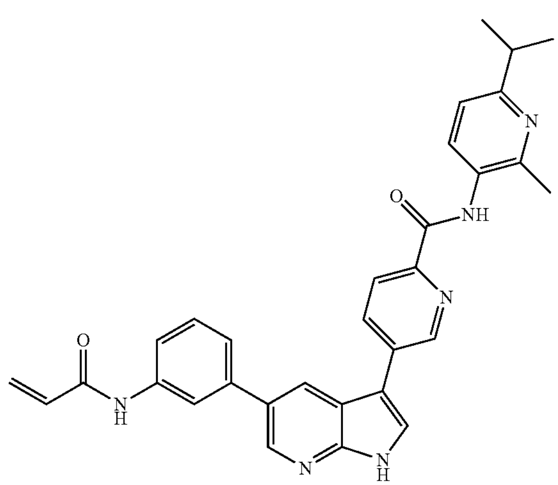 [SMILES: C=CC(=O)Nc1cccc(-c2cnc3[nH]cc(-c4ccc(C(=O)Nc5ccc(C(C)C)nc5C)nc4)c3c2)c1] | 5-(5-(3-acrylamidophenyl)-1H-pyrrolo[2,3-b]pyridin-3-yl)-N-(6-isopropyl-2-methylpyridin-3-yl)picolinamide |

TABLE 2-continued

| Structure | Name |
|---|---|
| 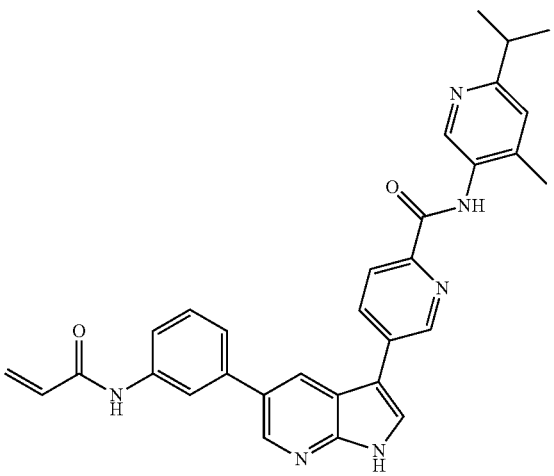 [SMILES: C=CC(=O)Nc1cccc(-c2cnc3[nH]cc(-c4ccc(C(=O)Nc5cnc(C(C)C)cc5C)nc4)c3c2)c1] | 5-(5-(3-acrylamidophenyl)-1H-pyrrolo[2,3-b]pyridin-3-yl)-N-(6-isopropyl-4-methylpyridin-3-yl)picolinamide |
| 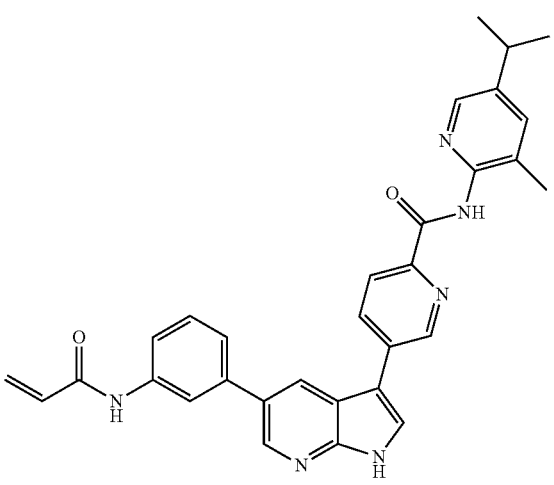 [SMILES: C=CC(=O)Nc1cccc(-c2cnc3[nH]cc(-c4ccc(C(=O)Nc5ncc(C(C)C)cc5C)nc4)c3c2)c1] | 5-(5-(3-acrylamidophenyl)-1H-pyrrolo[2,3-b]pyridin-3-yl)-N-(5-isopropyl-3-methylpyridin-2-yl)picolinamide |
| 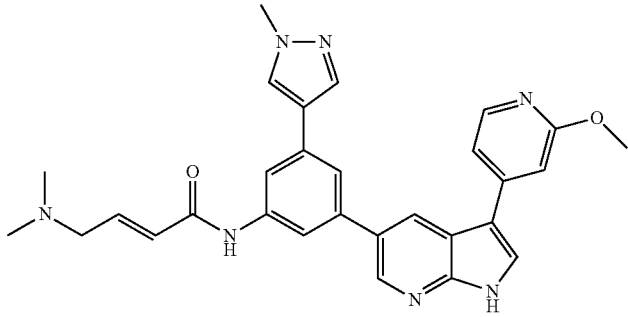 | (E)-4-(dimethylamino)-N-(3-(3-(2-methoxypyridin-4-yl)-1H-pyrrolo[2,3-b]pyridin-5-yl)-5-(1-methyl-1H-pyrazol-4-yl)phenyl)but-2-enamide |
| 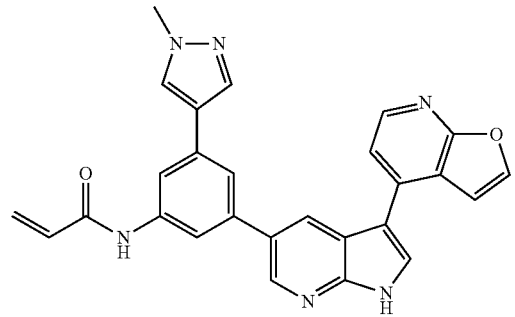 [SMILES: C=CC(=O)Nc1cc(-c2cnc3[nH]cc(-c4ccnc5occc45)c3c2)cc(-c2cnn(C)c2)c1] | N-(3-(3-(furo[2,3-b]pyridin-4-yl)-1H-pyrrolo[2,3-b]pyridin-5-yl)-5-(1-methyl-1H-pyrazol-4-yl)phenyl)acrylamide |

TABLE 2-continued

| Structure | Name |
|---|---|
| 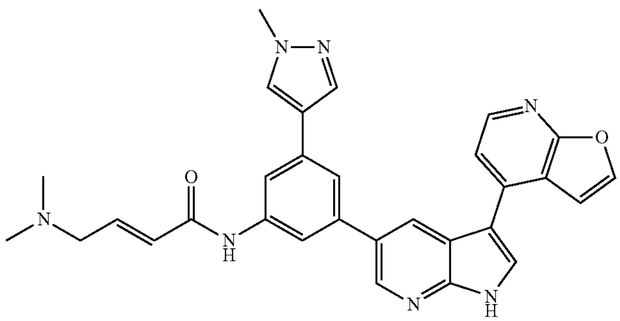 [SMILES: CN(C)C/C=C/C(=O)Nc1cc(-c2cnc3[nH]cc(-c4ccnc5occc45)c3c2)cc(-c2cnn(C)c2)c1] | (E)-4-(dimethylamino)-N-(3-(3-(furo[2,3-b]pyridin-4-yl)-1H-pyrrolo[2,3-b]pyridin-5-yl)-5-(1-methyl-1H-pyrazol-4-yl)phenyl)but-2-enamide |
| 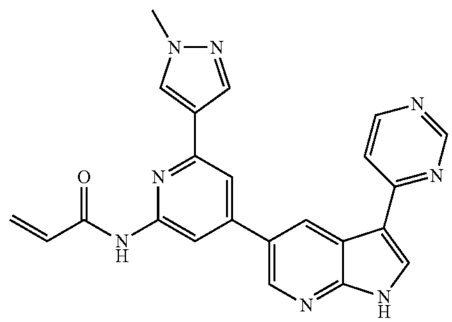 [SMILES: C=CC(=O)Nc1cc(-c2cnc3[nH]cc(-c4ccncn4)c3c2)cc(-c2cnn(C)c2)n1] | N-(6-(1-methyl-1H-pyrazol-4-yl)-4-(3-(pyrimidin-4-yl)-1H-pyrrolo[2,3-b]pyridin-5-yl)pyridin-2-yl)acrylamide |
| 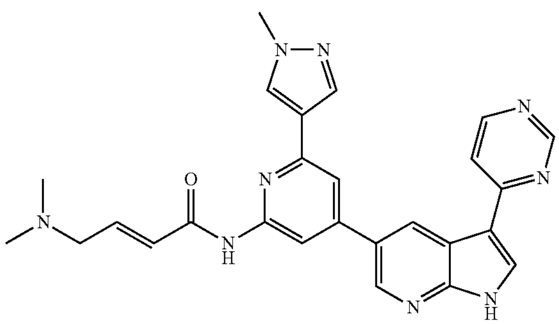 [SMILES: CN(C)C/C=C/C(=O)Nc1cc(-c2cnc3[nH]cc(-c4ccncn4)c3c2)cc(-c2cnn(C)c2)n1] | (E)-4-(dimethylamino)-N-(6-(1-methyl-1H-pyrazol-4-yl)-4-(3-(pyrimidin-4-yl)-1H-pyrrolo[2,3-b]pyridin-5-yl)pyridin-2-yl)but-2-enamide |
| 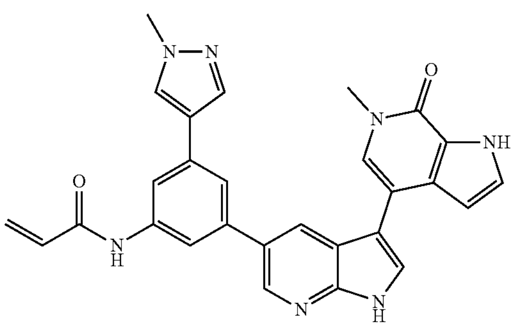 [SMILES: C=CC(=O)Nc1cc(-c2cnc3[nH]cc(-c4cn(C)c(=O)c5[nH]ccc45)c3c2)cc(-c2cnn(C)c2)c1] | N-(3-(1-methyl-1H-pyrazol-4-yl)-5-(3-(6-methyl-7-oxo-6,7-dihydro-1H-pyrrolo[2,3-c]pyridin-4-yl)-1H-pyrrolo[2,3-b]pyridin-5-yl)phenyl)acrylamide |
| 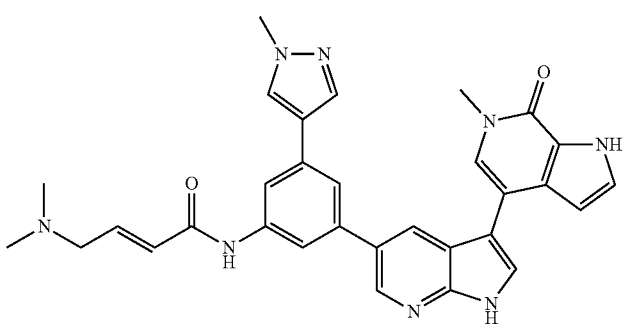 [SMILES: CN(C)C/C=C/C(=O)Nc1cc(-c2cnc3[nH]cc(-c4cn(C)c(=O)c5[nH]ccc45)c3c2)cc(-c2cnn(C)c2)c1] | (E)-4-(dimethylamino)-N-(3-(1-methyl-1H-pyrazol-4-yl)-5-(3-(6-methyl-7-oxo-6,7-dihydro-1H-pyrrolo[2,3-c]pyridin-4-yl)-1H-pyrrolo[2,3-b]pyridin-5-yl)phenyl)but-2-enamide |

TABLE 2-continued

| Structure | Name |
|---|---|
| 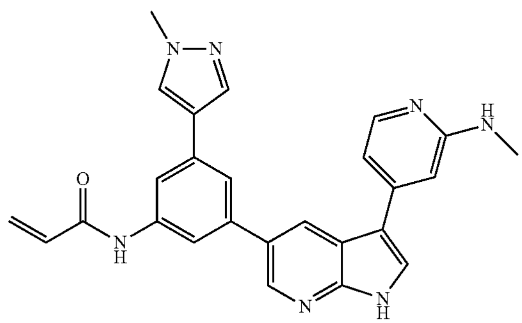 [SMILES: C=CC(=O)Nc1cc(-c2cnc3[nH]cc(-c4ccnc(NC)c4)c3c2)cc(-c2cnn(C)c2)c1] | N-(3-(1-methyl-1H-pyrazol-4-yl)-5-(3-(2-(methylamino)pyridin-4-yl)-1H-pyrrolo[2,3-b]pyridin-5-yl)phenyl)acrylamide |
| 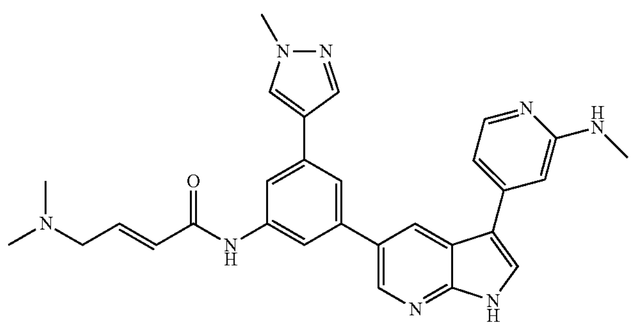 | (E)-4-(dimethylamino)-N-(3-(1-methyl-1H-pyrazol-4-yl)-5-(3-(2-(methylamino)pyridin-4-yl)-1H-pyrrolo[2,3-b]pyridin-5-yl)phenyl)but-2-enamide |
| 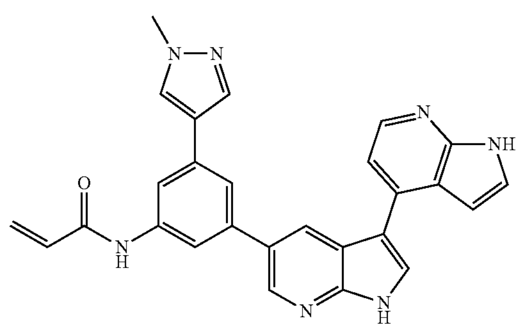 [SMILES: C=CC(=O)Nc1cc(-c2cnc3[nH]cc(-c4ccnc5[nH]ccc45)c3c2)cc(-c2cnn(C)c2)c1] | N-(3-(1H,1'H-[3,4'-bipyrrolo[2,3-b]pyridin]-5-yl)-5-(1-methyl-1H-pyrazol-4-yl)phenyl)acrylamide |
| 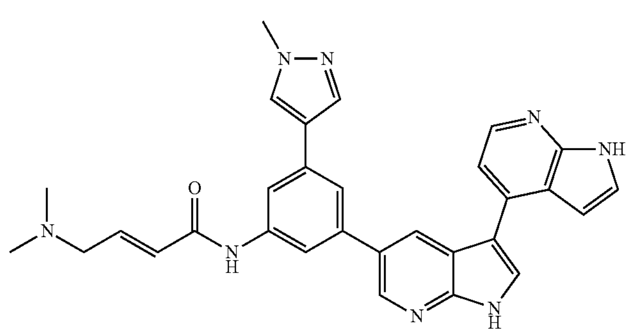 [SMILES: CN(C)C/C=C/C(=O)Nc1cc(-c2cnc3[nH]cc(-c4ccnc5[nH]ccc45)c3c2)cc(-c2cnn(C)c2)c1] | (E)-N-(3-(1H,1'H-[3,4'-bipyrrolo[2,3-b]pyridin]-5-yl)-5-(1-methyl-1H-pyrazol-4-yl)phenyl)-4-(dimethylamino)but-2-enamide |
| 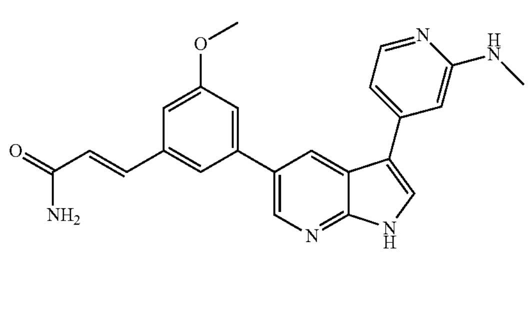 [SMILES: CNc1cc(-c2c[nH]c3ncc(-c4cc(/C=C/C(N)=O)cc(OC)c4)cc23)ccn1] | (E)-3-(3-methoxy-5-(3-(2-(methylamino)pyridin-4-yl)-1H-pyrrolo[2,3-b]pyridin-5-yl)phenyl)acrylamide |

TABLE 2-continued

| Structure | Name |
|---|---|
| 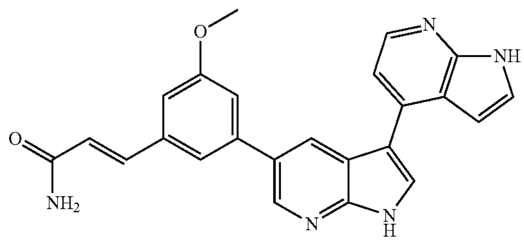 [SMILES: COc1cc(/C=C/C(N)=O)cc(-c2cnc3[nH]cc(-c4ccnc5[nH]ccc45)c3c2)c1] | (E)-3-(3-(1H,1'H-[3,4'-bipyrrolo[2,3-b]pyridin]-5-yl)-5-methoxyphenyl)acrylamide |
| 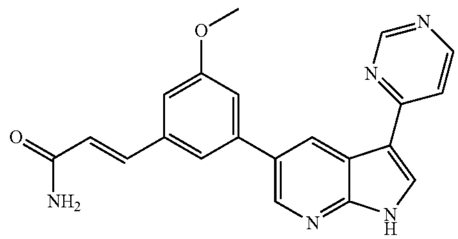 [SMILES: COc1cc(/C=C/C(N)=O)cc(-c2cnc3[nH]cc(-c4ccncn4)c3c2)c1] | (E)-3-(3-methoxy-5-(3-(pyrimidin-4-yl)-1H-pyrrolo[2,3-b]pyridin-5-yl)phenyl)acrylamide |
| 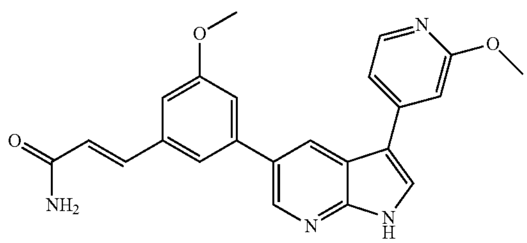 [SMILES: COc1cc(/C=C/C(N)=O)cc(-c2cnc3[nH]cc(-c4ccnc(OC)c4)c3c2)c1] | (E)-3-(3-methoxy-5-(3-(2-methoxypyridin-4-yl)-1H-pyrrolo[2,3-b]pyridin-5-yl)phenyl)acrylamide |
| 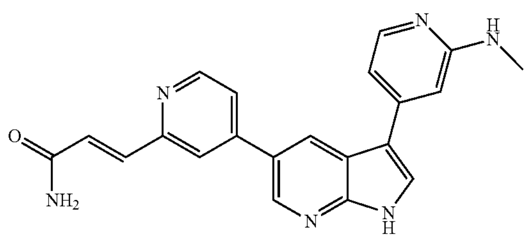 [SMILES: CNc1cc(-c2c[nH]c3ncc(-c4ccnc(/C=C/C(N)=O)c4)cc23)ccn1] | (E)-3-(4-(3-(2-(methylamino)pyridin-4-yl)-1H-pyrrolo[2,3-b]pyridin-5-yl)pyridin-2-yl)acrylamide |
| 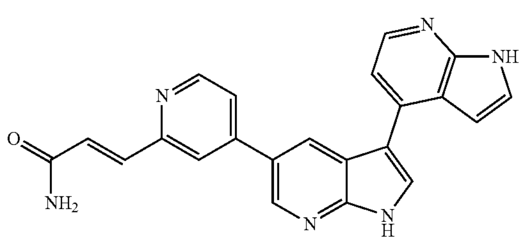 [SMILES: NC(=O)/C=C/c1cc(-c2cnc3[nH]cc(-c4ccnc5[nH]ccc45)c3c2)ccn1] | (E)-3-(4-(1H,1'H-[3,4'-bipyrrolo[2,3-b]pyridin]-5-yl)pyridin-2-yl)acrylamide |
| 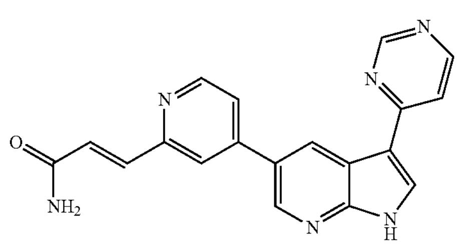 [SMILES: NC(=O)/C=C/c1cc(-c2cnc3[nH]cc(-c4ccncn4)c3c2)ccn1] | (E)-3-(4-(3-(pyrimidin-4-yl)-1H-pyrrolo[2,3-b]pyridin-5-yl)pyridin-2-yl)acrylamide |

TABLE 2-continued

| Structure | Name |
|---|---|
| 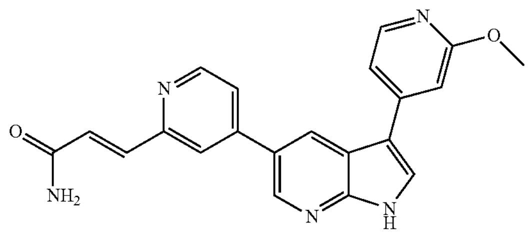 | (E)-3-(4-(3-(2-methoxypyridin-4-yl)-1H-pyrrolo[2,3-b]pyridin-5-yl)pyridin-2-yl)acrylamide |
| 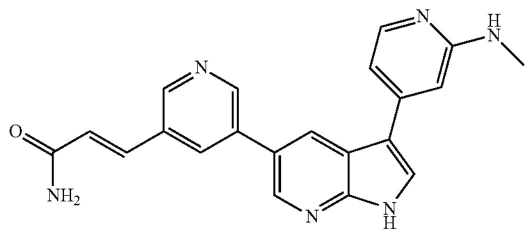 | (E)-3-(5-(3-(2-(methylamino)pyridin-4-yl)-1H-pyrrolo[2,3-b]pyridin-5-yl)pyridin-3-yl)acrylamide |
| 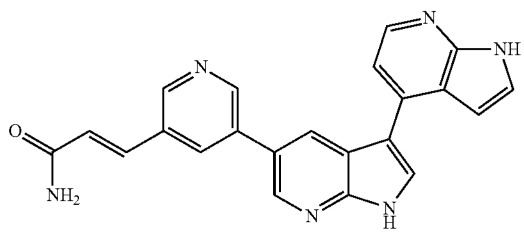 [SMILES: NC(=O)/C=C/c1cncc(-c2cnc3[nH]cc(-c4ccnc5[nH]ccc45)c3c2)c1] | (E)-3-(5-(1H,1'H-[3,4'-bipyrrolo[2,3-b]pyridin]-5-yl)pyridin-3-yl)acrylamide |
| 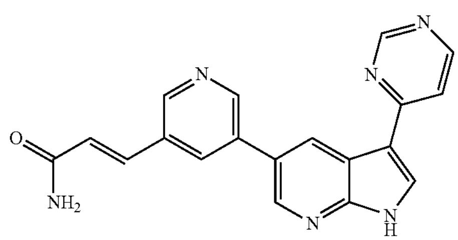 [SMILES: NC(=O)/C=C/c1cncc(-c2cnc3[nH]cc(-c4ccncn4)c3c2)c1] | (E)-3-(5-(3-(pyrimidin-4-yl)-1H-pyrrolo[2,3-b]pyridin-5-yl)pyridin-3-yl)acrylamide |
| 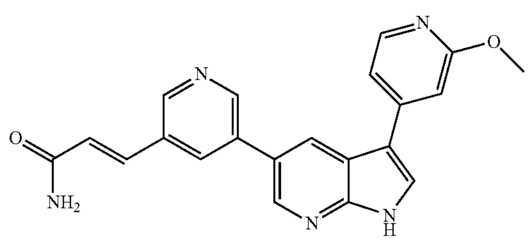 | (E)-3-(5-(3-(2-methoxypyridin-4-yl)-1H-pyrrolo[2,3-b]pyridin-5-yl)pyridin-3-yl)acrylamide |
| 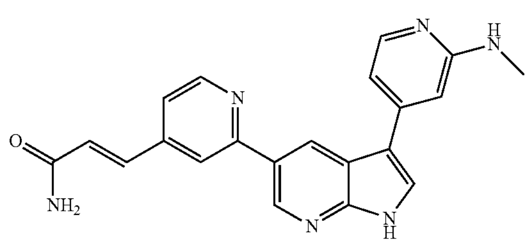 | (E)-3-(2-(3-(2-(methylamino)pyridin-4-yl)-1H-pyrrolo[2,3-b]pyridin-5-yl)pyridin-4-yl)acrylamide |

TABLE 2-continued

| Structure | Name |
|---|---|
| 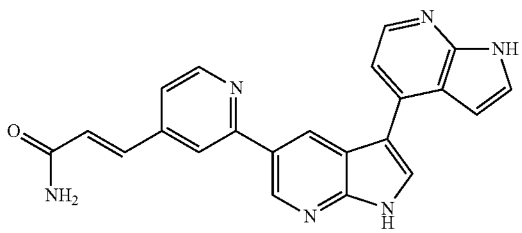 [SMILES: NC(=O)/C=C/c1ccnc(-c2cnc3[nH]cc(-c4ccnc5[nH]ccc45)c3c2)c1] | (E)-3-(2-(1H,1'H-[3,4'-bipyrrolo[2,3-b]pyridin]-5-yl)pyridin-4-yl)acrylamide |
| 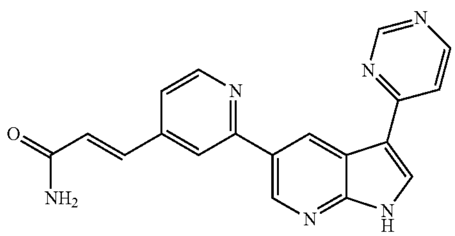 [SMILES: NC(=O)/C=C/c1ccnc(-c2cnc3[nH]cc(-c4ccncn4)c3c2)c1] | (E)-3-(2-(3-(pyrimidin-4-yl)-1H-pyrrolo[2,3-b]pyridin-5-yl)pyridin-4-yl)acrylamide |
| 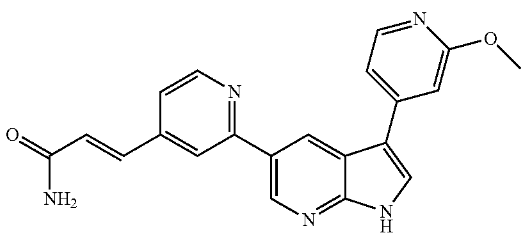 [SMILES: COc1cc(-c2c[nH]c3ncc(-c4cc(/C=C/C(N)=O)ccn4)cc23)ccn1] | (E)-3-(2-(3-(2-methoxypyridin-4-yl)-1H-pyrrolo[2,3-b]pyridin-5-yl)pyridin-4-yl)acrylamide |
| 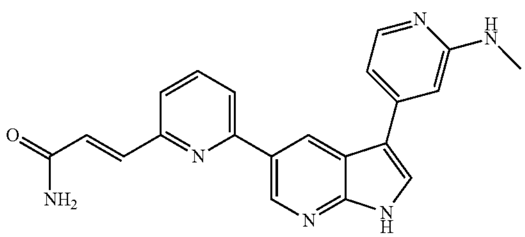 [SMILES: CNc1cc(-c2c[nH]c3ncc(-c4cccc(/C=C/C(N)=O)n4)cc23)ccn1] | (E)-3-(6-(3-(2-(methylamino)pyridin-4-yl)-1H-pyrrolo[2,3-b]pyridin-5-yl)pyridin-2-yl)acrylamide |
| 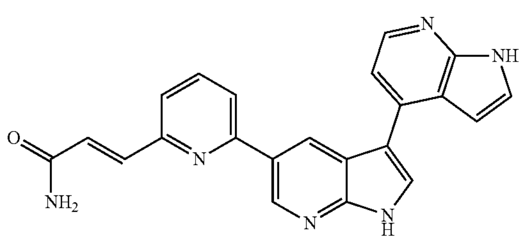 [SMILES: NC(=O)/C=C/c1cccc(-c2cnc3[nH]cc(-c4ccnc5[nH]ccc45)c3c2)n1] | (E)-3-(6-(1H,1'H-[3,4'-bipyrrolo[2,3-b]pyridin]-5-yl)pyridin-2-yl)acrylamide |
| 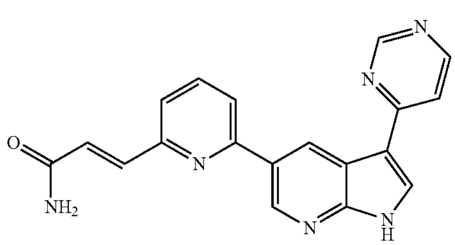 [SMILES: NC(=O)/C=C/c1cccc(-c2cnc3[nH]cc(-c4ccncn4)c3c2)n1] | (E)-3-(6-(3-(pyrimidin-4-yl)-1H-pyrrolo[2,3-b]pyridin-5-yl)pyridin-2-yl)acrylamide |

TABLE 2-continued

| Structure | Name |
|---|---|
| 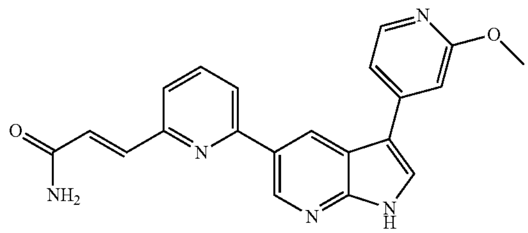 [SMILES: COc1cc(-c2c[nH]c3ncc(-c4cccc(/C=C/C(N)=O)n4)cc23)ccn1] | (E)-3-(6-(3-(2-methoxypyridin-4-yl)-1H-pyrrolo[2,3-b]pyridin-5-yl)pyridin-2-yl)acrylamide |
| 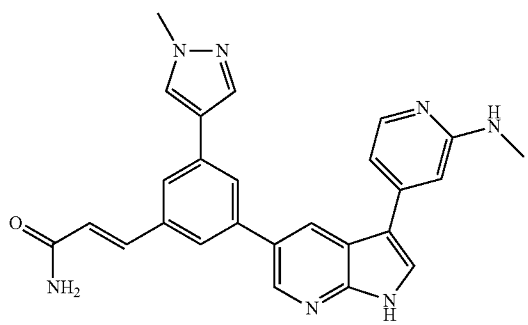 [SMILES: CNc1cc(-c2c[nH]c3ncc(-c4cc(/C=C/C(N)=O)cc(-c5cnn(C)c5)c4)cc23)ccn1] | (E)-3-(3-(1-methyl-1H-pyrazol-4-yl)-5-(3-(2-(methylamino)pyridin-4-yl)-1H-pyrrolo[2,3-b]pyridin-5-yl)phenyl)acrylamide |
| 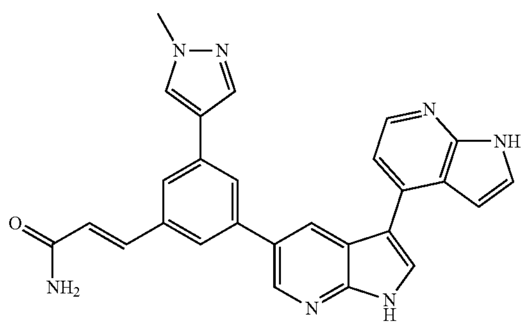 [SMILES: Cn1cc(-c2cc(/C=C/C(N)=O)cc(-c3cnc4[nH]cc(-c5ccnc6[nH]ccc56)c4c3)c2)cn1] | (E)-3-(3-(1H,1'H-[3,4'-bipyrrolo[2,3-b]pyridin]-5-yl)-5-(1-methyl-1H-pyrazol-4-yl)phenyl)acrylamide |
| 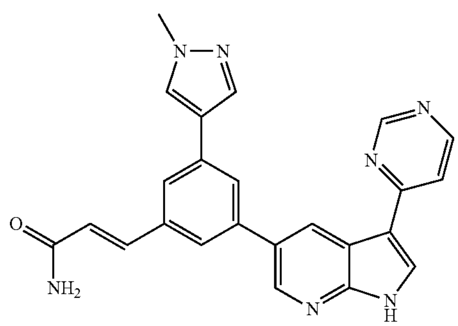 [SMILES: Cn1cc(-c2cc(/C=C/C(N)=O)cc(-c3cnc4[nH]cc(-c5ccncn5)c4c3)c2)cn1] | (E)-3-(3-(1-methyl-1H-pyrazol-4-yl)-5-(3-(pyrimidin-4-yl)-1H-pyrrolo[2,3-b]pyridin-5-yl)phenyl)acrylamide |
| 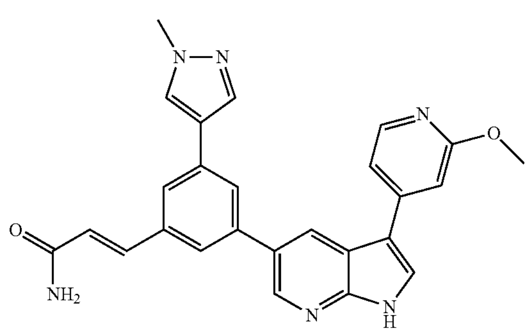 [SMILES: COc1cc(-c2c[nH]c3ncc(-c4cc(/C=C/C(N)=O)cc(-c5cnn(C)c5)c4)cc23)ccn1] | (E)-3-(3-(3-(2-methoxypyridin-4-yl)-1H-pyrrolo[2,3-b]pyridin-5-yl)-5-(1-methyl-1H-pyrazol-4-yl)phenyl)acrylamide |

Biological Activity Assays
ITK Inhibitor Binding Potency

The ability of candidate compounds to interact with ITK is quantitated by a competitive binding assay using the LanthaScreen technology developed by Life Technologies. This assay is based on the binding of a proprietary, Alexa Fluor® 647-labeled, ATP-competitive kinase inhibitor (kinase tracer-236) to the ITK expression construct in the presence of a Europium-conjugated antibody, resulting in a FRET (fluorescence resonance energy transfer) signal. Displacement of the kinase tracer by compound results in a lower emission ratio upon excitation of the Europium chelate. Candidate compounds are designed as potential irreversible inhibitors of ITK, capable of ligating to an active site cysteine residue resulting in time dependent covalent binding. The time dependent nature of irreversible inhibition is investigated by performing the binding assay with and without a pre-incubation of compound and ITK. An increase in potency in the pre-incubated assay suggests the candidate compound could be irreversibly modifying ITK or having a slowly reversible mechanism. The inhibitory potency of candidate compounds is measured in 20 mM HEPES pH 7.5, 10 mM $MgCl_2$, 0.01% BSA, 0.0005% Tween-20, and 2% DMSO in the presence of 10 nM ITK, 2 nM Eu-anti-GST antibody, and 50 nM kinase tracer-236 using a 384-well plate format. Background signal is defined in the absence of ITK and uninhibited signal is defined in the presence of vehicle (2% DMSO) alone. Compounds were evaluated in an 11 point dose-response ranging from 20 uM to 0.34 nM. The binding assays are performed under two preincubation conditions to evaluate time dependence of inhibition. For the pre-incubation assay, ITK and Eu-anti-GST antibody are pre-incubated with compound or vehicle for two hours prior to the addition of kinase tracer. The non-preincubated assay is run under conditions where ITK and Eu-anti-GST antibody are added to a mixture of compound and kinase tracer. $IC_{50}$ values of compounds are determined using a 4 parameter logistical fit of emission ratio as a function of the concentration of compound. Results are shown below in Table 3.

ITK Inhibitor Binding Kinetics

To obtain a better understanding of the kinetics of binding by inhibitor compounds to ITK, association and dissociation experiments were performed. Using the same TR-FRET buffer and conditions as described above, the kinetic rate constants for the binding of KT-236 to ITK were initially determined. Once knowing the association ($k_{on}$) and dissociation ($k_{off}$) rates of KT-236 binding, the binding kinetics for these candidate compounds could be further elucidated. The dissociation rates were determined by pre-incubating ITK for two hours with various concentrations of the candidate compounds. After this period of time, excess (200 nM final) KT-236 was added to the incubation and the resulting increase in fluorescence followed for approximately four hours. For the association rates, ITK was pre-incubated with KT-236 (50 nM) for 90-120 minutes and then various concentrations of candidate compound added. The resulting decrease in signal was then evaluated for the next two hours. Data from both sets of time course experiments was then analyzed using Dynafit software to obtain the kinetic rate constants ($k_{on}$, $k_{off}$, $k_{inact}$, $K_i$) utilizing multiple reaction models.

ITK Target Modulation PLC-γ Assay

Jurkat cells, an immortalized human T-lymphocyte cell line, were maintained in RPMI media, 10% FBS, 1% pen/strep/glutamine (growth media). Cells were plated in growth media plus 50 µM β-mercaptoethanol at 400,000 cells per well of a 96 well plate.

Compounds were serially diluted into DMSO, and then into media to concentrations 10× that of the final assay concentration. Compounds were then added to the cells with the final assay DMSO concentration being 0.1%. Cells were incubated for 1 hour at 37° C.

Following compound incubation, αCD3 Dynabeads were added at 1 bead/cell to each assay well and incubated at 37° C. for 7 minutes. Unstimulated control wells received media only. The plate was then placed on a 96-well magnetic plate for an additional 60 seconds (total assay stimulation time equals 8 minutes). The plate was then dumped and gently patted dry on a paper towel. 50 µl of complete Meso Scale Discovery (MSD) Lysis buffer was then added to each well. Samples were assayed for phospho-PLCγ1 using Meso Scale Discovery technology.

The assay stimulation time has been optimized for detection of Itk kinase-mediated phosphorylation of PLCγ1. The timing and detection reagents for this assay could be adjusted to capture phosphorylation events upstream (e.g., phospho-ZAP70) or downstream of the Itk/PLCγ1 node, provided the appropriate phospho-specific antibodies are available for building of an MSD assay. Results are shown below in Table 3.

ITK TH17 Activation Assay
Lymphocyte/CD4+ Cell Purification and Differentiation

CD4+ lymphocytes are prepared from the spleens of adult (>10 week old) C57BL/6 mice using conventional methodologies (Current Protocols in Immunology and Miltenyi Biotech), as starting material for in vitro differentiation of TH17 cells. Cultures are prepared using complete media (CM) and differentiation media (DM) as defined below. Purified CD4+ cells are washed twice with CM, and concentration adjusted to $6.7 \times 10^5$ cells per ml of DM. Prepare αCD3 coated tissue culture wells by diluting αCD3 antibody 1:100 in sterile PBS (10 µg/ml) with 1 ml per 6 well plate or 0.25 ml in a 24-well plate. Incubate 2 hours at 37° C. (Alternatively, wells can be coated the afternoon before use and incubated at 4° C.) Wash coated αCD3 plate 3× with DPBS. Do not aspirate final wash until cells are ready to be plated. Add 3 ml of cell suspension to αCD3 coated 6 well tissue culture plate ($2 \times 10^6$ cells per well) or 750 µl of cell suspension to a 24-well tissue culture plate ($5 \times 10^5$) and incubate at 37° C., 5% $CO_2$ for 3 days (72 hours). On Day 3, gently add 2 ml of freshly prepared DM for 6-well plate, or 500 µl of freshly prepared DM for 24-well plate, and continue to incubate for an additional 24 hours.

Re-Stimulation of Th17 T Cells

Prepare αCD3 coated tissue culture wells for by diluting αCD3 antibody 1:200 in sterile PBS (5 µg/ml) and add 5 µl per well, 96 well plate. Incubate 2 hours at 37° C. (Alternatively, wells can be coated the afternoon before use and incubated at 4° C.). On Day 4, harvest Th17 cells and wash 2× with fresh warmed CM. Count and re-suspend cells to $2.8 \times 10^5$ cells per ml. Distribute 0.18 ml of cell suspension per well into a 96 well tissue culture plate (not the αCD3 coated plate). Add 10× concentration of inhibitors in 0.02 ml of CM and incubate at 37° C. for one hour. Five minutes before this incubation step is finished, wash the αCD3 coated tissue culture plate 3× with sterile PBS. Leave last wash on the plates until ready to transfer cell suspension to avoid drying out. Re-suspend cells by gently pipetting up and down or placing plate on a mixer. Flick out the last PBS wash from the αCD3 coated plate and transfer 0.18 milliliters of cells in CM and inhibitors to αCD3 coated plate, omitting outer wells of plate. Fill outer wells with 0.18 milliliters PBS. Incubate overnight (~20 hours) at 37° C., 5% $CO_2$. The next morning, centrifuge plate at 1200 RPM for 5 minutes, then remove 150 µl of supernatant for cytokine level determination by Mesoscale. Freeze supernatants at −20° C. until use.

REFERENCES

ISOLATION AND FRACTIONATION OF SECTION MONONUCLEAR CELL POPULATIONS. Current Protocols in Immunology 3.1
CD4 (L3T4) MicroBeads, mouse, catalog no. 130-049-201—Miltenyi Biotech
Complete Media (CM)
RPMI1640 (Life Technologies, Cat. #A10491-01)
10% Heat Inactivated Fetal Bovine Serum
2 mM L-glutamine
1 mM Sodium Pyruvate
10 mM HEPES
1× Non-essential Amino Acids (NEAA)
50 uM 2-mercaptoethanol
1× pen/strep
Differentiation Media (DM)
Complete media (CM) supplemented with:
10 µg/ml anti-murine anti-CD-28 (BioLegend, Cat. #102112)
10 µg/ml anti-murine IFNγ (BioLegend, Cat. #505812)
10 µg/ml anti-murine IL4 (BioLegend, Cat. #504108)
1 ng/ml recombinant human TGFβ1 (BioLegend, Cat. #580704)
50 ng/ml recombinant murine IL-6 (BioLegend, Cat. #575704)
5 ng/ml recombinant murine IL-23 (BioLegend, Cat. #589004)
10 ng/ml recombinant murine IL-1β (R&D Systems, Cat. #401-ML-005)
Anti-IL4, anti-IFNγ, anti-CD28, and anti-CD3 stock solutions are maintained at 4° C. TGFβ1, IL-6, IL-23 and IL1β are single-use aliquots of 2 µl each. Add 198 µl of CM to obtain 100 fold dilution working solutions. Discard single-use aliquots after each use. Stored at −20° C.

TABLE 3

Biological Activity

| Example # | ITK Inhibition $IC_{50}$ uM<br>+ indicates ≤1 µM<br>− indicates >1 µM | PLC-γ Inhibition $IC_{50}$ uM<br>++ indicates ≤1 µM<br>+ indicates ≤1-5 µM<br>− indicates >5 µM |
|---|---|---|
| 1 | + | − |
| 2 | + |  |
| 3 | + |  |
| 4 | + | − |
| 5 | + | − |
| 6 | + | ++ |
| 7 | − |  |
| 8 | + | + |
| 9 | + | − |
| 10 | + | − |
| 11 | + | ++ |
| 12 | + | + |
| 13 | + |  |
| 14 | + | − |
| 15 | + | − |
| 16 | + |  |
| 17 | + | − |
| 18 | + |  |
| 19 | + | − |
| 20 | + | ++ |
| 21 | + | + |
| 22 | + | ++ |
| 23 | + | + |
| 24 | + | ++ |
| 25 | + | ++ |
| 26 | + | ++ |
| 27 | + |  |
| 28 | + | ++ |
| 29 | + | + |
| 30 | + | + |
| 31 | − | − |
| 32 | + | ++ |
| 33 | + | + |
| 34 | − | − |
| 35 | + | − |
| 36 | + | − |
| 37 | + | + |
| 38 | + | − |
| 39 | + | + |
| 40 | + |  |
| 41 | + | ++ |
| 42 | + | + |
| 43 | + | + |
| 44 | + | + |
| 45 | + | + |
| 46 | + | ++ |
| 47 | + |  |
| 48 | + | + |
| 49 | + | ++ |
| 50 | + | ++ |
| 51 | + | + |
| 52 | + | − |
| 53 | + | − |
| 54 | + | + |
| 55 | + | − |
| 56 | + | + |
| 57 | + | ++ |
| 58 | + | + |
| 59 | + | ++ |
| 60 | + | − |
| 61 | + | ++ |
| 62 | + | ++ |
| 63 | + | − |
| 64 | + | + |
| 65 | + | − |
| 66 | + | + |
| 67 | − | ++ |
| 68 | − | − |
| 69 | + | − |
| 70 | + | − |
| 71 | + | + |
| 72 | + | ++ |
| 73 | + | − |
| 74 | + | ++ |
| 75 | + | − |
| 76 | + | ++ |
| 77 | + | − |
| 78 | + | − |
| 79 | + | − |
| 80 | + | ++ |
| 81 | − | − |
| 82 | − | − |
| 83 | − | + |
| 84 | + | + |
| 85 | + | − |
| 86 | − | − |
| 87 | + | − |
| 88 | + | + |
| 89 | + | ++ |
| 90 | + | − |
| 91 | + | ++ |
| 92 | + | + |

Anti-inflammatory Efficacy—Rat Carrageenan Foot Pad Edema: The compounds of the present disclosure will be evaluated for efficacy in vivo in a model of inflammation. Methods to determine efficacy in rat carrageenan foot pad edema are described in U.S. Pat. No. 5,760,068.

Male Sprague Dawley rats are selected for equal average body weight per group. After fasting, with free access to water sixteen hours prior to test, animals are dosed orally (1 mL) with test compounds in a vehicle containing 0.5% methylcellulose and 0.025% surfactant. The control group is dosed with vehicle alone.

One hour after dosing, a subplantar injection of 0.1 mL of 1% solution of carrageenan/sterile 0.9% saline is administered in one foot, to all animals. The volume of the injected foot is measured using a displacement plethysmometer. Foot volume is measured again three hours after carrageenan injection. The three hour foot volume measurement is compared between treated and control groups; the percent inhibition of edema is calculated.

Anti-inflammatory Efficacy—Rat Carrageenan-Induced Analgesia Test: The compounds of the present disclosure will be evaluated for efficacy in vivo in a model of inflammatory analgesia. Methods to determine efficacy in rat carrageenan-induced analgesia test are described in U.S. Pat. No. 5,760,068.

Male Sprague Dawley rats are selected for equal average body weight per group. After fasting, with free access to water sixteen hours prior to test, animals are dosed orally (1 mL) with test compounds in vehicle containing 0.5% methylcellulose and 0.025% surfactant. Control groups are dosed with vehicle alone.

One hour after dosing, a subplantar injection of 0.1 mL of 1% solution of carrageenan/sterile 0.9% saline is administered in one foot, to all animals. Three hours after carrageenan injection, rats are placed in a plexiglass container with a high intensity lamp under the floor. After twenty minutes, thermal stimulation is begun on either the injected or the uninjected foot. Foot withdrawal is determined by a photoelectric cell. The time until foot withdrawal is measured and compared between treated and control groups. The percent inhibition of the hyperalgesic foot withdrawal is calculated.

Efficacy in Collagen-Induced Arthritis: The compounds of the present disclosure will be evaluated in a mouse autoimmune model of rheumatoid arthritis. Methods to determine efficacy in collagen-induced arthritis in the mouse are described by Grimstein, et al. (2011) J. Translational Med. 9, 1-13.

Six week-old male DBA/1J mice are obtained from The Jackson Laboratory. At eight weeks of age, mice are orally administered test compounds daily. Mice are immunized by intradermal injection, at twelve weeks of age, with 0.1 mL of emulsion containing 100 µg of bovine type II collagen (bCII). At 21 days following immunization, mice are boosted with 0.1 mL of bCII (100 µg) emulsified in equal volume of incomplete Freund's Adjuvant (IFA) (Difco, Detroit, Mich.). All mice are monitored three times for the incidence of arthritis and evaluation of a clinical score, ranging from 0-4 was used (0: no swelling or redness; 1: detectable arthritis with erythema; 2: significant swelling and redness; 3: severe swelling and redness from joint to digit; 4: joint stiffness or deformity with ankylosis). The score is calculated from the average cumulative value of all four paws. Severe arthritis is defined as a score >3.

For terminal evaluation of arthritis, mice are euthanized 28 days after initial immunization. The two hind limbs are removed, fixed in formalin, decalcified in RDO solution (Apex Engineering, Aurora, Ill.) for 10-20 min depending on tissue size and examined for pliability. Sections are cut (4 µm thick) and stained with hematoxylin and eosin. Histological evaluation is performed by examining for infiltration of immune cells, hyperplasia, pannus formation and bone deformation for each paw, using a scale ranging from 0-3, according to severity of pathological changes (0: normal, 1: mild, 2: moderate, 3: severe).

ITK IL-2 Release Assay

This assay was based on the ability of a compound to inhibit ITK mediated IL-2 release. Jurkat cells were placed in wells of a 96-well plate at 500,000 per well in 120 µL medium (same as above). Compounds were added as 15 µL per well of 10× working stock solutions in medium with 1% DMSO (or medium with 1% DMSO for controls) and placed in a 37° C. incubator for 2 hours. Stimulation used CD3/CD28 Dynabeads to activate the T cell receptor and mimic antigen presenting cells. Beads were added at a ratio of 1 bead per cell, in 15 µL medium (or medium alone for unstimulated control). After overnight incubation, the plates were centrifuged at 290×g for 5 min, then 100 µL per well of supernatant medium removed for IL-2 cytokine assay. To determine cell viability, to the remaining well contents 50 µL of CellTiter-Glo reagent was added and luminescence determined. The IL-2 cytokine assay utilized an electrochemiluminescence-based ELISA.

OTHER EMBODIMENTS

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

All references cited in this specification are hereby incorporated by reference. The discussion of the references herein is intended merely to summarize the assertions made by their authors and no admission is made that any reference constitutes prior art relevant to patentability. Applicant reserves the right to challenge the accuracy and pertinency of the cited references.

What is claimed is:
1. A compound, or a pharmaceutically acceptable salt, hydrate or solvate thereof, of Formula (I):

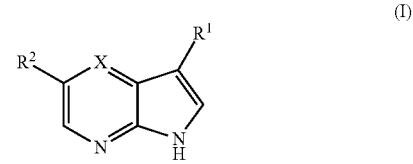

wherein:
$R^1$ is phenyl, wherein $R^1$ is substituted with one $R^3$ substituent;
$R^2$ is chosen from heterocycloalkyl, aryl, and heteroaryl, each of which is substituted with one $R^4$ substituent, and any of which is further optionally substituted with one or more R[8] substituents, or alternatively R[2] is NR[12]R[13];

R[3] is cyano;

R[4] is chosen from NR[5]R[6], —(CH$_2$)$_n$CR[7]=CR[9]C(O)CH$_3$, —(CH$_2$)$_n$CR[7]=CR[9]C(O)NR[7]R[7'], and —(CH$_2$)$_n$CR[7]=CR[9]CN;

R[5] is chosen from cyano, —C(O)CF$_3$, —C(O)CH=CH$_2$, —C(O)CR[7]=CH$_2$, —C(O)CH=CHR[7], —C(O)CR[7]=CHR[7], —C(O)CH=CR[7]R[7'], —C(O)CH=CHCH$_2$R[8], —C(O)CH=CHC(O)CH$_2$R[8], —COC(CN)=CHR[6], —C(O)(C(O)NH$_2$)=CHR[6], C(O)alkynylR[7], —S(O)$_2$CH=CH$_2$, —(CH$_2$)$_m$CR[7]=CR[9]C(O)CH$_3$, —(CH$_2$)$_m$CR[7]=CR[9]C(O)NR[7]R[7'], and —(CH$_2$)$_m$CR[7]=CR[9]CN;

R[6] and R[6'] are each independently chosen from hydrogen, C$_{1-4}$ alkyl, C$_{3-7}$ cycloalkylalkyl, and phenylC$_{1-4}$ alkyl;

R[7] and R[7'] are each independently chosen from hydrogen, cyano, C$_{1-4}$alkyl, hydroxyC$_{1-4}$alkyl, C$_{1-4}$alkoxyalkyl, C$_{3-7}$ cycloalkyl, C$_{3-7}$ heterocycloalkyl, C$_{3-7}$ heterocycloalkylalkyl, (NR[6]R[6'])C$_{1-4}$alkyl, aryl, and heteroaryl, wherein aryl and heteroaryl are optionally substituted with one or more R[9];

R[8] is chosen from hydrogen, halo, cyano, C$_{1-4}$alkyl, arylC$_{1-4}$ alkyl, heteroarylC$_{1-4}$alkyl, C$_{3-7}$cycloalkyl, hydroxyC$_{1-6}$ alkyl, heterocycloalkylC$_{1-4}$ alkyl, C$_{3-7}$ heterocycloalkyl, hydroxyl, C$_{1-4}$alkoxy, C$_{3-7}$ cycloalkoxy, C$_{3-7}$ cycloalkoxyalkyl, heteroaryloxy, aryloxy, (NR[6]R[6'])alkyl, arylalkoxy, C$_{1-4}$ alkoxyC$_{1-4}$alkyl, amino, C$_{1-4}$ alkylamino, di(C$_{1-4}$alkyl)amino, trifluoromethyl, aryl, and heteroaryl, wherein alkyl, heterocycloalkyl, aryl and heteroaryl are optionally substituted with one or more R[9];

R[9] is chosen from hydrogen, halo, hydroxyl, C$_{1-4}$ alkyl, cyano, trifluoromethyl, alkanoyl, amino, amido, and aryl;

R[11] is chosen from hydrogen, C$_{1-4}$ alkyl, C$_{3-7}$ cycloalkylalkyl, heterocycloalkylalkyl, arylC$_{1-4}$alkyl, and heteroarylC$_{1-4}$alkyl, wherein aryl and heteroaryl may be optionally substituted with one or more R[9];

R[12] is a nitrogen-containing C$_{3-7}$ heterocycloalkyl, wherein said nitrogen is further substituted by R[5];

R[13] is chosen from hydrogen, C$_{1-4}$ alkyl, and C$_{3-7}$ cycloalkylalkyl;

X is N or CR[11];

m is an integer chosen from 1, 2 and 3; and n is an integer chosen from 0, 1, 2, and 3.

2. A compound of claim 1, or a pharmaceutically acceptable salt, hydrate or solvate thereof, wherein R[2] is chosen from phenyl and pyridinyl, either of which is substituted with one R[4] substituent, and either of which is further optionally substituted with one or more R[8] substituents.

3. A compound according to claim 1, chosen from:
(E)-N-(3-(3-(3-cyanophenyl)-1H-pyrrolo[2,3-b]pyridin-5-yl)phenyl)-4-(dimethylamino)but-2-enamide, and
N-(3-(3-(3-cyanophenyl)-1H-pyrrolo[2,3-b]pyridin-5-yl)phenyl)acrylamide,
or a pharmaceutically acceptable salt, hydrate or solvate thereof.

4. A compound of claim 2, wherein the compound has formula (III):

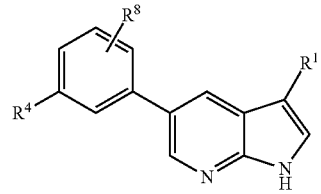

(III)

or a pharmaceutically acceptable salt, hydrate or solvate thereof, wherein:

R[1] is phenyl, wherein R[1] is substituted with one R[3] substituent;

R[3] is cyano,

R[4] is chosen from —NR[5]R[6], —(CH$_2$)$_n$CR[7]=CR[9]C(O)CH$_3$, —(CH$_2$)$_n$CR[7]=CR[9]C(O)NR[7]R[7'], and —(CH$_2$)$_n$CR[7]=CR[9]CN;

R[5] is chosen from cyano, —C(O)CF$_3$, —C(O)CH=CH$_2$, —C(O)CR[7]=CH$_2$, —C(O)CH=CHR[7], —C(O)CR[7]=CHR[7], —C(O)CH=CR[7]R[7'], —C(O)CH=CHCH$_2$R[8], —C(O)CH=CHC(O)CH$_2$R[8], —COC(CN)=CHR[6], —C(O)(C(O)NH$_2$)=CHR[6], —C(O)alkynylR[7], —S(O)$_2$CH=CH$_2$, —(CH$_2$)$_m$CR[7]=CR[9]C(O)CH$_3$, —(CH$_2$)$_m$CR[7]=CR[9]C(O)NR[7]R[7'], and —(CH$_2$)$_m$CR[7]=CR[9]CN;

R[6] and R[6'] are each independently chosen from hydrogen, C$_{1-4}$ alkyl, C$_{3-7}$ cycloalkylalkyl, and phenylC$_{1-4}$ alkyl;

R[7] and R[7'] are each independently chosen from hydrogen, cyano, C$_{1-4}$alkyl, hydroxyC$_{1-4}$alkyl, C$_{1-4}$alkoxyalkyl, C$_{3-7}$ cycloalkyl, C$_{3-7}$ heterocycloalkyl, C$_{3-7}$ heterocycloalkylalkyl, (NR[6]R[6'])C$_{1-4}$alkyl, aryl, and heteroaryl where aryl and heteroaryl are optionally substituted with one or more R[9];

R[8] is chosen from hydrogen, halo, cyano, C$_{1-4}$alkyl, arylC$_{1-4}$ alkyl, heteroarylC$_{1-4}$alkyl, C$_{3-7}$cycloalkyl, hydroxyC$_{1-6}$ alkyl, heterocycloalkylC$_{1-4}$ alkyl, C$_{3-7}$ heterocycloalkyl, hydroxyl, C$_{1-4}$alkoxy, C$_{3-7}$ cycloalkoxy, C$_{3-7}$ cycloalkoxyalkyl, heteroaryloxy, aryloxy, (NR[6]R[6'])alkyl, arylalkoxy, C$_{1-4}$ alkoxyC$_{1-4}$ alkyl, amino, C$_{1-4}$alkylamino, di(C$_{1-4}$alkyl)amino, trifluoromethyl, aryl, and heteroaryl, wherein alkyl, heterocycloalkyl, aryl and heteroaryl are optionally substituted with one or more R[9];

R[9] is chosen from hydrogen, halo, hydroxyl, C$_{1-4}$ alkyl, cyano, trifluoromethyl, C(O)CH$_3$, amido, and aryl;

m is an integer chosen from 1, 2 and 3; and n is an integer chosen from 0, 1, 2, and 3.

5. A compound according to claim 4, chosen from:
N-(3-(3-(3-cyanophenyl)-1H-pyrrolo[2,3-b]pyridin-5-yl)phenyl)acrylamide,
or a pharmaceutically acceptable salt, hydrate or solvate thereof.

6. A composition comprising a compound of claim 1, or a pharmaceutically acceptable salt, hydrate or solvate thereof, and a pharmaceutically acceptable carrier, adjuvant, or vehicle.

7. A method of inhibiting ITK activity in a biological sample comprising contacting the biological sample with a compound of claim 1, or a pharmaceutically acceptable salt, hydrate or solvate thereof.

* * * * *